(12) United States Patent
Studer et al.

(10) Patent No.: US 12,371,662 B2
(45) Date of Patent: Jul. 29, 2025

(54) CELL-BASED TREATMENT AND DRUG DISCOVERY IN HIRSCHSPRUNG'S DISEASE ENABLED BY PLURIPOTENT STEM CELL-DERIVED HUMAN ENTERIC NEURAL CREST LINEAGES

(71) Applicant: MEMORIAL SLOAN-KETTERING CANCER CENTER, New York, NY (US)

(72) Inventors: Lorenz Studer, New York, NY (US); Faranak Fattahi, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/015,748

(22) Filed: Jun. 22, 2018

(65) Prior Publication Data

US 2018/0291339 A1    Oct. 11, 2018

Related U.S. Application Data

(63) Continuation of application No. PCT/US2016/068430, filed on Dec. 22, 2016.

(60) Provisional application No. 62/387,468, filed on Dec. 23, 2015.

(51) Int. Cl.
| | | |
|---|---|---|
| *C12N 5/0793* | (2010.01) | |
| *A61K 35/30* | (2015.01) | |
| *C12N 5/073* | (2010.01) | |

(52) U.S. Cl.
CPC ............ *C12N 5/0619* (2013.01); *A61K 35/30* (2013.01); *C12N 5/0603* (2013.01); *C12N 2501/13* (2013.01); *C12N 2501/15* (2013.01); *C12N 2501/155* (2013.01); *C12N 2501/16* (2013.01); *C12N 2501/385* (2013.01); *C12N 2501/415* (2013.01); *C12N 2501/727* (2013.01); *C12N 2501/999* (2013.01); *C12N 2506/02* (2013.01); *C12N 2506/45* (2013.01); *C12N 2510/00* (2013.01)

(58) Field of Classification Search
CPC .. C12N 5/0623; C12N 5/0603; C12N 5/0606; C12N 2501/13; C12N 2501/15; C12N 2501/16; C12N 2501/115; C12N 2501/155; C12N 2501/415; C12N 2506/02; C12N 5/0667; C12N 5/0018; C12N 5/0618; C12N 5/0619; C12N 5/0696; C12N 2501/01; C12N 2501/727; C12N 2501/999; C12N 2506/03; C12N 2506/04; C12N 2510/00; C12N 2533/52; C12N 2501/385; C12N 2506/45; A61K 35/12; A61K 35/30; A61P 5/00; A61P 25/00; A61P 25/16; A61P 25/28; A61P 1/00; A61P 25/02; A61P 43/00

See application file for complete search history.

(56) References Cited

U.S. PATENT DOCUMENTS

| | | |
|---|---|---|
| 2008/0268019 A1 | 10/2008 | Badylak et al. |
| 2009/0123433 A1 | 5/2009 | Shroff |
| 2011/0296542 A1 | 12/2011 | Wang et al. |
| 2013/0183674 A1 | 7/2013 | Studer et al. |
| 2015/0159135 A1 | 6/2015 | Davis et al. |
| 2015/0285822 A1 | 10/2015 | Zhang et al. |

FOREIGN PATENT DOCUMENTS

| | | |
|---|---|---|
| WO | WO 2011/149762 A2 | 12/2011 |
| WO | WO 2015/077648 A1 | 5/2015 |

OTHER PUBLICATIONS

Menendez et al., Nature Protocols, vol. 8 No. 1.: 203-212, 2013 (Year: 2013).*
Sato et al., Nature Medicine, vol. 10, No. 1:55-63, 2004 (Year: 2004).*
Yan et al., Developmental Dynamics, 213:370-385, 1998 (Year: 1998).*
Kam and Lui, Develop. Growth Differ. 57:158-168 (Feb. 19, 2015) (Year: 2015).*
Menendez, PNAS, 108(48):19240-245, 2011 (Year: 2011).*
Simkin et al. PLoS One, vol. 8, Issue 5:e64077 (May 2013) (Year: 2013).*
Hutchins et al., Dev Biol. 444(Suppl 1):S98-109, Dec. 2018 (Year: 2018).*
Menendez et al., Nature Protocols, 8(1):203-212 (Year: 2013).*
Dickman et al., Development, 124:3111-3121 (Year: 1997).*
Elkenani et al., The FEBS Journal 288: 3317-3329 (Year: 2020).*
Hearn et al., "GDNF and ET-3 Differentially Modulate the Numbers of Avian Enteric Neural Crest Cells and Enteric Neurons in Vitro," Developmental Biology, 197:93-105 (1998).

(Continued)

*Primary Examiner* — Kimberly Ballard
*Assistant Examiner* — Stacey N MacFarlane
(74) *Attorney, Agent, or Firm* — Baker Botts L.L.P.

(57) ABSTRACT

The presently disclosed subject matter provides for in vitro methods of inducing differentiation of stem cells into enteric neural crest lineage cells, and enteric neural crest lineage cells by such methods. The presently disclosed subject matter also provides for uses of such enteric neural crest lineage cells for preventing and/or treating enteric nervous system disorders (e.g, Hirschsprung's disease), and for screening compounds suitable for preventing and/or treating enteric nervous system disorders (e.g., Hirschsprung's disease).

Figure 1A:
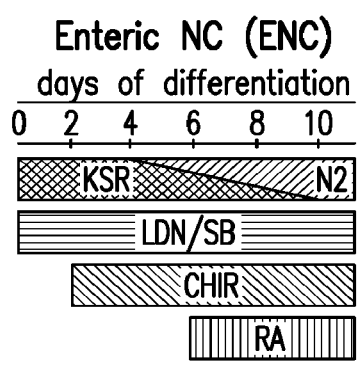

32 Claims, 36 Drawing Sheets
Specification includes a Sequence Listing.

(56) References Cited

OTHER PUBLICATIONS

Maury et al., "Combinatorial analysis of developmental cues efficiently converts human pluripotent stem cells into multiple neuronal subtypes," Nature Biotechnology, 33(1):89-96 (2015).
Micci et al., "Neural Stem Cell Transplantation in the Stomach Rescues Gastric Function in Neuronal Nitric Oxide Synthase-Deficient Mice," Gastroenterology, 129:1817-1824 (2005).
Micci et al., "Neural stem cells express RET, Produce Nitric Oxide, and Survive Transplantation in the Gastrointestinal Tract," Gastroenterology, 121:757-766 (2001).
Micci et al., "Neural Stem Cells for the Treatment of Disorders of the Enteric Nervous System: Strategies and Challenges," Developmental Dynamics., 236:33-43 (2007).
Rintala et al., "Sodium Cromoglycate in the Management of Chronic or Recurrent Enterocolitis in Patients with Hirschsprung's Disease," Journal of Pediatric Surgery., 36:1032-1035 (2001).
Supplementary Partial European Search Report dated Oct. 22, 2019 in Application.
Barthel et al., "Tissue Engineering of the Intestine in a Murine Model," J. Vis. Exp. (70):e4279 (2012).
Cadigan et al., "Wnt signaling: complexity at the surface," J Cell Sci. 119(3):395-402 (2006).
Calder et al., "Retinoic Acid-Mediated Regulation of GLI3 Enables Efficient Motoneuron Derivation from Human ESCs in the Absence of Extrinsic SHH Activation," J Neurosci. 35(33):11462-11481 (2015).
Chakravarti, "Endothelin receptor-mediated signaling in Hirschsprung disease," Hum Mol Genet 5(3):303-307 (1996).
Chalazonitis et al., "Neurotrophin-3 Induces Neural Crest-Derived Cells from Fetal Rat Gut to Develop in vitro as Neurons or Glia," J Neurosci 14(11):6571-6584 (1994).
Chambers et al., "Combined small-molecule inhibition accelerates developmental timing and converts human pluripotent stem cells into nociceptors," Nat Biotechnol 30(7):715-720 (2012).
Chambers et al., "Highly efficient neural conversion of human ES and iPS cells by dual inhibition of SMAD signaling," Nat Biotechnol 27(3):275-280 (2009).
Chan et al., "Hoxb3 Vagal Neural Crest-specific Enhancer Element for Controlling Enteric Nervous System Development," Dev Dynamics 233:473-483 (2005).
Chen et al., "Chemically defined conditions for human iPSC derivation and culture," Nat Methods 8(5):424-429 (2011).
Christ et al., "Gap junction-mediated intercellular diffusion of Ca2+ in cultured human corporal smooth muscle cells," Am J Physiol 263:C373-C383 (1992).
Cong et al., "Multiplex Genome Engineering Using CRISPR/Cas Systems," Science 339:819-823 (2013).
Cully, "Deal watch: Lilly buys back into the BACE race for Alzheimer's disease," Nature Reviews. Drug Discovery 13:804 (2014).
Cuny et al., "Structure-activity relationship study of bone morphogenetic protein (BMP) signaling inhibitors," Bioorg. Med. Chem. Lett. 18(15):4388-4392 (2008).
Di Lorenzo et al., "Colonic Motility after Surgery for Hirschsprung's Disease," The American Journal of Gastroenterology 95(7):1759-1764 (2000).
Doble et al., "GSK-3: tricks of the trade for a multi-tasking kinase," J Cell Sci. 116(7):1175-1186 (2003).
Drake et al., Gray's Anatomy for Students. Churchill Livingstone (2010).
Dreser et al., "Grouping of histone deacetylase inhibitors and other toxicants disturbing neural crest migration by transcriptional profiling," NeuroToxicology 50:56-70 (2015).
Fu et al., "HOXB5 Expression Is Spatially and Temporarily Regulated in Human Embryonic Gut During Neural Crest Cell Colonization and Differentiation of Enteric Neuroblasts," Dev Dyn 228:1-10 (2003).
Furness, "The enteric nervous system and neurogastroenterology," Nature Reviews Gastroenterology & Hepatology 9:286-294 (2012).
Gariepy et al., "Null mutation of endothelin receptor type B gene in spotting lethal rats causes aganglionic megacolon and white coat color," Proc. of the Natl. Acad. of Sci. USA 93:867-872 (1996).
Gershon et al., "The Serotonin Signaling System: From Basic Understanding to Drug Development for Functional GI Disorders," Gastroenterology 132:397-414 (2007).
Gershon, "Transplanting the enteric nervous system: a step closer to treatment for aganglionosis," Gut 56:459-461 (2007).
Haas, "Extending the Search for Folk Personality Constructs: The Dimensionality of the Personality-Relevant Proverb Domain," J Pers Soc Psychol 82(4):594-609 (2002).
Heanue et al., "Enteric nervous system development and Hirschsprung's disease advances in genetic and stem cell studies," Nat Rev Neurosci 8:466-479 (2007).
Hosoda et al., "Targeted and Natural (Piebald-Lethal) Mutations of Endothelin-B Spotted in Mice," Cell 79:1267-1276 (1994).
Hotta et al., "Transplanted progenitors generate functional enteric neurons in the postnatal colon," J Clin Invest 123(3):1182-1191 (2013).
Hotta et al., "Stem cells for GI motility disorders," Curr Opin Pharmacol, 11:617-623 (2011).
International Search Report May 3, 2017 in International Application No. PCT/US16/68430.
Iwashita et al., "Hirschsprung Disease Is Linked to Defects in Neural Crest Stem Cell Function," Science 301:972-976 (2003).
Jinek et al., "RNA-programmed genome editing in human cells," eLife 2:e00471 (2013).
Kikuchi et al., "Multiplicity of the interactions of Wnt proteins and their receptors," Cell Signalling 19:659-671 (2007).
Kruger et al., "Temporally Distinct Requirements for Endothelin Receptor B in the Generation and Migration of Gut Neural Crest Stem Cells," Neuron 40:917-929 (2003).
Laflamme et al., "Cardiomyocytes derived from human embryonic stem cells in pro-survival factors enhance function of infarcted rat hearts," Nat Biotechnol 25(9):1015-1024 (2007).
Lee et al., "Isolation and directed differentiation of neural crest stem cells derived from human embryonic stem cells," Nat Biotechnol 25(12):1468-1475 (2007).
Menendez et al., "Wnt signaling and a Smad pathway blockade direct the differentiation of human pluripotent stem cells to multipotent neural crest cells," PNAS 108(48):19240-19245 (2011).
Mica et al., "Modeling Neural Crest Induction, Melanocyte Specification, and Disease-Related Pigmentation Defects in hESCs and Patient-Specific iPSCs," Cell Rep 3:1140-1152 (2013).
Nathan et al., "The contribution of Islet1-expressing splanchnic mesoderm cells to distinct branchiomeric muscles reveals significant heterogeneity in head muscle development," Development 135:647-657 (2008).
Ran et al., "Double Nicking by RNA-Guided CRISPR Cas9 for Enhanced Genome Editing Specificity," Cell 154:1380-1389 (2013).
Schafer et al., "Neural stem cell transplantation in the enteric nervous system: roadmaps and roadblocks," Neurogastroenterol Motil 21:103-112 (2009).
Takahashi et al., "Induction of Pluripotent Stem Cells from Mouse Embryonic and Adult Fibroblast Cultures by Defined Factors," Cell 126:663-676 (2006).
Tobin et al., "Inhibition of neural crest migration underlies craniofacial dysmorphology and Hirschsprung's disease in Bardet-Biedl syndrome," PNAS 105(18):6714-6719 (2008).
Torii et al., "In vivo knockdown of ErbB3 in mice inhibits Schwann cell precursor migration," Biochem Biophys Res Commun 452:782-788 (2014).
Vassar et al., "Function, therapeutic potential and cell biology of BACE proteases: current status and future prospects," J Neurochem 130:4-28 (2014).
Wakatsuki et al., "Neuregulin-1/glial growth factor stimulates Schwann cell migration by inducing α5 β1 integrin-ErbB2-focal adhesion kinase complex formation," Genes to Cells 19:66-77 (2014).
Wichterle et al., "Directed Differentiation of Embryonic Stem Cells into Motor Neurons," Cell 110:385-397 (2002).
Yoshida et al., "Pepstatin A, an Aspartic Proteinase Inhibitor, Suppresses RANKL-Induced Osteoclast Differentiation," J Biochem 139:583-590 (2006).

(56) References Cited

OTHER PUBLICATIONS

Yu et al., "BMP type I receptor inhibition reduces heterotopic ossification," Nat Med 14(12):1363-1369 (2008).
Zeltner et al., "Feeder-free Derivation of Neural Crest Progenitor Cells from Human Pluripotent Stem Cells," J. Vis. Exp. (87):e51609 (2014).
Zhang et al., "Phactr4 regulates directional migration of enteric neural crest through PP1, integrin signaling, and cofilin activity," Genes Dev 26:69-81 (2012).
Laranjeira et al., "Glial cells in the mouse enteric nervous system can undergo neurogenesis in response to injury," J. Clin. Invest., 121(9):3412-3424 (2011).
Heanue et al., "Prospective Identification and Isolation of Enteric Nervous System Progenitors Using Sox2," Stem Cells 29:128-140 (2011).

\* cited by examiner

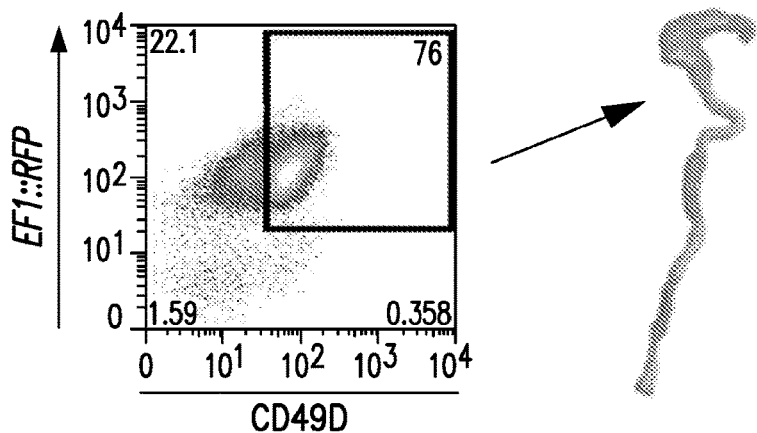
FIG. 6A
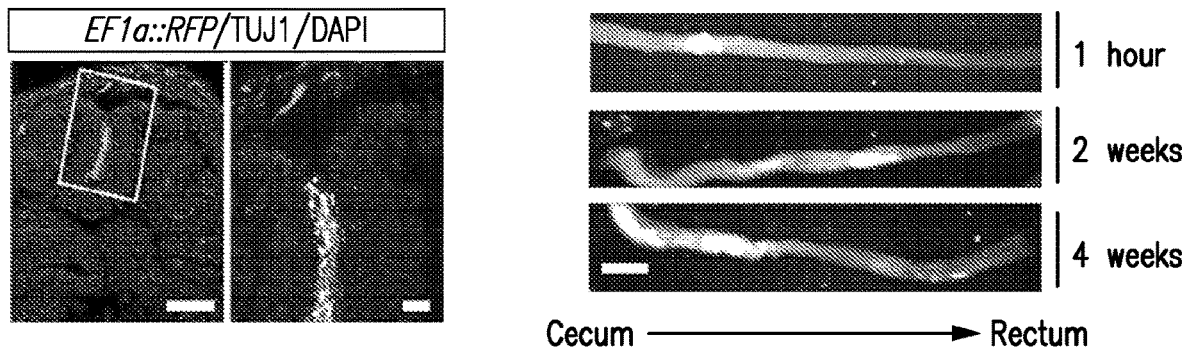
FIG. 6C
FIG. 6B
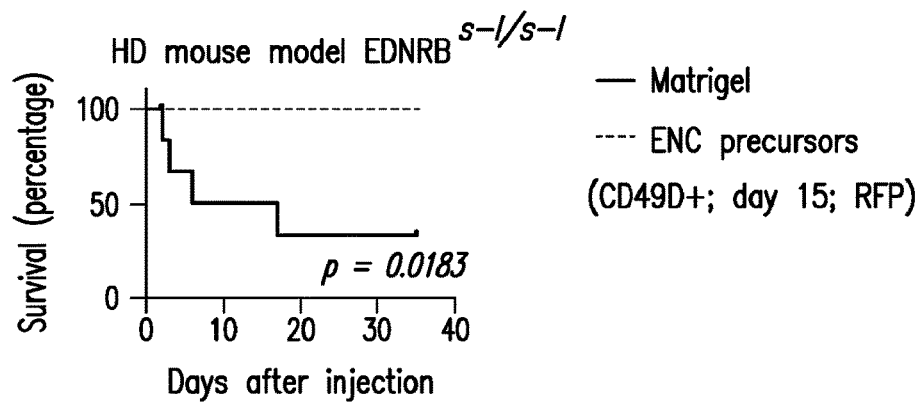
FIG. 6D

FIG. 11A

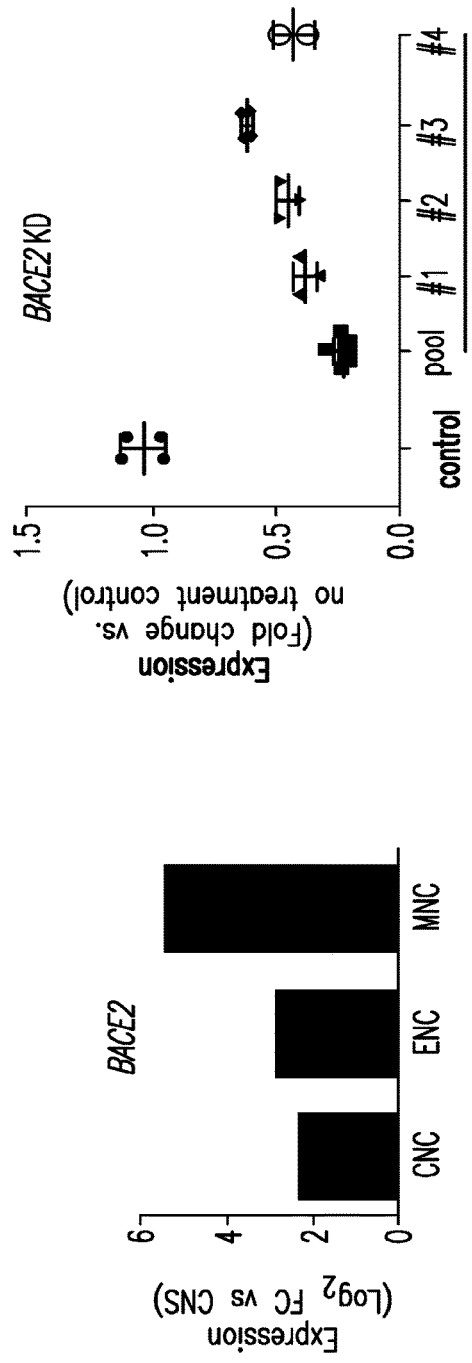
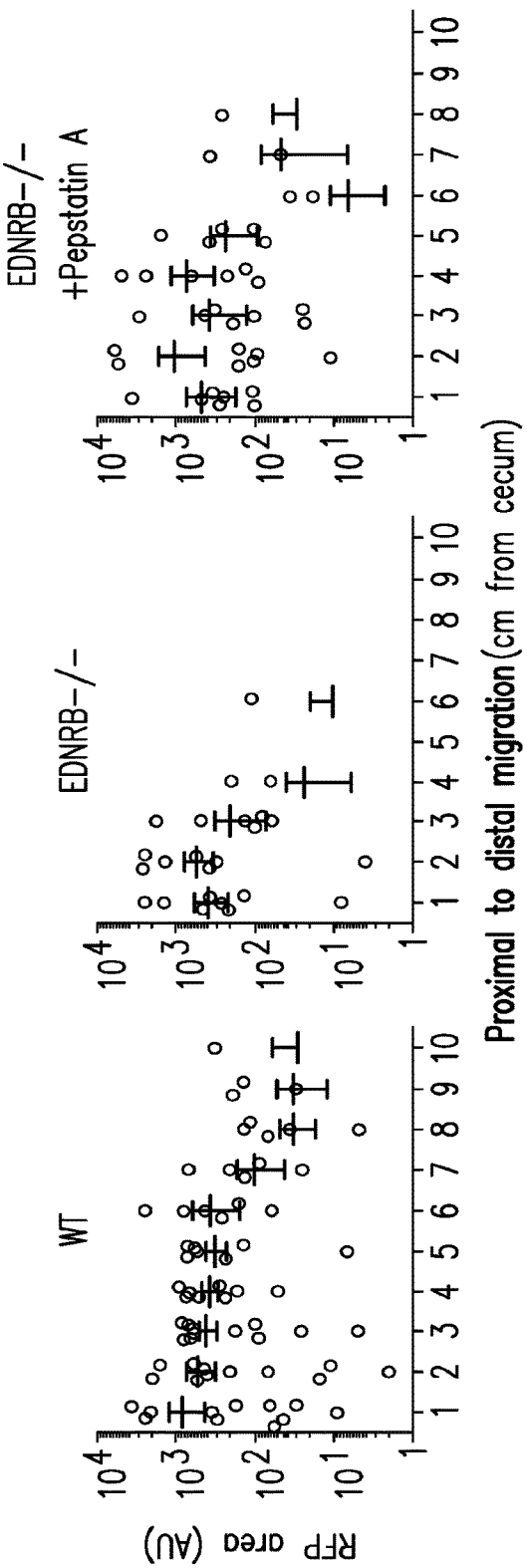
FIG. 13A
FIG. 13B
FIG. 13C

CELL-BASED TREATMENT AND DRUG DISCOVERY IN HIRSCHSPRUNG'S DISEASE ENABLED BY PLURIPOTENT STEM CELL-DERIVED HUMAN ENTERIC NEURAL CREST LINEAGES

CROSS-REFERENCE TO RELATED APPLICATION

This application is a Continuation of International Patent Application No. PCT/US16/068430 filed Dec. 22, 2016, which claims priority to U.S. Provisional Application Ser. No. 62/387,468 filed on Dec. 23, 2015, the contents of each of which are incorporated by reference in their entirety, and to each of which priority is claimed.

SEQUENCE LISTING

The specification further incorporates by reference the Sequence Listing submitted herewith via EFS on Jun. 22, 2018. Pursuant to 37 C.F.R. § 1.52(e)(5), the Sequence Listing text file, identified as 0727340744SL.txt, is 1,205 bytes and was created on Jun. 22, 2018. The Sequence Listing, electronically filed herewith, does not extend beyond the scope of the specification and thus does not contain new matter.

1. INTRODUCTION

The presently disclosed subject matter relates to enteric neural crest lineage cells derived from stem cells (e.g., human stem cells) and uses thereof for cell-based treatment and drug discovery in diseases of the enteric nervous system, such as Hirschsprung's disease.

2. BACKGROUND OF THE SUBJECT MATTER

The enteric nervous system (ENS) is critical for normal gastrointestinal (GI) function. It is the largest and most diverse component of the autonomic nervous system with cells expressing more than 30 different neurotransmitters and with neuron numbers surpassing those in the spinal cord[1]. The ENS can function largely independent of inputs from the brain and spinal cord and has therefore been called the "second brain"[1] given its autonomy and complex cytoarchitecture. Defects in ENS development are responsible for a range of human disorders[2] including Hirschsprung's disease (HD). HD is a debilitating genetic disorder caused by the developmental failure of ENS progenitors to migrate into the GI tract in particular the distal colon[3]. The development of the human ENS lineage remains poorly understood due to the lack of a suitable model system and the limited access to primary tissue.

Small molecule-based protocols for the derivation of central nervous system (CNS) and peripheral nervous system (PNS) lineages from human pluripotent stem cells (hPSCs) including neural crest (NC) were established previously[4-7]. However, despite extensive efforts and the important medical implications of GI disorders, the in vitro derivation of human ENS lineages has remained elusive. Therefore, there remains a need for an in vitro method and protocol of generating ENS precursors directly from human stem cells.

3. SUMMARY OF THE SUBJECT MATTER

The presently disclosed subject matter relates to enteric neural crest lineage cells derived from stem cells (e.g., human stem cells), e.g., by in vitro differentiation.

In certain embodiments, the presently disclosed subject matter provides for in vitro methods for inducing differentiation of stem cells (e.g., human stem cells). In certain embodiments, the in vitro method for inducing differentiation of stem cells comprises contacting a population of stem cells with effective amounts of one or more inhibitor of transforming growth factor beta (TGFβ)/Activin-Nodal signaling and one or more activator of wingless (Wnt) signaling, and further contacting said population of cells with an effective amount(s) of one or more molecule that induces vagal neural crest patterning for at least about 2 days to produce a population of differentiated cells that express one or more enteric neural crest lineage marker.

In certain embodiments, the in vitro method for inducing differentiation of stem cells comprises contacting a population of stem cells with effective amounts of one or more inhibitor of TGFβ/Activin-Nodal signaling and one or more activator of Wnt signaling, and, within about 8 days from initial contact of the stem cells with the one or more inhibitor of TGFβ/Activin-Nodal signaling, further contacting said population of cells with an effective amount(s) of one or more molecule that induces vagal neural crest patterning for at least about 2 days, between about 2 days and about 20 days, or between about 2 days and about 6 days, to produce a population of differentiated cells that express one or more enteric neural crest lineage marker. In certain embodiments, initial contact of said population of cells with an effective amount(s) of the one or more activator of Wnt signaling occurs within an about four day period beginning with the initial contact of the population of stem cells with the one or more inhibitor of TGFβ/Activin-Nodal signaling. For clarity, the one or more activator of Wnt signaling may be added the same day as the one or more inhibitor of TGFβ/Activin-Nodal signaling or one, or two, or three days later. In certain embodiments, the cells are contacted with one or more activator of Wnt signaling and the one or more inhibitor of TGFβ/Activin-Nodal signaling within a 96 hour period.

In time periods set forth herein, if one or more agents are added on the same day (in the same 24 hour period), they may be added in any order unless specified herein to the contrary.

The presently disclosed subject matter also provides for a population of in vitro differentiated cells expressing one or more enteric neural crest lineage marker. In certain embodiments, the differentiated cell population is derived from a population of stem cells by a method comprising contacting a population of stem cells with effective amounts of one or more inhibitor of TGFβ/Activin-Nodal signaling and one or more activator of Wnt signaling, and further contacting said cells with an effective amount(s) of one or more molecule that induces vagal neural crest patterning for at least about 2 days. The presently disclosed subject matter further provides for compositions comprising such a differentiated cell population.

In certain embodiments, the differentiated cell population is derived from a population of stem cells by a method comprising contacting a population of stem cells with effective amounts of one or more inhibitor of TGFβ/Activin-Nodal signaling and one or more activator of Wnt signaling, and within an about 8 day period from initial contact of the stem cells with the one or more inhibitor of TGFβ/Activin-Nodal signaling further contacting said population of cells with an effective amount(s) of one or more molecule that induces vagal neural crest patterning for at least about 2 days, between about 2 days and about 20 days, or between about 2 days and about 6 days. In certain embodiments, initial contact of said population of cells with an effective amount(s) of the one or more activator of Wnt signaling occurs within about a four day period beginning with the initial contact of the population of stem cells with the one or more inhibitor of TGFβ/Activin-Nodal signaling. The presently disclosed subject matter further provides for compositions comprising such a differentiated cell population.

Furthermore, the presently disclosed subject matter provides for kits for inducing differentiation of stem cells. In certain embodiments, the kit comprises (a) one or more inhibitor of TGFβ/Activin-Nodal signaling, (b) one or more activator of Wnt signaling, and (c) one or more molecule that induces vagal neural crest patterning. In certain embodiments, the kit further comprises (d) instructions for inducing differentiation of the stem cells into a population of differentiated cells that express one or more enteric neural crest lineage marker, wherein said instructions comprise directions to contact said population of cells with an effective amount(s) of said one or more molecule that induces vagal neural crest patterning for at least about 2 days. In certain non-limiting embodiments, said instructions comprise directions (i) to initially contact said population of cells with said one or more molecule that induces vagal neural crest patterning within about 8 days from the initial contact of said population of stem cells with said one or more inhibitor of TGFβ/Activin-Nodal signaling, and (ii) to contact said population of stem cells with said one or more molecule that induces vagal neural crest patterning for at least about 2 days, for between about 2 days and about 20 days, or for between about 2 days and about 6 days. In certain embodiments, the instructions comprise directions to initially contact said population of cells with said one or more activator of Wnt signaling within about 0 to 4 days from the initial contact of said population of stem cells with said one or more inhibitor of TGFβ/Activin-Nodal signaling.

In certain embodiments, the method comprises contacting said population of cells with said one or more molecule that induces vagal neural crest patterning for about 6 days.

In certain embodiments, the method comprises initially contacting said population of cells with said one or more molecule that induces vagal neural crest patterning within about an 8 day period beginning with the day of initially contacting said population of cells with said one or more activator of Wnt signaling.

In certain embodiments, the method comprises initially contacting said population of cells with said one or more molecule that induces vagal neural crest patterning at least about 2 days after the initial contact of said population of cells with said one or more activator of Wnt signaling.

In certain embodiments, the method comprises initially contacting said population of cells with said one or more molecule that induces vagal neural crest patterning about 4 days after the initial contact of said population of cells with said one or more activator of Wnt signaling.

In certain embodiments, said population of stem cells have been differentiated into a population of differentiated cells that express one or more said enteric neural crest lineage marker on or after about 11 days after their initial contact with said one or more inhibitor of TGFβ/Activin-Nodal signaling.

In certain embodiments, the method comprises contacting said population of stem cells with one or more inhibitor of Small Mothers Against Decapentaplegic (SMAD) signaling.

In certain embodiments, the method comprises contacting said population of stem cells with said one or more inhibitor of TGFβ/Activin-Nodal signaling and said one or more inhibitor of SMAD signaling concurrently.

In certain embodiments, the method comprises initially contacting said population of cells with said one or more activator of Wnt signaling no later than about 4 days from the initial contact of said population of stem cells with said one or more inhibitor of TGFβ/Activin-Nodal signaling. In certain embodiments, the method comprises initially contacting said population of cells with said one or more activator of Wnt signaling about 2 days after the initial contact of said population of stem cells with said one or more inhibitor of TGFβ/Activin-Nodal signaling.

In certain embodiments, the method comprises initially contacting said population of stem cells with an effective amount(s) of said one or more inhibitor of TGFβ/Activin-Nodal signaling on the same day (within the same 24 hour period) as the initial contact of said population of stem cells with an effective amount(s) of said one or more activator of Wnt signaling.

In certain embodiments, said one or more inhibitor of TGFβ/Activin-Nodal signaling is a small molecule selected from the group consisting of SB431542, derivatives thereof, and mixtures thereof. In certain embodiments, the inhibitor of TGFβ/Activin-Nodal signaling is SB431542.

In certain embodiments, said one or more inhibitor of SMAD signaling is a small molecule selected from the group consisting of LDN193189, derivatives thereof, and mixtures thereof. In certain embodiments, the inhibitor of SMAD signaling is LDN193189.

In certain embodiments, said one or more activator of Wnt signaling lowers glycogen synthase kinase 3β (GSK3β) for activation of Wnt signaling. In certain embodiments, said one or more activator of Wnt signaling is a small molecule selected from the group consisting of CHIR99021, derivatives thereof, and mixtures thereof. In certain embodiments, the activator of Wnt signaling is CHIR99021.

In certain embodiments, said one or more molecule that induces vagal neural crest patterning is selected from the group consisting of retinoic acid, retinol, retinal, tretinoin, isotretinoin, alitretinoin, etretinate, acitretin, tazarotene, bexarotene, adapalene. In certain embodiments, said one or more molecule that induces vagal neural crest patterning is selected from the group consisting of activators of fibroblast growth factor (FGF) signaling, Wnt activators, and combinations thereof. In certain embodiments, the molecule that induces vagal neural crest patterning is retinoic acid.

In certain embodiments, said population of stem cells are contacted with an effective amount of retinoic acid that induces vagal neural crest patterning. In certain embodiments, said population of stem cells are contacted with two or more species of molecule that induce vagal neural crest patterning, which are one or more activator of FGF signaling and one or more Wnt activator. In certain embodiments, said activators of FGF signaling are selected from the group consisting of FGF2, FGF4, FGF7, and FGF8. In certain embodiments, said Wnt activators are selected from the group consisting of CHIR99021 and WNT3A.

In certain embodiments, said vagal neural crest patterning is characterized by expression of one or more regional specific homoebox (HOX) gene. In certain embodiments, said one or more regional specific HOX gene is selected from the group consisting of HOXB2, HOXB3, HOXB4, and HOXB5.

In certain embodiments, said one or more enteric neural crest lineage marker is selected from the group consisting of PAX3, EDNRB, RET, PHOX2A, PHOX2B, NTRK-3, HAND2, HOXB3, HOXB5 and ASCL1. In certain embodiments, said population of differentiated cells further express one or more SOX10+ neural crest lineage marker. In certain embodiments, said SOX10+ neural crest lineage marker is CD49D.

In certain embodiments, said stem cells are human stem cells. In certain embodiments, said stem cells are non-human stem cells, for example non-human primate stem cells, rodent stem cells, dog stem cells, cat stem cells, etc. In certain embodiments, said stem cells are pluripotent stem cells. In certain embodiments, said human stem cells are selected from the group consisting of human embryonic stem cells, human induced pluripotent stem cells, human parthenogenetic stem cells, primoridal germ cell-like pluripotent stem cells, epiblast stem cells, F-class pluripotent stem cells.

In certain embodiments, the method further comprises subjecting said population of differentiated cells to conditions favoring maturation of said differentiated cells into a population of enteric neurons. In certain embodiments, said conditions favoring maturation comprise culturing said population of differentiated cells in a suitable cell culture medium. In certain embodiments, said conditions favoring maturation comprise contacting said population of differentiated cells with one or more molecule that enhances maturation of enteric nervous system precursors into enteric neurons. In certain embodiments, said one or more molecule that enhances maturation of enteric nervous system precursors into enteric neurons are selected from the group consisting of growth factors and Wnt activators. In certain embodiments, said growth factors are selected from the group consisting of activators of FGF signaling ("FGF activators"), glial cell line derived neurotrophic factor (GDNF), and ascorbic acid. In certain embodiments, said conditions favoring maturation comprise contacting said population of differentiated cells with one or more FGF activator and one or more Wnt activator. In certain embodiments, said conditions favoring maturation comprise contacting said population of differentiated cells with one or more FGF activator and one or more Wnt activator for at least 1 day. In certain embodiments, said conditions favoring maturation comprise contacting said population of differentiated cells with one or more FGF activator and one or more Wnt activator for about 4 days. In certain embodiments, said conditions favoring maturation comprise contacting said population of differentiated cells with GDNF and ascorbic acid. In certain embodiments, said conditions favoring maturation comprise contacting said population of differentiated cells with GDNF and ascorbic acid for about 10 days, for about 15 days, or for about 45 days.

In certain embodiments, said population of differentiated cells express one or more enteric neuron marker. In certain embodiments, said one or more enteric neuron marker is selected from the group consisting of Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

The presently disclosed subject matter further provides for methods of preventing and/or treating an enteric nervous system disorder in a subject. In certain embodiments, the method comprises administering an effective amount of the differentiated cell population described herein into a subject suffering from an enteric nervous system disorder.

The presently disclosed subject matter further provides for differentiated cell population described herein for preventing and/or treating an enteric nervous system disorder in a subject.

The presently disclosed subject matter further provides for uses of the differentiated cell population described herein in the manufacture of a medicament for preventing and/or treating an enteric nervous system disorder.

In certain embodiments, the enteric nervous system disorder is Hirschsprung's disease.

In certain embodiments, the enteric nervous system disorder is toxic megacolon.

Additionally, the presently disclosed subject matter provides for in vitro methods of identifying a compound suitable for preventing and/or treating Hirschsprung's disease, and/or a Hirschsprung's disease-related genetic defect, and/or another enteric nervous system disorder. In certain embodiments, the method comprises identifying a compound that is capable of rescuing at least one migration defect presented by a differentiated cell and/or cell population described herein (population of differentiated cells expressing one or more enteric neural crest lineage marker, and/or population of differentiated cells expressing one or more enteric neuron marker), wherein the pre-differentiated stem cells comprise homozygous loss-of-function mutations in endothelin receptor type B (EDNRB). In certain embodiments, the method comprises (a) providing (i) said differentiated cell or cell population, and (ii) a test compound; (b) contacting said differentiated cell or cell population with said test compound; and (c) measuring the migration behavior of said differentiated cell or cell population. In certain embodiments, said differentiated cell or cell population is contacted with said test compound for at least about 6, 12, or 24 hours.

The presently disclosed subject matter also provides for a composition comprising a population of in vitro differentiated cells, wherein at least about 70% (e.g., at least about 75%, at least about 80%, at least about 85%, at least about 90%, at least about 95%, or at least about 99%, or at least about 99.5%) of the population of cells express one or more enteric neural crest lineage marker and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cell markers, CNS markers, Cranial Neural Crest (CNC) markers, Melanocyte-competent Neural Crest (MNC) markers, neuronal cell markers, and mesenchymal precursor markers.

The presently disclosed subject matter also provides for a composition comprising a population of in vitro differentiated cells, wherein at least about 70% (e.g., at least about 75%, at least about 80%, at least about 85%, at least about 90%, at least about 95%, or at least about 99%, or at least about 99.5%) of the population of cells express one or more enteric neuron marker and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cell markers, enteric neural crest lineage markers, CNS markers, Cranial Neural Crest (CNC) markers, Melanocyte-competent Neural Crest (MNC) markers, neuronal cell markers, and mesenchymal precursor markers.

In certain non-limiting embodiments, the enteric neural crest lineage markers are selected from the group consisting PAX3, EDNRB, RET, PHOX2A, PHOX2B, NTRK-3, HAND2, HOXB3, HOXB5 and ASCL1.

In certain non-limiting embodiments, the enteric neuron markers are selected from the group consisting of Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

In certain non-limiting embodiments, the stem cell markers are selected from the group consisting of OCT4, NANOG, SOX2, LIN28, SSEA4 and SSEA3.

In certain non-limiting embodiments, the CNS markers are selected from the group consisting of PAX6, NESTIN, Vimentin, FOXG1, SOX2, TBR1, TBR2 and SOX1.

In certain non-limiting embodiments, the CNC markers are selected from the group consisting of PAX6, NESTIN, Vimentin, FOXG1, SOX2, TBR1, TBR2 and SOX1.

In certain non-limiting embodiments, the MNC markers are selected from the group consisting of PAX6, NESTIN, Vimentin, FOXG1, SOX2, TBR1, TBR2 and SOX1.

In certain non-limiting embodiments, the neuronal cell markers are selected from the group consisting of TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

In certain non-limiting embodiments, the mesenchymal precursor markers are selected from the group consisting of SMA, Vimentin, HLA-ABC, CD105, CD90 and CD73.

In certain non-limiting embodiments, the composition comprises a population of from about $1\times10^4$ to about $1\times10^{10}$ cells expressing said one or more enteric neural crest lineage marker.

In certain non-limiting embodiments, the composition comprises a population of from about $1\times10^5$ to about $1\times10^7$ cells expressing said one or more enteric neural crest lineage marker.

The presently disclosed subject matter also provides a method of preventing and/or treating an ENS disorder (e.g., HD) comprising administering to a subject in need thereof an effective amount of an inhibitor of β-secretase (BACE). In certain embodiments, the inhibitor of BACE is selected from the group consisting of inhibitors of BACE2, LY450139, LY2886721, LY2811376, Verubecestat (MK-8931), and AZD3839. In certain embodiments, the inhibitor of BACE is a inhibitor of BACE2. In certain embodiments, the inhibitor of BACE2 is BACE inhibitor IV(BACE inhibitor C3). Said inhibitor may be administered to a subject systemically or may be locally infused into the gastrointestinal tract (e.g. the colon) and/or a blood vessel infusing the gastrointestinal tract (e.g. colon).

Furthermore, the presently disclosed subject matter provides a method of preventing and/or treating an ENS disorder (e.g., HD) comprising administering to a subject in need thereof an effective amount of an inhibitor of acid protease. In certain embodiments, the inhibitor of acid protease is selected from the group consisting of Pepstatin A, Ritonavir, Indinavir, Zankiren, Aliskiren and LY-450139. In certain embodiments, the inhibitor of acid protease is Pepstatin A. Said inhibitor may be administered to a subject systemically or may be locally infused into the gastrointestinal tract (e.g. the colon) and/or a blood vessel infusing the gastrointestinal tract (e.g. colon).

Furthermore, the presently disclosed subject matter provides for uses of a BACE inhibitor for preventing and/or treating an ENS disorder.

In addition, the presently disclosed subject matter provides for uses of an inhibitor of acid protease for preventing and/or treating an ENS disorder.

A. In certain non-limiting embodiments, the presently disclosed subject matter provides for an in vitro method for inducing differentiation of stem cells, comprising contacting a population of stem cells with effective amounts of one or more inhibitor of TGFβ/Activin-Nodal signaling and one or more activator of Wnt signaling ("Wnt activator"), and further contacting said population of cells with an effective amount(s) of one or more molecule that induces vagal neural crest patterning for at least about 2 days to produce a population of differentiated cells that express one or more enteric neural crest lineage marker ("enteric nervous system (ENS) precursors").

A1. The foregoing method of A, comprising contacting said population of cells with said an effective amount(s) one or more molecule that induces vagal neural crest patterning for about 6 days.

A2. The foregoing method of A, comprising initially contacting said population of cells with said one or more molecule that induces vagal neural crest patterning within about an 8 day period from the initial contact of said population of stem cells with said one or more activator of Wnt signaling.

A3. The foregoing method of A, comprising initially contacting said population of cells with said one or more molecule that induces vagal neural crest patterning at least about 2 days from the initial contact of said population of stem cells with said one or more activator of Wnt signaling.

A4. The foregoing method of A, comprising initially contacting said population of cells with said one or more molecule that induces vagal neural crest patterning is about 4 days from the initial contact of said population of stem cells with said one or more activator of Wnt signaling.

A5. The foregoing method of A, wherein said population of stem cells have been differentiated into a population of differentiated cells that express one or more said enteric neural crest lineage marker on or after about 11 days after their initial contact with said one or more inhibitor of TGFβ/Activin-Nodal signaling.

A6. The foregoing method of A, comprising contacting said population of stem cells with one or more inhibitor of SMAD signaling.

A7. The foregoing method of A, comprising contacting said population of stem cells with said one or more inhibitor of TGFβ/Activin-Nodal signaling and said one or more inhibitor of SMAD signaling concurrently.

A8. The foregoing method of A, comprising initially contacting said population of stem cells with said one or more activator of Wnt signaling within about a 4 day period beginning with the initial contact of said population of stem cells with said one or more inhibitor of TGFβ/Activin-Nodal signaling.

A9. The foregoing method of A, comprising initially contacting said population of stem cells with said one or more activator of Wnt signaling about 2 days from the initial contact of said population of stem cells with said one or more inhibitor of TGFβ/Activin-Nodal signaling.

A10. The foregoing method of A, comprising initially contacting said population of stem cells with said one or more inhibitor of TGFβ/Activin-Nodal signaling the same day as the initial contact of said population with said one or more activator of Wnt signaling.

A11. The foregoing method of A, wherein said one or more inhibitor of TGFβ/Activin-Nodal signaling is a small molecule selected from the group consisting of SB431542, derivatives thereof, and mixtures thereof.

A12. The foregoing method of A, wherein said one or more inhibitor of SMAD signaling is a small molecule selected from the group consisting of LDN193189, derivatives thereof, and mixtures thereof.

A13. The foregoing method of A, wherein said one or more activator of Wnt signaling lowers glycogen synthase kinase 3β (GSK3β) for activation of Wnt signaling.

A14. The foregoing method of A, wherein said one or more activator of Wnt signaling is a small molecule selected from the group consisting of CHIR99021, derivatives thereof, and mixtures thereof.

A15. The foregoing method of A, wherein said one or more molecule that induces vagal neural crest patterning is selected from the group consisting of retinoic acid, retinol, retinal, tretinoin, isotretinoin, alitretinoin, etretinate, acitretin, tazarotene, bexarotene, adapalene, and combinations thereof.

A16. The foregoing method of A, wherein said one or more molecule that induces vagal neural crest patterning is selected from the group consisting of activators of FGF signaling and activators of Wnt signaling, and combinations thereof.

A17. The foregoing method of A, comprising contacting said population of cells with one molecule that induces vagal neural crest patterning.

A18. The foregoing method of A, wherein said one molecule that induces vagal neural crest patterning is retinoic acid.

A19. The foregoing method of A, comprising contacting said population of cells with two or more species of molecule that induce vagal neural crest patterning.

A20. The foregoing method of A, wherein said two or more species of molecule that induce vagal neural crest patterning are one or more activator of FGF signaling and one or more Wnt activator.

A21. The foregoing method of A, wherein said activators of FGF signaling are selected from the group consisting of FGF2, FGF4, FGF7, and FGF8.

A22. The foregoing method of A, wherein said Wnt activators are selected from the group consisting of CHIR99021 and WNT3A.

A23. The foregoing method of A, wherein said vagal neural crest patterning is characterized by expression of one or more regional specific homoebox (HOX) gene.

A24. The foregoing method of A, wherein said one or more regional specific HOX gene is selected from the group consisting of HOXB2, HOXB3, HOXB4, and HOXB5.

A25. The foregoing method of A, wherein said one or more enteric neural crest lineage marker is selected from the group consisting of PAX3, EDNRB, RET, PHOX2A, PHOX2B, NTRK-3, HAND2, HOXB3, HOXB5 and ASCL1.

A26. The foregoing method of A, wherein said population of differentiated cells further express one or more SOX10$^+$ neural crest lineage marker.

A27. The foregoing method of A, wherein said SOX10$^+$ neural crest lineage marker is CD49D.

A28. The foregoing method of A, wherein said stem cells are human stem cells.

A29. The foregoing method of A, wherein said human stem cells are selected from the group consisting of human embryonic stem cells, human induced pluripotent stem cells, human parthenogenetic stem cells, primoridal germ cell-like pluripotent stem cells, epiblast stem cells, and F-class pluripotent stem cells.

A30. The foregoing method of A, wherein said stem cells are non-human stem cells. A31. The foregoing method of A, comprising subjecting said population of differentiated cells to conditions favoring maturation of said differentiated cells into a population of cells that express one or more enteric neuron marker.

A32. The foregoing method of A, wherein said conditions favoring maturation of said differentiated cells into said population of enteric neurons comprise culturing said differentiated cells in a suitable cell culture medium.

A33. The foregoing method of A, wherein said suitable cell culture medium comprises one or more molecule that enhances maturation of ENC precursors to enteric neurons.

A34. The foregoing method of A, wherein said one or more molecule that enhances maturation of ENC precursors to enteric neurons is selected from the group consisting of growth factors and Wnt activators.

A35. The foregoing method of A, wherein said growth factors are selected from the group consisting of activators of FGF signaling, glial cell line derived neurotrophic factor (GDNF), and ascorbic acid.

A36. The foregoing method of A, wherein said suitable cell culture medium comprises one or more activator of FGF signaling and one or more activator of Wnt signaling.

A37. The foregoing method of A, wherein said differentiated cells are cultured in said suitable cell culture medium comprising said one or more activator of FGF signaling and said one or more activator of Wnt signaling for about 4 days.

A38. The foregoing method of A, wherein the one or more activator of FGF signaling is selected from the group consisting of FGF2, FGF4, FGF8, and FGF7.

A39. The foregoing method of A, wherein said one or more enteric neuron marker is selected from the group consisting of Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

B. In certain embodiments, the presently disclosed subject matter provides for a population of in vitro differentiated cells expressing one or more enteric neural crest lineage marker ("ENS precursors"), wherein said differentiated cell population is derived from a population of stem cells after:

contacting a population of stem cells with effective amounts of one or more inhibitor of TGFβ/Activin-Nodal signaling and one or more activator of Wnt signaling, and further contacting said population of cells with an effective amount(s) of one or more molecule that induces vagal neural crest patterning for at least about 2 days.

B1. The foregoing differentiated cell population of B, wherein said population of cells are contacted with said one or more molecule that induces vagal neural crest patterning for about 6 days.

B2. The foregoing differentiated cell population of B, wherein the initial contact of said population of cells with said one or more molecule that induces vagal neural crest patterning occurs within about an 8 day period from the initial contact of said population of cells with said one or more activator of Wnt signaling.

B3. The foregoing differentiated cell population of B, wherein the initial contact of said population of cells with said one or molecule that induces vagal neural crest patterning is at least about 2 days from the initial contact of said population of cells with said one or more activator of Wnt signaling.

B4. The foregoing differentiated cell population of B, wherein the initial contact of said population of cells with said one or more molecule that induces vagal neural crest patterning is about 4 days from the initial contact of said population of cells with said one or more activator of Wnt signaling.

B5. The foregoing differentiated cell population of B, wherein said population of stem cells have been differentiated into a population of differentiated cells that express one or more said enteric neural crest lineage marker on or after about 11 days after their initial contact with said one or more inhibitor of TGFβ/Activin-Nodal signaling.

B6. The foregoing differentiated cell population of B, wherein said population of stem cells are contacted with one or more inhibitor of SMAD signaling.

B7. The foregoing differentiated cell population of B, wherein said population of stem cells are contacted with said one or more inhibitor of TGFβ/Activin-Nodal signaling and said one or more inhibitor of SMAD signaling concurrently.

B8. The foregoing differentiated cell population of B, wherein the initial contact of said population of cells with said one or more activator of Wnt signaling occurs within about a 4 day period beginning with the initial contact of said population of stem cells with said one or more inhibitor of TGFβ/Activin-Nodal signaling.

B9. The foregoing differentiated cell population of B, wherein the initial contact of said population of stem cells with said one or more activator of Wnt signaling is about 2 days from the initial contact of said population of stem cells with said one or more inhibitor of TGFβ/Activin-Nodal signaling.

B10. The foregoing differentiated cell population of B, wherein the initial contact of said population of stem cells with said one or more inhibitor of TGFβ/Activin-Nodal signaling is the same day as the initial contact of said population of stem cells with said one or more activator of Wnt signaling.

B11. The foregoing differentiated cell population of B, wherein said one or more inhibitor of TGFβ/Activin-Nodal signaling is a small molecule selected from the group consisting of SB431542, derivatives thereof, and mixtures thereof.

B12. The foregoing differentiated cell population of B, wherein said one or more inhibitor of SMAD signaling is a small molecule selected from the group consisting of LDN193189, derivatives thereof, and mixtures thereof.

B13. The foregoing differentiated cell population of B, wherein said one or more activator of Wnt signaling lowers glycogen synthase kinase 3β (GSK3β) for activation of Wnt signaling.

B14. The foregoing differentiated cell population of B, wherein said one or more activator of Wnt signaling is a small molecule selected from the group consisting of CHIR99021, derivatives thereof, and mixtures thereof.

B15. The foregoing differentiated cell population of B, wherein said one or more molecule that induces vagal neural crest patterning is selected from the group consisting of retinoic acid, retinol, retinal, tretinoin, isotretinoin, alitretinoin, etretinate, acitretin, tazarotene, bexarotene, adapalene, activators of FGF signaling, Wnt activators, and combinations thereof.

B16. The foregoing differentiated cell population of B, wherein said one or more molecule that induces vagal neural crest patterning is selected from the group consisting of activators of FGF signaling, activators of Wnt signaling, and combinations thereof.

B17. The foregoing differentiated cell population of B, wherein said population of cells are contacted with one molecule that induces vagal neural crest patterning.

B18. The foregoing differentiated cell population of B, wherein said one molecule that induces vagal neural crest patterning is retinoic acid.

B19. The foregoing differentiated cell population of B, wherein said population of cells are contacted with two or more species of molecule that induce vagal neural crest patterning.

B20. The foregoing differentiated cell population of B, wherein said two or more species of molecule that induce vagal neural crest patterning are one or more activator of FGF signaling and one or more Wnt activator.

B21. The foregoing differentiated cell population of B, wherein said activators of FGF signaling are selected from the group consisting of FGF2, FGF4, FGF7, and FGF8.

B22. The foregoing differentiated cell population of B, wherein said Wnt activators are selected from the group consisting of CHIR99021 and WNT3A.

B23. The foregoing differentiated cell population of B, wherein said one or more enteric neural crest lineage marker is selected from the group consisting of PAX3, EDNRB, RET, PHOX2A, PHOX2B, NTRK-3, HAND2, HOXB3, HOXB5 and ASCL1.

B24. The foregoing differentiated cell population of B, wherein said vagal neural crest patterning is characterized by expression of one or more regional specific homeobox (HOX) gene.

B25. The foregoing differentiated cell population of B, wherein said one or more regional specific HOX gene is selected from the group consisting of HOXB2, HOXB3, HOXB4, and HOXB5.

B26. The foregoing differentiated cell population of B, wherein said differentiated cell population further express one or more SOX10$^+$ neural crest lineage marker.

B27. The foregoing differentiated cell population of B, wherein said SOX10$^+$ neural crest lineage marker is CD49D.

B28. The foregoing differentiated cell population of B, wherein said stem cells are human stem cells.

B29. The foregoing differentiated cell population of B, wherein said human stem cells are selected from the group consisting of human embryonic stem cells, human induced pluripotent stem cells, human parthenogenetic stem cells, primoridal germ cell-like pluripotent stem cells, epiblast stem cells, and F-class pluripotent stem cells.

C. In certain embodiments, the presently disclosed subject matter provides for a composition comprising the foregoing differentiated cell population expressing one or more enteric neural crest lineage marker.

D. In certain embodiments, the presently disclosed subject matter provides a population of in vitro differentiated cells expressing one or more enteric neuron marker, wherein said differentiated cell population is derived from the foregoing population of cells expressing one or more enteric neural crest lineage marker.

D1. The foregoing differentiated cell population of D, wherein said differentiated cell population is derived from the foregoing population of cells expressing one or more enteric neural crest lineage marker after culturing the foregoing population of cells expressing one or more enteric neural crest lineage marker in a suitable cell culture medium.

D2. The foregoing differentiated cell population of D, wherein said differentiated cell population is derived from the foregoing population of cells expressing one or more enteric neural crest lineage marker after culturing the foregoing population of cells expressing one or more enteric neural crest lineage marker in a suitable cell culture medium for at least about 1 day.

D3. The foregoing differentiated cell population of D, wherein said suitable cell culture medium comprises one or more molecule that enhances maturation of ENC precursors to enteric neurons.

D4. The foregoing differentiated cell population of D, wherein said one or more molecule that enhances maturation of ENC precursors to enteric neurons is selected from the group consisting of growth factors and Wnt activators.

D5. The foregoing differentiated cell population of D, wherein said growth factors are selected from the group consisting of activators of FGF signaling, glial cell line derived neurotrophic factor (GDNF), and ascorbic acid.

D6. The foregoing differentiated cell population of D, wherein said suitable cell culture medium comprises one or more activator of FGF signaling and one or more activator of Wnt signaling.

D7. The foregoing differentiated cell population of D, wherein said differentiated cell population is derived from the foregoing population of cells expressing one or more enteric neural crest lineage marker after culturing the foregoing population of cells expressing one or more enteric neural crest lineage marker in a suitable cell culture medium comprising said one or more activator of FGF signaling and said one or more activator of Wnt signaling for about 4 days.

D8. The foregoing differentiated cell population of D, wherein said suitable cell culture medium comprises GDNF and ascorbic acid.

D9. The foregoing differentiated cell population of D, wherein said differentiated cell population is derived from the foregoing population of cells expressing one or more enteric neural crest lineage marker after culturing the foregoing population of cells expressing one or more enteric neural crest lineage marker in a suitable cell culture medium comprising GDNF and ascorbic acid for about 10 days, for about 25 days, or for about 45 days.

D10. The foregoing differentiated cell population of D, wherein said one or more activator of FGF signaling is selected from the group consisting of FGF2, FGF4, FGF8, and FGF7.

D11. The foregoing differentiated cell population of D, wherein said one or more Wnt activator is selected from the group consisting of CHIR99021 and WNT3A.

D12. The foregoing differentiated cell population of D, wherein said one or more enteric neuron marker is selected from the group consisting of Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

E. In certain embodiments, the presently disclosed subject matter provides for a composition comprising the foregoing differentiated cell population expressing one or more enteric neuron marker.

F. In certain embodiments, the presently disclosed subject matter provides for a method of preventing and/or treating an enteric nervous system disorder in a subject, comprising administering to a subject suffering from an enteric nervous system disorder an effective amount of one of the followings:
(a) the foregoing population of differentiated ENS precursors;
(b) a composition comprising the foregoing population of differentiated ENS precursors;
(c) the foregoing population of enteric neurons; and
(d) a composition comprising the foregoing population of enteric neurons.

F1. The foregoing method of F, wherein the enteric nervous system disorder is Hirschsprung's disease.

F2. The foregoing method of F, wherein the enteric nervous system disorder is toxic megacolon.

G. In certain embodiments, the presently disclosed subject matter provides for the foregoing population of differentiated ENS precursors for preventing and/or treating an enteric nervous system disorder in a subject.

G1. The foregoing differentiated cell population of G, wherein the enteric nervous system disorder is Hirschsprung's disease.

G2. The foregoing differentiated cell population of G, wherein the enteric nervous system disorder is toxic megacolon.

H. In certain embodiments, the presently disclosed subject matter provides for use of the foregoing population of differentiated ENS precursors in the manufacture of a medicament for preventing and/or treating an enteric nervous system disorder.

H1. The foregoing use of H, wherein the enteric nervous system disorder is Hirschsprung's disease.

H2. The foregoing use of H, wherein the enteric nervous system disorder is toxic megacolon.

I. In certain embodiments, the presently disclosed subject matter provides for a composition comprising the foregoing population of differentiated ENS precursors for preventing and/or treating an enteric nervous system disorder in a subject.

I1. The foregoing composition of I, wherein the enteric nervous system disorder is Hirschsprung's disease.

I2. The foregoing composition of I, wherein the enteric nervous system disorder is toxic megacolon.

J. In certain embodiments, the presently disclosed subject matter provides for the foregoing population of differentiated enteric neurons for preventing and/or treating an enteric nervous system disorder in a subject.

J1. The foregoing differentiated cell population of J, wherein the enteric nervous system disorder is Hirschsprung's disease.

J2. The foregoing differentiated cell population of J, wherein the enteric nervous system disorder is toxic megacolon.

K. In certain embodiments, the presently disclosed subject matter provides for use of the foregoing population of differentiated enteric neurons in the manufacture of a medicament for preventing and/or treating an enteric nervous system disorder.

K1. The foregoing use of K, wherein the enteric nervous system disorder is Hirschsprung's disease.

K2. The foregoing use of K, wherein the enteric nervous system disorder is toxic megacolon.

L. In certain embodiments, the presently disclosed subject matter provides for a composition comprising the foregoing population of differentiated enteric neurons for preventing and/or treating an enteric nervous system disorder in a subject.

L1. The foregoing composition of L, wherein the enteric nervous system disorder is Hirschsprung's disease.

L2. The foregoing composition of I, wherein the enteric nervous system disorder is toxic megacolon.

M. In certain embodiments, the presently disclosed subject matter provides for a method of screening a compound suitable for preventing and/or treating Hirschsprung's disease and/or a Hirschsprung's disease-related genetic defect in vitro, comprising identifying a compound that is capable of rescuing at least one migration defect presented by a population of cells that are selected from the foregoing differentiated ENS precursors, the foregoing differentiated enteric neurons and a combination thereof, wherein the stem cells comprise homozygous loss-of-function mutations in endothelin receptor type B (EDNRB).

M1. The foregoing method of M, comprising:
(a) providing (i) said population of cells, and (ii) a test compound;
(b) contacting said population of cells with said test compound; and
(c) measuring the migration behavior of said population of cells.

M2. The foregoing method of M, wherein said population of cells are a population of ENS precursors.

M3. The foregoing method of M, wherein said population of cells are contacted with said test compound for at least about 24 hours.

N. In certain embodiments, the presently disclosed subject matter provides for a kit for inducing differentiation of stem cells, comprising:
(a) one or more inhibitor of TGFβ/Activin-Nodal signaling,
(b) one or more activator of Wnt signaling,
(c) one or more molecule that induces vagal neural crest patterning, and
(d) instructions for inducing differentiation of the stem cells into a population of differentiated cells that express one or more enteric neural crest lineage marker, wherein said instructions comprise directions to contact said population of cells with said an effective amount of one or more molecule that induces vagal neural crest patterning for at least about 2 days.

N1. The foregoing kit of N, wherein said instructions comprise directions to contact said population of cells with said one or more molecule that induces vagal neural crest patterning for about 6 days.

N2. The foregoing kit of N, wherein said instructions comprise directions to initially contact said population of cells with said one or more molecule that induces vagal neural crest patterning within an about 8 day period from the initial contact of said population of cells with said one or more activator of Wnt signaling.

N3. The foregoing kit of N, wherein said instructions comprise directions to initially contact said population of cells with said one or more molecule that induces vagal neural crest patterning at least about 2 days from the initial contact of said population of stem cells with said one or more activator of Wnt signaling.

N4. The foregoing kit of N, wherein said instructions comprise directions to initially contact said population of cells with said one or more molecule that induces vagal neural crest patterning about 4 days from the initial contact of said population of cells with said one or more activator of Wnt signaling.

N5. The foregoing kit of N, further comprising one or more inhibitor of SMAD signaling.

N6. The foregoing kit of N, wherein said instructions comprise directions to contact said population of stem cells with said one or more inhibitor of TGFβ/Activin-Nodal signaling and said one or more inhibitor of SMAD signaling concurrently.

N7. The foregoing kit of H, wherein said instructions comprise directions to initially contact said population of cells with said one or more activator of Wnt signaling within an about 4 day period beginning with the initial contact of said population of stem cells with said one or more inhibitor of TGFβ/Activin-Nodal signaling.

N8. The foregoing kit of N, wherein said instructions comprise directions to initially contact said population of cells with said one or more activator of Wnt signaling about 2 days from the initial contact of said population of stem cells with said one or more inhibitor of TGFβ/Activin-Nodal signaling.

N9. The foregoing kit of N, wherein said instructions comprise directions to initially contact said population of stem cells with said one or more inhibitor of TGFβ/Activin-Nodal signaling the same day as the initial contact of said population of cells with said one or more activator of Wnt signaling.

N10. The foregoing kit of N, wherein said one or more inhibitor of TGFβ/Activin-Nodal signaling is a small molecule selected from the group consisting of SB431542, derivatives thereof, and mixtures thereof.

N11. The foregoing kit of N, wherein said one or more inhibitor of SMAD signaling is a small molecule selected from the group consisting of LDN193189, derivatives thereof, and mixtures thereof.

N12. The foregoing kit of N, wherein said one or more activator of Wnt signaling lowers glycogen synthase kinase 3β (GSK3β) for activation of Wnt signaling.

N13. The foregoing kit of N, wherein said one or more activator of Wnt signaling is a small molecule selected from the group consisting of CHIR99021, derivatives thereof, and mixtures thereof.

N14. The foregoing kit of N, wherein said one or more molecule that induces vagal neural crest patterning is selected from the group consisting of retinoic acid, retinol, retinal, tretinoin, isotretinoin, alitretinoin, etretinate, acitretin, tazarotene, bexarotene, adapalene, activators of FGF signaling, Wnt activators, and combinations thereof.

N15. The foregoing kit of N, wherein said one or more molecule that induces vagal neural crest patterning is selected from the group consisting of activators of FGF signaling, activators of Wnt signaling, and combinations thereof.

N16. The foregoing kit of N, comprising one molecule that induces vagal neural crest patterning.

N17. The foregoing kit of N, wherein said one molecule that induces vagal neural crest patterning is retinoic acid.

N18. The foregoing kit of N, comprising two or more species of molecule that induce vagal neural crest patterning.

N19. The foregoing kit of N, wherein said two or more species of molecule that induce vagal neural crest patterning are one or more activator of FGF signaling and one or more Wnt activator.

N20. The foregoing kit of N, wherein said activators of FGF signaling are selected from the group consisting of FGF2, FGF4, FGF7, and FGF8.

N21. The foregoing kit of N, wherein said Wnt activators are selected from the group consisting of CHIR99021 and WNT3A.

O. In certain non-limiting embodiments, the presently disclosed subject matter provides for an in vitro method for inducing differentiation of stem cells, comprising contacting a population of stem cells with effective amounts of one or more inhibitor of TGFβ/Activin-Nodal signaling and one or more activator of Wnt signaling, and further contacting said population of cells with an effective amount(s) of one or more molecule that induces vagal neural crest patterning for at least about 2 days, for between about 2 days and about 20 days, or for between about 2 days and about 6 days, to produce a population of differentiated cells that express one or more enteric neural crest lineage marker, wherein the initial contact of said population of cells with said one or more molecule that induces vagal neural crest patterning is within an about 8 day period from the initial contact of said population of cells with said one or more activator of Wnt signaling.

O1. The foregoing method of O, comprising initially contacting said population of cells with said one or more activator of Wnt signaling within an about 4 day period from the initial contact of said population of stem cells with said one or more inhibitor of TGFβ/Activin-Nodal signaling.

P. In certain non-limiting embodiments, the presently disclosed subject matter provides for a population of in vitro differentiated cells expressing one or more enteric neural crest lineage marker, wherein said differentiated cell population is derived from a population of stem cells after: contacting a population of stem cells with effective amounts of one or more inhibitor of TGFβ/Activin-Nodal signaling and one or more activator of Wnt signaling, and further contacting said population of cells with an effective amount(s) of one or more molecule that induces vagal neural crest patterning for at least about 2 days, for between about 2 days and about 20 days, or for between about 2 days and about 6 days, wherein the initial contact of said population of cells with said one or more molecule that induces vagal neural crest patterning is within an about 8 day period from the initial contact of said population of cells with said one or more activator of Wnt signaling.

P1. The foregoing differentiated cell population of P, wherein the initial contact of said population of cells with said one or more activator of Wnt signaling is within an about 4 day period from the initial contact of said population of stem cells with said one or more inhibitor of TGFβ/Activin-Nodal signaling.

Q. In certain non-limiting embodiments, the presently disclosed subject matter provides for a kit for inducing differentiation of stem cells, comprising (a) one or more inhibitor of TGFβ/Activin-Nodal signaling, (b) one or more activator of Wnt signaling, (c) one or more molecule that induces vagal neural crest patterning, and (d) instructions for inducing differentiation of the stem cells into a population of differentiated cells that express one or more enteric neural crest lineage marker, wherein said instructions comprise directions to initially contact said population of cells with said one or more molecule that induces vagal neural crest patterning within an about 8 day period from the initial contact of said population of cells with said one or more activator of Wnt signaling, and to contact said population of cells with said one or more molecule that induces vagal neural crest patterning for at least about 2 days, for between about 2 days and about 20 days, or for between about 2 days and about 6 days.

Q1. The foregoing kit of Q, wherein said instructions comprise directions to initially contact said population of cells with said one or more activator of Wnt signaling within an about 4 day period beginning with the initial contact of said population of stem cells with said one or more inhibitor of TGFβ/Activin-Nodal signaling.

R. A composition comprising a population of in vitro differentiated cells,
wherein at least about 70% (e.g., at least about 75%, at least about 80%, at least about 85%, at least about 90%, at least about 95%, at least about 99%, or at least about 99.5%) of the population of cells express one or more enteric neural crest lineage marker and
wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cell markers, CNS markers, Cranial Neural Crest (CNC) markers, Melanocyte-competent Neural Crest (MNC) markers, neuronal cell markers, and mesenchymal precursor markers.

R1. The foregoing of the composition of R, wherein the enteric neural crest lineage markers are selected from the group consisting of PAX3, EDNRB, RET, PHOX2A, PHOX2B, NTRK-3, HAND2, HOXB3, HOXB5 and ASCL1.

R2. The foregoing of the composition of R, wherein the stem cell markers are selected from the group consisting of OCT4, NANOG, SOX2, LIN28, SSEA4 and SSEA3.

R3. The foregoing of the composition of R, wherein the CNS markers are selected from the group consisting of PAX6, NESTIN, Vimentin, FOXG1, SOX2, TBR1, TBR2 and SOX1.

R4. The foregoing of the composition of R, wherein the CNC markers are selected from the group consisting of PAX6, NESTIN, Vimentin, FOXG1, SOX2, TBR1, TBR2 and SOX1.

R5. The foregoing of the composition of R, wherein the MNC markers are selected from the group consisting of PAX6, NESTIN, Vimentin, FOXG1, SOX2, TBR1, TBR2 and SOX1.

R6. The foregoing of the composition of R, wherein the neuronal cell markers are selected from the group consisting of TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

R7. The foregoing of the composition of R, wherein the mesenchymal precursor markers are selected from the group consisting of SMA, Vimentin, HLA-ABC, CD105, CD90 and CD73.

R8. The foregoing of the composition of R, comprising a population of from about $1 \times 10^4$ to about $1 \times 10^{10}$ cells expressing said one or more enteric neural crest lineage marker.

S. A composition comprising a population of in vitro differentiated cells,
wherein at least about 70% (e.g., at least about 75%, at least about 80%, at least about 85%, at least about 90%, at least about 95%, at least about 99%, or at least about 99.5%) of the population of cells express one or more enteric neuron marker and
wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cell markers, enteric neural crest lineage markers, CNS markers, Cranial Neural Crest (CNC) markers, Melanocyte-competent Neural Crest (MNC) markers, neuronal cell markers, and mesenchymal precursor markers.

S1. The foregoing of the composition of S, wherein the enteric neural crest lineage markers are selected from the group consisting of PAX3, EDNRB, RET, PHOX2A, PHOX2B, NTRK-3, HAND2, HOXB3, HOXB5 and ASCL1.

S2. The foregoing of the composition of S, wherein the enteric neuron markers are selected from the group consisting of Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

S3. The foregoing of the composition of S, wherein the stem cell markers are selected from the group consisting of OCT4, NANOG, SOX2, LIN28, SSEA4 and SSEA3.

S4. The foregoing of the composition of S, wherein the CNS markers are selected from the group consisting of PAX6, NESTIN, Vimentin, FOXG1, SOX2, TBR1, TBR2 and SOX1.

S5. The foregoing of the composition of S, wherein the CNC markers are selected from the group consisting of PAX6, NESTIN, Vimentin, FOXG1, SOX2, TBR1, TBR2 and SOX1.

S6. The foregoing of the composition of S, wherein the MNC markers are selected from the group consisting of PAX6, NESTIN, Vimentin, FOXG1, SOX2, TBR1, TBR2 and SOX1.

S7. The foregoing of the composition of S, wherein the neuronal cell markers are selected from the group consisting of TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

S8. The foregoing of the composition of S, wherein the mesenchymal precursor markers are selected from the group consisting of SMA, Vimentin, HLA-ABC, CD105, CD90 and CD73.

S9. The foregoing of the composition of S, comprising a population of from about $1\times10^5$ to about $1\times10^7$ cells expressing said one or more enteric neuron marker.

T. In certain embodiments, the presently disclosed subject matter provides a method of preventing and/or treating an ENS disorder (e.g., HD) comprises administering to a subject in need thereof an effective amount of an inhibitor of β-secretase (BACE).

T1. The foregoing method of T, wherein the inhibitor of BACE is selected from the group consisting of inhibitors of BACE2, LY450139, LY2886721, LY2811376, Verubecestat (MK-8931), and AZD3839.

T2. The foregoing method of T, wherein the inhibitor of BACE is an inhibitor of BACE2.

T3. The foregoing method of T, wherein the inhibitor of BACE2 is BACE inhibitor IV (BACE inhibitor C3).

U. In certain embodiments, the presently disclosed subject matter provides a method of preventing and/or treating an ENS disorder (e.g., HD) comprises administering to a subject in need thereof an effective amount of an inhibitor of acid protease.

U1. The foregoing method of U, wherein the inhibitor of acid protease is selected from the group consisting of Pepstatin A, Ritonavir, Indinavir, Zankiren, Aliskiren and LY-450139.

U2. The foregoing method of U, wherein the inhibitor of acid protease is Pepstatin A.

V. In certain embodiments, the presently disclosed subject matter provides for uses of a BACE inhibitor for preventing and/or treating an ENS disorder.

W. In certain embodiments, the presently disclosed subject matter provides for uses of an inhibitor of acid protease for preventing and/or treating an ENS disorder.

4. BRIEF DESCRIPTION OF THE FIGURES

FIGS. 1A-1J: Induction of ENC precursors from hESCs. (A) Schematic illustration of the protocol (day 0-11) developed for the induction of enteric NC (ENC) cells. (B) Flow cytometry of ENC for SOX10::GFP and CD49D expression at day 11 of differentiation following protocol detailed in (A). (C) qRT-PCR for SOX10, vagal NC markers HOXB2 through HOXB5 and HOXB9 for CD49D+ sorted ENC compared to CNC (no RA). (D) Quantification of immunofluorescence staining for PAX3, RET and EDNRB in CD49D+ ENC. (E and F) Unsupervised clustering and principle component analysis of CD49D+NC versus matched CNS precursor (day 11 of differentiation). (G) Top 10 and selected additional (in Bold) most differentially expressed transcripts in CD49D+ ENC versus CNS precursors. (H) RFP+ and CD49D+ ENC are FACS purified for transplantation (day 11) into the developing chick embryos. (I and J) Migration of RFP+ cells within the embryo; subset of cells in the developing gut. (I) whole mount epifluorescence showing distribution of RFP+ cells at 24 hours after injection. (J) Cross section images of the embryos at the trunk level show location of the RFP+ cells in the gut anlage (left panel) and zoom in (right panel) of the boxed area. Scale bars=25 μm in h (middle panel); 200 μm in i; 10 μm in j;.p-values are: * p<0.05;  p<0.01; * p<0.001 (t-test, ENC compared to CNC; n=3)

FIGS. 2A-2I: Characterization of hESC-derived NC populations (A) Schematic illustration of Cranial NC (CNC) and Melanocyte competent NC (MNC) induction protocols[5]. (B) Flow cytometry for CD49D and SOX10::GFP in CNC and MNC cells. (C) Immunofluorescence of unsorted and CD49D sorted differentiated NC cells for SOX10. (D) Flow cytometry for CD49D in ENC derived from H9 hESCs and control and Familial Dysautonomia hiPSCs. (E and F) Representative immunofluorescence images and flow cytometry in hESC-derived ENC for enteric precursor lineage marker at day11. (G) List of the top 10 and selected additional most differentially expressed transcripts from the RNASeq analysis of CNC compared to stage matched CNS precursors[11]. (H) Lists of the top 10 and selected additional most differentially expressed transcripts from the RNASeq analysis of MNC compared to stage matched CNS precursors.[11] (I) Distribution of CNC and MNC cells in developing chick embryos at 24-36 hours after injection. Right panel: Higher power image of the clusters of MNC cells in the developing surface ectoderm. Abbreviations: NT=Neural Tube, NotoC=Notochord, S=Somite, Scale bars=50 μm in c; 25 μm in e; 1 mm in i-left panel; 50 μm in middle and 25 μm in right panel.

FIGS. 3A-3K: Differentiation of hESC-derived ENC precursors into various enteric neuron subtypes. (A) Schematic illustration of the protocol developed for neuronal differentiation and maturation of ENC precursors. (B) Image of SOX10::GFP expressing 3D whole spheroids aggregated from purified ENC before monolayer differentiation along enteric neuron lineage with expression of TUJ1 and PHOX2A. (C and D) Phase contrast and immunofluorescence images and the quantification of ENC lineage cells at day 40. Cells are shown to express TRKC, ASCL, and PHOX2A/B. PHOX2B expression was further confirmed using an H9 hESC-based PHOX2B::GFP reporter line (kindly provided by G. Lee; Johns Hopkins University). (E and F) Immunofluorescence analysis and quantification showing expression of diverse neurotransmitters. Note: all cells were derived from CD49D+, FACS purified NC to ensure NC lineage origin. (G) Schematic illustration of the light-stimulated activation of ENC-derived neurons via expression of Channelrhodopsin-2 (ChR2). (H) Phase contrast and live fluorescence images of the culture subjected to light stimulation after co-cultured with ENC-derived neurons. (I) Diagrams representing extent of contraction of SMCs before light stimulation and during stimulation with different 450 nm light pulse frequencies. (J) Schematic illustration for generation of tissue engineered colon (TEC). (K) TEC stained for human cytoplasmic marker SC121 and human specific Synaptophysin (hSYN). Dotted line shows approximate location of border between muscle and epithelial/submucosal-like layers. Scale bars=100 µm in b, (all panels); 50 µm in c, e, h; 20 µm in k-left and middle panels; 40 µm in k-right panel.

FIGS. 4A-4E: Characterization of hESC-derived enteric neural lineages (A) Flow Cytometry for TRKC and PHOX2A expression. (B) Immunofluorescence for PHOX2A and ASCL1 for TRKC positive and TRKC negative hESC-derived ENC precursors. (C) Time course qRT-PCR analysis of enteric lineage markers during more extended in vitro differentiation periods. (D and E) Flow cytometric quantification of enteric neuron precursor and neuronal markers in ENC-derived neurons at day 40 and 60 of differentiation. Scale bars=50 µm; Abbreviation: FC=Fold Change.

FIGS. 5A-5E: CNC gives rise to neurons enriched in autonomic lineage (A-C) Representative immunofluorescence images for expression of 5-HT (Serotonin), TUJ1 and TH in CNC-derived neurons. In contrast to ENC-derived lineages, no serotonergic (5HT$^+$) neurons were detected under cranial conditions despite the presence of many Tuj1+ neurons and increased percentages of TH$^+$ cells. (E and E) Flow Cytometry for TRKB and TRKC under CNC and ENC conditions. Scale bars=50 µm.

FIGS. 6A-6H: human ENC precursors migrate extensively in normal and HD adult colon (A) Schematic illustration of the transplantation paradigm into the colon of adult murine hosts. (B) Whole mount fluorescence imaging of the grafted RFP$^+$ hESC-derived ENC precursors inside the adult NSG colon wall. (C) Immunofluorescence staining of a cross section of an NSG colon transplanted with RFP+ hESC-derived ENC precursors showing TUJ1 staining. (D) Survival curve of EDNRB$^{s-l/s-l}$ animals grafted with hESC-derived enteric NC precursors versus those receiving matrigel-only. (E) Megacolon-like phenotype in control animals versus animals receiving hESC-derived ENC transplants. (F) Immunofluorescence staining of cross sections of normal or HD colons transplanted with matrigel or RFP+ hESC-derived ENC precursors showing distribution of hESC-derived ENC precursors in myenteric and submucosal layers similar to normal ENS. The dashed lines indicate the border between submucosal and muscle layers. (G) Immunofluorescence staining of cross sections of HD colons transplanted with matrigel or RFP+ hESC-derived ENC precursors showing expression of SC121 and human specific Synaptophysin (hSYN). (H) Representative images of grafted hESC-derived ENC precursors after transplantation into the colon of EDNRB$^{s-l/s-l}$ HD mice, showing expression of GABA and 5HT in a subset of human (SC121 immunoreactive) cells. All in vivo experiments were performed in a blinded manner. EDNRB$^{s-l/s-l}$ mutation was confirmed in all grafted animals. Scale bars=1 cm in b; 500 µm in c-left panel; 100 µm in c-right panel, f and g and 25 µm in h; Abbreviation: AU=Arbitrary Unit. p-value for survival analysis is given numerically, log-rank (Mantel-Cox) test; n=6 each.

FIGS. 7A-7E: Functional characterization of hESC-derived enteric neurons in co-culture with SMCs (A) Schematic illustration of smooth muscle cell (SMC) differentiation protocol. (B) Immunofluorescence staining of SMC progenitors for SMA and ISL1. (C) Association of various ENC-derived neuron subtypes with SMA+ cells. (D) Synapsin::EYFP expression in ENC-derived neurons at 40 days of co-culture with SMCs and stage matched neurons in the absence of SMCs. (E) Monoculture of SMCs versus co-cultures of SMCs with ENC-derived neurons. Upper panels: phase contrast images showing morphological changes of SMCs in Co-culture. Lower panels: Immunofluorescence staining of mature SMC markers MYH11 and Acetylcholine Receptor (AchR) in monoculture of SMCs versus co-cultures of SMCs with ENC-derived neurons. Scale bars=50 µm in b, c, e; 100 µm in d.

Figure 8A:
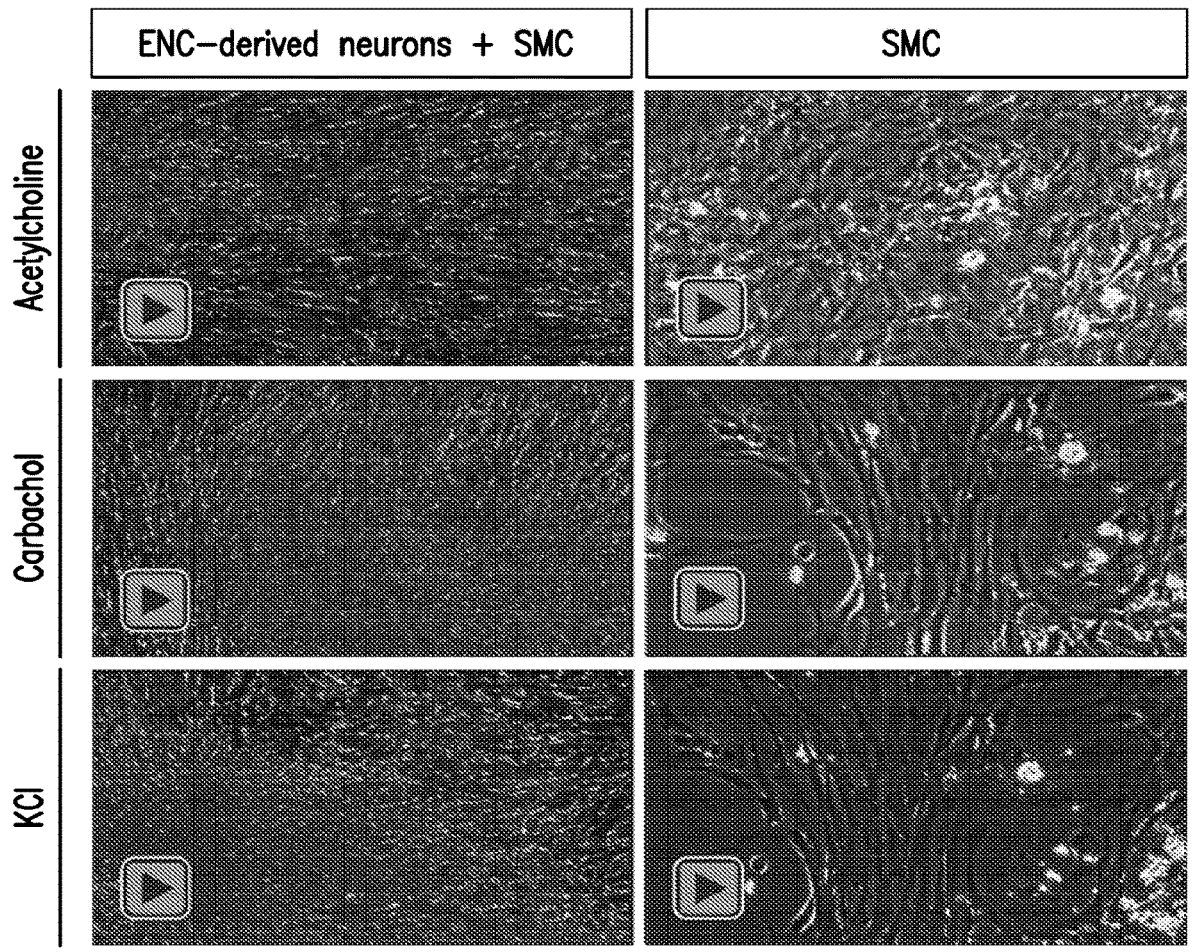
Figure 8C:
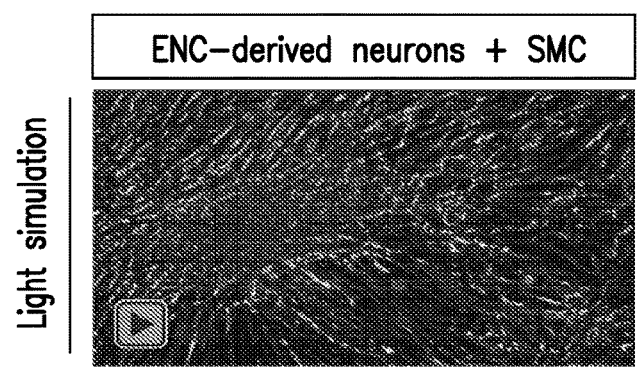
Figure 8B:
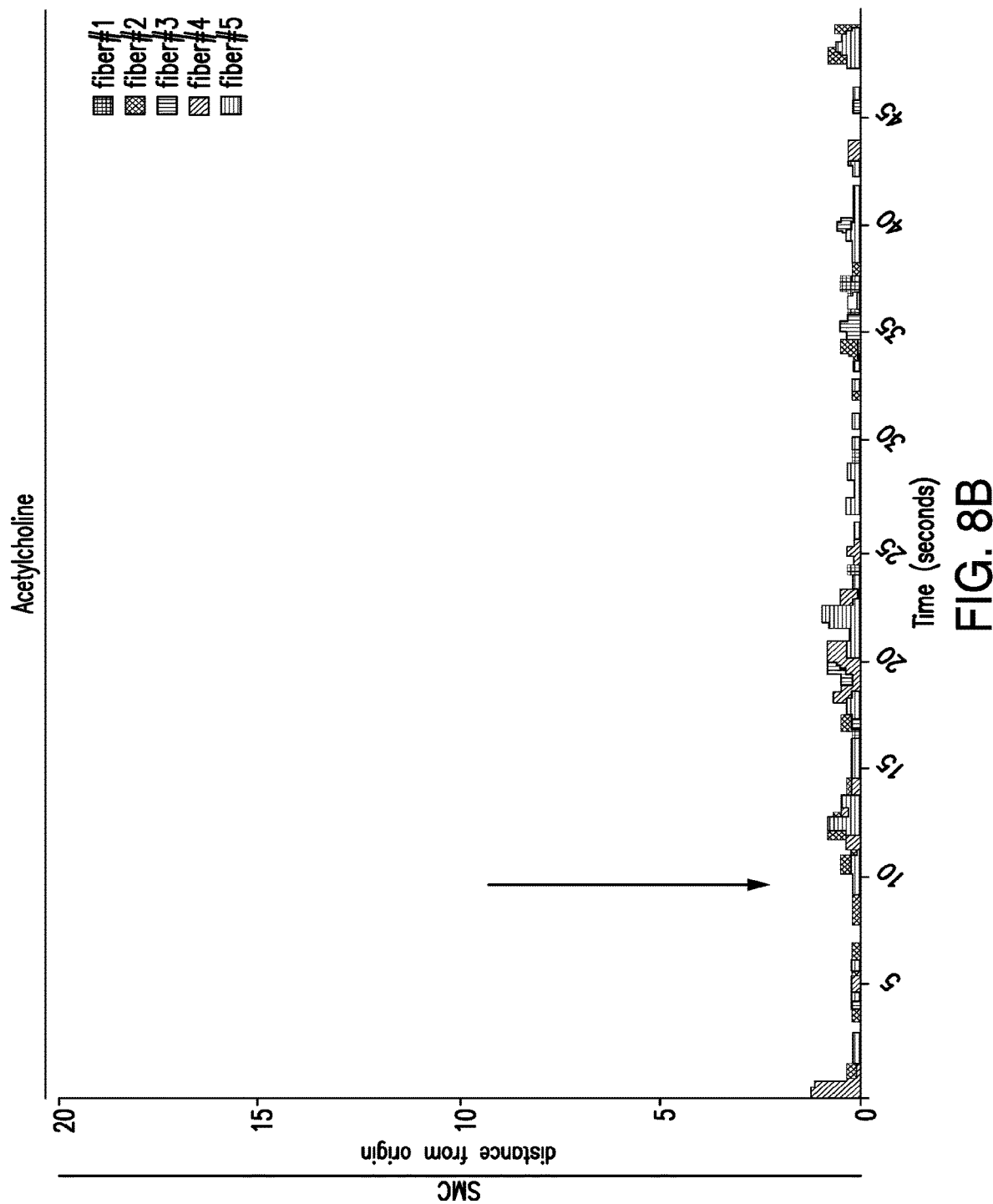
Figure 8B:
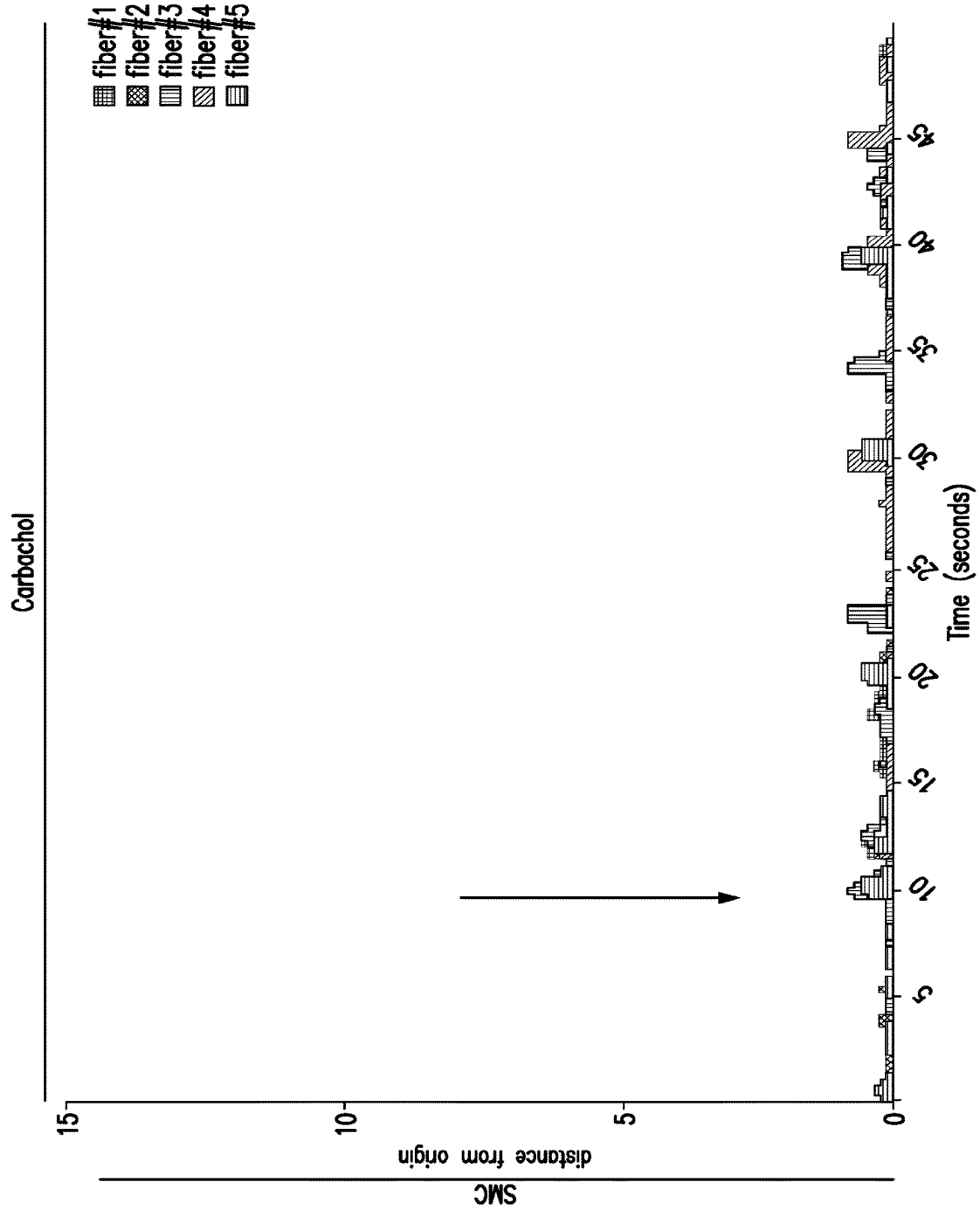
Figure 8B:
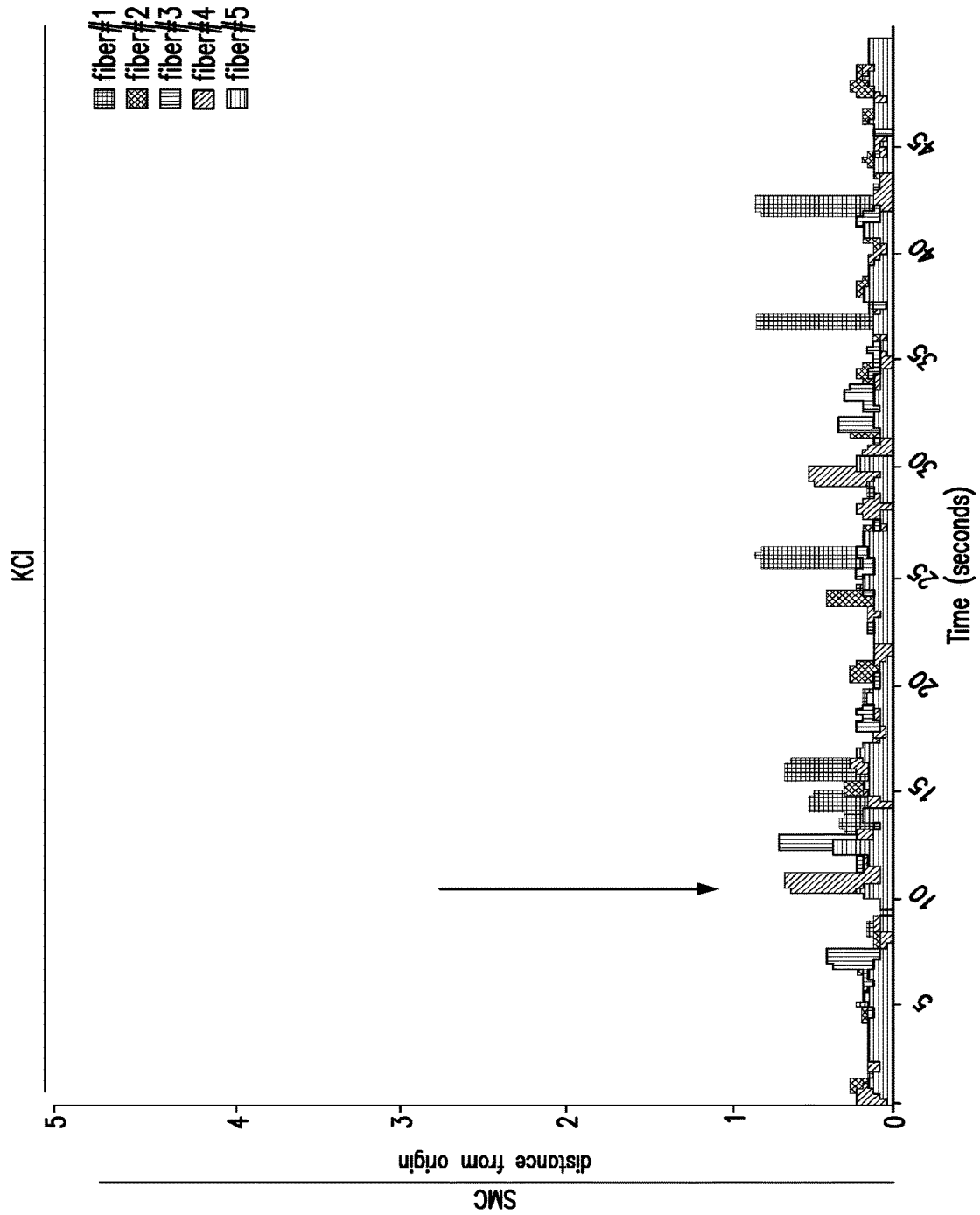
Figure 8B:
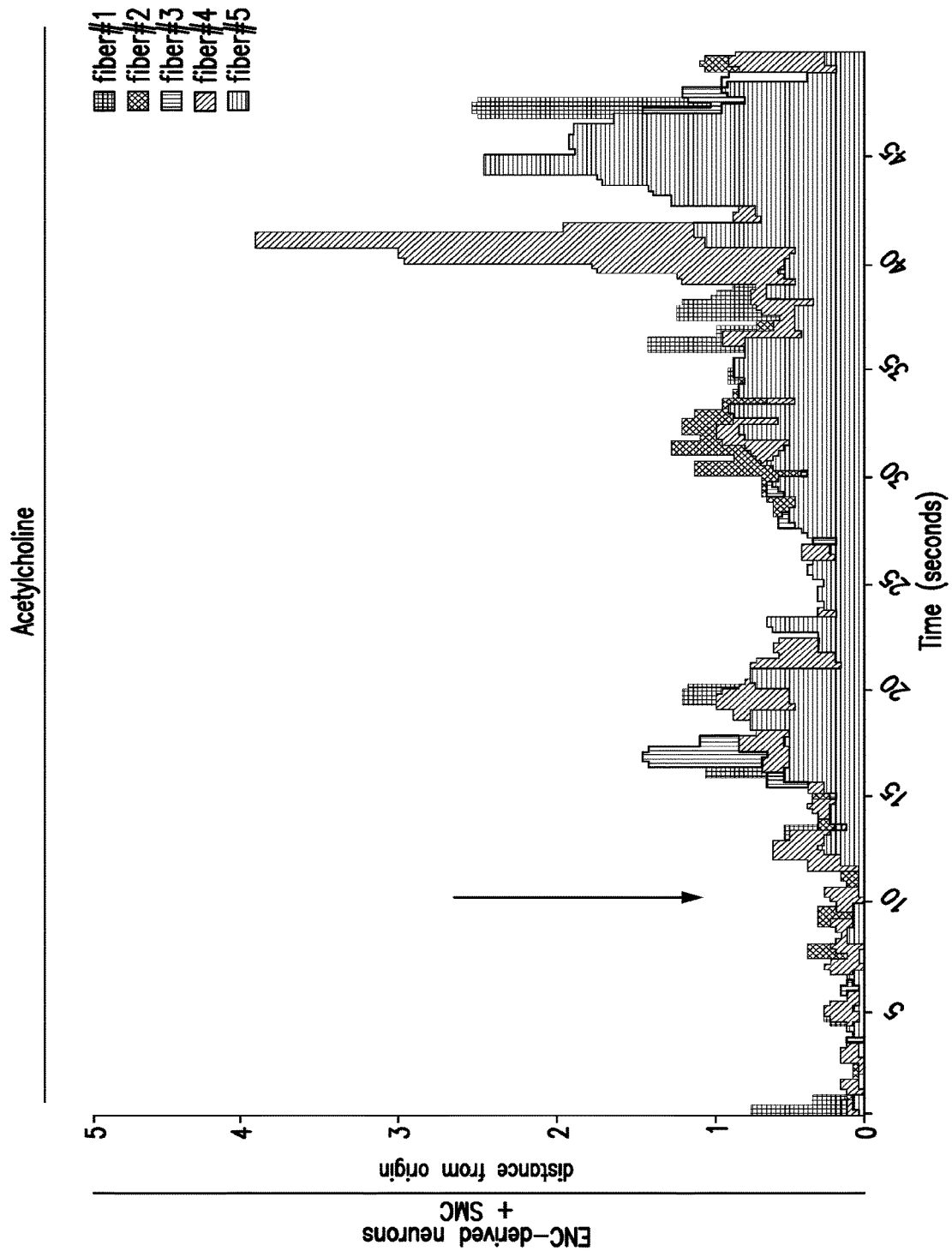
Figure 8B:
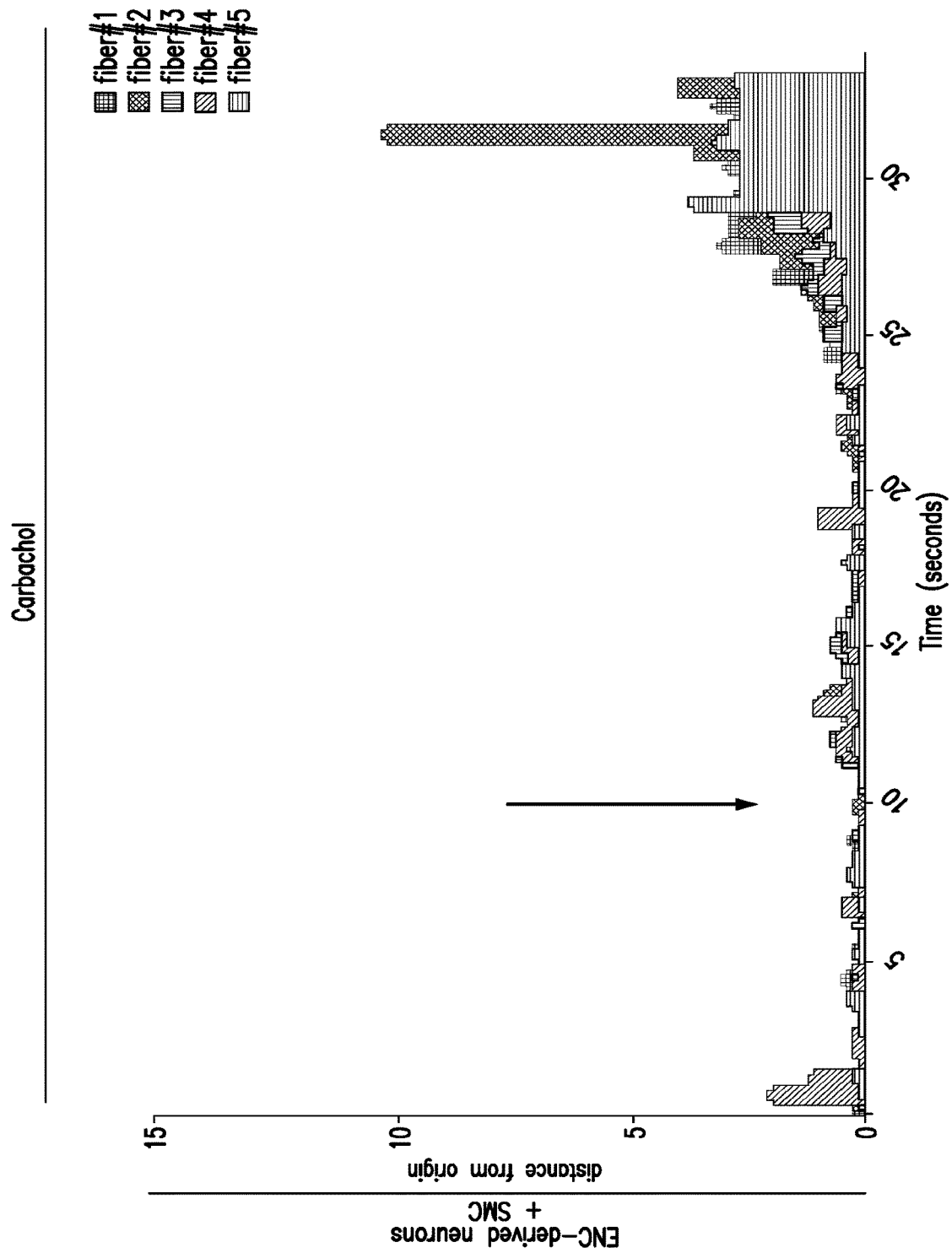
Figure 8B:
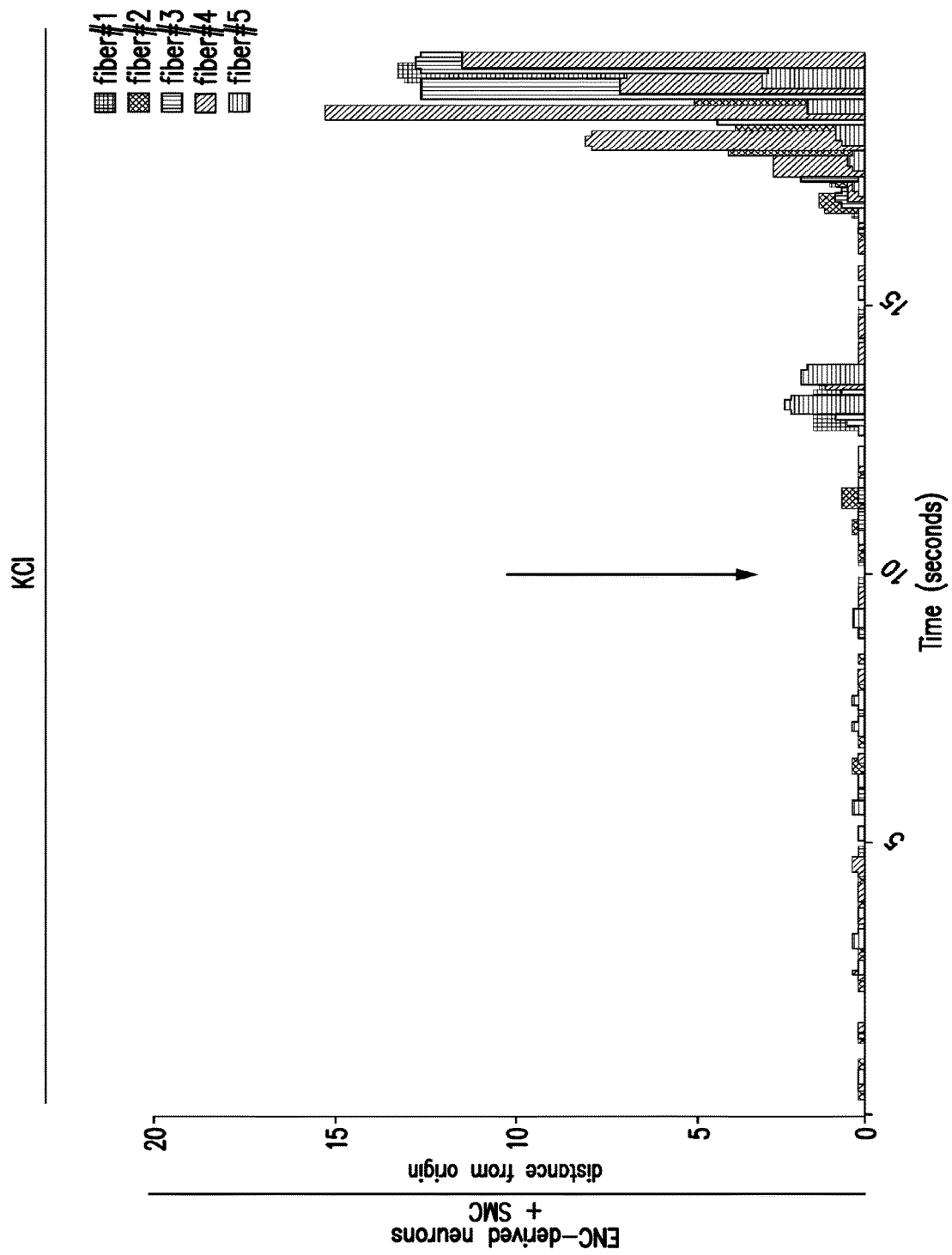

FIGS. 8A-8C: contraction of hESC-derived SMCs in co-culture with ENC-derived neuron (A) Movie snapshots showing contractile response of co-cultures of SMCs with SMCs with ENC-derived neurons versus monoculture of SMCs following exposure to Acetylcholine, Carbachol or KCl-mediated depolarization. (B) Diagrams representing extent of contraction of SMC+ tissue. Arrows indicate the time of pharmacological stimulation. (C) Movie snapshotsshowing contractile response of SMCs before light stimulation and during stimulation with different 450 nm light pulse frequencies. For quantification of response following optogenetic activation see FIG. 3I. Yellow dots represent pseudo-coloring generated by software based on phase contrast and used for quantification of movements. All movies are 5× faster than real time.

FIGS. 9A-9J: Characterization of transplanted hESC-ENC precursors in adult colon of NSG and EDNRB$^{s-l/s-l}$ mice (A) Whole mount microscopy of colon transplanted with RFP$^+$ CD49D purified hESC-ENC precursors to track RFP expression at injection site at 1 hour after transplantation to ensure that cells were injected at proper location, and at 2 weeks to show dispersal of the cells and congregation of subset of cells distinct clusters. The dashed lines indicate the outer border of the intact colon tissue. (B and C) Whole mount fluorescence imaging and quantification of migration of grafted RFP$^+$ hESC-derived CNS precursors and CD49D purified CNC precursors inside the adult colon wall. (D and E) Whole mount fluorescence imaging and quantification of migration of grafted RFP$^+$ CD49D purified hESC-ENC precursors in colon of EDNRB$^{s-l/s-l}$ mice. (F) Total GI transit times by carmine dye gavage of EDNRB$^{s-l/s-l}$ mice grafted with RFP+CD49D purified hESC-ENC precursors versus matrigel only grafted mice. (G and H) Representative images of grafted hESC-derived enteric NC precursors at 3 months after transplantation into the colon of EDNRB$^{s-l/s-l}$ mice co-expressing TUJ1 and SC121 (F) and human specific GFAP (SC123) in (G). The dashed lines indicate the border between submucosal and muscle layers. (I and J) Representative images of grafted hESC-derived ENC precursors at 6 weeks after transplantation into the colon of NSG (WT) and EDNRB$^{s-l/s-l}$ mice. The dashed lines indicate the border between submucosal and muscle layers. Scale bars=200 µm in a; 1 cm in b and d; 100 µm in g-j; Abbreviation: AU=Arbitrary Unit. p-value for (F) is given numerically, t-test with Welch's correction; n=3.

FIGS. 10A-10L: EDNRB signaling regulates human ENC precursor cell migration (A) Illustration of the in vitro HD disease modeling paradigm based on targeting EDNRB. (B and C) Representative images and subsequent quantification of the scratch assay in RFP+CD49D purified WT and EDNRB$^{-/-}$ hESC-derived ENC (clones 1-4). (D) Schematic illustration of chemical compound screening paradigm. (E) Dose response for effects of Pepstatin A on migration of CD49D purified EDNRB$^{-/-}$ hESC-derived ENC. (F and G) Representative images and quantification of CD49D purified EDNRB$^{-/-}$ hESC-derived ENC migration following treatment with Pepstatin A (10 µM) and BACE inhibitor IV (1 (H and I) Representative images and quantification of cell migration following BACE2 knockdown using a pool of 5 different siRNAs and 4 individual siRNAs against BACE2 in CD49D purified EDNRB$^{-/-}$ hESC-derived ENC. (J) Schematic illustration of Pepstatin A pre-transplantation treatment paradigm. (K) Whole mount images of the colon of NSG mice transplanted with RFP+CD49D purified WT and EDNRB$^{-/-}$ hESC-derived ENC precursors with or without Pepstatin A pre-treatment. (L) Quantification of the fraction of animals with human cells present in colon at increasing distance from injection site—compare to (K) and to raw data of RFP signal in FIG. S9C. Scale bars=200 µm in b, f and h; 1 cm in j. p-values in c and in i are: * p<0.001; ** p<0.0001 (ANOVA; Dunnett test (compared to wt)). p-values for analysis in L (fraction of animals with cells at a given distance from injection site) is given numerically, Log-rank (Mantel-Cox) test; n≥8 per for each group.

FIGS. 11A-11E: Establishing and characterizing EDNRB null hESC lines (A) Sequences of WT and Cas9-nickase induced bi-allelic nonsense mutations in targeted region of EDNRB$^{-/-}$ clones. (B) Western blot analysis for EDNRB in hESC-derived ENC precursors showing lack of protein expression in mutant clones C1-C4. (C) EDNRB$^{-/-}$ hESCs can be efficiently differentiated into CD49D+ hESC-derived ENC based on CD49D expression (C) and expression of SOX10 (data not shown). (D) proliferation of EDNRB$^{-/-}$ hESC-derived ENC versus WT-derived cells. (E) LDH activity measurement of cell viability in EDNRB$^{-/-}$ hESC-derived ENC versus WT-derived cells. p-value in (D) is: * p<0.05, t-test, n=3.

FIGS. 12A-12D: Chemical screening for compounds that rescue migration of EDNRB$^{-/-}$ hESC-derived NC precursors (A) Schematic illustration of the time line and experimental steps involved in the chemical screening assay and migration scoring system. (B) Example of a screening plate layout and locations of DMSO control wells. (C) Migration scores of Prestwick library compounds and DMSO controls. (D) migration assay and scores for EDNRB$^{-/-}$ hESCs-derived ENC precursors treated with primary hit compounds. Z-score for primary hit compounds in (C) is given numerically (compared to DMSO control, n=224)

FIGS. 13A-13F: Pharmacological modulation of migration in hESC-derived ENC precursors (A) BACE2 expression in the various hESC-derived NC sublineages at day 11 as compared to stage-matched CNS precursors. (B) qRT-PCR analysis to confirm knockdown of the BACE2 in CD49D purified EDNRB$^{-/-}$ hESC-derived ENC after siRNA transfection compared to control siRNA. (C) Quantification of whole mount images of the colon of NSG mice transplanted with RFP$^+$ CD49D purified WT and EDNRB$^{-/-}$ hESC-derived ENC precursors with or without Pepstatin A pre-treatment (compare to FIG. 3*l*). (D) Representative images of WT CD49D purified hESC-derived ENC treated with EDN3 and BQ-788 (EDNRB inhibitor). (E) Colon migration assay in WT hESC-derived ENC precursors following pretreatment with BQ788. (F) Quantification of the data in (E). Scale bar=1 cm in e; Abbreviations: AU=Arbitrary Unit.

5. DETAILED DESCRIPTION OF THE SUBJECT MATTER

The presently disclosed subject matter relates to in vitro methods for inducing differentiation of stem cells (e.g., human stem cells) to cells that express one or more enteric neural crest lineage marker (enteric nervous system (ENS) precursors), which can further induced in vitro to enteric neurons, cells (ENS precursors and enteric neurons) produced by such methods and compositions comprising such cells. Also provided are uses of such cells for preventing and/or treating Hirschsprung's disease and for screening compounds suitable for preventing and/or treating Hirschsprung's disease.

For purposes of clarity of disclosure and not by way of limitation, the detailed description is divided into the following subsections:
5.1. Definitions
5.2. Method of Differentiating Stem Cells
5.3. Compositions Comprising Differentiated Cell Populations
5.4 Method of Preventing and/or Treating Enteric Nervous System Disorders
5.5. Method of Screening Therapeutic Compounds
5.6. Kits

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "signaling" in reference to a "signal transduction protein" refers to a protein that is activated or otherwise affected by ligand binding to a membrane receptor protein or some other stimulus. Examples of signal transduction protein include, but are not limited to, a SMAD, a wingless (Wnt) complex protein, including beta-catnin, NOTCH, transforming growth factor beta (TGFβ), Activin, Nodal and glycogen synthase kinase 3β (GSK3P) proteins. For many cell surface receptors or internal receptor proteins, ligand-receptor interactions are not directly linked to the cell's response. The ligand activated receptor can first interact with other proteins inside the cell before the ultimate physiological effect of the ligand on the cell's behavior is produced. Often, the behavior of a chain of several interacting cell proteins is altered following receptor activation or inhibition. The entire set of cell changes induced by receptor activation is called a signal transduction mechanism or signaling pathway.

As used herein, the term "signals" refer to internal and external factors that control changes in cell structure and function. They can be chemical or physical in nature.

As used herein, the term "ligands" refers to molecules and proteins that bind to receptors, e.g., transforming growth factor-beta (TFGβ), Activin, Nodal, bone morphogenic proteins (BMPs), etc.

As used herein, the term "inhibitor", refers to a compound or molecule (e.g., small molecule, peptide, peptidomimetic, natural compound, siRNA, anti-sense nucleic acid, aptamer, or antibody) that interferes with (e.g., reduces, decreases, suppresses, eliminates, or blocks) the signaling function of the molecule or pathway. An inhibitor can be any compound or molecule that changes any activity of a named protein (signaling molecule, any molecule involved with the named signaling molecule, a named associated molecule, such as a glycogen synthase kinase 3β (GSK3β)) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein). Inhibitors also include molecules that indirectly regulate SMAD biological activity by intercepting upstream signaling molecules (e.g., within the extracellular domain, examples of a signaling molecule and an effect include: Noggin which sequesters bone morphogenic proteins, inhibiting activation of ALK receptors 1, 2, 3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFb signaling molecules. Antibodies that block activins, nodal, TGFb, and BMPs are contemplated for use to neutralize extracellular activators of SMAD signaling, and the like. Inhibitors are described in terms of competitive inhibition (binds to the active site in a manner as to exclude or reduce the binding of another known binding compound) and allostenc inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. An inhibitor can be a "direct inhibitor" that inhibits a signaling target or a signaling target pathway by actually contacting the signaling target.

As used herein, the term "activator", refers to compounds that increase, induce, stimulate, activate, facilitate, or enhance activation the signaling function of the molecule or pathway, e.g., Wnt signaling As used herein, the term "derivative" refers to a chemical compound with a similar core structure.

As used herein, the term "a population of cells" or "a cell population" refers to a group of at least two cells. In non-limiting examples, a cell population can include at least about 10, at least about 100, at least about 200, at least about 300, at least about 400, at least about 500, at least about 600, at least about 700, at least about 800, at least about 900, at least about 1000 cells. The population may be a pure population comprising one cell type, such as a population of enteric nervous system precursors, or a population of undifferentiated stem cells. Alternatively, the population may comprise more than one cell type, for example a mixed cell population.

As used herein, the term "stem cell" refers to a cell with the ability to divide for indefinite periods in culture and to give rise to specialized cells. A human stem cell refers to a stem cell that is from a human.

As used herein, the term "enteric nervous system precursor", "ENS precursor", "enteric neural crest precursor, "enteric NC precursor" or "ENC precursor" refers to a cell expressing one or more enteric neural crest lineage marker. An ENS precursor is a cell with the ability to mature into an enteric neuron. A human ENS precursor refers to an ENS precursor that is from a human. Non-limiting examples of enteric neural crest lineage markers include PAX3, EDNRB, RET, PHOX2A, PHOX2B, NTRK-3, HAND2, HOXB3, HOXB5 and ASCL1.

As used herein, the term "enteric neuron" refers to a cell expressing one or more enteric neuron marker. A human enteric neuron refers to an enteric neuron that is from a human. Non-limiting examples of enteric neuron markers include Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

As used herein, the term "embryonic stem cell" refers to a primitive (undifferentiated) cell that is derived from pre-implantation-stage embryo, capable of dividing without differentiating for a prolonged period in culture, and are known to develop into cells and tissues of the three primary germ layers. A human embryonic stem cell refers to an embryonic stem cell that is from a human. As used herein, the term "human embryonic stem cell" or "hESC" refers to a type of pluripotent stem cells derived from early stage human embryos, up to and including the blastocyst stage, that is capable of dividing without differentiating for a prolonged period in culture, and are known to develop into cells and tissues of the three primary germ layers.

As used herein, the term "embryonic stem cell line" refers to a population of embryonic stem cells which have been cultured under in vitro conditions that allow proliferation without differentiation for up to days, months to years.

As used herein, the term "totipotent" refers to an ability to give rise to all the cell types of the body plus all of the cell types that make up the extraembryonic tissues such as the placenta.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

As used herein, the term "induced pluripotent stem cell" or "iPSC" refers to a type of pluripotent stem cell, similar to an embryonic stem cell, formed by the introduction of certain embryonic genes (such as a OCT4, SOX2, and KLF4 transgenes) (see, for example, Takahashi and Yamanaka Cell 126, 663-676 (2006), herein incorporated by reference) into a somatic cell, for examples, CI 4, C72, and the like.

As used herein, the term "somatic cell" refers to any cell in the body other than gametes (egg or sperm); sometimes referred to as "adult" cells.

As used herein, the term "somatic (adult) stem cell" refers to a relatively rare undifferentiated cell found in many organs and differentiated tissues with a limited capacity for both self renewal (in the laboratory) and differentiation. Such cells vary in their differentiation capacity, but it is usually limited to cell types in the organ of origin.

As used herein, the term "neuron" refers to a nerve cell, the principal functional units of the nervous system. A neuron consists of a cell body and its processes—an axon and one or more dendrites. Neurons transmit information to other neurons or cells by releasing neurotransmitters at synapses.

As used herein, the term "proliferation" refers to an increase in cell number.

As used herein, the term "undifferentiated" refers to a cell that has not yet developed into a specialized cell type.

As used herein, the term "differentiation" refers to a process whereby an unspecialized embryonic cell acquires the features of a specialized cell such as a heart, liver, or muscle cell. Differentiation is controlled by the interaction of a cell's genes with the physical and chemical conditions outside the cell, usually through signaling pathways involving proteins embedded in the cell surface.

As used herein, the term "directed differentiation" refers to a manipulation of stem cell culture conditions to induce differentiation into a particular (for example, desired) cell type, such as enteric neuron precursors.

As used herein, the term "directed differentiation" in reference to a stem cell refers to the use of small molecules, growth factor proteins, and other growth conditions to promote the transition of a stem cell from the pluripotent state into a more mature or specialized cell fate (e.g. enteric neuron precursors, enteric neurons, etc.).

As used herein, the term "inducing differentiation" in reference to a cell refers to changing the default cell type (genotype and/or phenotype) to a non-default cell type (genotype and/or phenotype). Thus, "inducing differentiation in a stem cell" refers to inducing the stem cell (e.g., human stem cell) to divide into progeny cells with characteristics that are different from the stem cell, such as genotype (e.g., change in gene expression as determined by genetic analysis such as a microarray) and/or phenotype (e.g., change in expression of a protein, such as SOX10, and CD49D).

As used herein, the term "cell culture" refers to a growth of cells in vitro in an artificial medium for research or medical treatment.

As used herein, the term "culture medium" refers to a liquid that covers cells in a culture vessel, such as a Petri plate, a multi-well plate, and the like, and contains nutrients to nourish and support the cells. Culture medium may also include growth factors added to produce desired changes in the cells.

As used herein, the term "contacting" cells with a compound (e.g., one or more inhibitor, activator, and/or inducer) refers to placing the compound in a location that will allow it to touch the cell. The contacting may be accomplished using any suitable methods. For example, contacting can be accomplished by adding the compound to a tube of cells. Contacting may also be accomplished by adding the compound to a culture medium comprising the cells. Each of the compounds (e.g., the inhibitors, activators, and molecules that induce vagal neural crest patterning disclosed herein) can be added to a culture medium comprising the cells as a solution (e.g., a concentrated solution). Alternatively or additionally, the compounds (e.g., the inhibitors, activators, and molecules that induce vagal neural crest patterning disclosed herein) as well as the cells can be present in a formulated cell culture medium.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "expressing" in relation to a gene or protein refers to making an mRNA or protein which can be observed using assays such as microarray assays, antibody staining assays, and the like.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type.

As used herein, the term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vitro, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

5.2 Method of Differentiating Stem Cells

The presently disclosed subject matter provides for in vitro methods for inducing differentiation of stem cells (e.g., human stem cells). In certain embodiments, the stem cells are human stem cells. Non-limiting examples of human stem cells include human embryonic stem cells (hESC), human pluripotent stem cell (hPSC), human induced pluripotent stem cells (hiPSC), human parthenogenetic stem cells, primoridal germ cell-like pluripotent stem cells, epiblast stem cells, F-class pluripotent stem cells, somatic stem cells, cancer stem cells, or any other cell capable of lineage specific differentiation. In certain embodiments, the human stem cell is a human embryonic stem cell (hESC). In certain embodiments, the human stem cell is a human induced pluripotent stem cell (hiPSC). In certain embodiments, the stem cells are non-human stem cells. Non-limiting examples of non-human stem cells non-human primate stem cells, rodent stem cells, dog stem cells, cat stem cells. In certain embodiments, the stem cells are pluripotent stem cells. In certain embodiments, the stem cells are embryonic stem cells. In certain embodiments, the stem cells are induced pluripotent stem cells.

The inventors previously disclosed the use of dual SMAD inhibition for inducing differentiation of stem cells (e.g., hPSC) to one type of neural lineage (Chambers (2009), which is incorporated by reference in its entirety). Furthermore, the inventors previously disclosed differentiation of stem cells to nociceptors (neural crest derived cell lineage) by sequential inhibition of SMAD signaling followed by activation of Wnt signaling (Chambers (2012); WO2011/149762, which are incorporated by reference in their entireties). These neural crest (NC) differentiation methods and protocols result in SOX10+ NC precursors that are HOX negative, which is indicative of anterior/cranial identify; cranial NC (CNCs), and these methods and protocols primarily give rise to sensory and nociceptive neurons.

The presently disclosed subject matter herein discloses a novel finding that enteric nervous system (ENS) precursors (e.g., cells that express one or more enteric neural crest lineage marker) can be differentiated from stem cells (e.g., human stem cells) by sequential inhibition of SMAD signaling followed by activation of Wnt signaling, which is followed by inducing vagal neural crest identify. The ENS develops from both the vagal and sacral neural crest (NC). A major function of the ENS is control of peristaltic gut movements via coordinated activation of smooth muscle layers. The vagal neural crest (NC) generates the majority of the ENS and migrates caudally to colonize the entire length of the bowel[3].

In Vitro Differentiation of Stem Cells to ENS Precursors

In certain embodiments, the method of in vitro inducing differentiation of stem cells to cells expressing one or more enteric neural crest lineage marker (ENS precursors) comprises contacting a population of stem cells (e.g., human stem cells) with an effective amount(s) of one or more inhibitor of transforming growth factor beta (TGFβ)/Activin-Nodal signaling. In certain embodiments, the inhibitor of TGFβ/Activin-Nodal signaling neutralizes the ligands including TGFβs, bone morphogenetic proteins (BMPs), Nodal, and activins, or blocking their signal pathways through blocking the receptors and downstream effectors. Non-limiting examples of inhibitors of TGFβ/Activin-Nodal signaling are disclosed in WO2011/149762, Chambers (2009), and Chambers (2012), which are incorporated by reference in their entireties. In certain embodiments, the one or more inhibitor of TGFβ/Activin-Nodal signaling is a small molecule selected from the group consisting of SB431542, derivatives thereof, and mixtures thereof.

In certain embodiments, the inhibitor of TGFβ/Activin-Nodal signaling is SB431542. "SB431542" refers to a molecule with a number CAS 301836-41-9, a molecular formula of $C_{22}H_{18}N_4O_3$, and a name of 4-[4-(1,3-benzodioxol-5-yl)-5-(2-pyridinyl)-1H-imidazol-2-yl]-benzamide, for example, see structure below:

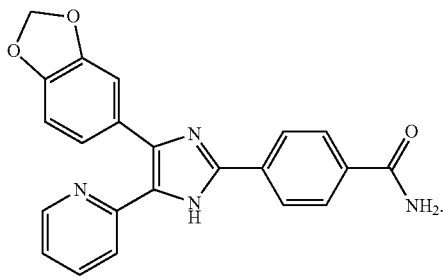 [SMILES: NC(=O)c1ccc(-c2nc(-c3ccc4c(c3)OCO4)c(-c3ccccn3)[nH]2)cc1]

The stem cells can be contacted with the one or more inhibitor of TGFβ/Activin-Nodal signaling for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days, to produce a population of cells expressing one or more enteric neural crest lineage marker (ENS precursors). In certain embodiments, the stem cells are contacted with the one or more inhibitor of TGFβ/Activin-Nodal signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce a population of cells expressing one or more enteric neural crest lineage marker (ENS precursors). In certain embodiments, the stem cells are contacted with the one or more inhibitor of TGFβ/Activin-Nodal signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days, to produce a population of cells expressing one or more enteric neural crest lineage marker (ENS precursors). In certain embodiments, the stem cells are contacted with the one or more inhibitor of TGFβ/Activin-Nodal signaling for between 10 days and about 15 days, to produce a population of cells expressing one or more enteric neural crest lineage marker (ENS precursors). In certain embodiments, the stem cells are contacted with the one or more inhibitor of TGFβ/Activin-Nodal signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day, to produce a population of cells expressing one or more enteric neural crest lineage marker (ENS precursors). In certain embodiments, the stem cells are contacted with the one or more inhibitor of TGFβ/Activin-Nodal signaling for about 11 days, to produce a population of cells expressing one or more enteric neural crest lineage marker (ENS precursors).

In certain embodiments, the stem cells are contacted with the one or more inhibitor of TGFβ/Activin-Nodal signaling in a concentration of from about 1 nM to about 300 nM, from about 5 nM to about 250 nM, from about 10 nM to about 200 nM, from about 10 nM to about 50 nM, from about 50 nM to about 150 nM, from about 80 nM to about 120 nM, from about 90 nM to about 110 nM, from about 50 nM to about 100 nM, from about 100 nM to about 150 nM, from about 150 nM to about 200 nM, from about 200 nM to about 250 nM, or from about 250 nM to about 300 nM, to produce ENS precursors. In certain embodiments, the stem cells are contacted with the one or more inhibitor of TGFβ/Activin-Nodal signaling in a concentration of from about 80 nM to about 120 nM, to produce ENS precursors. In certain embodiments, the stem cells are contacted with the one or more inhibitor of TGFβ/Activin-Nodal signaling in a concentration of about 100 nM, to produce ENS precursors. In certain embodiments, the stem cells are contacted with the one or more inhibitor of TGFβ/Activin-Nodal signaling in any one of the above-described concentrations daily. In certain embodiments, the stem cells are contacted with the one or more inhibitor of TGFβ/Activin-Nodal signaling in a concentration of about 100 nM daily, to produce ENS precursors.

In certain embodiments, the method of in vitro inducing differentiation of stem cells to cells expressing one or more enteric neural crest lineage marker (ENS precursors) comprises contacting the stem cells with an effective amount(s) of one or more inhibitor of Small Mothers Against Decapentaplegic (SMAD) signaling. Non-limiting examples of inhibitors of SMAD signaling are disclosed in WO2011/149762, Chambers (2009), and Chambers (2012), which are incorporated by reference in their entireties. In certain embodiments, the one or more inhibitor of SMAD signaling is a small molecule selected from the group consisting of LDN193189, derivatives thereof, and mixtures thereof.

In certain embodiments, the inhibitor of SMAD signaling is LDN193189. "LDN193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$ with the following formula.

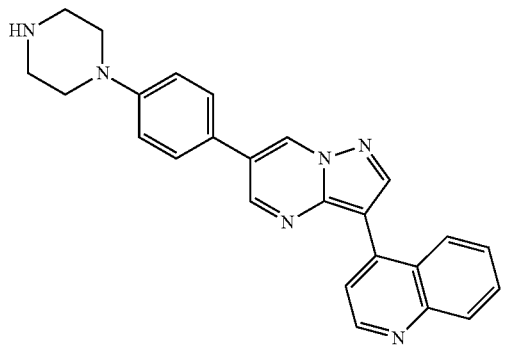 [SMILES: c1ccc2c(-c3cnn4cc(-c5ccc(N6CCNCC6)cc5)cnc34)ccnc2c1]

LDN193189 is capable of functioning as a SMAD signaling inhibitor. LDN193189 is also highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of Smad1, Smad5, and Smad8 (Yu et al. (2008) Nat Med 14:1363-1369; Cuny et al. (2008) Bioorg. Med. Chem. Lett. 18: 4388-4392, herein incorporated by reference).

The stem cells can be contacted with the one or more inhibitor of SMAD signaling for at least about 3 days, at least about 4 days, at least about 5 days, at least about 6 days, at least about 7 days, at least about 8 days, at least about 9 days, at least about 10 days, at least about 11 days, at least about 12, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days, to produce a population of cells expressing one or more enteric neural crest lineage marker (ENS precursors). In certain embodiments, the stem cells are contacted with the one or more inhibitor of SMAD signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, for up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce a population of cells expressing one or more enteric neural crest lineage marker (ENS precursors). In certain embodiments, the stem cells are contacted with the one or more inhibitor of SMAD signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days, to produce a population of cells expressing one or more enteric neural crest lineage marker (ENS precursors). In certain embodiments, the stem cells are contacted with the one or more inhibitor of SMAD signaling for between 10 days and about 15 days, to produce a population of cells expressing one or more enteric neural crest lineage marker (ENS precursors). In certain embodiments, the stem cells are contacted with the one or more inhibitor of SMAD signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day, to produce a population of cells expressing one or more enteric neural crest lineage marker (ENS precursors). In certain embodiments, the stem cells are contacted with the one or more inhibitor of SMAD signaling for about 11 days, to produce a population of cells expressing one or more enteric neural crest lineage marker (ENS precursors).

In certain embodiments, the stem cells are contacted with the one or more inhibitor of SMAD signaling in a concentration of from about 1 μM to 100 μM, from about 1 μM to 20 μM, from about 1 μM to 15 μM, from about 1 μM to 10 μM, from about 1 μM to 5 μM, from about 5 μM to 10 μM, from about 5 μM to 15 μM, from about 15 μM to 20 μM, from about 20 μM to 30 μM, from about 30 μM to 40 μM, from about 40 μM to 50 μM, from about 50 μM to 60 μM, from about 60 μM to 70 μM, from about 70 μM to 80 μM, from about 80 μM to 90 μM, or from about 90 μM to 100

µM, to produce ENS precursors. In certain embodiments, the stem cells are contacted with the one or more inhibitor of SMAD signaling in a concentration of from about from about 5 µM to 15 µM, to produce ENS precursors. In certain embodiments, the stem cells are contacted with the one or more inhibitor of SMAD signaling in a concentration of about 10 µM, to produce ENS precursors. In certain embodiments, the stem cells are contacted with the one or more inhibitor of SMAD signaling in any one of the above-described concentrations daily. In certain embodiments, the stem cells are contacted with the one or more inhibitor of SMAD signaling in a concentration of about 10 µM daily, to produce ENS precursors.

In certain embodiments, the method of in vitro inducing differentiation of stem cells to cells expressing one or more enteric neural crest lineage marker (ENS precursors) comprises contacting the cells with an effective amount(s) of one or more activator of wingless (Wnt) signaling (also referred to as "Wnt activators"). As used herein, the term "WNT" or "wingless" in reference to a ligand refers to a group of secreted proteins (i.e. Intl (integration 1) in humans) capable of interacting with a WNT receptor, such as a receptor in the Frizzled and LRPDerailed/RYK receptor family. As used herein, the term "WNT" or "wingless" in reference to a signaling pathway refers to a signal pathway composed of Wnt family ligands and Wnt family receptors, such as Frizzled and LRPDerailed/RYK receptors, mediated with or without β-catenin. For the purposes described herein, a preferred WNT signaling pathway includes mediation by β-catenin, e.g., WNT/-catenin.

In certain embodiments, the one or more activator of Wnt signaling lowers glycogen synthase kinase 3β (GSK3β) for activation of Wnt signaling. Thus, the activator of Wnt signaling can be a GSK3β inhibitor. A GSK3P inhibitor is capable of activating a WNT signaling pathway, see e.g., Cadigan, et al., J Cell Sci. 2006; 119:395-402; Kikuchi, et al., Cell Signalling. 2007; 19:659-671, which are incorporated by reference herein in their entireties. As used herein, the term "glycogen synthase kinase 3β inhibitor" refers to a compound that inhibits a glycogen synthase kinase 3β enzyme, for example, see, Doble, et al., J Cell Sci. 2003; 116:1175-1186, which is incorporated by reference herein in its entirety.

Non-limiting examples of activators of Wnt signaling or GSK3β inhibitors are disclosed in WO2011/149762, Chambers (2012), and Calder et al., J Neurosci. 2015 Aug. 19; 35(33):11462-81, which are incorporated by reference in their entireties. In certain embodiments, the one or more activator of Wnt signaling is a small molecule selected from the group consisting of CHIR99021, WNT3A, derivatives thereof, and mixtures thereof.

In certain embodiments, the Wnt activator is CHIR99021. "CHIR99021" (also known as or "aminopyrimidine" or "3-[3-(2-Carboxyethyl)-4-methylpyrrol-2-methylidenyl]-2-indolinone") refers to IUPAC name 6-(2-(4-(2,4-dichlorophenyl)-5-(4-methyl-1H-imidazol-2-yl)pyrimidin-2-ylamino) ethylamino)nicotinonitrile with the following formula.

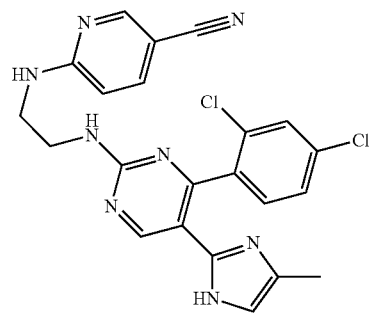 [SMILES: Cc1c[nH]c(-c2cnc(NCCNc3ccc(C#N)cn3)nc2-c2ccc(Cl)cc2Cl)n1]

CHIR99021 is highly selective, showing nearly thousand-fold selectivity against a panel of related and unrelated kinases, with an IC50=6.7 nM against human GSK3β and nanomolar IC50 values against rodent GSK3β homologs.

The stem cells can be contacted with the one or more activator of Wnt signaling for at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, or at least about 29 days, at least about 30 days, to produce a population of cells expressing one or more enteric neural crest lineage marker (ENS precursors). In certain embodiments, the stem cells are contacted with the one or more activator of Wnt signaling for up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce a population of cells expressing one or more enteric neural crest lineage marker (ENS precursors). In certain embodiments, the stem cells are contacted with the one or more activator of Wnt signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days, to produce a population of cells expressing one or more enteric neural crest lineage marker (ENS precursors). In certain embodiments, the stem cells are contacted with the one or more activator of Wnt signaling for between 5 days and about 15 days, to produce a population of cells expressing one or more enteric neural crest lineage marker (ENS precursors). In certain embodiments, the stem cells are contacted with the one or more activator of Wnt signaling for about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day, to produce a population of cells expressing one or more enteric neural crest lineage marker (ENS precursors). In certain embodiments, the stem cells are contacted with the one or more activator of Wnt signaling for about 11 days, to produce a population of cells expressing one or more enteric neural crest lineage marker (ENS precursors). In certain embodiments, the stem cells are contacted with the one or more activator of Wnt signaling for about 10 days, to produce a population of cells expressing one or more enteric neural crest lineage marker (ENS precursors). In certain embodiments, the stem cells are contacted with the one or more activator of Wnt signaling for about 9 days, to produce a population of cells expressing one or more enteric neural crest lineage marker (ENS precursors).

In certain embodiments, the stem cells are contacted with the one or more activator of Wnt signaling in a concentration of from about 1 µM to 100 µM, from about 1 µM to 20 µM, from about 1 µM to 15 µM, from about 1 µM to 10 µM, from about 1 µM to 5 µM, from about 5 µM to 10 µM, from about 5 µM to 15 µM, from about 15 µM to 20 µM, from about 20 µM to 30 µM, from about 30 µM to 40 µM, from about 40 µM to 50 µM, from about 50 µM to 60 µM, from about 60 µM to 70 µM, from about 70 µM to 80 µM, from about 80 µM to 90 µM, or from about 90 µM to 100 µM, to produce ENS precursors. In certain embodiments, the stem cells are contacted with the one or more activator of Wnt signaling in a concentration of from about 1 µM to 5 µM, to produce ENS precursors. In certain embodiments, the stem cells are contacted with the one or more activator of Wnt signaling in a concentration of about 3 µM, to produce ENS precursors. In certain embodiments, the stem cells are contacted with the one or more activator of Wnt signaling in any one of the above-described concentrations daily. In certain embodiments, the stem cells are contacted with the one or more activator of Wnt signaling in a concentration of about 3 µM daily, to produce ENS precursors.

In certain embodiments, the method of in vitro inducing differentiation of stem cells to cells expressing one or more enteric neural crest lineage marker (ENS precursors) comprises contacting the cells with an effective amount(s) of one or more molecule that induces vagal neural crest patterning to produce a population of differentiated cells that express one or more enteric neural crest lineage marker. Vagal NC patterning can be characterized by the expression of one or more regional specific homeobox (HOX) gene, including, but not limited to, homeobox B2 (HOXB2), homeobox B3 (HOXB3)[8], homeobox B4 (HOXB4), and homeobox B5 (HOXB5)[9].

In certain embodiments, the one or more molecule that induces vagal neural crest patterning is selected from the group consisting of retinoic acid (RA), retinol, retinal, tretinoin, isotretinoin, alitretinoin, etretinate, acitretin, tazarotene, bexarotene, adapalene, and combinations thereof. In certain embodiments, the one or more molecule that induces vagal neural crest patterning is selected from the group consisting of activators of FGF signaling, activators of Wnt signaling, and combinations thereof.

In certain embodiments, the molecule that induces vagal neural crest patterning is retinoic acid (RA). RA has been previously used as an extrinsic factor to shift the regional identity of CNS precursors from anterior to more caudal fates such as during motoneuron specification[10]. The inventors discovered that RA not only directs the regional identity in neural crest lineages, but also induces the expression of vagal markers. See Example 1 (e.g., FIG. 1A).

The cells can be contacted with the one or more molecule that induces vagal neural crest patterning for at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, or at least about 21 days, to produce a population of cells expressing one or more enteric neural crest lineage marker (ENS precursors). In certain embodiments, the cells are contacted with the one or more molecule that induces vagal neural crest patterning for at least about 2 days, to produce a population of cells expressing one or more enteric neural crest lineage marker (ENS precursors). In certain embodiments, the cells are contacted with the one or more molecule that induces vagal neural crest patterning for up to about 2 days, up to 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, or up to about 21 days, to produce a population of cells expressing one or more enteric neural crest lineage marker (ENS precursors). In certain embodiments, the cells are contacted with the one or more one or more molecule that induces vagal neural crest patterning for between about 2 days and about 21 days, between about 2 days and about 20 days, between about 2 days to about 10 days, between about 10 days and about 15 days, between about 15 days and about 21 days, between about 2 days and about 6 days, between about 2 days and about 5 days, or between about 5 days and about 10 days, to produce a population of cells expressing one or more enteric neural crest lineage marker (ENS precursors). In certain embodiments, the cells are contacted with the one or more molecule that induces vagal neural crest patterning for between about 5 days and about 10 days, to produce a population of cells expressing one or more enteric neural crest lineage marker (ENS precursors). In certain embodiments, the cells are contacted with the one or more molecule that induces vagal neural crest patterning for between 5 days and about 20 days, to produce a population of cells expressing one or more enteric neural crest lineage marker (ENS precursors). In certain embodiments, the cells are contacted with the one or more molecule that induces vagal neural crest patterning for between about 2 days and about 6 days, to produce a population of cells expressing one or more enteric neural crest lineage marker (ENS precursors). In certain embodiments, the stem cells are contacted with the one or more molecule that induces vagal neural crest patterning for between about 2 days and about 10 days, to produce a population of cells expressing one or more enteric neural crest lineage marker (ENS precursors). In certain embodiments, the cells are contacted with the one or more molecule that induces vagal neural crest patterning for up to about 20 days, to produce a population of cells expressing one or more enteric neural crest lineage marker (ENS precursors). In certain embodiments, the cells are contacted with the one or more molecule that induces vagal neural crest patterning for about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days, to produce a population of cells expressing one or more enteric neural crest lineage marker (ENS precursors). In certain embodiments, the cells are contacted with the one or more molecule that induces vagal neural crest patterning for about 6 days, to produce a population of cells expressing one or more enteric neural crest lineage marker (ENS precursors). In certain embodiments, the cells are contacted with the one or more molecule that induces vagal neural crest patterning for about 5 days, to produce a population of cells expressing one or more enteric neural crest lineage marker (ENS precursors).

In certain embodiments, the cells are contacted with the one or more molecule that induces vagal neural crest patterning in a concentration of from about 1 µM to 100 µM, from about 1 µM to 20 µM, from about 1 µM to 15 µM, from about 1 µM to 10 µM, from about 1 µM to 5 µM, from about 5 µM to 10 µM, from about 5 µM to 15 µM, from about 15 µM to 20 µM, from about 20 µM to 30 µM, from about 30 µM to 40 µM, from about 40 µM to 50 µM, from about 50 µM to 60 µM, from about 60 µM to 70 µM, from about 70 µM to 80 µM, from about 80 µM to 90 µM, or from about 90 µM to 100 to produce ENS precursors. In certain embodiments, the cells are contacted with the one or more molecule that induces vagal neural crest patterning in a concentration of from about from about 5 µM to 15 µM, to produce ENS precursors. In certain embodiments, the cells are contacted with the one or more molecule that induces vagal neural crest patterning in a concentration of about 10 µM, to produce ENS precursors. In certain embodiments, the cells are contacted with the one or more molecule that induces vagal neural crest patterning in any one of the above-described concentrations daily. In certain embodiments, the cells are contacted with the one or more molecule that induces vagal neural crest patterning in a concentration of about 10 µM daily, to produce ENS precursors.

In certain embodiments, the stem cells are contacted with one or more inhibitor of TGFβ/Activin-Nodal signaling and the one or more inhibitor of SMAD signaling for about 12 days; with the one or more activator of Wnt signaling for about 10 days; and with the one or more molecule that induces vagal neural crest patterning for about 6 days, to produce a population of cells expressing one or more enteric neural crest lineage marker (ENS precursors). In certain embodiments, the stem cells are contacted with one or more inhibitor of TGFβ/Activin-Nodal signaling and the one or more inhibitor of SMAD signaling for about 11 days; with the one or more activator of Wnt signaling for about 9 days; and with the one or more molecule that induces vagal neural crest patterning for about 5 days, to produce a population of cells expressing one or more enteric neural crest lineage marker (ENS precursors).

In certain embodiments, with one or more inhibitor of TGFβ/Activin-Nodal signaling and the one or more activator of Wnt signaling for about 12 days; and with the one or more molecule that induces vagal neural crest patterning for about 6 days, to produce a population of cells expressing one or more enteric neural crest lineage marker (ENS precursors). In certain embodiments, with one or more inhibitor of TGFβ/Activin-Nodal signaling and the one or more activator of Wnt signaling for about 11 days; and with the one or more molecule that induces vagal neural crest patterning for about 5 days, to produce a population of cells expressing one or more enteric neural crest lineage marker (ENS precursors).

Enteric nervous system (ENS) precursors (e.g., cells that express one or more enteric neural crest lineage marker) can be differentiated from stem cells in less than about 20 days, less than about 19 days, less than about 18 days, less than about 17 days, less than about 16 days, less than about 15 days, less than about 14 days, less than about 13 days, less than about 12 days, less than about 11 days, less than about 10 days, less than about 9 days, less than about 8 days, less than about 7 days, less than about 6 days, less than about 5 days, or less than about 4 days after their initial contact with at least one of the inhibitor(s) of TGFβ/Activin-Nodal signaling, inhibitor(s) of SMAD signaling, activator(s) of Wnt signaling, and molecule(s) inducing vagal neural crest patterning. In certain embodiments, ENS precursors are differentiated from stem cells on or after about 11 days after their initial contact with at least one of the inhibitor(s) of TGFβ/Activin-Nodal signaling, inhibitor(s) of SMAD signaling, activator(s) of Wnt signaling, and molecule(s) inducing vagal neural crest patterning. In certain embodiments, ENS precursors are differentiated from stem cells on about 11 days after their initial contact with at least one of the inhibitor(s) of TGFβ/Activin-Nodal signaling, inhibitor(s) of SMAD signaling, activator(s) of Wnt signaling, and molecule(s) inducing vagal neural crest patterning.

In certain embodiments, the two or molecules that induce vagal neural crest patterning are one or more activator of FGF signaling and one or more Wnt activator. Non-limiting examples of activators of FGF signaling include FGF2, FGF4, and FGF8. Non-limiting examples of Wnt activators include CHIR99021 and WNT3A.

In Vitro Induction of ENS Precursors to Enteric Neurons

ENS precursors are unique in their ability to give rise to diverse neuron subsets producing dozens of distinct neurotransmitters and hormones. The ENS precursors can be further induced/matured in vitro to enteric neurons. Enteric neurons can be immature enteric neurons, mature enteric neurons, or a combination thereof. The differentiated ENS precursors can be subjected to conditions favoring maturation of ENS precursors into a population of enteric neurons.

In certain embodiments, the conditions favoring maturation comprises culturing the differentiated ENS precursors in a suitable cell culture medium. In certain embodiments, the suitable cell culture medium is an NB medium. In certain embodiments, the suitable cell culture medium is an NB medium supplemented with L-Glutamine (e.g., from Gibco, 25030-164), N2 (e.g., from Stem Cell Technologies, 07156), and B27 (e.g., from Life Technologies, 17504044). The differentiated ENS precursors can be cultured in the suitable cell culture medium for at least about 1 day, for at least about 2 days, for at least about 3 days, for at least about 4 days, for at least about 5 days, for at least about 6 days, for at least about 7 days, for at least about 8 days, for at least about 9 days, for at least about 10 days, for at least about 11 days, for at least about 12 days, for at least about 13 days, for at least about 14 days, for at least about 15 days, for at least about 16 days, for at least about 17 days, for at least about 18 days, for at least about 19 days, for at least about 20 days, for at least about 25 days, for at least about 30 days, for at least about 35 days, for at least about 40 days, for at least about 45 days, or for at least about 50 days, to produce enteric neurons.

In certain embodiments, the suitable cell culture medium comprises one or more molecule that enhances maturation of ENS precursors to enteric neurons. In certain embodiments, the conditions favoring maturation comprises contacting the differentiated ENS precursors with one or more molecule that enhances maturation of ENS precursors to enteric neurons. In certain embodiments, the one or more molecule that enhances maturation of ENS precursors to enteric neurons is selected from the group consisting of growth factors and Wnt activators described herein. Non-limiting examples of growth factors include activators of FGF signaling (FGF activators), glial cell line derived neurotrophic factor (GDNF), and ascorbic acid. In certain embodiments, the differentiated ENS precursors are contacted with one or more activator of FGF signaling and one or more WNt activator to produce a population of enteric neurons. In certain embodiments, the suitable cell culture medium comprises one or more FGF activator and one or more WNT activator. Non-limiting examples of activators of FGF signaling include FGF2, FGF4, FGF8, and FGF7. In certain embodiments, the one or more FGF activator is FGF2. In certain embodiments, the one or more WNT activator is CHIR99021.

In certain embodiments, the ENS precursors are contacted with the one or more FGF activator and one or more Wnt activator for at least about 1 day, at least about 2 days, at least about 3 days, at least about 4 days, at least about 5 days, at least about 6 days, at least about 7 days, at least about 8 days, at least about 9 days, or at least about 10 days, to produce enteric neurons. In certain embodiments, the ENS precursors are contacted with the one or more FGF activator and one or more Wnt activator for between about 1 day and about 10 days, between about 1 day and about 5 days, between about 5 days and about 10 days, to produce enteric neurons. In certain embodiments, the ENS precursors are contacted with the one or more FGF activator and one or more Wnt activator for between about 1 day and about 5 days to produce enteric neurons. In certain embodiments, the ENS precursors are contacted with the one or more FGF activator and one or more Wnt activator for about 4 days to produce enteric neurons.

In certain embodiments, the ENS precursors are contacted with the one or more activator of FGF signaling in a concentration of from about 1 nM to 100 nM, from about 1 nM to 20 nM, from about 1 nM to 15 nM, from about 1 nM to 10 nM, from about 1 nM to 5 nM, from about 5 nM to 10 nM, from about 5 nM to 15 nM, from about 15 nM to 20 nM, from about 20 nM to 30 nM, from about 30 nM to 40 nM, from about 40 nM to 50 nM, from about 50 nM to 60 nM, from about 60 nM to 70 nM, from about 70 nM to 80 nM, from about 80 nM to 90 nM, or from about 90 nM to 100 nM, to produce enteric neurons. In certain embodiments, the ENS precursors are contacted with the one or more activator of FGF signaling in a concentration of from about from about 5 nM to 15 nM to produce enteric neurons. In certain embodiments, the ENS precursors are contacted with the one or more activator of FGF signaling in a concentration of about 10 nM to produce enteric neurons. In certain embodiments, the ENS precursors are contacted with the one or more activator of FGF signaling in any one of the above-described concentrations daily, every other day or every two days to produce enteric neurons. In certain embodiments, the ENS precursors are contacted with the one or more activator of FGF signaling in a concentration of about 10 nM daily to produce enteric neurons.

In certain embodiments, the ENS precursors are contacted with the one or more Wnt activator in a concentration of from about 1 µM to 100 µM, from about 1 µM to 20 µM, from about 1 µM to 15 µM, from about 1 µM to 10 µM, from about 1 µM to 5 µM, from about 5 µM to 10 µM, from about 5 µM to 15 µM, from about 15 µM to 20 µM, from about 20 µM to 30 µM, from about 30 µM to 40 µM, from about 40 µM to 50 µM, from about 50 µM to 60 µM, from about 60 µM to 70 µM, from about 70 µM to 80 µM, from about 80 µM to 90 µM, or from about 90 µM to 100 µM, to produce enteric neurons. In certain embodiments, the ENS precursors are contacted with the one or more Wnt activator in a concentration of from about from about 1 µM to 5 µM to produce enteric neurons. In certain embodiments, the ENS precursors are contacted with the one or more Wnt activator in a concentration of about 3 µM to produce enteric neurons. In certain embodiments, the ENS precursors are contacted with the one or more Wnt activator in any one of the above-described concentrations daily, every other day or every two days to produce enteric neurons. In certain embodiments, the ENS precursors are contacted with the one or more Wnt activator in a concentration of about 3 µM daily to produce enteric neurons.

In certain embodiments, the ENS precursors are contacted with the one or more FGF activator and one or more Wnt activator in a cell culture medium to produce enteric neurons. In certain embodiments, the cell culture medium is an NB medium. In certain embodiments, the cell culture medium is an NB medium supplemented with L-Glutamine (e.g., from Gibco, 25030-164), N2 (e.g., from Stem Cell Technologies, 07156), and B27 (e.g., from Life Technologies, 17504044).

In certain embodiments, the differentiated ENS precursors are contacted with GDNF and ascorbic acid to produce a population of enteric neurons. In certain embodiments, the suitable cell culture medium comprises GDNF and ascorbic acid.

In certain embodiments, the ENS precursors are contacted with GDNF and ascorbic acid for at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days, at least about 25 days, at least about 30 days, at least about 35 days, at least about 40 days, at least about 45 days, or at least about 50 days, to produce enteric neurons. In certain embodiments, the ENS precursors are contacted with GDNF and ascorbic acid for between about 1 day and about 50 days, between about 1 day and about 10 days, between about 20 days and about 30 days, between about 30 days and about 40 days, or between about 40 days and about 50 days, to produce enteric neurons. In certain embodiments, the ENS precursors are contacted with GDNF and ascorbic acid for between about 10 day and about 20 days to produce enteric neurons. In certain embodiments, the ENS precursors are contacted with GDNF and ascorbic acid for between about 20 day and about 30 days to produce enteric neurons. In certain embodiments, the ENS precursors are contacted with GDNF and ascorbic acid for between about 40 day and about 50 days to produce enteric neurons. In certain embodiments, the ENS precursors are contacted with GDNF and ascorbic acid for about 10 days to produce enteric neurons. In certain embodiments, the ENS precursors are contacted with GDNF and ascorbic acid for about 25 days to produce enteric neurons. In certain embodiments, the ENS precursors are contacted with GDNF and ascorbic acid for about 45 days to produce enteric neurons.

In certain embodiments, the ENS precursors are contacted with GDNF in a concentration of from about 1 nM to 100 nM, from about 1 ng/mL to 100 ng/mL, from about 1 ng/mL to 20 ng/mL, from about 20 ng/mL to 30 ng/mL, from about 30 ng/mL to 40 ng/mL, from about 40 ng/mL to 50 ng/mL, from about 50 ng/mL to 60 ng/mL, from about 60 ng/mL to 70 ng/mL, from about 70 ng/mL to 80 ng/mL, from about 80 ng/mL to 90 ng/mL, or from about 90 ng/mL to 100 ng/mL, to produce enteric neurons. In certain embodiments, the ENS precursors are contacted with GDNF in a concentration of from about from about 20 ng/mL to 30 ng/mL to produce enteric neurons. In certain embodiments, the ENS precursors are contacted with GDNF in a concentration of about 25 ng/mL to produce enteric neurons. In certain embodiments, the ENS precursors are contacted with GDNF signaling in any one of the above-described concentrations daily, every other day or every two days to produce enteric neurons. In certain embodiments, the ENS precursors are contacted with GDNF of FGF signaling in a concentration of about 25 ng/mL daily to produce enteric neurons.

In certain embodiments, the ENS precursors are contacted with ascorbic acid in a concentration of from about 50 µM to 200 µM, from about 50 µM to 100 µM, or from about 100 µM to 200 µM, to produce enteric neurons. In certain embodiments, the ENS precursors are contacted with ascorbic acid in a concentration of from about from about 50 µM to 200 µM to produce enteric neurons. In certain embodiments, the ENS precursors are contacted with ascorbic acid in a concentration of about 100 µM to produce enteric neurons. In certain embodiments, the ENS precursors are contacted with ascorbic acid in any one of the above-described concentrations daily, every other day or every two days to produce enteric neurons. In certain embodiments, the ENS precursors are contacted with ascorbic acid in a concentration of about 100 µM daily to produce enteric neurons.

In certain embodiments, the ENS precursors are contacted with GDNF and ascorbic acid in a cell culture medium to produce enteric neurons. In certain embodiments, the cell culture medium is an NB medium. In certain embodiments, the cell culture medium is an NB medium supplemented with L-Glutamine (e.g., from Gibco, 25030-164), N2 (e.g., from Stem Cell Technologies, 07156), and B27 (e.g., from Life Technologies, 17504044).

In certain embodiments, the ENS precursors are contacted with one or more FDF activator and one or more WNT activator, and are subsequently contacted with GDNF and ascorbic acid. In certain embodiments, the ENS precursors are contacted with FGF2 and CHIR990214, and are subsequently contacted with GDNF and ascorbic acid. In certain embodiments, the enteric neurons are immature enteric neurons. In certain embodiments, the immature enteric neurons express one or more enteric neuron marker, including, but not limited to, beta 3 class III tubulin (Tuj1), paired-like homeobox 2A (PHOX2A), paired-like homeobox 2B (PHOX2B), neurotrophic tyrosine kinase receptor type 3 (TRKC), ASCL1, heart and neural crest derivatives expressed 2 (HAND2), and EDNRB.

The immature enteric neurons can further differentiate to mature enteric neurons. In certain embodiments, the enteric neurons are mature enteric neurons. In certain embodiments, the mature enteric neurons express one or more enteric neuron marker, including, but not limited to, 5-hydroxytryptamine (5HT), gamma-aminobutyric acid (GABA), nitric oxide synthase (NOS), somatostatin (SST), tyrosine hydroxylase (TH), and choline 0-acetyltransferase (CHAT).

In certain embodiments, the enteric neurons are a mixture or combination of immature enteric neurons and mature enteric neurons.

In certain embodiments, the conditions favoring maturation further comprises aggregating the differentiated ENS precursors into 3D spheroids, and culturing the 3D spheroids in suspension culture. In certain embodiments, the 3D spheroids are cultured in suspension culture for about 1 day, about 2 days, about 3 days, about 4 days, about 5 days, about 6 days, about 7 days, about 8 days, about 9 days, or about 10 days. In certain embodiments, the 3D spheroids are cultured in suspension for about 4 days. In certain embodiments, the suspension culture medium is a Neurobasal medium supplemented with N2 supplement, and B27® supplement comprising CHIR99021 and fibroblast growth factor 2 (FGF2).

In certain embodiments, the conditions favoring maturation further comprises culturing the 3D spheroids in adherent culture in the presence of ascorbic acid (AA) and GDNF for spontaneous differentiation following culturing the 3D spheroids in suspension culture.

The 3D spheroids can be cultured in adherent culture for about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In certain embodiments, the 3D spheroids are cultured in adherent culture for about 3 weeks, e.g., about 20 days. In certain embodiments, the 3D spheroids are cultured in adherent culture for about 6 weeks, e.g., about 40 days. In certain embodiments, the adherent culture medium is a Neurobasal medium supplemented with N2 supplement, and B27® supplement comprising GDNF and ascorbic acid. In certain non-limiting embodiment, the adherent culture is performed on a surface with a suitable coating, for example, poly ornithine, laminin, fibronectin, or a combination thereof (e.g., the methods described in Zeltner, et al., (2014), which is incorporated herein by reference in its entirety). In certain embodiments, the cells aggregated to the 3D spheroids first differentiate to a population of immature neurons in the adherent culture and migrate out of the 3D spheroids.

Cell Culture Media

In certain embodiments, the above-described inhibitors, activators and molecules are added to a cell culture medium comprising the stem cells. Suitable cell culture media include, but are not limited to, Knockout® Serum Replacement ("KSR") medium, N2 medium, and an Essential 8®/Essential 6® ("E8/E6") medium, and a Neurobasal (NB) medium (e.g., a NB medium supplemented with N2 and B-27® Supplement). KSR medium, N2 medium, E8/E6 medium and NB medium are commercially available.

In certain embodiments, a medium for in vitro differentiation of stem cells to cells expressing one or more enteric neural crest lineage marker (ENS precursors) is a medium selected from the group consisting of a KSR medium, a N2 medium, and a combination thereof. In certain embodiments, a medium for in vitro differentiation of stem cells to cells expressing one or more enteric neural crest lineage marker (ENS precursors) is an E8/E6 medium. In certain embodiments, a medium for in vitro induction of cells expressing one or more enteric neural crest lineage marker (ENS precursors) to cells expressing one or more enteric neuron marker (enteric neurons) is an NB medium.

KSR medium is a defined, serum-free formulation optimized to grow and maintain undifferentiated hESC cells in culture. The components of a KSR medium are disclosed in WO2011/149762. In certain embodiments, a KSR medium comprises Knockout DMEM, Knockout Serum Replacement, L-Glutamine, Pen/Strep, MEM, and 13-mercaptoethanol. In certain embodiments, 1 liter of KSR medium can comprise 820 mL of Knockout DMEM, 150 mL of Knockout Serum Replacement, 10 mL of 200 mM L-Glutamine, 10 mL of Pen/Strep, 10 mL of 10 mM MEM, and 55 µM of 13-mercaptoethanol.

In certain embodiments, the stem cells are initially cultured in a KSR medium, which is gradually replaced with increasing amount of a N2 medium from about 1, about 2, about 3, about 4, about 5, about 6, about 7 about 8 days after the initial contact of the stem cells with at least one of the above-described inhibitors, activators, and molecules that induce vagal neural crest patterning. In certain embodiments, the stem cells are initially cultured in a KSR medium, which is gradually replaced with increasing amount of a N2 medium from about day 4 after the initial contact of the stem cells with at least one of the above-described inhibitors, activators, and molecules that induce vagal neural crest patterning (e.g., 4 days after the initial contact of the stem cells with the one or more inhibitor of TGFβ/Activin-Nodal signaling).

In certain embodiments, the stem cells are contacted with one or more inhibitor of TGFβ/Activin-Nodal signaling, one or more inhibitor of SMAD signaling, one or more activator of Wnt signaling, and one or more molecule that induces vagal patterning. In certain embodiments, one or more inhibitor of TGFβ/Activin-Nodal signaling, one or more inhibitor of SMAD signaling, one or more activator of Wnt signaling, and one or more molecule that induces vagal patterning are added to a cell culture medium comprising the stem cells. In certain embodiments, the cell culture medium is a KSR medium.

E8/E6 medium is a feeder-free and xeno-free medium that supports the growth and expansion of human pluripotent stem cells. E8/E6 medium has been proven to support somatic cell reprogramming. In addition, E8/E6 medium can be used as a base for the formulation of custom media for the culture of PSCs. One example E8/E6 medium is described in Chen et al., Nat Methods. 2011 May; 8(5):424-9, which is incorporated by reference in its entirety. One example E8/E6 medium is disclosed in WO15/077648, which is incorporated by reference in its entirety. In certain embodiments, an E8/E6 cell culture medium comprises DMEM/F12, ascorbic acid, selenum, insulin, NaHCO$_3$, transferrin, FGF2 and TGFβ. The E8/E6 medium differs from a KSR medium in that E8/E6 medium does not include an active BMP or Wnt ingredient. Thus, in certain embodiments, when an E8/E6 medium is used to culture the presently disclosed population of stem cells to differentiate into a population of enteric neural crest precursors (ENS precursors), one or more inhibitor of SMAD signaling (e.g., those inhibiting BMP) is not required to be added to the E8/E6 medium. In certain embodiments, the stem cells are contacted with one or more inhibitor of TGFβ/Activin-Nodal signaling, one or more activator of Wnt signaling, and one or more molecule that induces vagal patterning. In certain embodiments, one or more inhibitor of TGFβ/Activin-Nodal signaling, one or more activator of Wnt signaling, and one or more molecule that induces vagal patterning are added to a cell culture medium comprising the stem cells. In certain embodiments, the cell culture medium is an E8/E6 medium.

N2 supplement is a chemically defined, animal-free, supplement used for expansion of undifferentiated neural stem and progenitor cells in culture. N2 Supplement is intended for use with DMEM/F12 medium. The components of a N2 medium are disclosed in WO2011/149762. In certain embodiments, a N2 medium comprises a DMEM/F12 medium supplemented with glucose, sodium bicarbonate, putrescine, progesterone, sodium selenite, transferrin, and insulin. In certain embodiments, 1 liter of a N2 medium comprises 985 ml dist. H$_2$O with DMEM/F12 powder, 1.55 g of glucose, 2.00 g of sodium bicarbonate, putrescine (100 uL aliquot of 1.61 g dissolved in 100 mL of distilled water), progesterone (20 uL aliquot of 0.032 g dissolved in 100 mL 100% ethanol), sodium selenite (60 uL aliquot of 0.5 mM solution in distilled water), 100 mg of transferrin, and 25 mg of insulin in 10 mL of 5 mM NaOH.

The cell culture medium used for culturing the presently disclosed population of stem cells not only determines the inhibitor(s) to be contacted with the stem cells (e.g., for a KSR medium, one or more inhibitor of TGFβ/Activin-Nodal signaling and one or more inhibitor of SMAD signaling are required; and for an E8/E6 medium, only one or more inhibitor of TGFβ/Activin-Nodal signaling is required), but also determines the sequence of contacting the above-described inhibitor(s), activator(s) and molecule(s) with the stem cells.

In certain embodiments, the initial contact of the cells with an effective amount(s) of the one or more activator of Wnt signaling occurs within about a 4 day period (e.g., concurrently (on the same day), about 1 day, about 2 days, about 3 days, or about 4 days) beginning within the initial contact of the stem cells with the one or more inhibitor of TGFβ/Activin-Nodal signaling. The one or more activator of Wnt signaling may be added the same day as the one or more inhibitor of TGFβ/Activin-Nodal signaling or one, or two, or three days later. In certain embodiments, the cells are contacted with one or more activator of Wnt signaling and the one or more inhibitor of TGFβ/Activin-Nodal signaling within a 96 hour period.

In time periods set forth herein, if one or more agents (activators, inhibitors, molecules) are added on the same day (in the same 24 hour period), they may be added in any order unless specified herein to the contrary.

In certain embodiments, the initial contact of the stem cells with the one or more inhibitor of TGFβ/Activin-Nodal signaling, with the one or more inhibitor of SMAD signaling, and with the one or more activator of Wnt signaling is on the same day, e.g., by initially adding these inhibitors and the Wnt signaling activator(s) to a cell culture medium comprising the stem cells on the same day. In certain embodiments, the cell culture medium is a KSR medium.

In certain embodiments, the initial contact of the stem cells with the one or more inhibitor of TGFβ/Activin-Nodal signaling is the same day as the initial contact of the stem cells with the one or more inhibitor of SMAD signaling, e.g., by initially adding these inhibitors to a cell culture medium comprising the stem cells on the same day. In certain embodiments, the cell culture medium is a KSR medium. In certain embodiments, the initial contact of the cells with the one or more activator of Wnt signaling is between about 1 and about 4 days (e.g., about 1 day, about 2 days, about 3 days, or about 4 days) from the initial contact of the stem cells with the one or more inhibitor of TGFβ/Activin-Nodal signaling. In certain embodiments, the cell culture medium is a KSR medium. In certain embodiments, the initial contact of the cells with the one or more activator of Wnt signaling is about 2 days from the initial contact with the one or more inhibitor of TGFβ/Activin-Nodal signaling.

In certain embodiments, the cell culture medium for in vitro differentiation of stem cells to cell expressing one or more enteric neural crest lineage marker is an E8/E6 medium, and the initial contact of the cells with the one or more Wnt activator is the same day as the initial contact of the stem cells with the one or more inhibitor of TGFβ/Activin-Nodal signaling, e.g., by initially adding the Wnt activator(s) and inhibitor(s) of TGFβ/Activin-Nodal signaling to a cell culture medium comprising the stem cells on the same day. In certain embodiments, a bone morphogenetic protein (BMP) active agent is added to the E8/E6 medium.

In certain embodiments, the BMP active agent is withdrawn from the medium after about 1 day, about 2 days, about 3 days, about 4 days, about 5 days, about 6 days, about 7 days, about 8 days, about 9 days, or about 10 days of culture. In certain embodiments, the BMP active agent is withdrawn from the medium after about 3 days of culture. In certain embodiments, the BMP active agent is present in the culture medium at a concentration of from between about 0.5 and about 20 ng/mL, or between about 1 and about 15 ng/ml, or between about 2 and about 10 ng/ml, or between about 3 and about 5 ng/ml. In certain embodiments the BMP active agent is present in the culture medium at a concentration of about 5 ng/ml.

In certain embodiments, the initial contact of the cells with the one or more molecule that induces vagal neural crest patterning is within an about 8 day period (no later than about 8 days) from or beginning with the initial contact of the cells with the one or more activator of Wnt signaling. In certain embodiments, the initial contact of the stem cells with the one or more molecule that induces vagal neural crest patterning is at least about 2 days from the initial contact of the cells with the one or more activator of Wnt signaling. In certain embodiments, initial contact of the cells with the one or more molecule that induces vagal neural crest patterning is about 1 day, about 2 days, about 3 days, about 4 days, about 5 days, about 6 days, about 7 days or about 8 days from the initial contact of stem cells with the one or more activator of Wnt signaling.

In certain embodiments, the initial contact of the cells with the one or more molecule that induces vagal neural crest patterning is about 4 days from the initial contact of the cells with the one or more activator of Wnt signaling. In certain embodiments, the initial contact of the stem cells with the one or more inhibitor of TGFβ/Activin-Nodal signaling is on day 0, the initial contact of the stem cells with the one or more inhibitor of SMAD signaling is on day 0, the initial contact of the cells with the one or more activator of Wnt signaling on day 2, and the initial contact of the cells with the one or more molecule that induces vagal neural crest patterning is on day 6. In certain embodiments, the cell culture is a KSR medium, a N2 medium, or a combination thereof.

In certain embodiments, the initial contact of stem cells with the one or more molecule that induces vagal neural crest patterning is about 6 days from the initial contact of the cells with the one or more activator of Wnt signaling. In certain embodiments, the initial contact of the stem cells with the one or more inhibitor of TGFβ/Activin-Nodal signaling is on day 0, the initial contact of the cells with the one or more activator of Wnt signaling is on day 0, and the initial contact of the cells with the one or more molecule that induces vagal neural crest patterning is on day 6. In certain embodiments, the cell culture is an E8/E6 medium.

Markers and Reporters

The differentiated ENS precursors express one or more enteric neural crest lineage marker. Non-limiting examples of enteric neural crest lineage markers include paired box 3 (PAX3), endothelin receptor type B (EDNRB) and ret proto-oncogene (RET), paired-like homeobox 2A (PHOX2A), paired-like homeobox 2B (PHOX2B), neurotrophic tyrosine kinase receptor type 3 (NTRK-3), achaete-scute complex homolog 1 (ASCL1), heart and neural crest derivatives expressed 2 (HAND2), homeobox B3 (HOXB3), homeobox B5 (HOXB5).

In certain embodiments, the differentiated ENS precursors further express one or more general neural crest marker. Non-limiting examples of general neural crest marker include forkhead box D3 (FOXD3), transcription factor AP-2 alpha (TFAP2A), T-box 2 (TBX2), RP4-792G4.2, RNA, 28S ribosomal 5 (RNA28S5), transcription factor AP-2 beta (TFAP2B), inscuteable homolog (INSC), RP11-200A13.2, cilia and flagella associated protein 126 (C1orf192), retinoid X receptor gamma (RXRG), complement factor H (CFH), and SOX10.

In certain embodiments, the differentiated ENS precursors further express one or more vagal marker. Non-limiting examples of vagal markers include HOXB2, HOXB2, HOXB3, HOXB4, and HOXB5.

In certain embodiments, the differentiated ENS precursors cells further express one or more SOX10$^+$ neural crest lineage marker. In certain embodiments, the SOX10$^+$ neural crest lineage marker is CD49D.

The enteric neurons express one or more enteric neuron marker. Non-limiting examples of enteric neuron markers include Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

The differentiated ENS precursors or enteric neurons can further express one or more reporter. Non-limiting examples of reporters include fluorescent proteins (such as green fluorescent protein (GFP), blue fluorescent protein (EBFP, EBFP2, Azurite, mKalamal), cyan fluorescent protein (ECFP, Cerulean, CyPet, mTurquoise2), and yellow fluorescent protein derivatives (YFP, Citrine, Venus, YPet, EYFP)), β-galactosidase (LacZ), chloramphenicol acetyltransferase (cat), neomycin phosphotransferase (neo), enzymes (such as oxidases and peroxidases), and antigenic molecules. As used herein, the terms "reporter gene" or "reporter construct" refer to genetic constructs comprising a nucleic acid encoding a protein that is easily detectable or easily assayable, such as a colored protein, fluorescent protein such as GFP or an enzyme such as beta-galactosidase (lacZ gene). In certain embodiments, the reporter can be driven by a recombinant promotor of a enteric neural crest lineage marker gene, for example, a SOX10 promoter.

The differentiated ENS precursors and further matured enteric neurons can be purified after differentiation, e.g., in a cell culture medium. As used herein, the terms "purified," "purify," "purification," "isolated," "isolate," and "isolation" refer to the reduction in the amount of at least one contaminant from a sample. For example, a desired cell type is purified by at least 10%, by at least 30%, by at least 50%, by at least 75%, and by at least 90%>, with a corresponding reduction in the amount of undesirable cell types. The term "purify" can refer to the removal of certain cells (e.g., undesirable cells) from a sample. The removal or selection of non-nociceptor cells results in an increase in the percent of desired nociceptor cells in the sample. In certain embodiments, the cells are purified by sorting a mixed cell population into cells expressing at least one SOX10$^+$ neural crest lineage marker, e.g., CD49D. In certain embodiments, the cells are purified by sorting a mixed cell population into cells expressing at least one enteric neural crest lineage marker, e.g., PAX3, EDNRB, RET, PHOX2A, PHOX2B, NTRK-3, HAND2, HOXB3, HOXB5 and/or ASCL1.

The presently disclosed subject matter also provides a population of in vitro differentiated cells expressing one or more enteric neural crest lineage marker produced by the methods described herein, and compositions comprising such in vitro differentiated cells. The presently disclosed subject matter also provides a population of in vitro differentiated cells expressing one or more enteric neural marker produced by the methods described herein, and compositions comprising such in vitro differentiated cells.

5.3 Compositions Comprising Differentiated Cell Populations

The presently disclosed subject matter provides compositions comprising a population of differentiated enteric neural crest lineage cells (or "ENS precursors") produced by the in vitro differentiation methods described herewith. Furthermore, the presently disclosed subject matter provides compositions comprising a population of enteric neurons matured from the in vitro differentiated enteric neural crest lineage cells (or "ENS precursors") described herewith.

Furthermore, the presently disclosed subject matter provides compositions comprising a population of in vitro differentiated cells, wherein at least about 70% (e.g., at least about 75%, at least about 80%, at least about 85%, at least about 90%, at least about 95%, at least about 99%, or at least about 99.5%) of the population of cells express one or more enteric neural crest lineage markers, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cell markers, CNS markers, Cranial Neural Crest (CNC) markers, Melanocyte-competent Neural Crest (MNC) markers, enteric neuron markers, neuronal cell markers, and mesenchymal precursor markers.

Furthermore, the presently disclosed subject matter provides compositions comprising a population of in vitro differentiated cells, wherein at least about 70% (e.g., at least about 75%, at least about 80%, at least about 85%, at least about 90%, at least about 95%, at least about 99%, or at least about 99.5%)) of the population of cells express one or more enteric neuron markers, and wherein less than about 15% (e.g., less than about 10%, less than about 5%, less than about 4%, less than about 3%, less than about 2%, less than about 1%, less than about 0.5%, or less than about 0.1%) of the population of cells express one or more marker selected from the group consisting of stem cell markers, enteric neural crest lineage markers, CNS markers, Cranial Neural Crest (CNC) markers, Melanocyte-competent Neural Crest (MNC) markers, neuronal cell markers, and mesenchymal precursor markers.

Non-limiting examples of enteric neural crest lineage markers include PAX3, EDNRB, RET, PHOX2A, PHOX2B, NTRK-3, HAND2, HOXB3, HOXB5 and ASCL1.

Non-limiting examples of enteric neuron markers include Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

Non-limiting examples of stem cell markers include OCT4, NANOG, SOX2, LIN28, SSEA4 and SSEA3.

Non-limiting examples of CNS markers include PAX6, NESTIN, Vimentin, FOXG1, SOX2, TBR1, TBR2 and SOX1.

Non-limiting examples of neuronal cell markers include TUJ1, MAP2, NFH, BRN3A, ISL1, TH, ASCL1, CHAT, PHOX2B, PHOX2A, TRKA, TRKB, TRKC, 5HT, GABA, NOS, SST, TH, CHAT, DBH, Substance P, VIP, NPY, GnRH, and CGRP.

Non-limiting examples of mesenchymal precursor markers are SMA, Vimentin, HLA-ABC, CD105, CD90 and CD73.

Non-limiting examples of CNC markers include PAX6, NESTIN, Vimentin, FOXG1, SOX2, TBR1, TBR2 and SOX1.

Non-limiting examples of MNC markers include PAX6, NESTIN, Vimentin, FOXG1, SOX2, TBR1, TBR2 and SOX1.

In certain embodiments, the composition comprises a population of from about $1\times10^4$ to about $1\times10^{10}$, from about $1\times10^4$ to about $1\times10^5$, from about $1\times10^5$ to about $1\times10^9$, from about $1\times10^5$ to about $1\times10^6$, from about $1\times10^5$ to about $1\times10^7$, from about $1\times10^6$ to about $1\times10^7$, from about $1\times10^6$ to about $1\times10^8$, from about $1\times10^7$ to about $1\times10^8$, from about $1\times10^8$ to about $1\times10^9$, from about $1\times10^8$ to about $1\times10^{10}$, or from about $1\times10^9$ to about $1\times10^{10}$ of the presently disclosed stem-cell-derived enteric neural crest lineage cells or matured enteric neurons. In certain embodiments, the composition comprises a population of from about $1\times10^5$ to about $1\times10^7$ of the presently disclosed stem-cell-derived enteric neural crest lineage cells or matured enteric neurons.

In certain non-limiting embodiments, the composition further comprises a biocompatible scaffold or matrix, for example, a biocompatible three-dimensional scaffold that facilitates tissue regeneration when the cells are implanted or grafted to a subject. In certain non-limiting embodiments, the biocompatible scaffold comprises extracellular matrix material, synthetic polymers, cytokines, collagen, polypeptides or proteins, polysaccharides including fibronectin, laminin, keratin, fibrin, fibrinogen, hyaluronic acid, heparin sulfate, chondroitin sulfate, agarose or gelatin, and/or hydrogel. (See, e.g., U.S. Publication Nos. 2015/0159135, 2011/0296542, 2009/0123433, and 2008/0268019, the contents of each of which are incorporated by reference in their entireties).

In certain embodiments, the composition is a pharmaceutical composition that comprises a pharmaceutically acceptable carrier, excipient, diluent or a combination thereof. The compositions can be used for preventing and/or treating enteric neuron related disorders, e.g., Hirschsprung disease (HSCR).

5.4 Method of Preventing and/or Treating Enteric Nervous System Disorders

The in vitro differentiated cells that express one or more enteric neural crest lineage marker (also referred to as "stem-cell-derived enteric neural crest (NC) precursors" or "ENS precursors") can be used for preventing and/or treating enteric nervous system disorders (ENSs). The enteric neurons matured from the in vitro differentiated ENS precursors can also be used for preventing and/or treating ENSs. The presently disclosed subject matter provides for methods of preventing and/or treating an ENS disorder comprising administering to a subject suffering from an ENS disorder an effective amount of one or more of the followings:

(a) a population of differentiated presently disclosed stem-cell-derived enteric NC precursors (ENS precursors) described herein;

(b) a composition comprising such stem-cell-derived enteric NC precursors (ENS precursors);

(c) a population of enteric neurons matured from the presently disclosed stem-cell-derived enteric NC precursors (ENS precursors) described herein; and (d) a composition comprising such enteric neurons.

Furthermore, the presently disclosed subject matter provides for uses of the presently disclosed stem-cell-derived enteric NC precursors (ENS precursors) or a composition comprising thereof, or the presently disclosed enteric neurons matured from the stem-cell-derived enteric NC precursors (ENS precursors) for preventing and/or treating an ENS disorder. Non-limiting examples of ENS disorders include Hirschsprung's disease (HD), toxic megacolon, any intestinal aganglionosis, irritable bowel syndrome, inflammatory bowel disease, gastroparesis, bowel-related drug side effects or other treatment complications. In certain embodiments, the ENS disorder is Hirschsprung's disease (HD). In certain embodiments, the stem-cell-derived enteric NC precursors express the cell surface marker CD49D.

Children suffering from HD are currently treated by surgical removal of the aganglionic portion of the gut. While life-saving, the surgery does not address permanent dysfunction of the remaining GI tract in surviving patients[17]. A major challenge in developing a cell therapy for HD, is the need to repopulate the ENS over extensive distances. In adult individuals, the length of the small and large intestines is approximately 5 meters and 1.5 meters respectively[18]. Therefore, any candidate cell type for transplantation may require extraordinary migratory properties. Previous studies tested the transplantation of variety of candidate cell sources into the fetal or postnatal colon[19-21]. Murine, fetal-derived ENC precursors resulted in the most promising data with evidence for functional integration but limited in vivo migration potential[22]. Furthermore, primary ENC precursors are of very limited scalability and cannot be readily obtained from human sources.

One key functional property of the enteric neural crest (ENC) is the ability to migrate extensively after delaminating from the neural tube at the vagal NC level and to colonize the entire length of the gut[3]. The presently disclosed stem-cell-derived enteric NC precursors have extensive in vivo migratory potential in the colon (e.g., migrate extensively within the colon) of a subject (e.g., an adult human). The presently disclosed stem-cell-derived enteric NC precursors repopulate the gut and the colon of a subject (e.g., a subject suffering from an ENS disorder (e.g., HD)). In certain embodiments, administration of the presently disclosed stem-cell-derived enteric NC precursors repopulates the colon of a subject suffering from an ENS disorder (e.g., HD) over its entire length from the cecum to the rectum. Widespread engraftment of the presently disclosed stem-cell-derived enteric NC precursors may enable permanent, bona fide repair of the aganglionic portions of the gut. The presently disclosed stem-cell-derived enteric NC precursors may also impact paracrine cytokine release, immunomodulation, and/or changes in barrier function, which may contribute to prevent HD-related death. Therefore, the presently disclosed stem-cell-derived enteric NC precursors provide novel therapeutic opportunities for ENS disorders (e.g., HD).

The presently disclosed stem-cell-derived enteric NC precursors can be administered or provided systemically or directly to a subject for treating or preventing an ENS disorder. In certain embodiments, the presently disclosed stem-cell-derived enteric NC precursors are directly injected into an organ of interest (e.g., an organ affected by an ENS disorder (e.g., HD)). The presently disclosed stem-cell-derived enteric NC precursors can be administered (injected) directly to a subject's intestine region, e.g., small intestine, colon, cecum, and/or rectum the. In certain embodiments, the presently disclosed stem-cell-derived enteric NC precursors are administered to the cecum of a subject suffering from an ENS disorder (e.g., HD). In addition, the presently disclosed stem-cell-derived enteric NC precursors can be administered (injected) directly to the wall, smooth muscle, connective issue and/or lyphatic ducts of small intestine, colon, cecum, and/or rectum. In certain embodiments, the presently disclosed stem-cell-derived enteric NC precursors are administered to the wall of the cecum of a subject suffering from an ENS disorder (e.g., HD). The injected cells can migrate to the smooth muscle of small intestine, colon, cecum and/or rectum, and form functional neuromuscular junction.

The presently disclosed stem-cell-derived enteric NC precursors and/or enteric neurons can be administered in any physiologically acceptable vehicle. Pharmaceutical compositions comprising the presently disclosed stem-cell-derived enteric NC precursors and/or enteric neurons and a pharmaceutically acceptable carrier are also provided. The presently disclosed stem-cell-derived enteric NC precursors and/or enteric neurons and the pharmaceutical compositions comprising thereof can be administered via localized injection, orthotropic (OT) injection, systemic injection, intravenous injection, or parenteral administration. In certain embodiments, the presently disclosed stem-cell-derived enteric NC precursors and/or enteric neurons are administered to a subject suffering from an ENS disorder (e.g., HD) via orthotropic (OT) injection.

The presently disclosed stem-cell-derived enteric NC precursors and/or enteric neurons and the pharmaceutical compositions comprising thereof can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof. Sterile injectable solutions can be prepared by incorporating the compositions of the presently disclosed subject matter, e.g., a composition comprising the presently disclosed stem-cell-derived enteric NC precursors and/or enteric neurons, in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin. According to the presently disclosed subject matter, however, any vehicle, diluent, or additive used would have to be compatible with the presently disclosed stem-cell-derived enteric NC precursors.

Viscosity of the compositions, if desired, can be maintained at the selected level using a pharmaceutically acceptable thickening agent. Methylcellulose can be used because it is readily and economically available and is easy to work with. Other suitable thickening agents include, for example, xanthan gum, carboxymethyl cellulose, hydroxypropyl cellulose, carbomer, and the like. The concentration of the thickener can depend upon the agent selected. The important point is to use an amount that will achieve the selected viscosity. Obviously, the choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Those skilled in the art will recognize that the components of the compositions should be selected to be chemically inert and will not affect the viability or efficacy of the presently disclosed stem-cell-derived enteric NC precursors. This will present no problem to those skilled in chemical and pharmaceutical principles, or problems can be readily avoided by reference to standard texts or by simple experiments (not involving undue experimentation), from this disclosure and the documents cited herein.

One consideration concerning the therapeutic use of the presently disclosed stem-cell-derived enteric NC precursors is the quantity of cells necessary to achieve an optimal effect. An optimal effect include, but are not limited to, repopulation of gut, repopulation of colon, and repopulation of gut and colon of a subject suffering from an ENS disorder (e.g., HD), and/or improved function of the subject's intestine.

An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the ENS disorder (e.g., HD), or otherwise reduce the pathological consequences of the ENS disorder (e.g., HD). The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

In certain embodiments, an effective amount is an amount that is sufficient to repopulate gut, repopulate colon, or repopulate gut and colon of a subject suffering from an ENS disorder (e.g., HD). In certain embodiments, an effective amount is an amount that is sufficient to improve the function of the intestine of a subject suffering from an ENS disorder (e.g., HD), e.g., the improved function can be about 1%, about 5%, about 10%, about 20%, about 30%, about 40%, about 50%, about 60%, about 70%, about 80%, about 90%, about 95%, about 98%, about 99% or about 100% of the function of a normal person's intestine.

The quantity of cells to be administered will vary for the subject being treated. In certain embodiments, from about $1 \times 10^4$ to about $1 \times 10^{10}$, from about $1 \times 10^4$ to about $1 \times 10^5$, from about $1 \times 10^5$ to about $1 \times 10^9$, from about $1 \times 10^5$ to about $1 \times 10^6$, from about $1 \times 10^5$ to about $1 \times 10^7$, from about $1 \times 10^6$ to about $1 \times 10^7$, from about $1 \times 10^6$ to about $1 \times 10^8$, from about $1 \times 10^7$ to about $1 \times 10^8$, from about $1 \times 10^8$ to about $1 \times 10^9$, from about $1 \times 10^8$ to about $1 \times 10^{10}$, or from about $1 \times 10^9$ to about $1 \times 10^{10}$ the presently disclosed stem-cell-derived enteric NC precursors and/or enteric neurons are administered to a subject. In certain embodiments, from about $1 \times 10^5$ to about $1 \times 10^7$ the presently disclosed stem-cell-derived enteric NC precursors and/or enteric neurons are administered to a subject suffering from an ENS disorder (e.g., HD). In certain embodiments, about $2 \times 10^5$ the presently disclosed stem-cell-derived enteric NC precursors and/or enteric neurons are administered to a subject suffering from an ENS disorder (e.g., HD). In certain embodiments, from about $1 \times 10^6$ to about $1 \times 10^7$ the presently disclosed stem-cell-derived enteric NC precursors and/or enteric neurons are administered to a subject suffering from an ENS disorder (e.g., HD). In certain embodiments, from about $2 \times 10^6$ to about $4 \times 10^6$ the presently disclosed stem-cell-derived enteric NC precursors and/or enteric neurons are administered to a subject suffering from an ENS disorder (e.g., HD). The precise determination of what would be considered an effective dose may be based on factors individual to each subject, including their size, age, sex, weight, and condition of the particular subject. Dosages can be readily ascertained by those skilled in the art from this disclosure and the knowledge in the art.

In certain embodiments, the cells that are administered to a subject suffering from an ENS disorder (e.g., HD) for preventing and/or treating an ENS disorder are a population of the presently disclosed stem-cell-derived enteric NC precursors. In certain embodiments, the cells that are administered to a subject suffering from an ENS disorder (e.g., HD) for preventing and/or treating an ENS disorder are a population of enteric neurons that are differentiated/matured from the presently disclosed stem-cell-derived enteric NC precursors. In certain embodiments, the cells that are administered to a subject suffering from an ENS disorder (e.g., HD) for treating an ENS disorder are a population of enteric ganglia, sensory neurons and motor neurons differentiated/matured from the presently disclosed stem-cell-derived enteric NC precursors.

In certain embodiment, the method of preventing and/or treating an ENS disorder (e.g., HD) comprises administering to a subject in need thereof an effective amount of an inhibitor of β-secretase (BACE).

In certain embodiment, the method of preventing and/or treating an ENS disorder (e.g., HD) comprises administering to a subject in need thereof an effective amount of an inhibitor of acid protease.

Furthermore, the presently disclosed subject matter provides for uses of a BACE inhibitor for preventing and/or treating an ENS disorder. In addition, the presently disclosed subject matter provides for uses of an inhibitor of acid protease for preventing and/or treating an ENS disorder Non-limiting examples of BACE inhibitors include inhibitors of BACE2, LY450139, LY2886721, LY2811376, Verubecestat (MK-8931), and AZD3839. In certain embodiments, the BACE2 inhibitor is BACE inhibitor IV (BACE inhibitor C3).

Non-limiting examples of acid protease inhibitors include inhibitors of Pepstatin A, Ritonavir, Indinavir, Zankiren, Aliskiren and LY-450139.

An inhibitor of acid protease (e.g., Pepstatin A) is capable of rescuing migration defects of the presently disclosed stem-cell derived enteric NC precursors comprising homozygous loss-of-function mutations in EDNRB. In certain embodiments, the rescuing effect of Pepstatin A is a BACE2-mediated effect.

In addition, a BACE inhibitor (e.g., a BACE2 inhibitor, e.g., BACE inhibitor IV) is capable of rescuing migration defects of the presently disclosed stem-cell derived enteric NC precursors comprising homozygous loss-of-function mutations in EDNRB.

Therefore, inhibitors of acid protease (e.g., Pepstatin A), and BACE inhibitors (e.g., a BACE2 inhibitor, e.g., BACE inhibitor IV) can be used for preventing and/or treating an ENS disorder.

5.5 Methods of Identifying Therapeutic Compounds

The presently disclosed stem-cell-derived enteric NC precursors and/or the matured enteric neurons can be used to model an ENS disorder (e.g., HD) and serve as a platform to screen for candidate compounds that can overcome disease related migration defects. The capacity of a candidate compound to alleviate an ENS disorder (e.g., HD) can be determined by assaying the candidate compound's ability to rescue a physiological or cellular defect caused by a genetic mutation, which causes an ENS disorder (e.g., HD). The inventors' identification of Pepstatin A and BACE2 inhibition in rescuing HD-related migration defects represents a proof-of-concept for the use of presently disclosed stem-cell-derived enteric NC precursors in drug discovery. See Example 1.

The presently disclosed subject matter provides for in vitro methods of identifying or screening compounds suitable for preventing and/or treating an ENS disorder (e.g., HD and/or a HD-related genetic defect). In certain embodiments, the method comprises identifying a compound that is capable of rescuing at least one migration defect presented by a population of cells comprising homozygous loss-of-function mutations in a gene related to cell mobility, e.g., endothelin receptor type B (EDNRB), wherein the population of cells are selected from the group consisting of presently disclosed enteric NC precursors derived from stem cells (e.g., pluripotent stem cells), presently disclosed enteric neurons derived from the stem-cell derived enteric NC precursors, and a combination or mixture thereof. Loss of function mutations in EDNRB is a well-known genetic cause in a subset of HD patients[28].

In certain embodiments, the method comprise: (a) providing (i) a population of cells comprising homozygous loss-of-function mutations in EDNRB, wherein the population of cells are selected from the group consisting of presently disclosed enteric NC precursors derived from stem cells (e.g., pluripotent stem cells), presently disclosed enteric neurons derived from the stem-cell derived enteric NC precursors, and a combination or mixture thereof, and (ii) a test compound; (b) contacting the population of cells with the test compound; and (c) measuring the migration behavior of the population of cells. In certain embodiments, the population of cells (e.g., enteric NC precursors and/or enteric neurons) are contacted with the test compound for at least about 6 hours, about 12 hours, about 24 hours (1 day), e.g., about 24 hours (1 day), about 2 days, about 3 days, about 4 days, about 5 days, about 6 days, about 7 days, about 8 days, about 9 days, or about 10 days.

In certain embodiments, the population of cells are enteric NC precursors derived from stem cells.

Any suitable migration assays can be used for measuring the migration behavior of the enteric NC precursors include, e.g., scratch assays (e.g., migration to an open space of a cell culture plate), wound healing assays, transmigration assays (e.g., cross through micropores), cell exclusion zone assays, microfluidic assays, and Oris® cell migration assays. In addition, the methods for measuring the migration behavior of the enteric NC precursors include measuring the ability of the enteric NC precursors to migrate in a semi-solid culture medium, e.g., a hydrogel culture medium. In certain embodiments, the enteric NC precursors are fixed before being measured for their migration behavior.

In certain embodiments, the method further comprises determining a causal genetic mutation of an ENS disorder (e.g., HD or toxic megacolon). Methods for determining a causal genetic mutation of HD are known in the art, including, but not limited to, genetic lineage analyses among familial patient groups, forward and reverse genetics using mouse model.

5.6. Kits

The presently disclosed subject matter provides for kits for inducing differentiation of stem cells. In certain embodiments, the kit comprises an effective amount(s) of one or more inhibitor of transforming growth factor beta (TGFβ/Activin-Nodal signaling, an effective amount(s) of one or more activator of wingless (Wnt) signaling, an effective amount(s) of one or more molecule that induces vagal neural crest patterning, and instructions for inducing differentiation of the stem cells into a population of differentiated cells that express one or more enteric neural crest lineage marker.

In certain embodiments, the instructions comprise directions to contact the stem cells with the inhibitor(s), activator(s) and molecule(s) in a specific sequence. The sequence of contacting the inhibitor(s), activator(s) and molecule(s) can be determined by the cell culture medium used for culturing the stem cells.

In certain embodiments, the instructions comprise directions to contact the population of cells with an effective amount(s) of the one or more molecule that induces vagal neural crest patterning for at least about 2 days. In certain embodiments, the instructions comprise directions to contact the population of cells with the one or more molecule that induces vagal neural crest patterning for about 6 days. In certain embodiments, the instructions comprise directions to contact the population of cells with the one or more molecule that induces vagal neural crest patterning for about 5 days. In certain embodiments, the instructions comprise directions to initially contact the cells with an effective amount(s) of the one or more activator of Wnt signaling within an about 4 day period (e.g., concurrently (on the same day), about 1 day, about 2 days, about 3 days, or about 4 days) from or beginning with the initial contact of stem cells with the one or more inhibitor of TGFβ/Activin-Nodal signaling. In certain embodiments, the instructions comprise directions to initially contact the stem cells with the one or more inhibitor of TGFβ/Activin-Nodal signaling the same day as the initial contact of the cells with the one or more activator of Wnt signaling.

In certain embodiments, the kit further comprises an effective amount(s) of one or more inhibitor of Small Mothers Against Decapentaplegic (SMAD) signaling. In certain embodiments, the instructions comprise directions to contact the stem cells with the one or more inhibitor of TGFβ/Activin-Nodal signaling and the one or more inhibitor of SMAD signaling concurrently. In certain embodiments, the instructions comprise directions to contact the stem cells with the one or more inhibitor of TGFβ/Activin-Nodal signaling, the one or more inhibitor of SMAD signaling, and the one or more activator of Wnt signaling concurrently. In certain embodiments, the instructions comprise directions to initially contact the cells with one or more activator of Wnt signaling within about 1 to about 4 days from the initial contact of the stem cells with the one or more inhibitor of TGFβ/Activin-Nodal signaling. In certain embodiments, the instructions comprise directions to initially contact the cells with the one or more activator of Wnt signaling about 2 days from the initial contact of the stem cells with the one or more inhibitor of TGFβ/Activin-Nodal signaling.

In certain embodiments, the instructions comprise directions to initially contact the cells with the one or more molecule that induces vagal neural crest patterning within an about 8 day period from or beginning with the initial contact of the cells with the one or more activator of Wnt signaling. In certain embodiments, the instructions comprise directions to initially contact the cells with the one or more molecule that induces vagal neural crest patterning at least about 2 days from the initial contact of the stem cells with the one or more activator of Wnt signaling. In certain embodiments, the instructions comprise directions to initially contact the cells with the one or more molecule that induces vagal neural crest patterning about 1 day, about 2 days, about 3 days, about 4 days, about 5 days, about 6 days, about 7 days or about 8 days from the initial contact of the cells with the one or more activator of Wnt signaling.

In certain embodiments, the instructions comprise directions to initially contact the cells with the one or more molecule that induces vagal neural crest patterning about 6 days from the initial contact of the cells with the one or more activator of Wnt signaling. In certain embodiments, the instructions comprise directions to initially contact the stem cells with the one or more inhibitor of TGFβ/Activin-Nodal signaling on day 0, directions to initially contact the cells with the one or more activator of Wnt signaling on day 0, and directions to initially contact the cells with the one or more molecule that induces vagal neural crest patterning on day 6.

In certain embodiments, the instructions comprise directions to initially contact the cells with the one or more molecule that induces vagal neural crest patterning about 4 days from the initial contact of the cells with the one or more activator of Wnt signaling. In certain embodiments, the instructions comprise directions to initially contact the stem cells with the one or more inhibitor of TGFβ/Activin-Nodal signaling on day 0, directions to initially contact the stem cells the one or more inhibitor of SMAD signaling on day 0, directions to initially contact the cells with the one or more activator of Wnt signaling on day 2, and directions to initially contact the cells with the one or more molecule that induces vagal neural crest patterning on day 6.

In certain embodiments, the instructions comprise directions to contact the stem cells with the one or more inhibitor of TGFβ/Activin-Nodal signaling for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days, to produce ENS precursors. In certain embodiments, the instructions comprise directions to contact the stem cells with the one or more inhibitor of TGFβ/Activin-Nodal signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce ENS precursors. In certain embodiments, the instructions comprise directions to contact the stem cells with the one or more inhibitor of TGFβ/Activin-Nodal signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days, to produce ENS precursors. In certain embodiments, the instructions comprise directions to contact the stem cells with the one or more inhibitor of TGFβ/Activin-Nodal signaling for between 10 days and about 15 days, to produce ENS precursors. In certain embodiments, the instructions comprise directions to contact the stem cells with the one or more inhibitor of TGFβ/Activin-Nodal signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day, to produce ENS precursors. In certain embodiments, the instructions comprise directions to contact the stem cells with the one or more inhibitor of TGFβ/Activin-Nodal signaling for about 11 days, to produce ENS precursors.

In certain embodiments, the instructions comprise directions to contact the stem cells with the one or more inhibitor of SMAD signaling for at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, at least about 29 days, or at least about 30 days, to produce ENS precursors. In certain embodiments, the instructions comprise directions to contact the stem cells with the one or more inhibitor of SMAD signaling for up to about 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce ENS precursors. In certain embodiments, the instructions comprise directions to contact the stem cells with the one or more inhibitor of SMAD signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days, to produce ENS precursors. In certain embodiments, the instructions comprise directions to contact the stem cells with the one or more inhibitor of SMAD signaling for between 10 days and about 15 days, to produce ENS precursors. In certain embodiments, the instructions comprise directions to contact the stem cells with the one or more inhibitor of SMAD signaling for about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day, to produce ENS precursors. In certain embodiments, the instructions comprise directions to contact the stem cells with the one or more inhibitor of SMAD signaling for about 11 days, to produce ENS precursors.

In certain embodiments, the instructions comprise directions to contact the cells with the one or more activator of Wnt signaling for at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 21 days, at least about 22 days, at least about 23 days, at least about 24 days, at least about 25 days, at least about 26 days, at least about 27 days, at least about 28 days, or at least about 29 days, at least about 30 days, to produce ENS precursors. In certain embodiments, the instructions comprise directions to contact the cells with the one or more activator of Wnt signaling for up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, up to about 21 days, up to about 22 days, up to about 23 days, up to about 24 days, up to about 25 days, up to about 26 days, up to about 27 days, up to about 28 days, up to about 29 days, or up to about 30 days, to produce ENS precursors. In certain embodiments, the instructions comprise directions to contact the cells with the one or more activator of Wnt signaling for between about 4 days and about 30 days, between about 4 days to about 27 days, between about 4 days and about 26 days, between about 4 days and about 25 days, between about 4 days and about 24 days, between about 4 days and about 20 days, between about 4 days and about 15 days, between about 4 days and about 10 days, between about 5 days and about 15 days, between about 5 days and about 10 days, between about 10 days and about 15 days, between about 15 days and about 20 days, between about 10 days and about 20 days, between about 20 days and about 25 days, or between about 25 days and about 30 days, to produce ENS precursors. In certain embodiments, the instructions comprise directions to contact the cells with the one or more activator of Wnt signaling for between 5 days and about 15 days, to produce ENS precursors. In certain embodiments, the instructions comprise directions to contact the cells with the one or more activator of Wnt signaling for about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 day, to produce ENS precursors. In certain embodiments, the instructions comprise directions to contact the cells with the one or more activator of Wnt signaling for about 11 days, to produce ENS precursors. In certain embodiments, the instructions comprise directions to contact the cells with the one or more activator of Wnt signaling for about 10 days, to produce ENS precursors. In certain embodiments, the instructions comprise directions to contact the cells with the one or more activator of Wnt signaling for about 9 days, to produce ENS precursors.

In certain embodiments, the instructions comprise directions to contact the cells with the one or more molecule that induces vagal neural crest patterning for at least about 2 days, at least about 3 days, at least about 4 days, at least about 5 days, at least about 6 days, at least about 7 days, at least about 8 days, at least about 8 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, or at least about 21 days, to produce ENS precursors. In certain embodiments, the instructions comprise directions to contact the cells with the one or more molecule that induces vagal neural crest patterning for at least about 2 days. In certain embodiments, the instructions comprise directions to contact the cells with the one or more molecule that induces vagal neural crest patterning for up to about 2 days, up to 3 days, up to about 4 days, up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, up to about 20 days, or up to about 21 days, to produce ENS precursors. In certain embodiments, the instructions comprise directions to contact the cells with the one or more molecule that induces vagal neural crest patterning for up to about 20 days. In certain embodiments, the instructions comprise directions to contact the cells with the one or more one or more molecule that induces vagal neural crest patterning for between about 2 days and about 21 days, between about 2 days and about 20 days, between about 2 days to about 10 days, between about 10 days and about 15 days, between about 15 days and about 21 days, between about 2 days and about 6 days, between about 2 days and about 5 days, or between about 5 days and about 10 days, to produce ENS precursors. In certain embodiments, the instructions comprises directions to contact the cells with the one or more molecule that induces vagal neural crest patterning for between about 5 days and about 10 days, to produce ENS precursors. In certain embodiments, the instructions comprise directions to contact the cells with the one or more molecule that induces vagal neural crest patterning for between 5 days and about 20 days, to produce ENS precursors. In certain embodiments, the instructions comprise directions to contact the cells with the one or more molecule that induces vagal neural crest patterning for between about 2 days and about 6 days, to produce ENS precursors. In certain embodiments, the instructions comprise directions to contact the cells with the one or more molecule that induces vagal neural crest patterning for between about 2 days and about 10 days, to produce ENS precursors. In certain embodiments, the instructions comprise directions to contact the cells with the one or more molecule that induces vagal neural crest patterning for about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days, to produce ENS precursors. In certain embodiments, the instructions comprise directions to contact the cells with the one or more molecule that induces vagal neural crest patterning for about 6 days, to produce ENS precursors. In certain embodiments, the instructions comprise directions to contact the cells with the one or more molecule that induces vagal neural crest patterning for about 5 days, to produce ENS precursors.

In certain embodiments, the instructions comprise directions to contact the stem cells with one or more inhibitor of TGFβ/Activin-Nodal signaling and the one or more inhibitor of SMAD signaling for about 12 days; directions to contact the cells with the one or more activator of Wnt signaling for about 10 days; and directions to contact the cells with the one or more molecule that induces vagal neural crest patterning for about 6 days, to produce ENS precursors. In certain embodiments, the instructions comprise directions to contact the stem cells with one or more inhibitor of TGFβ/Activin-Nodal signaling and the one or more inhibitor of SMAD signaling for about 11 days; directions to contact the cells with the one or more activator of Wnt signaling for about 9 days; and directions to contact the cells with the one or more molecule that induces vagal neural crest patterning for about 5 days, to produce ENS precursors.

In certain embodiments, the instructions comprise directions to contact the stem cells with one or more inhibitor of TGFβ/Activin-Nodal signaling and the one or more activator of Wnt signaling for about 12 days; and directions to contact the cells with the one or more molecule that induces vagal neural crest patterning for about 6 days, to produce ENS precursors. In certain embodiments, the instructions comprise directions to contact the stem cells with one or more inhibitor of TGFβ/Activin-Nodal signaling and the one or more activator of Wnt signaling for about 11 days; and directions to contact the cells with the one or more molecule that induces vagal neural crest patterning for about 5 days, to produce ENS precursors.

In certain embodiments, the kit further comprise instructions for inducing maturation of ENS precursors to enteric neurons.

In certain embodiments, the instructions for inducing maturation of ENS precursors to enteric neurons comprise culturing the ENS precursors in a suitable cell culture medium. In certain embodiments, the kit further comprise one or more molecule that enhances maturation of ENS precursors to enteric neurons and the instructions for inducing maturation of ENS precursors to enteric neurons comprise contacting the ENS precursors with the one or more molecule that enhances maturation of ENS precursors to enteric neurons. In certain embodiments, the one or more molecule that enhances maturation of ENS precursors to enteric neurons is selected from the group consisting of growth factors and WNT activators. In certain embodiments, the growth factors are selected from the group consisting of FGF activators, GDNF, and ascorbic acid.

In certain embodiments, the instructions for inducing maturation of ENS precursors to enteric neurons comprise directions to contact the ENS precursors with the one or more FGF activator and the one or more Wnt activator for at least about 1 day, at least about 2 days, at least about 3 days, at least about 4 days, at least about 5 days, at least about 6 days, at least about 7 days, at least about 8 days, at least about 9 days, or at least about 10 days, to produce enteric neurons. In certain embodiments, the instructions for inducing maturation of ENS precursors to enteric neurons comprise directions to contact the ENS precursors with the one or more FGF activator and the one or more Wnt activator for about 1 day and about 10 days, between about 1 day and about 5 days, between about 5 days and about 10 days, to produce enteric neurons. In certain embodiments, the instructions for inducing maturation of ENS precursors to enteric neurons comprise directions to contact the ENS precursors with the one or more FGF activator and the one or more Wnt activator for between about 1 day and about 5 days to produce enteric neurons. In certain embodiments, the instructions for inducing maturation of ENS precursors to enteric neurons comprise directions to contact the ENS precursors with the one or more FGF activator and one or more Wnt activator for about 4 days to produce enteric neurons.

In certain embodiments, the instructions for inducing maturation of ENS precursors to enteric neurons comprise directions to contact the ENS precursors with GDNF and ascorbic acid. In certain embodiments, the instructions for inducing maturation of ENS precursors to enteric neurons comprise directions to contact the ENS precursors with GDNF and ascorbic acid for at least about 1 day, at least about 2 days, at least about 3 days, at least about 4 days, at least about 5 days, at least about 6 days, at least about 7 days, at least about 8 days, at least about 9 days, at least about 10 days, at least about 15 days, at least about 20 days, at least about 25 days, at least about 30 days, at least about 35 days, at least about 40 days, at least about 45 days, or at least about 50 days, to produce enteric neurons. In certain embodiments, the instructions for inducing maturation of ENS precursors to enteric neurons comprise directions to contact the ENS precursors with GDNF and ascorbic acid for between about 1 day and about 50 days, between about 1 day and about 10 days, between about 20 days and about 30 days, between about 30 days and about 40 days, or between about 40 days and about 50 days, to produce enteric neurons. In certain embodiments, the ENS precursors are contacted with GDNF and ascorbic acid for between about 10 day and about 20 days to produce enteric neurons. In certain embodiments, the instructions for inducing maturation of ENS precursors to enteric neurons comprise directions to contact the ENS precursors with GDNF and ascorbic acid for between about 40 day and about 50 days to produce enteric neurons. In certain embodiments, the instructions for inducing maturation of ENS precursors to enteric neurons comprise directions to contact the ENS precursors with GDNF and ascorbic acid for about 10 days to produce enteric neurons. In certain embodiments, the instructions for inducing maturation of ENS precursors to enteric neurons comprise contacting the ENS precursors with GDNF and ascorbic acid for about 25 days to produce enteric neurons. In certain embodiments, the instructions for inducing maturation of ENS precursors to enteric neurons comprise directions to contact the ENS precursors with GDNF and ascorbic acid for about 45 days to produce enteric neurons. Furthermore, the presently disclosed subject matter provides for kits for preventing and/or treating or preventing an ENS disorder (e.g., HD). In certain embodiments, the kit comprises an effective amount of a population of the presently disclosed stem-cell-derived enteric NC precursors or a composition comprising such precursors in unit dosage form. In certain embodiments, the kit comprises a sterile container which contains the therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit comprises instructions for administering a population of the presently disclosed stem-cell-derived enteric NC precursors or a composition comprising thereof to a subject suffering from an ENS disorder (e.g., HD). The instructions can comprise information about the use of the cells or composition for preventing and/or treating an ENS disorder (e.g., HD). In certain embodiments, the instructions comprise at least one of the following: description of the therapeutic agent; dosage schedule and administration for preventing and/or treating an ENS disorder (e.g., HD) or symptoms thereof; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container.

6. EXAMPLES

The presently disclosed subject matter will be better understood by reference to the following Example, which is provided as exemplary of the presently disclosed subject matter, and not by way of limitation.

6.1 Example 1

Summary

The efficient derivation and isolation of ENS progenitors from human pluripotent stem cells (hPSCs) and their further differentiation into functional enteric neurons of diverse neurotransmitter phenotypes are demonstrated herein. In vitro derived ENS precursors showed an ability for targeted migration in the developing chick embryo and extensive colonization of the adult mouse colon as described below. Transplanted hPSC-derived ENS precursors migrated and engrafted in the colon of a mouse model of HD (EDNRB$^{s-l/s-l}$) and triggered rescue from disease-related mortality. Finally, establishing EDNRB mutant ENS precursors enabled the modeling of HD-related migration defects and the identification of Pepstatin A and other BACE inhibitors as new candidate therapeutics. The studies described hereinestablished a hPSC-based platform for the study of human ENS development and reveals novel cell and drug-based strategies for the treatment of HD.

Methods

Differentiation of hESC and hiPSC lines into NC cells was based on dual SMAD inhibition[11] and activation of WNT signaling[5] via CHIR99021-mediated GSK3b inhibition. Vagal/enteric NC (ENC) was induced in the presence of RA during NC induction. ENC precursors were further differentiated into neurons via a brief (4 day) 3D culture step in non-adherent plates ($1\times10^5$ cells/cm$^2$). Neuronal differentiation was carried out in N2 medium containing GDNF and AA. Cranial and melanocyte-biased NC precursors[5], RA-induced ENC precursors and differentiated neurons were characterized by immunocytochemistry, Flow Cytometry, qRT-PCR and global gene expression analysis using RNA sequencing. In vivo migratory function of the ENC precursors was assessed by transplantation in the developing chick embryo at HH14 stage and analyzed 24-36 hours later. For in vitro connectivity studies, hESCs were differentiated into SMCs following Activin A and BMP4 exposure and treatment with TGFβ[13]. Functional assays were performed by stimulating ENC-derived neurons generated from H9-SYN::ChR2-YFP hES cells with 450 nm light pulses (4 ms, 2-10 Hz, 2-4 mW). Functional interaction of the differentiated ENC precursors with primary murine intestinal tissue was evaluated using an in vivo colon tissue engineering approach by re-aggregating murine primary intestinal organoid units[16] with human hESC-ENC precursors followed by implantation in NOD-scid IL2Rgamma$^{null}$ (NSG) mice. For in vivo migration and differentiation studies the ENC precursors were orthotopically transplanted into the adult cecum (NSG or EDNRB$^{s-l/s-l}$ mice). The colon tissue was harvested at various time points for whole mount fluorescence and histological analysis. High throughput screening of the Prestwick Chemical Library® was performed using the scratch assay in 96 well format using ENC precursors derived from EDNRB$^{-/-}$ hESC lines, established via CRISPR/Cas based targeting. Dose-response curves and mechanistic studies were performed for Pepstatin A, a primary hit from the screen. BACE inhibitor IV and siRNA mediated knockdown of BACE-2 was performed on CD49D+ ENC precursors. Data are presented as mean+/−SEM and derived from at least 3 independent experiments if not noted otherwise. Table 1 presents a short description of the experimental details for each of the Figures.

TABLE 1

Summary of the experiments and methods presented in the corresponding Figures. For additional details see supplementary methods section

Figure 1B:
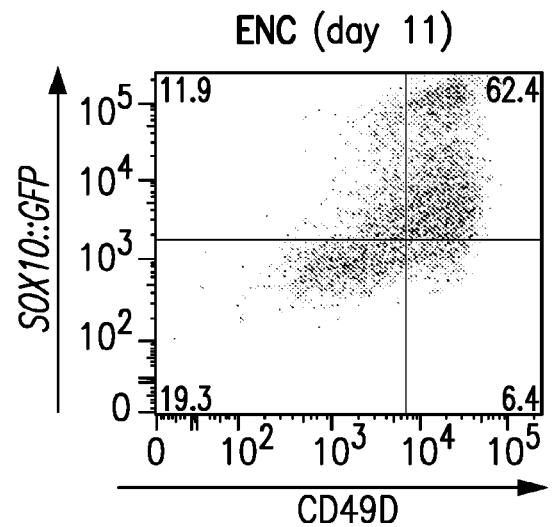
Figure 1C:
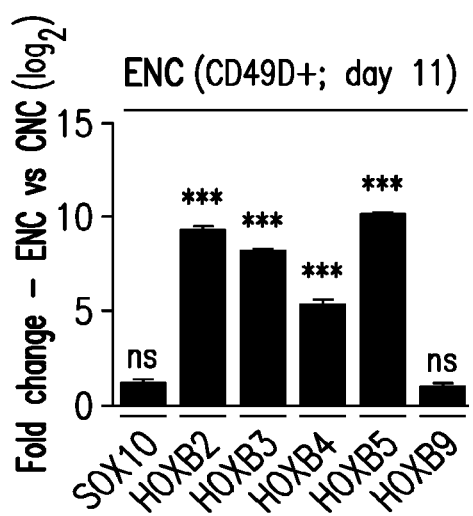
Figure 1D:
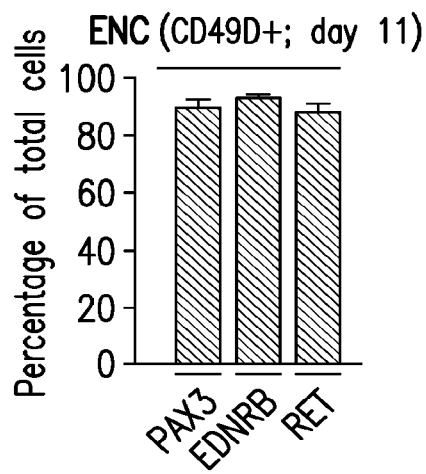
Figure 1E:
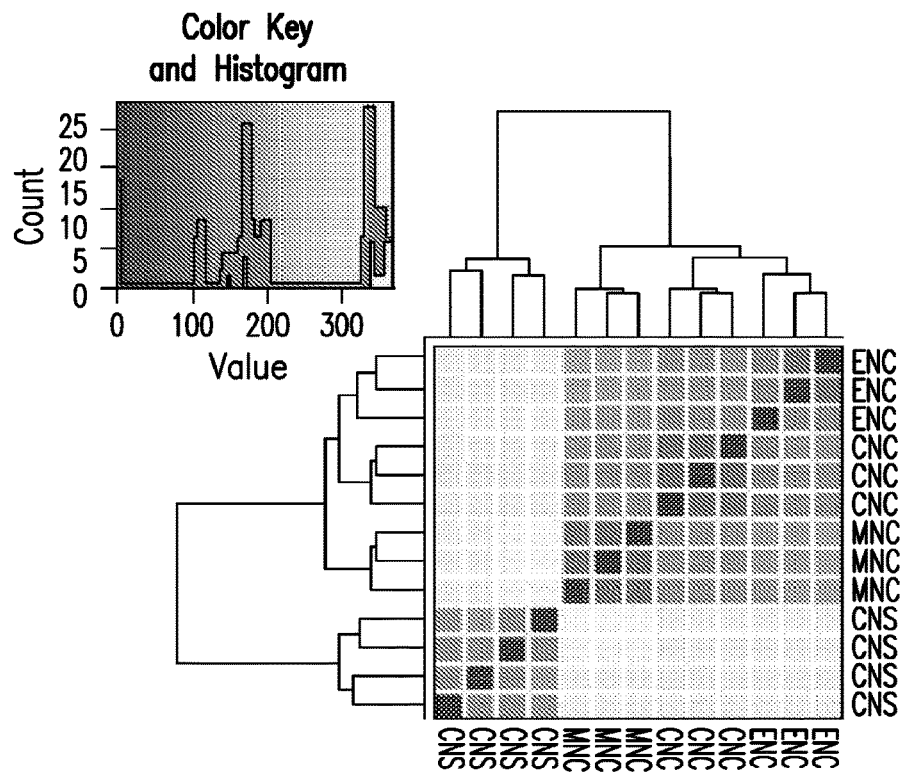
Figure 1F:
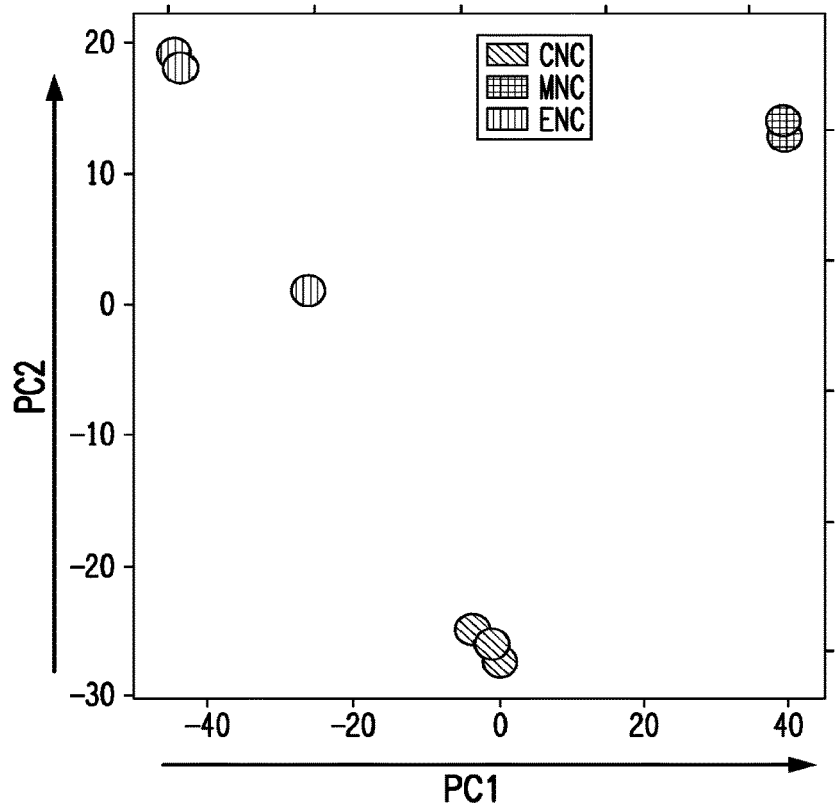
Figure 1G:
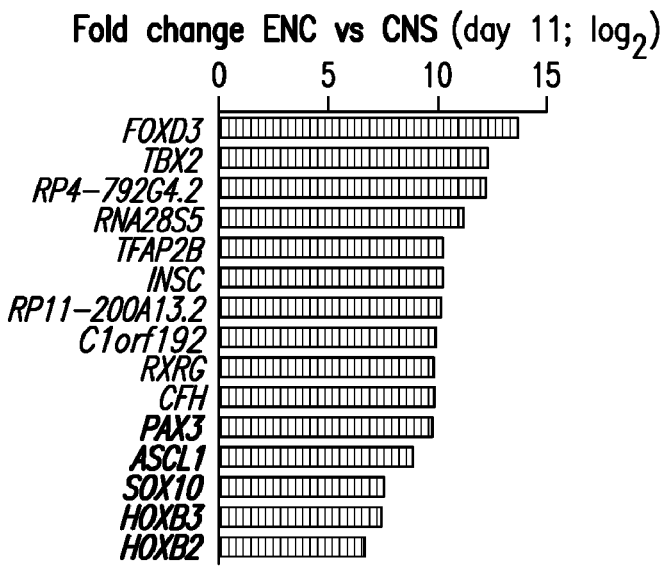
Figure 1H:
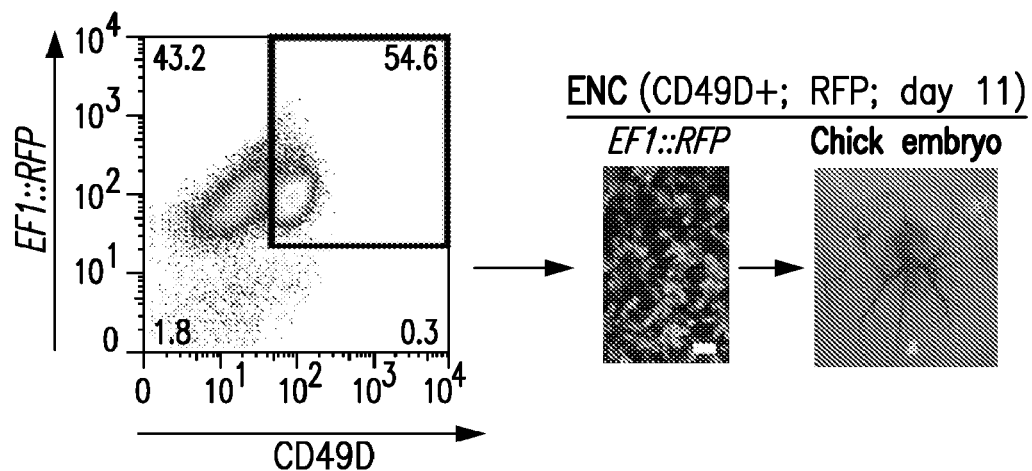
Figure 1I:
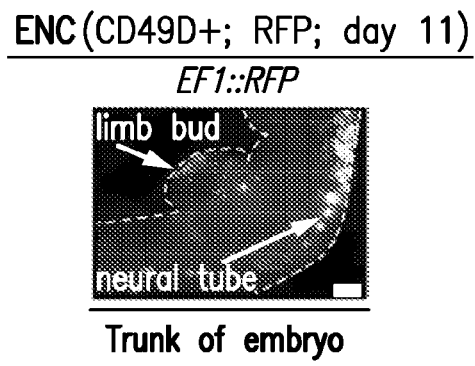
Figure 1J:
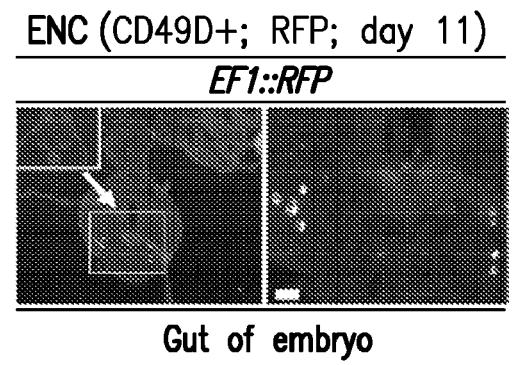
Figure 2A:
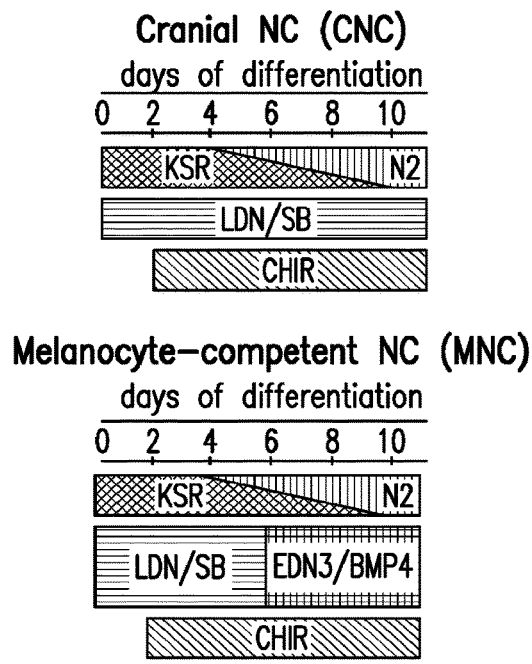
Figure 2B:
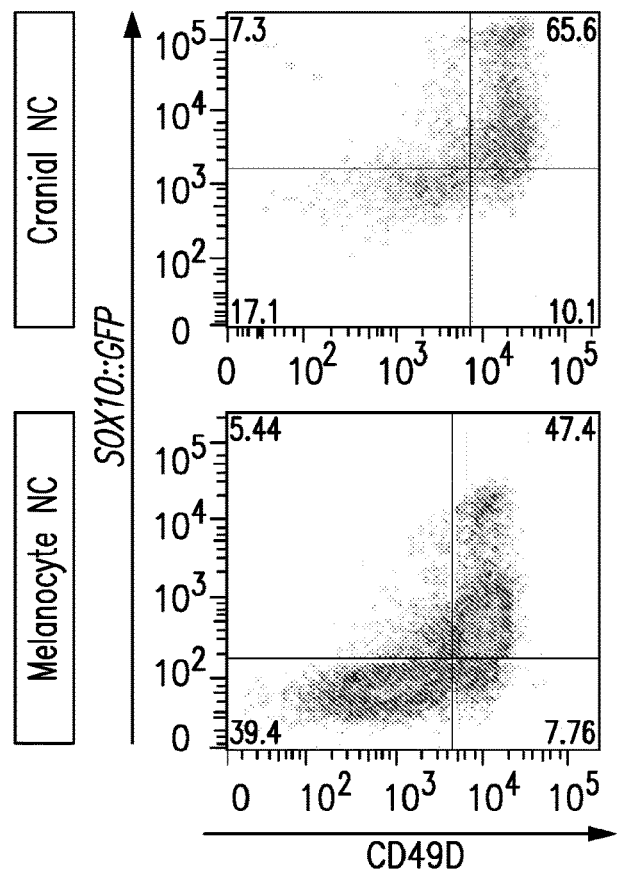
Figure 2C:
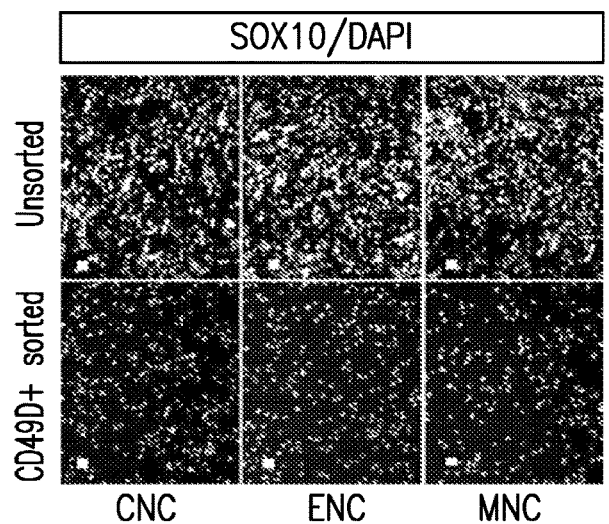

| FIGS. 1 and 2 | |
|---|---|
| FIGS. 1A and 1B FIGS. 2A-2C | SOX10::GFP reporter hESC line is differentiated under ENC, CNC and MNC conditions (FIG. 1A and FIG. 2A, respectively) and analyzed for expression of SOX10::GFP and CD49D at day 11 by flow cytometry (FIG. 1B and FIG. 2B). The differentiated cells were sorted for CD49D at day 11 of differentiation and stained for SOX10 to confirm enrichment of this NC marker in the various subtypes of hESC- derived NC cells (FIG. 1C). |

TABLE 1-continued

Summary of the experiments and methods presented in the corresponding Figures. For additional details see supplementary methods section

Figure 2D:
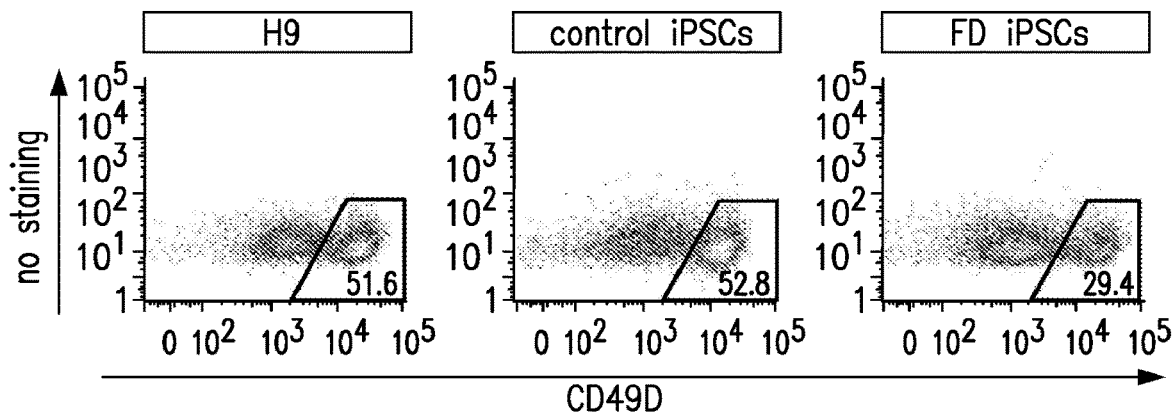
Figure 2E:
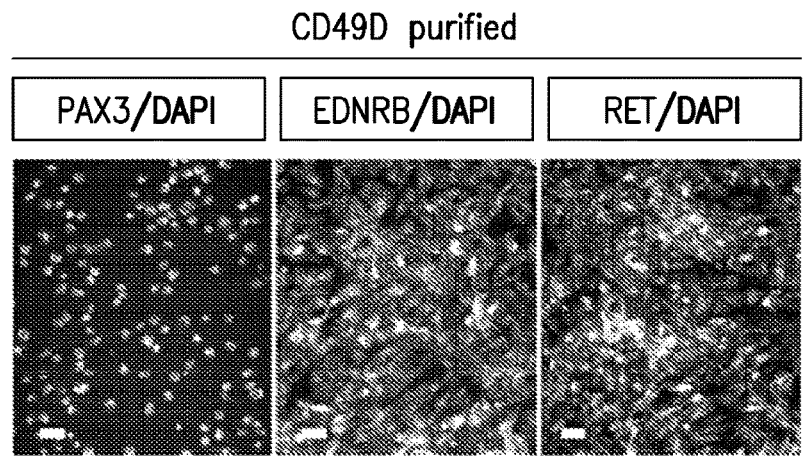
Figure 2F:
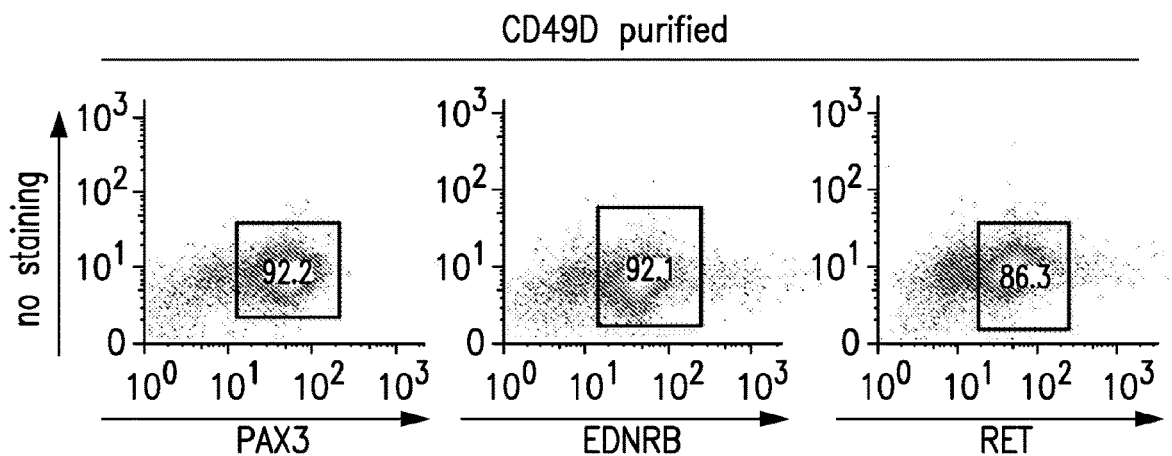
Figures 2G, 2H:
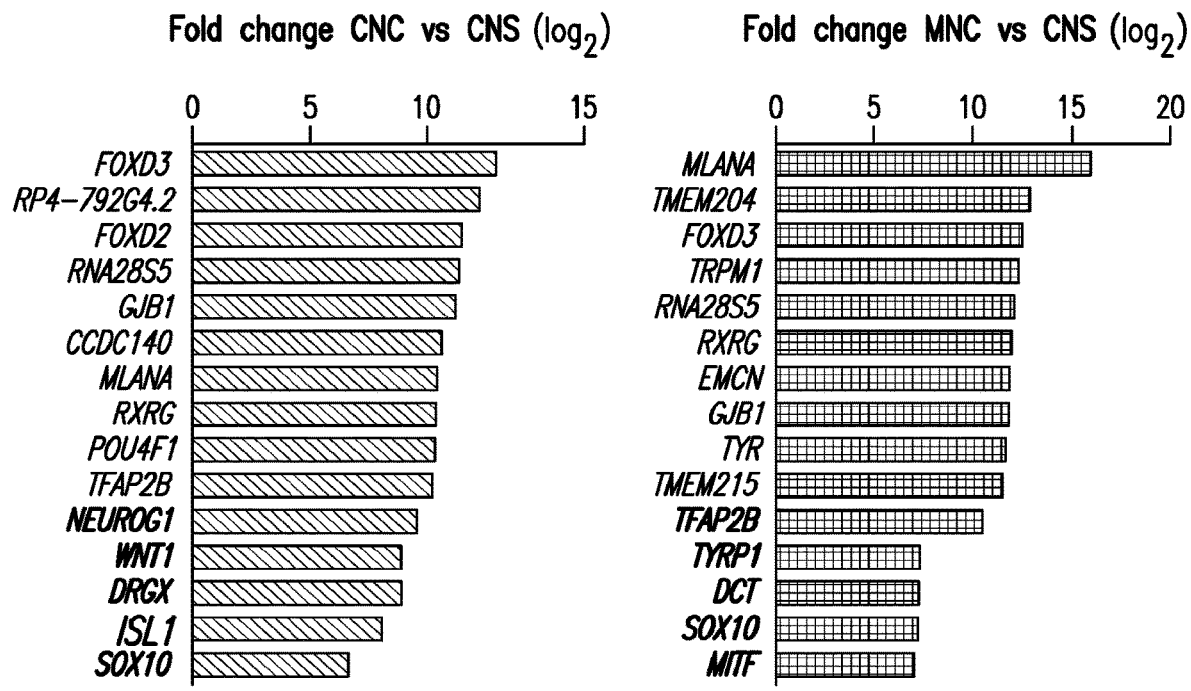
Figure 2I:
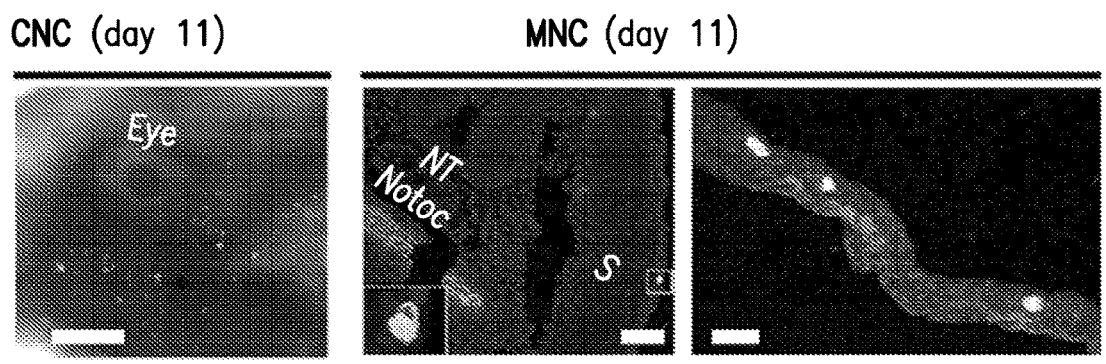
Figure 3A:
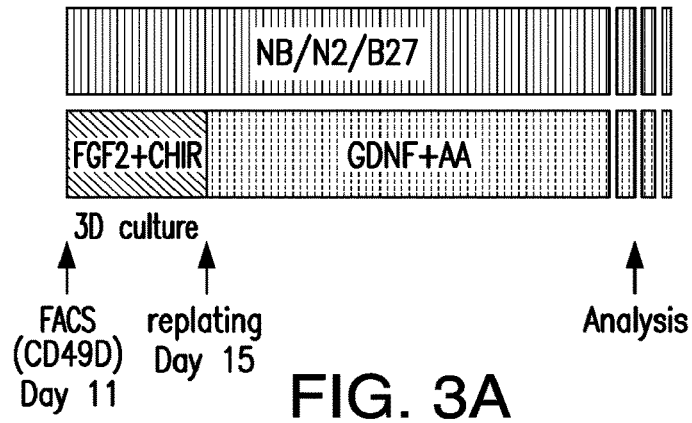
Figure 3B:
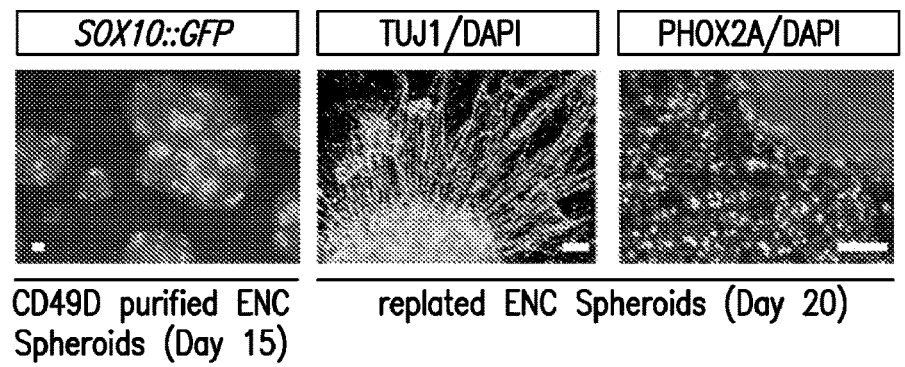
Figure 3C:
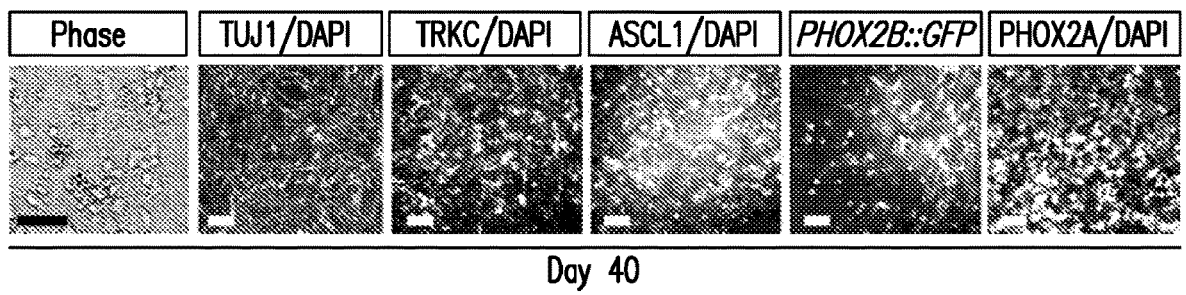
Figure 3D:
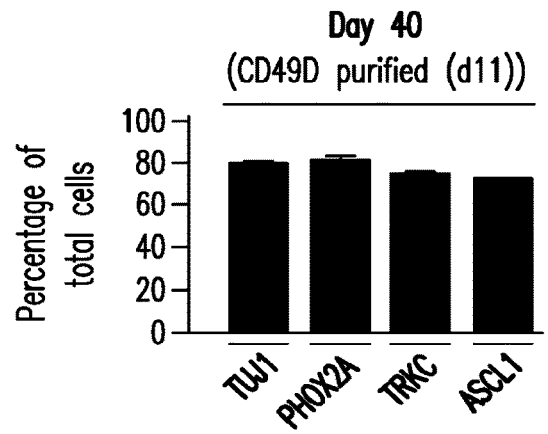
Figure 3E:
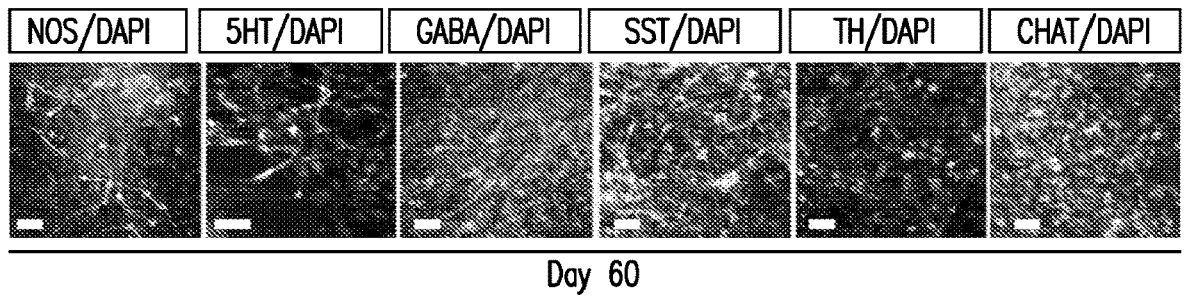
Figure 3F:
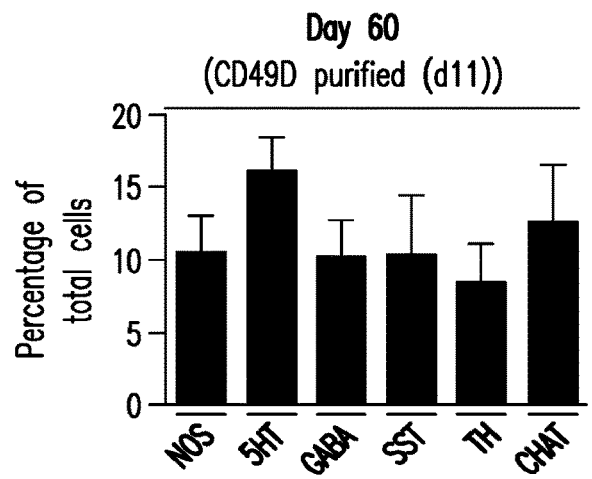
Figure 3G:
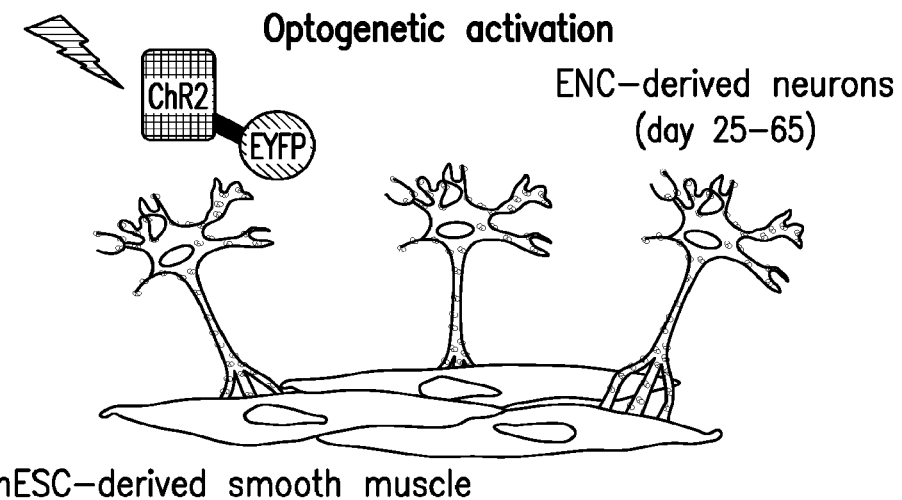
Figure 3H:
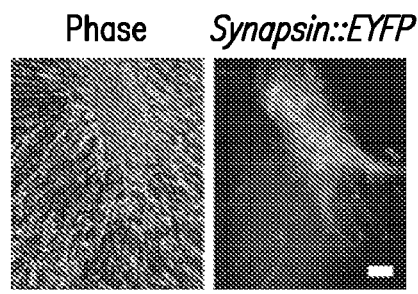
Figure 3I:
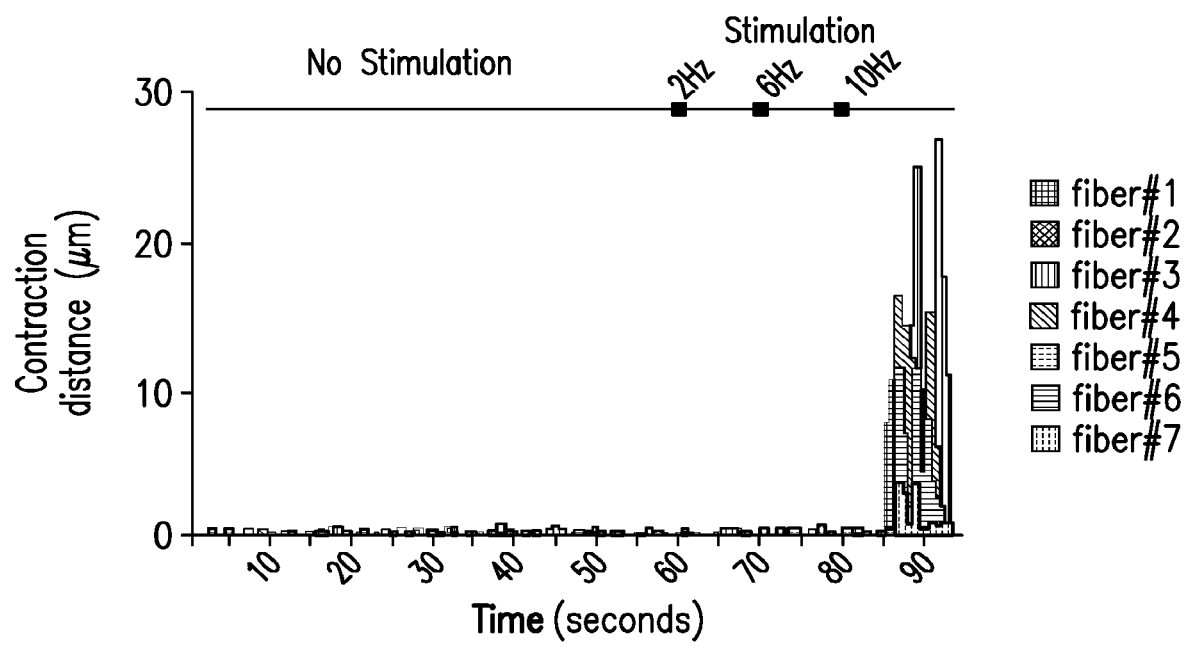
Figure 3J:
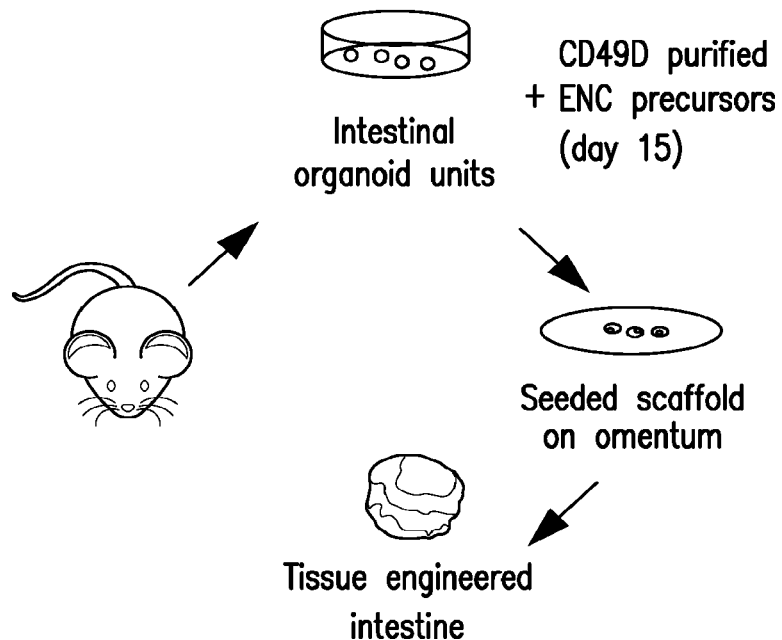
Figure 3K:
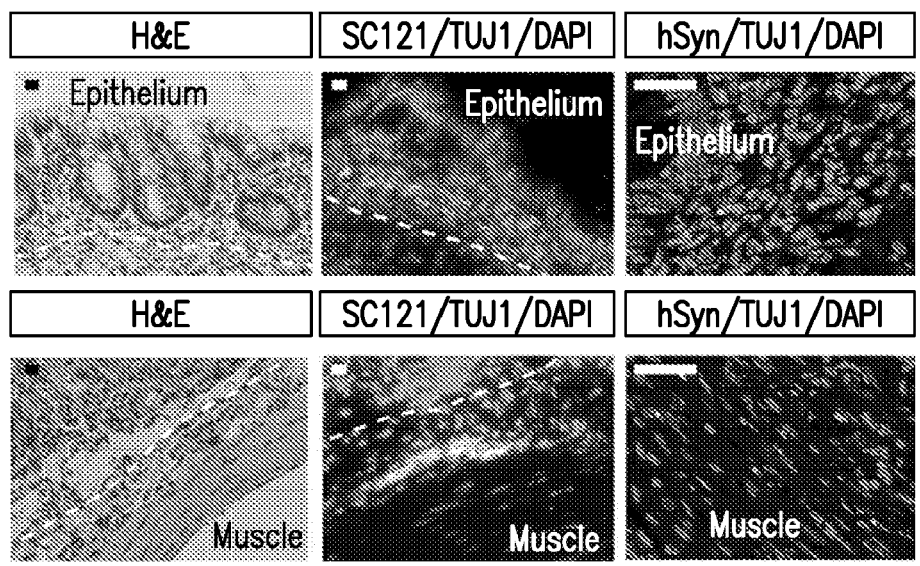
Figure 4A:
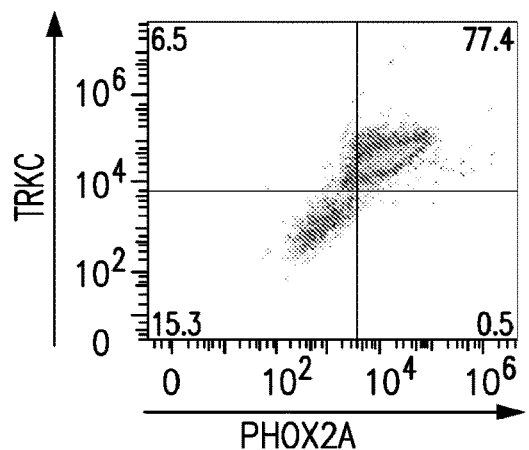
Figure 4B:
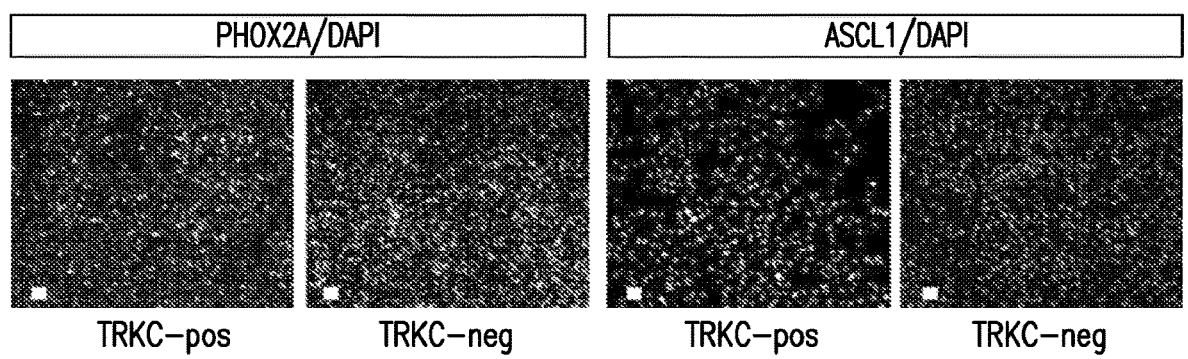
Figure 4C:
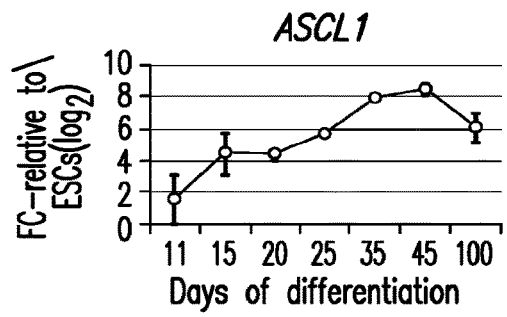
Figure 4C:
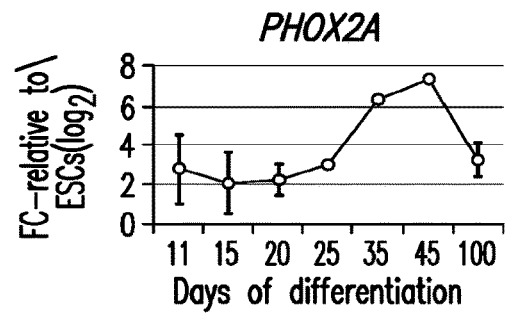
Figure 4C:
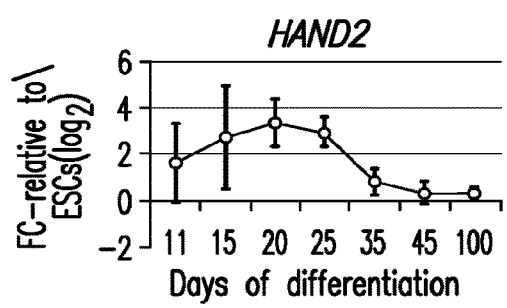
Figure 4C:
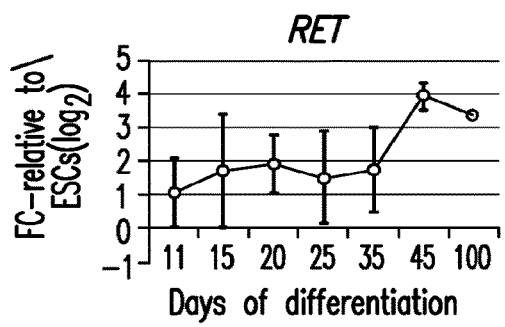
Figure 4C:
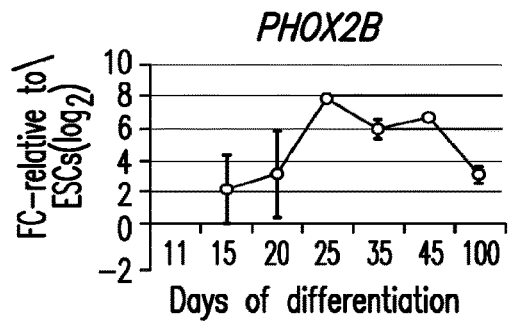
Figure 4C:
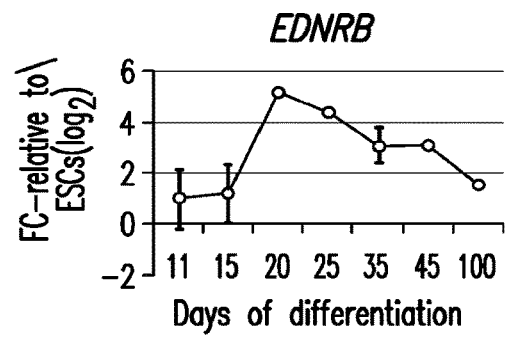
Figure 4C:
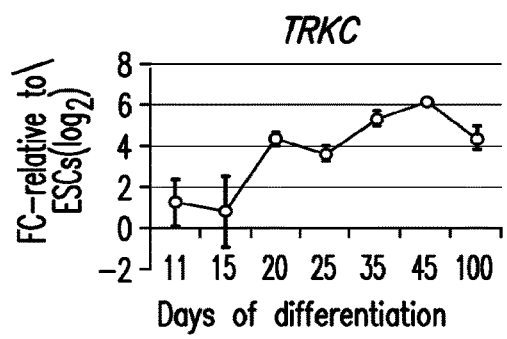
Figure 4D:
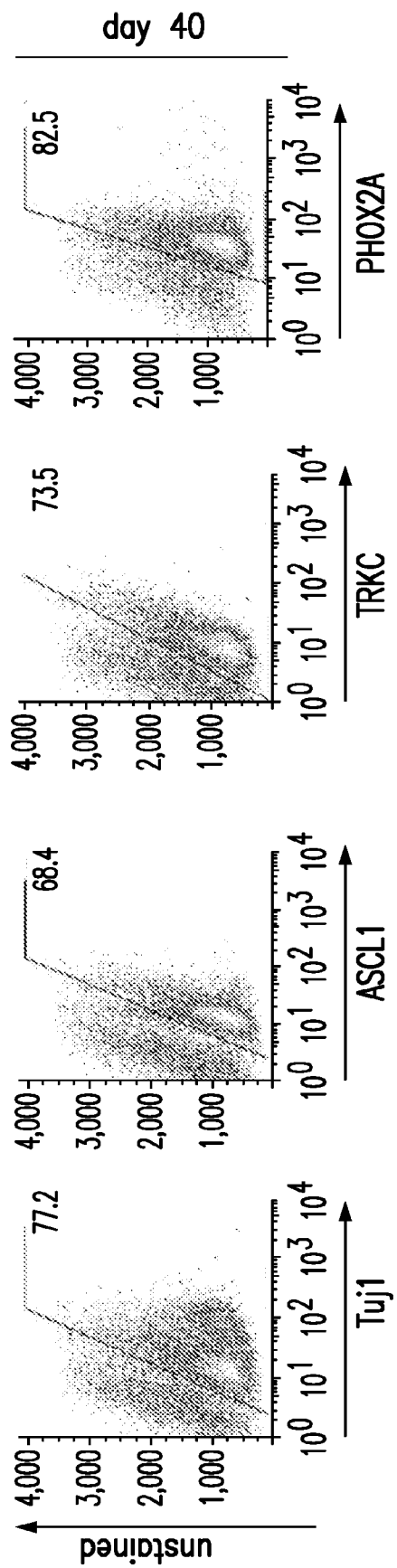
Figure 4E:
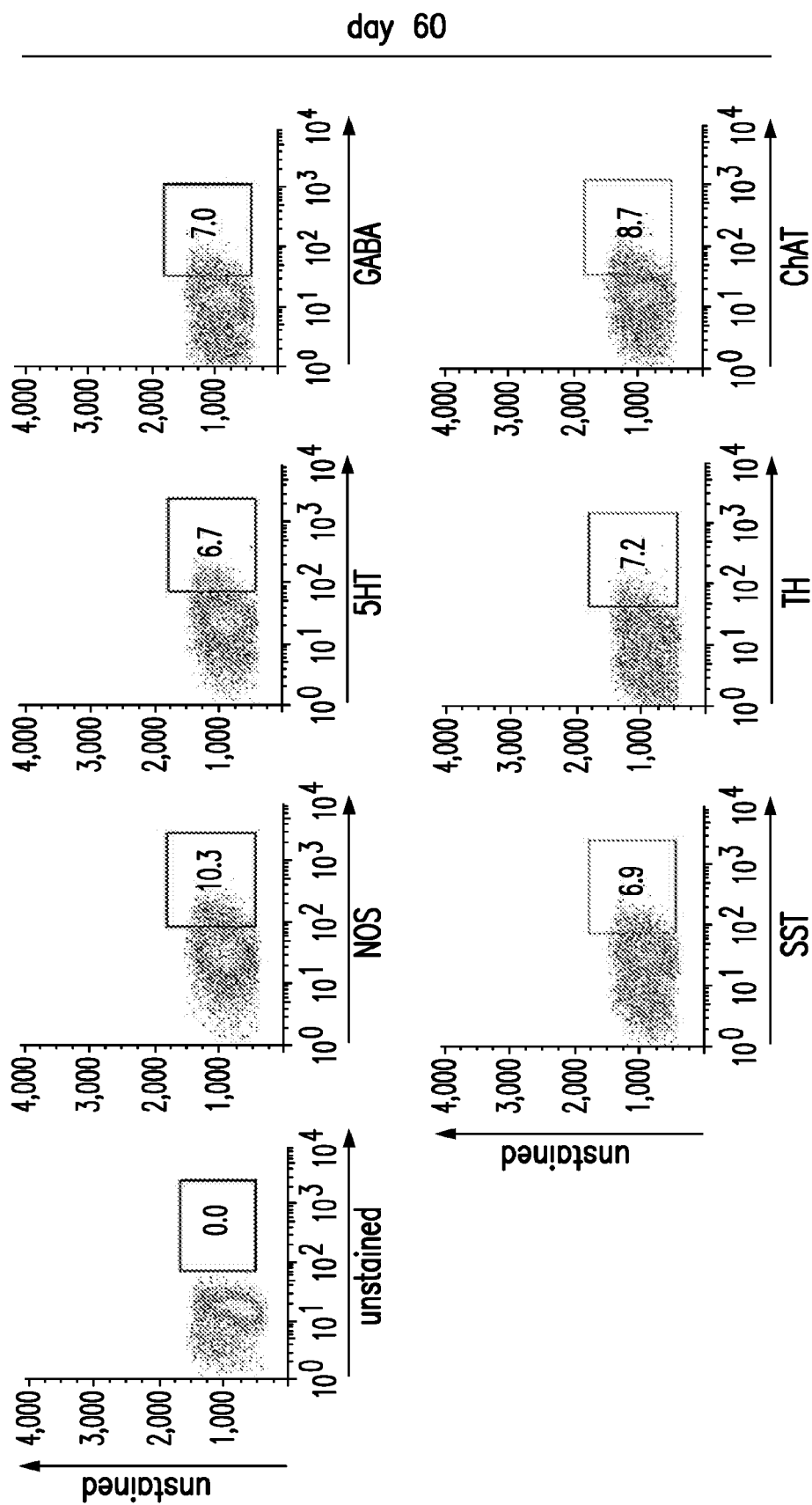
Figures 5A, 5B, 5C:
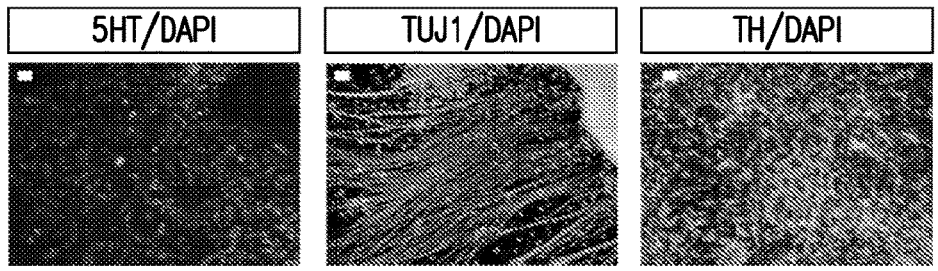
Figure 5D:
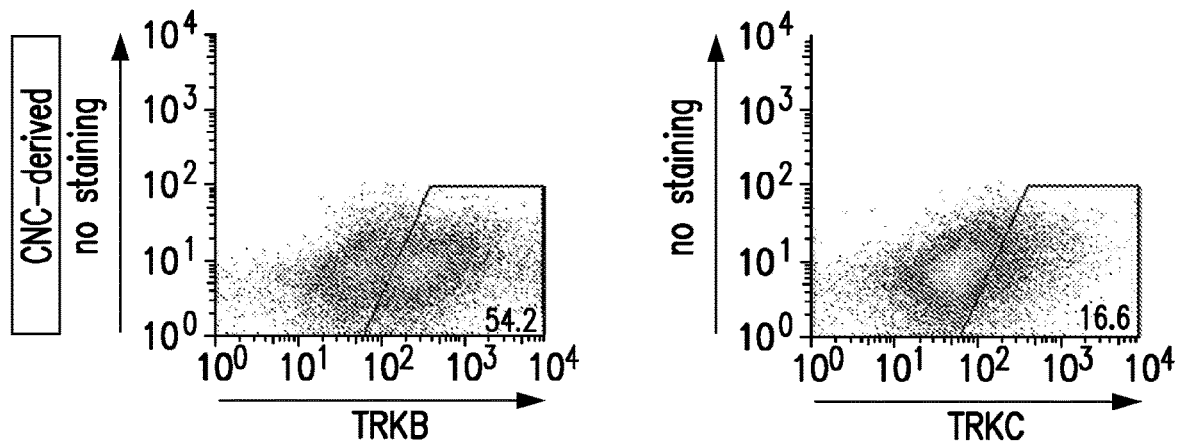
Figure 5E:
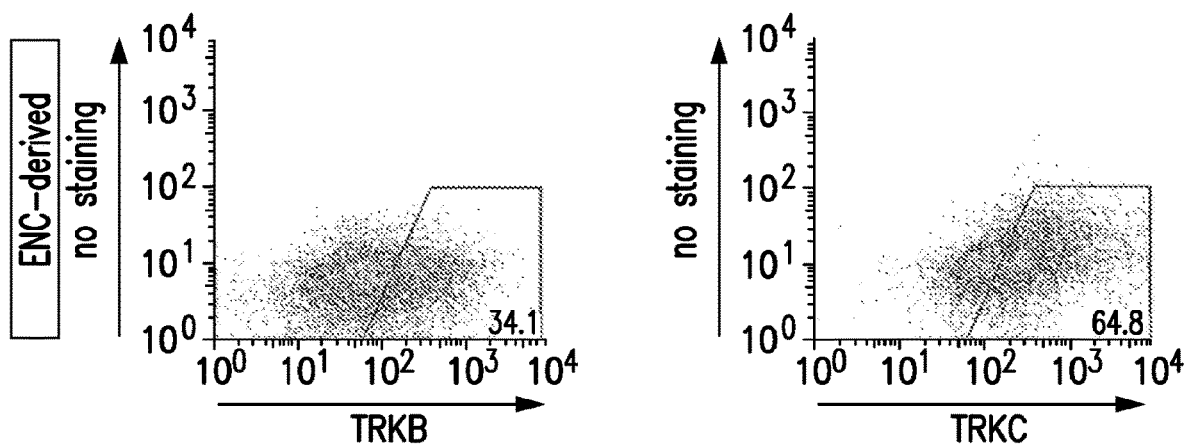
Figure 7A:
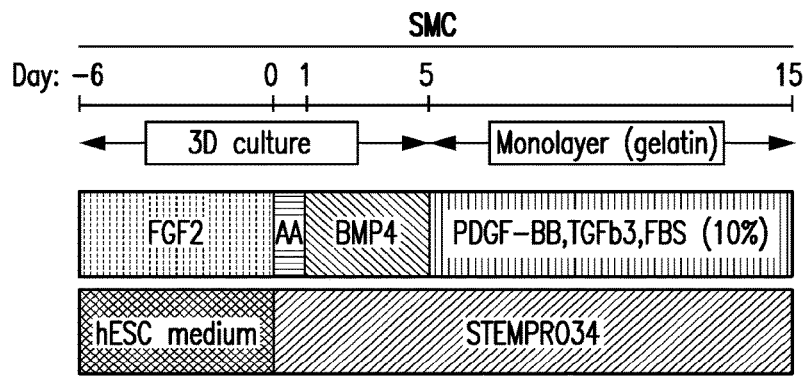

| | |
|---|---|
| FIG. 2D | To confirm the reproducibility of induction of ENCs across various hPSC lines, the differentiation was carried out on other hPSC lines. Flow cytometry plots for the H9 hESC line as well as for control and familial dysautonomia (FD) hiPSC lines are shown. |
| FIG. 1C | H9 hESCs were differentiated under the ENC conditions for 11 days, then sorted for CD49D and harvested for RNA purification. The levels of SOX10 and various HOX mRNAs in the purified cells were quantified using qRT-PCR (n = 3 independent experiments). |
| FIG. 1D and FIGS. 2E and 2F | H9 hESCs were differentiated under the ENC conditions for 11 days, then sorted for CD49D and stained for ENC markers PAX3, EDNRB and RET. The bar graph in FIG. 1D corresponds to Flow plots in FIG. 2F (n = 3 independent experiments). |
| FIGS. 1E-1G FIGS. 2G and 2H | H9 hESCs were differentiated under the CNC, MNC and ENC conditions for 11 days, then sorted for CD49D and harvested for RNA purification and sequencing for global gene expression analysis. Unsupervised clustering and principle component analysis was performed in FIGS. 1E and 1F. List of top 10 upregulated genes and selected highly expressed genes in ENC, CNC and MNC is shown in FIG. 1G and FIGS. 2G and 2G. |
| FIGS. 1H-1J FIG. 2I | EF1::RFP hESCs were differentiated under the CNC, MNC and ENC conditions for 11 days, then sorted for CD49D and injected in the developing chick embryos to compare their migration patterns. |
| | FIGS. 3, 4, 5, 7 and 8 |
| FIGS. 3A-3F | H9 hESCs were differentiated under the ENC condition for 11 days, then sorted for CD49D and cultured in 3D for 4 days. The ENC derived precursors were then plated and differentiated into neuronal precursors and neurons as illustrated in FIG. 3A. The cells were immunostained for various enteric lineage markers at the time points of differentiation indicated on the Figures (Day 15 and 20 in FIG. 3B, day 40 in FIGS. 3C and 3D and Day 60 in FIGS. 3E and 3F). |
| FIG. 4A | H9 hESCs were differentiated under the ENC conditions for 11 days, then sorted for CD49D and cultured in 3D for 4 days. The ENC derived precursors were then plated and differentiated into neurons for an additional 5 days. At day 20, the cells are analyzed for coexpression of TRKC and PHOX2A by flow cytometry (FIG. 4A). |
| FIG. 4B | TRKC positive and negative cells were sorted and stained for PHOX2A and ASCL1 to confirm enrichment of enteric neuron precursors in the TRKC positive fraction (FIG. 4B). Data were replicated in 3 independent experiments. |
| FIG. 4C | H9 hESCs were differentiated under the ENC conditions for 11 days, then sorted for CD49D and cultured in 3D for 4 days. The ENC derived precursors were then plated and differentiated into neurons as illustrated in FIG. 3A. The cells were harvested for RNA purification at different time points during the differentiation (see x-axis). The mRNA levels of several enteric lineage markers in the purified cells were quantified using qRT-PCR. (n = 3 independent experiments) |
| FIGS. 4D and 4E | H9 hESCs were differentiated under the ENC conditions for 11 days, then sorted for CD49D and cultured in 3D for 4 days. The ENC derived precursors were then plated and differentiated into neurons as illustrated in FIG. 3A. The differentiated cells were analyzed by flow cytometry for expression of several enteric lineage markers at day 40 (FIG. 4D) and neurotransmitters at day 60 (FIG. 4E). Data were replicated in >3 independent experiments. |
| FIG. 5 | H9 hESCs were differentiated under the CNC and ENC conditions for 11 days, then sorted for CD49D and cultured in 3D for 4 days. The cells were then plated and differentiated into neurons as illustrated in FIG. 3A. The CNC derived differentiated cells were analyzed by immunofluorescence staining for expression of 5HT, TUJ1 and TH at day 40 (FIGS. 5A-5C). The CNC and ENC derived cells were analyzed by flow cytometry for TRKB and TRKC expression at day 40 (FIGS. 5D and 5E). Data were replicated in >3 independent experiments. |
| FIGS. 7A and 7B | H9 hESCs were differentiated into SMC precursors as illustrated in FIG. 7A and analyzed for expression of smooth muscle progenitor markers SMA and ISL1 at day 15. |
| FIG. 7C | H9 hESCs were differentiated into SMC precursors as illustrated in FIG. 7A and cocultured with SYN::ChR2-EYFP ENC-derived neuron precursors at day 25. The cells are co-cultured for 40 days (day 65 after pluripotent stage for neurons) and immunostained for smooth muscle marker SMA and neuronal markers TUJ1, 5HT and GABA. |
| FIG. 7D | Day 40 co-cultures (65 days after the pluripotent stage) of H9 hESCs derived SMC precursors and SYN::ChR2-EYFP derived ENC neuronal precursors were compared to age-matched enteric neuron precursors monocultures, for expression of SYN::EYFP reporter. |
| FIG. 7E | Day 40 co-cultures (65 days after the pluripotent stage) of H9 hESCs derived SMC precursors and SYN::ChR2-EYFP derived ENC neuronal precursors were compared to age-matched SMC precursors monocultures, for expression of SMA, MYH11 and AchR. |

TABLE 1-continued

Summary of the experiments and methods presented in the corresponding Figures. For additional details see supplementary methods section

Figure 9A:
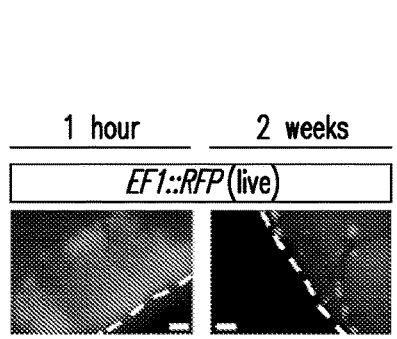
Figure 9B:
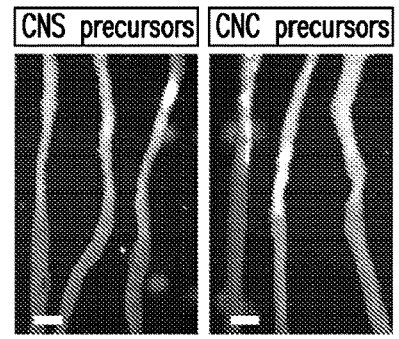
Figure 9C:
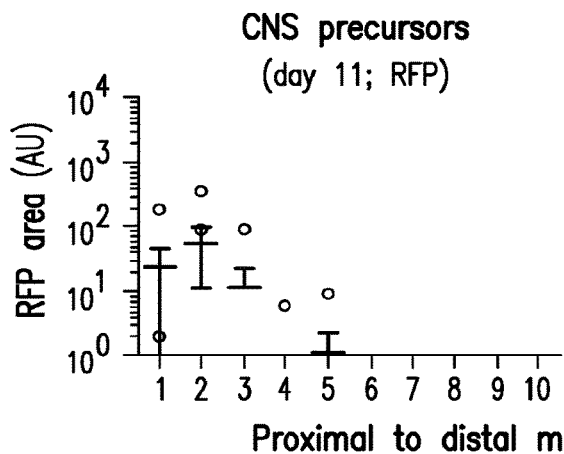
Figure 9D:
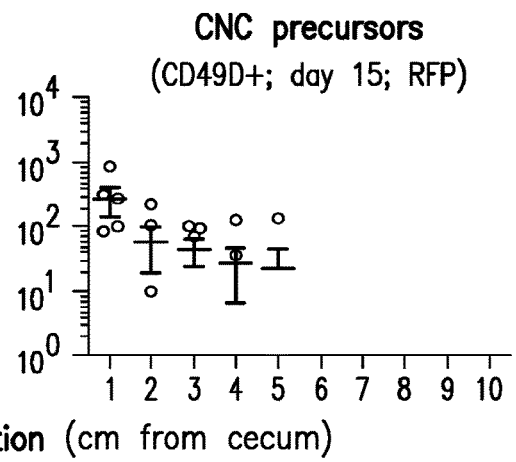
Figure 9D:
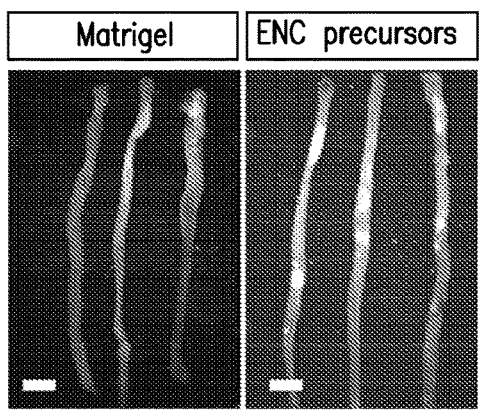
Figure 9E:
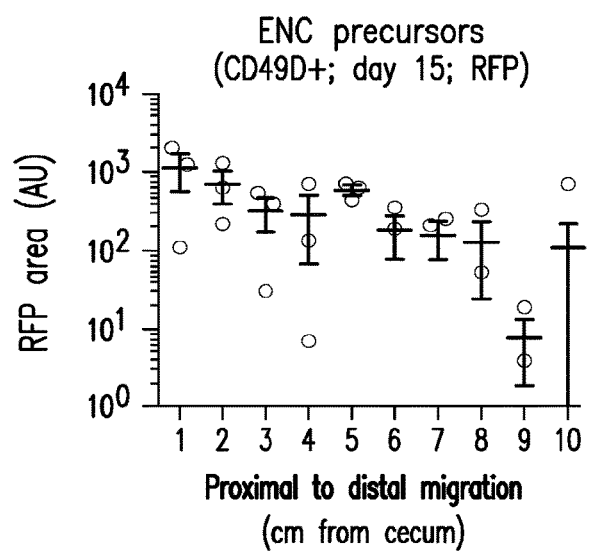
Figure 9F:
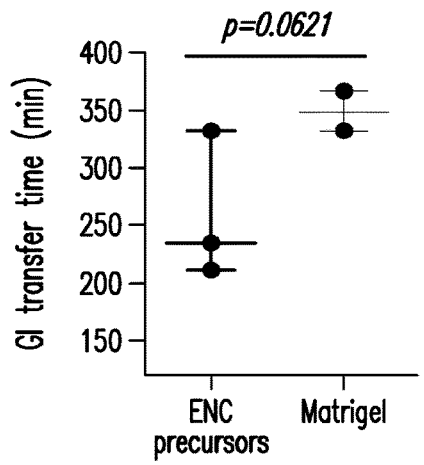
Figures 9G, 9H:
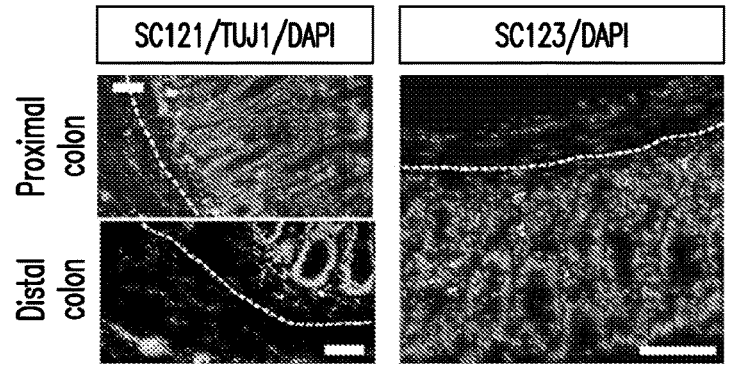
Figure 9I:
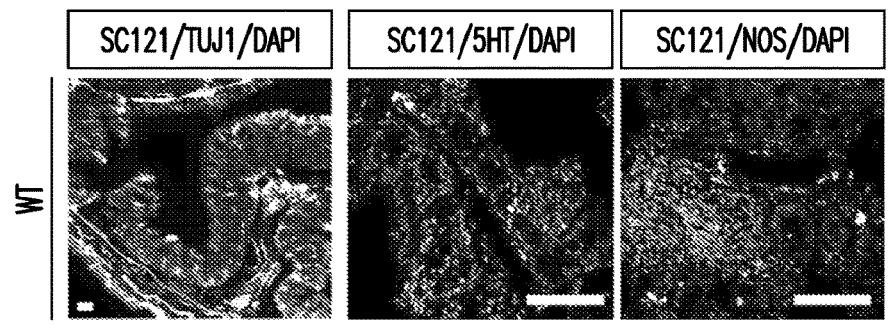

| | |
|---|---|
| FIGS. 8A and 8B | Day 90 co-cultures (115 days after the pluripotent stage) of H9 hESCs derived SMC precursors and SYN::ChR2-EYFP derived ENC neuronal precursors and age-matched SMC precursors monocultures were stimulated with Acetycholine, Carbachol and KCl. The contraction movies are shown in FIG. 8A and quantified in FIG. 8B. |
| FIGS. 3G-3I; FIGS. 8C | Day 90 co-cultures (115 days after the pluripotent stage) of H9 hESCs derived SMC precursors and SYN::ChR2-EYFP derived ENC neuronal precursors and age-matched SMC precursors monocultures were stimulated with light at 10 Hz. The contraction movies are shown in FIG. 8C and quantified in FIG. 3I. |
| FIGS. 3J and 3K | H9 hESCs were differentiated under the ENC conditions for 11 days, then sorted for CD49D and cultured in 3D for 4 days. The ENC derived precursors (day 15) were mixed with murine primary partially digested colon tissue (organoid units) and seeded onto biodegradable scaffolds. The seeded scaffolds were implanted onto the omentum of a recipient mouse and harvested 4 weeks later for histological analysis. The tissue was sectioned and stained for human specific cytoplasmic marker SC121 as well as neuronal markers TUJ1 and human specific Synaptophysin (hSYN). |
| FIGS. 6 and 9 | |
| FIGS. 6A-6C; FIG. 9A | EF1::RFP hESCs were differentiated under the ENC conditions for 11 days, then sorted for CD49D and cultured in 3D for 4 days. The ENC derived precursors were resuspended in matrigel and grafted into the wall of the adult NSG (5-8 weeks old animals) cecum. The grafted colons were then harvested at different time points and analyzed by whole mount fluorescence imaging and histological analysis. A total of n = 102 NSG mice were transplanted across all treatment groups. |
| FIGS. 9B and 9C | EF1::RFP hESCs were differentiated under CNC conditions for 11 days then sorted for CD49D and cultured in 3D for 4 days. Similarly, CNS precursors were generated from EF1::RFP hESCs for 11 days using standard dual-SMAD inhibition protocol (see material & methods). The differentiated CNC derived precursors and CNS precursors were grafted in the muscle layer of the 5-8 weeks old NSG cecum. The grafted colons were then analyzed by whole mount fluorescence imaging 2 weeks post injection to assess survival and migration compared to ENC derived precursors. |
| FIGS. 6D and 6E; FIGS. 9D, 9E, 9I and 9J | EF1::RFP hESCs were differentiated under the ENC conditions for 11 days, then sorted for CD49D and cultured in 3D for 4 days. The ENC derived precursors were resuspended in matrigel and grafted in the muscle layer of EDNRB$^{s-l/s-l}$ cecum (2-3 week old animals). The injected animals were monitored for 6 weeks and their survival was compared to animals injected only with matrigel. The colon tissue was then harvested and analyzed by whole mount imaging and histology. n = 6 animals each for treatment and control group. (Note: FIG. 9I shows matched histology after grafting into wt host and not EDNRB$^{s-l/s-l}$ cecum). |
| FIG. 9F | Preliminary studies measuring total GI transit time in EDNRB$^{s-l/s-l}$ animals injected with ENC derived precursors versus matrigel. GI transit time was assessed by carmine dye gavage and monitoring of stool color. Animals were assessed for GI transit time, 6 weeks after transplantation. N = 3 for grafted animals, N = 2 for matrigel group. Note: n = 2 for matrigel group was due to the fact that nearly all matrigel injected animals died due to their disease phenotype (EDNRB mutation) prior to being able to measure GI transit. |
| FIGS. 6F-6H; FIGS. 9G-9J. | EF1::RFP hESCs were differentiated under the ENC conditions for 11 days, then sorted for CD49D and cultured in 3D for 4 days. The ENC derived precursors were resuspended in matrigel and grafted in the muscle layer of EDNRB$^{s-l/s-l}$ cecum. The colons were harvested 6 weeks (FIG. 9J) or 3 months (FIGS. 6F-6H; FIG. 9G) later for histology. (Note: FIG. S6i shows matched histology after grafting into wt cecum and instead of EDNRB$^{s-l/s-l}$ cecum). |
| FIGS. 10, 11, 12, and 13 | |
| FIGS. 10A-10C; FIGS. 11A-11C | EDNRB locus was targeted in EF1::RFP hESCs using the double nickase CRISPR/Cas strategy. Targeted EDNRB−/− clones were identified by sequencing and western blot analysis for EDNRB (FIGS. 11A and 11B). The WT and EDNRB−/− EF1::RFP hESCs were differentiated under the ENC conditions for 11 days, then sorted for CD49D and analyzed for changes in migration capacity using scratch assay (n > 3 independent experiments). |
| FIGS. 11D and 11E | EDNRB−/− EF1::RFP hESCs were differentiated under the ENC conditions for 11 days and sorted for CD49D. Proliferation of CD49D purified (day 11) cells (wt ENC versus EDNRB−/− ENC (clone #1)) was assessed using the CyQUANT NF cell proliferation Assay Kit (FIG. 11D). Proliferation was assessed every 24 hours for a total of 72 hours. Cell viability of the cells was assessed by measuring LDH activity of ENC (day 11) using the CytoTox 96 cytotoxicity assay kit (FIG. 11E. |

TABLE 1-continued

Summary of the experiments and methods presented in the corresponding Figures. For additional details see supplementary methods section

Figure 10C:
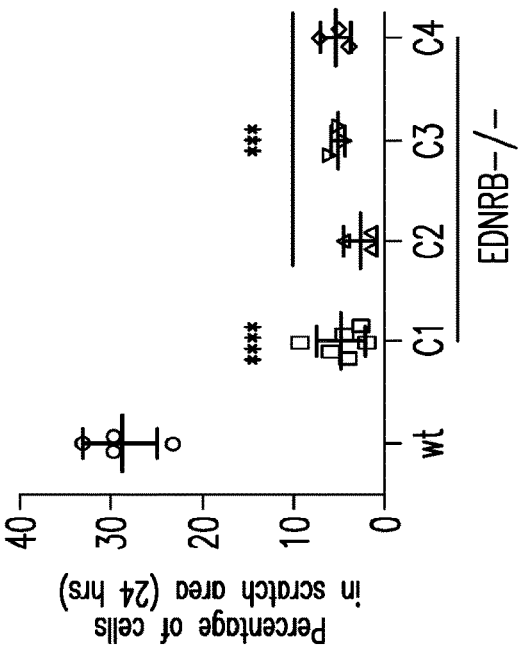
Figure 10E:
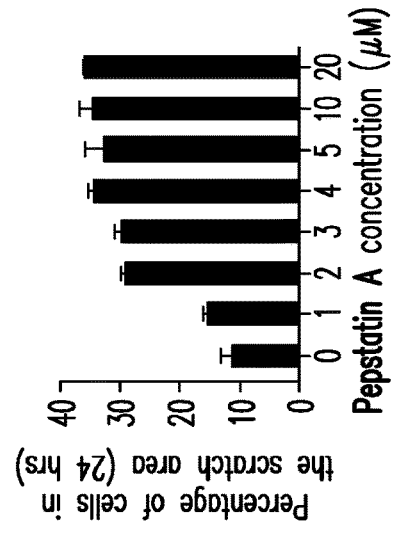
Figure 10B:
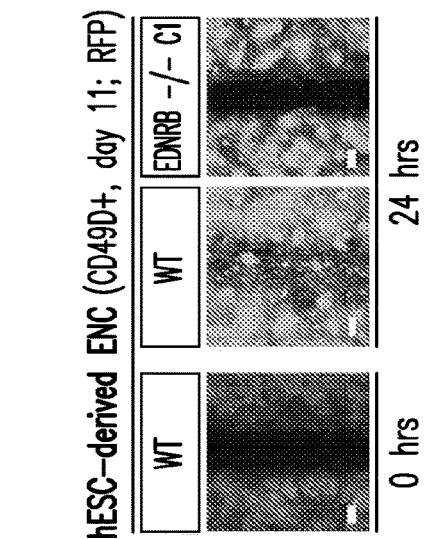
Figure 10D:
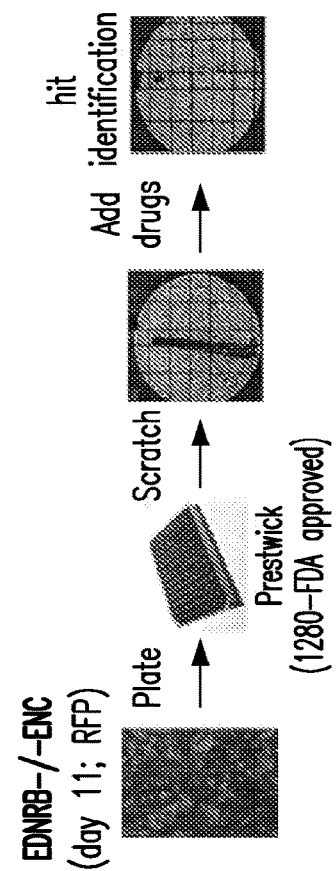
Figure 13D:
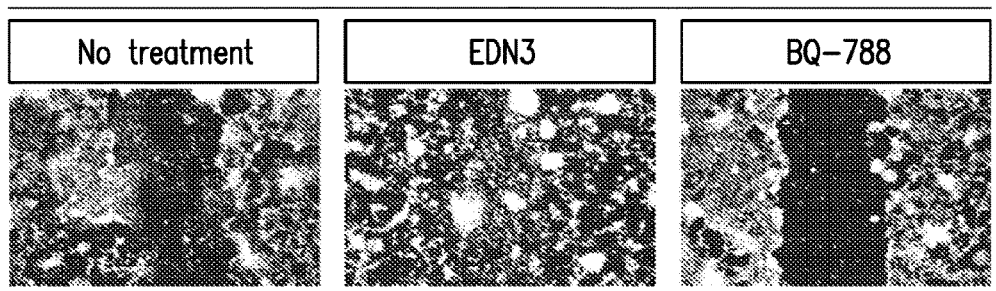

| | |
|---|---|
| FIG. 10D and FIG. 12 | EDNRB−/− EF1::RFP hESCs were differentiated under the ENC conditions for 11 days and plated in 96 well plated for high throughput chemical compound screening using the scratch assay platform. The plates are imaged 24 hrs after compound treatment and individual wells are scored based on their viability and migration status (as shown in FIG. 12A, right panel). Statistical data (z-score) on the robustness of the assay and the resulting candidate hits is presented in FIGS. 12B and 12C. The scratch assay pictures for primary hit compounds are shown in FIG. 12D. |
| FIG. 10E | EDNRB−/− EF1::RFP hESCs were differentiated under the ENC conditions for 11 days and sorted for CD49D. The effect of Pepstatin A on migration of EDNRB−/− hESC-derived ENCs was measured across a range of different concentrations. Pepstatin A treatment was started 24 hrs before scratching and continued during the assay. |
| FIGS. 10F and 10G | EDNRB−/− EF1::RFP hESCs were differentiated under the ENC conditions for 11 days and sorted for CD49D. The effect of Pepstatin A on migration of EDNRB−/− hESC-derived ENCs was compared to a second structurally unrelated inhibitor BACE inhibitor (n = 3 independent experiments). |
| FIG. 13A | The levels of BACE2 mRNA in CNC, MNC and ENC compared to CNS precursors based on the RNA sequencing data described in FIG. 1 (RNAseq data are derived from 3 independent replicates for each of the NC subtypes). |
| FIGS. 10H and 10I; FIG. 13BS9b | EDNRB−/− EF1::RFP hESCs were differentiated under the ENC conditions for 11 days and sorted for CD49D. CD49D purified ENCs were transfected with BACE2 siRNAs and analyzed for migration using scratch assay. Knock-down is confirmed by qRT-PCR measurement (FIG. 13B) of BACE2 mRNA (n = 3 independent experiments). |
| FIGS. 10J-10L; FIG. 13C | WT and EDNRB−/− EF1::RFP hESCs were differentiated under the ENC conditions for 11 days and sorted for CD49D. CD49D purified EDNRB−/− ENCs were treated with Pepstatin A for 3 days and transplanted in adult NSG cecum as detailed in FIG. 4j. The colons were harvested 2 weeks later and analyzed by whole mount fluorescence imaging to compare migration of WT, EDNRB−/− and Pepstatin A treated EDNRB−/− ENC derived precursors, n ≥ 8 animals for each of the treatment groups. For statistical analysis of the data presented in FIG. 13C - see FIG. 10L. |
| FIGS. 13D and 13F | H9 hESCs were differentiated under the ENC conditions for 11 days, then sorted for CD49D and assayed for migration in presence of EDN3 and EDNRB inhibitor BQ-788 (FIG. 13A). CD49D purified ENCs were treated with BQ-788 for 3 days and transplanted in adult NSG cecum. The tissue is harvested 2 weeks later and analyzed by whole mount fluorescence imaging to compare migration of BQ-788 treated and untreated ENC derived precursors. (n = 3 independent experiments). |

Culture of Undifferentiated Human Embryonic Stem Cells (hESCs)

hESC line H9 (WA-09) and derivatives (SOX10::GFP; SYN::ChR2-YFP; SYN::YFP; PHOX2B:GFP; EF1::RFP EDNRB−/−) as well as 2 independent hiPSC lines (healthy and Familial Dysautonomia, Sendai-based, OMSK (Cytotune)) were maintained on mouse embryonic fibroblasts (MEF, Global Stem, Rockville, MD) in KSR (Life Technologies, 10828-028) containing hESC medium as described previously[11]. Cells were subjected to mycoplasma testing at monthly intervals and STR profiled to confirm cell identity at the initiation of the study.

Neural Crest Induction.

hESCs were plated on matrigel (BD Biosciences, 354234) coated dishes ($10^5$ cells/cm$^2$) in hESC medium containing 10 nM FGF2 (R&D Systems, 233-FB-001MG/CF). Differentiation was initiated in knockout serum replacement (KSR) medium (KO DMEM+15% KSR, L-glutamine (Life Technologies, 25030-081), NEAA (Life Technologies, 11140-050) containing LDN193189 (100 nM, Stemgent, Cambridge, MA) and SB431542 (10 µM, Tocris, Ellisville, MI). The KSR medium was gradually replaced with increasing amounts of N2 medium from day 4 through day 10 as described previously[11]. For Cranial NC (CNC) induction, cells were treated with 3 uM CHIR99021 (Tocris Bioscience, 4423) in addition to LDN and SB from day 2 through day 11. Enteric NC (ENC) differentiation involved additional treatment with Retinoic Acid (10 µM) from day 6 through day11. For deriving Melanocyte-competent NC (MNC), LDN was replaced with BMP4 (10 nM-R&D, 314-bp) and EDN3 (10 nM, American Peptide company, 88-5-10B) from day 6 through day11[5]. The differentiated cells were sorted for CD49D at day 11. CNS precursor control cells were generated by treatment with LDN and SM from day 0 through day 11 as previously described[11]. Throughout the manuscript, day 0 is the day the medium was switched from hESC medium to LDN and SB containing medium. Days of differentiation in text and figures refer to the number of days since the pluripotent stage (day 0).

FACS and Immunofluorescence Analysis (IF).

For IF, the cells were fixed with 4% paraformaldehyde (PFA) (Affymetrix-USB, 19943) for 20 minutes, then blocked and permeabilized using 1% Bovine Serum Albumin (BSA) (Thermo Scientific, 23209) and 0.3% triton X-100 (Sigma, T8787). The cells were then incubated in primary antibody solutions overnight at 4° C. (Celsius) and stained with fluorophore conjugated secondary antibodies at RT for 1 hour, the stained cells were then incubated with DAPI (1 ng/ml, Sigma, D9542-5MG) and washed several times before imaging. For Flow Cytometry analysis, the cells were dissociated with Accutase (Innovative Cell Technologies, AT104) and fixed and permeabilized using BD Cytofix/Cytoperm (BD Bioscience, 554722) solution, then washed, blocked and permeabilized using BD Perm/Wash buffer (BD Bioscience, 554723) according to manufacturer's instructions. The cells were then stained with primary (overnight at 4) and secondary (30 min at room temperature) antibodies and analyzed using a flow Cytometer (Flowjo software). A list of primary antibodies and working dilutions is provided in Table 2. The PHOX2A antibody was contributed by Dr. J-F Brunet (Rabbit, 1:800 dilution).

TABLE 2

List of primary antibodies and working dilutions

| Antibody | Catalog number | Source | Dilution |
|---|---|---|---|
| CD49D | 304314 | Biolegend | 1:800 |
| PAX3 | PAX3 | DSHB | 1:150 |
| EDNRB | AF4496 | R&D systems | 1:50 |
| RET | MAB718 | R&D systems | 1:50 |
| TUJ1 | MRB-435P | Covance | 1:1000 |
| TRKC | AF373 | R&D systems | 1:500 |
| ASCL1 | 556604 | BD Pharmingen | 1:200 |
| NOS | sc-648 | Santa Cruz Biotech | 1:200 |
| 5HT | S5545 | Sigma | 1:1000 |
| GABA | A2052 | Sigma | 1:1000 |
| SST | A0566 | Dako | 1:2000 |
| TH | P40101-0 | pel freeze | 1:1000 |
| CHAT | AB144P | Millipore | 1:1000 |
| SC121 | Stem121 | StemCells Inc | 1:1000 |
| SC123 (hGFAP) | Stem 123 | StemCells Inc | 1:1000 |
| SOX10 | sc-17342 | Santa Cruz Biotech | 1:200 |
| PHOX2A | | Gift from JF Brunet Lab. | 1:800 |
| MYH11 | M7786 | Sigma | 1:1000 |
| AChR | sc-27293 | Santa Cruz Biotech | 1:200 |
| hSYN | ADI-905-782-100 | ENZO life science | 1:1000 |
| SMA | A5228 | Sigma | 1:1000 |
| ISL1 | 39.4D5 | DSHB | 1:100 |

In Vivo Transplants.

Fertilized eggs (from Charles River farms) were incubated at 37 for 50 hours before injections. $2 \times 10^5$ CD49D sorted, RFP labeled NC cells were injected into the intersomitic space of the vagal region of the embryos targeting a region between somite 2 and 6 (HH 14 embryo, 20-25 somite stage). The embryos were harvested 36 hours later for whole mount epifluorescence and histological analyses.

Gene Expression Analysis.

For RNA sequencing, total RNA was extracted using RNeasy RNA purification kit (Qiagen, 74106). For qRT-PCR assay, total RNA samples were reverse transcribed to cDNA using Superscript II Reverse Transcriptase (Life Technologies, 18064-014). qRT-PCR reactions were set up using QuantiTect SYBR Green PCR mix (Qiagen, 204148). Each data point represents three independent biological replicates.

In Vitro Differentiation of ENC to Enteric Neurons.

The ENC cells were aggregated into 3D spheroids (5 million cells/well) in Ultra Low Attachment 6-well culture plates (Fisher Scientific, 3471) and cultured in Neurobasal (NB) medium supplemented with L-Glutamine (Gibco, 25030-164), N2 (Stem Cell Technologies, 07156) and B27 (Life Technologies, 17504044) containing CHIR (3 uM, Tocris Bioscience, 4423) and FGF2 (10 nM, R&D Systems, 233-FB-001MG/CF). after 4 days of suspension culture, the spheroids were plated on Poly Ornithine/Laminin/Fibronectin (PO/LM/FN) coated dishes (prepared as described previously[38]) in Neurobasal (NB) medium supplemented with L-Glutamine (Gibco, 25030-164), N2 (Stem Cell Technologies, 07156) and B27 (Life Technologies, 17504044) containing GDNF (25 ng/ml, Peprotech, 450-10) and Ascorbic acid (100 uM, Sigma, A8960-5G). The ENC precursors migrated out of the plated spheroids and differentiated into neurons in 1-2 weeks. The cells were fixed for immunostaining or harvested for gene expression analysis at Day 25, Day 40 and Day 60 of differentiation.

Induction of SMCs.

Mesoderm specification was carried out in STEMPRO-34 (Gibco, 10639-011) medium. The hESCs were subjected to Activin A treatment (100 ng/ml, R&D, 338-AC-010) for 24 hours followed by BMP4 treatment (long/ml, R&D, 314-bp) for four days[13]. The Cells were then differentiated into SMC progenitors by treatment with PDGF-BB (5 ng/ml, Peprotech, 100-14B), TGFb3 (5 ng/ml, R&D systems, 243-B3-200) and 10% FBS. The SMC progenitors were expandable in DMEM supplemented with 10% FBS.

EN-SMC Co-Culture.

The SMC progenitors were plated on PO/LM/FN coated culture dishes (prepared as described previously[38]) three days before addition of ENC-derived neurons. The neurons were dissociated (using accutase, Innovative Cell Technologies, AT104) at day 30 of differentiation and plated onto the SMC monolayer cultures. The culture was maintained in Neurobasal (NB) medium supplemented with L-Glutamine (Gibco, 25030-164), N2 (Stem Cell Technologies, 07156) and B27 (Life Technologies, 17504044) containing GDNF (25 ng/ml, Peprotech, 450-10) and Ascorbic acid (100 uM, Sigma, A8960-5G). Functional connectivity was assessed at 8-16 weeks of co-culture.

Pharmacological and Optogenetic Stimulations of Co-Cultured SMCs.

SMC only and SMC-ENC-derived neuron co-cultures were subjected to Acetylcholine chloride (50 μM, Sigma, A6625), Carbamoylcholine chloride (10 μM, Sigma, C4382) and KCl (55 mM) Fisher scientific, BP366-500) treatment, 3 months after initiating the co-culture. Optogenetic stimulations were performed using a 450 nm pigtailed diode pumped solid state laser (OEM Laser, PSU-III LED, OEM Laser Systems, Inc) achieving an illumination between 2 and 4 mW/mm². The pulse width was 4 ms and stimulation frequencies ranged from 2 to 10 Hz. For the quantification of movement, images were assembled into a stack using Metamorph software and regions with high contrast were identified (labeled yellow in FIG. 8). The movement of 5 representative high contrast regions per field was automatically traced (Metamorph software). Data are presented in kinetograms as movement in pixels in x and y direction (distance) with respect to the previous frame. Automatic tracing of movement sometimes did not capture the strongest movements in cultures with >2× increase in movements. Therefore these data might partially underestimate the actual movement.

Generation of Chimeric Tissue Engineered Colon (TEC).

A previously described method was used for generation of TEC[16]. Briefly, the donor colon tissue was harvested and digested into organoid units using dispase (Life Technologies, 17105-041) and collagenase type 1 (Worthington, CLS-1). The organoid units were then mixed immediately (without any in vitro culture) with CD49D purified hESC-derived ENC precursors (day 15 of differentiation) and seeded onto biodegradable Polyglycolic Acid Scaffolds (2-mm sheet thickness, 60 mg cm-3 bulk density; porosity >95%, Concordia Fibers, Coventry RI) shaped into 2 mm long tubes with Poly-L Lactide (PLLA) (Durect Corporation). The seeded scaffolds were then placed onto and wrapped in the greater omentum of the adult (>2 months old) NSG mice. Just prior to the implantation, these mice were irradiated with 350 cGY. The seeded scaffolds were differentiated into colon-like structures inside the omentum for 4 additional weeks before they were surgically removed for tissue analysis.

Transplantation of ENC Precursors in Adult Colon.

All mouse procedures were performed following NIH guidelines, and were approved by the local Institutional Animal Care and Use Committee (IACUC), the Institutional Biosafety Committee (IBC) as well as the Embryonic Stem Cell Research Committee (ESCRO). 3-6 week old male NSG (NOD.Cg-Prkdc$^{scid}$ Il2rg$^{tm1Wjl}$/SzJ) mice or 2-3 weeks old EDNRB$^{s-l/s-l}$ (SSL/LeJ) mice[39] (n=12, 6 male, 6 female) were used for these studies. Animal numbers were based on availability of homozygous hosts and on sufficient statistical power to detect large effects between treatment versus control (EDNRB$^{s-l/s-l}$) as well as for demonstrating robustness of migration behavior (NSG). Animals were randomly selected for the various treatment paradigms (NSG and EDNRB$^{s-l/s-l}$) but assuring for equal distribution of male/female ratio in each group (EDNRB$^{s-l/s-l}$). Animals were anesthetized with isoflurane (1%) throughout the procedure, a small abdominal incision was made, abdominal wall musculature lifted and the cecum is exposed and exteriorized. Warm saline was used to keep the cecum moist. 20 μl of cell suspension (2-4 million RFP+CD49D purified hESC-derived ENC precursors) in 70% matrigel (BD Biosciences, 354234) in PBS or 20 μl of 70% matrigel in PBS only (control grafted animals) were slowly injected into the cecum (targeting the muscle layer) using a 27-gauge needle. Use of 70% matrigel as carrier for cell injection assured that the cells stayed in place following the injection and prevented backflow into peritoneum. After injection that needle was withdrawn, and a Q-tip was placed over the injection site for 30 seconds to prevent bleeding. The cecum was returned to the abdominal cavity and the abdominal wall was closed using 4-0 vicryl and a taper needle in an interrupted suture pattern and the skin was closed using sterile wound clips. After wound closure animals were put on paper on top of their bedding and attended until conscious and preferably eating and drinking. The tissue was harvested at different time points (ranging from two weeks to four months) after transplantation for histological analysis. EDNRB$^{s-l/s-l}$ mice were immunosuppressed by daily injections of cyclosporine (10 mg/kg i.p, Sigma, 30024).

Whole Mount Fluorescence Imaging and Histology

The harvested colon samples were fixed in 4% PFA at 4° C. overnight before imaging. Imaging was performed using Maestro fluorescence imaging system (Biotechniques). The tissue samples were incubated in 30% sucrose (Fisher Scientific, BP220-1) solutions at 4° C. for 2 days then embedded in OCT (Fisher Scientific, NC9638938) and cryosectioned. The sections were then blocked with 1% BSA (Thermo Scientific, 23209) and permeabilized with 0.3% Triton X-100 (Sigma, T8787). The sections were then stained with primary antibody solution at 4° C. overnight and fluorophore conjugated secondary antibody solutions at room temperature for 30 minutes. The stained sectioned were then incubated with DAPI (1 ng/ml, Sigma, D9542-5MG) and washed several times before they were mounted with Vectashield Mounting Medium (vector, H1200) and imaged using fluorescent (Olympus IX70) or confocal microscopes (Zeiss SP5).

Total GI Transit Time

Mice were gavaged with 0.3 ml of dye solution containing 6% carmine (Sigma, C1022-5G), 0.5% methylcellulose (Sigma, 274429-5G) and 0.9 NaCl, using a #24 round-tip feeding needle. The needle was held inside the mouse esophagus for a few seconds after gavage to prevent regurgitation. 1 hour later, the stool color was monitored for gavaged mice every 10 minutes. For each mouse, total GI transit time was between the time of gavage and the time when red stool was observed.

Gene Targeting

The double nickase CRISPR/Cas9 system[40] was used to target the EDNRB locus in EF1::RFP H9 hESCs. Two guide RNAs were designed (using the CRISPR design tool http://crispr.mit.edu/) to target the coding sequence with PAM targets ~20 bp apart (qRNA #1 target specific sequence: AAGTCTGTGCGGACGCGCCCTGG [SEQ ID NO:1], RNA #2 target specific sequence: CCAGATCCGCGACAGGCCGCAGG [SEQ ID NO:2]). The cells were transfected with gRNA constructs and GFP-fused Cas9-D10A nickase. The GFP expressing cells were FACS purified 24 hours later and plated in low density (150 cells/cm$^2$) on MEFs. The colonies were picked 7 days later and passaged twice before genomic DNA isolation and screening. The targeted region of EDNRB gene was PCR amplified (forward primer: ACGCCTTCTG-GAGCAGGTAG [SEQ ID NO:3], reverse primer: GTCAGGCGGGAAGCCTCTCT [SEQ ID NO:4]) and cloned into Zero Blunt TOPO vector (Invitrogen, 450245). To ensure that both alleles (from each hESC colony) are represented and sequenced, 10 bacterial clones (for each hESC clone) were selected for plasmid purification and subsequent sequencing. The clones with bi-allelic nonsense mutations were expanded and differentiated for follow-up assays.

Migration Assay

The ENC cells were plated on PO/LM/FN coated (prepared as described previously[38]) 96 well or 48 well culture plates (30,000/cm$^2$). 24 hours later the culture lawn was scratched manually using a pipette tip. The cells were given an additional 24-48 hours to migrate into the scratch area and fixed for imaging and quantification. The quantification was based on the percentage of the nuclei that are located in the scratch area after the migration period. The scratch area was defined using a reference well that was fixed immediately after scratching. Migration of cells were quantified using the open source data analysis software KNIME[41] (http://knime.org) with the "Quantification in ROI" plug-in as described in detail elsewhere[42].

Proliferation Assay

To quantify proliferation, FACS purified ENC cells were assayed using CyQUANT NF cell proliferation Assay Kit (Life Technologies, C35006) according to manufacturer's instructions. Briefly, to generate a standard, cells were plated at various densities and stained using the fluorescent DNA binding dye reagent. Total fluorescence intensity was then measured using a plate reader (excitation at 485 nm and emission detection at 530 nm). After determining the linear range, the CD49D+WT and EDNRB$^{-/-}$ ENC precursors were plated (6000 cell/cm$^2$) and assayed at 0, 24, 48 and 72 hrs. The cells were cultured in Neurobasal (NB) medium supplemented with L-Glutamine (Gibco, 25030-164), N2 (Stem Cell Technologies, 07156) and B27 (Life Technologies, 17504044) containing CHIR (3 uM, Tocris Bioscience, 4423) and FGF2 (10 nM, R&D Systems, 233-FB-001MG/CF) during the assay.

Viability Assay

To monitor the viability of WT and EDNRB$^{-/-}$ ENC precursors, cells were assayed for LDH activity using Cyto-Tox 96 cytotoxicity assay kit (Promega, G1780). Briefly, the cells were plated in 96 well plates at 30,000/cm$^2$. The supernatant and the cell lysate were harvested 24 hours later and assayed for LDH activity using a plate reader (490 nm absorbance). Viability was calculated by dividing the LDH signal of the lysate by total LDH signal (from lysate plus supernatant). The cells were cultured in Neurobasal (NB) medium supplemented with L-Glutamine (Gibco, 25030-164), N2 (Stem Cell Technologies, 07156) and B27 (Life Technologies, 17504044) containing CHIR (3 µM, Tocris Bioscience, 4423) and FGF2 (10 nM, R&D Systems, 233-FB-001MG/CF) during the assay.

High Throughput Screening

The chemical compound screening was performed using the Prestwick Chemical Library®. The ENC cells were plated in 96 well plates (30,000/cm$^2$) and scratched manually 24 hours before addition of the compounds. The cells were treated with two concentrations of the compounds (10 µM and 1 µM). The plates were fixed 24 hours later for total plate imaging. The compounds were scores based on their ability to promote filling of the scratch in 24 hours. The compounds that showed toxic effects (based on dramatic reduction in cell numbers assessed by DAPI staining) were scored 0, compound with no effects were scored 1, compound with moderate effects were scored 2 and compound with strong effects (that resulted in complete filling of the scratch area) were scored 3 and identified as hit compounds. The hits were further validated to ensure reproducibility. The cells were treated with various concentrations of the selected hit compound (Pepstatin A) for dose response analysis. The optimal dose (10 µM-based on optimal response and viability) was used for follow-up experiments. For the pre-treatment experiments, cells were CD49D purified at day 11 and treated with Pepstatin A from day 12 through day 15 followed by transplantation into the colon wall of NSG mice. The cells were cultured in Neurobasal (NB) medium supplemented with L-Glutamine (Gibco, 25030-164), N2 (Stem Cell Technologies, 07156) and B27 (Life Technologies, 17504044) containing CHIR (3 uM, Tocris Bioscience, 4423) and FGF2 (10 nM, R&D Systems, 233-FB-001MG/CF) during the assay.

BACE2 Inhibition and Knockdown

To inhibit BACE2, the ENC precursors were treated with 1 µM β-Secretase Inhibitor IV (CAS 797035-11-1—Calbiochem). To Knockdown BACE2, cells were dissociated using accutase (Innovative Cell Technologies, AT104) and reverse-transfected (using Lipofectamine RNAiMAX-Life Technologies, 13778-150) with a siRNA pool (SMARTpool: ON-TARGETplus BACE2 siRNA, Dharmacon, L-003802-00-0005) or 4 different individual siRNAs (Dharmacon, LQ-003802-00-0002 2 nmol). The Knockdown was confirmed by qRT-PCR measurement of BACE2 mRNA levels in cells transfected with the BACE2 siRNAs vs. the control siRNA pool (ON-TARGETplus Non-targeting Pool, Dharmacon, D-001810-10-05). The transfected cells were scratched 24 hours after plating and fixed 48 hours later for migration quantification. The cells were cultured in Neurobasal (NB) medium supplemented with L-Glutamine (Gibco, 25030-164), N2 (Stem Cell Technologies, 07156) and B27 (Life Technologies, 17504044) containing CHIR (3 uM, Tocris Bioscience, 4423) and FGF2 (10 nM, R&D Systems, 233-FB-001MG/CF) during the assay.

Statistical Analysis

Data are presented as mean±SEM and were derived from at least 3 independent experiments. Data on replicates (n) is given in figure legends and in Table 1. Statistical analysis was performed using the Student t-test (comparing 2 groups) or ANOVA with Dunnett test (comparing multiple groups against control). Distribution of the raw data approximated normal distribution (Kolmogorov Smirnov normality test) for data with sufficient number of replicates to test for normality. Survival analysis was performed using log rank (Mantel-Cox) test. Z-scores for primary hits were calculated as $Z=(x-\mu)/\sigma$. X is the migration score value and is 3 for all hit compounds. µ is the mean migration score value and σ is the standard deviation for all compounds and DMSO controls (n=224).

Results

Current NC differentiation protocols[4,5] result in SOX10$^+$ NC precursors that are HOX negative (indicative of anterior/cranial identity; cranial NC (CNCs)) and primarily give rise to sensory and nociceptive neurons. In contrast, vagal NC identity is characterized by the expression of specific, regionally restricted HOX genes including HOXB3[8] and HOXB5[9]. Retinoic acid (RA) has been previously used as an extrinsic factor to shift the regional identity of CNS precursors from anterior to more caudal fates such as during motoneuron specification[10]. The inventors tested whether the addition of RA can similarly direct the regional identity in NC lineages and induce the expression of vagal markers (FIG. 1A). Upon RA exposure Sox10::GFP+NC precursors were obtained with yields comparable to CNC conditions, indicating that RA treatment does not interfere with overall NC induction (FIG. 1B; FIG. 2B). To facilitate the isolation of pure NC populations across various hPSC lines, a candidate surface marker screen was performed and CD49D (α4-integrin) was identified as an epitope that reliably marks early SOX10$^+$ NC lineages (FIG. 1Bb, FIGS. 2A-2C). CD49D was used as a marker to validate NC induction in the presence of RA for additional hPSC lines (both human embryonic stem cells (hESCs) and human induced pluripotent stem cells (hiPSCs), confirming robustness (FIG. 2D). Purified CD49D+NC precursors, derived in the presence of RA, expressed HOXB2-B5 indicative of vagal identity[8,9]but not the more caudal HOX transcripts such as HOXB9 (FIG. 1C). In further agreement with vagal identity, CD49D$^+$, RA-treated NC precursors expressed markers of early enteric NC (ENC) lineages[3] including PAX3, EDNRB and RET (FIG. 1Dd, FIGS. 2E and 2F). Given the paucity of developmental data on human enteric NC development, RNAseq analysis was performed to define global gene expression profiles in hESC-derived enteric NC precursors, in cranial NC (CNC) (no RA), and in melanocyte-biased NC (MNC) (FIG. 2A) as well as in stage-matched CNS precursors[11]. Unsupervised clustering and principle component analysis reliably segregated the transcriptomes of all hPSC-derived NC populations away from CNS lineage cells (FIG. 1E) and further sorted out the various NC sublineages (FIGS. 1E and 1F). The most differentially expressed genes in the ENC compared to CNS lineage included general NC markers such as FOXD3 or TFAP2A but also PAX3 and HOX genes specifically related to the ENC lineage (FIG. 1G). CNC and MNC were also enriched in general NC markers but showed high levels of NEUROG1, ISL1 or MLANA, TYR, DCT expression respectively compatible with their NC subtype identity (FIGS. 2G and 2H). Direct comparison of the various NC lineages yielded novel candidate marker of human vagal NC/ENC lineage (FIG. 1G). A list of the top 200 most enriched transcripts for each of the NC lineage is provided as Tables 3-5. Raw RNAseq data are available at GEO http://www.ncbi.nlm.nih.gov/geo/ accession#: GSE66148.

TABLE 3

Top 200 most differentially expressed transcripts
in hESC-derived ENC (vagal/enteric NC) (day 11) versus
hESC-derived CNS (day 11) from RNA seq data

| Gene ID | log2FoldChange | pval |
|---|---|---|
| FOXD3 | 13.64 | 8.01E−199 |
| TBX2 | 12.30 | 6.25E−74 |
| RP4-792G4.2 | 12.17 | 5.81E−151 |
| RNA28S5 | 11.18 | 1.67E−92 |
| TFAP2B | 10.24 | 4.43E−244 |
| INSC | 10.22 | 1.39E−194 |
| RP11-200A13.2 | 10.15 | 1.92E−77 |
| C1orf192 | 9.90 | 1.30E−72 |
| RXRG | 9.82 | 2.71E−136 |
| CFH | 9.81 | 0.000347368 |
| PAX3 | 9.79 | 8.08E−222 |
| OR7E12P | 9.73 | 2.48E−71 |
| UGT2B7 | 9.72 | 3.25E−69 |
| CERKL | 9.54 | 8.82E−155 |
| SYNC | 9.41 | 4.51E−104 |
| TMEM204 | 9.39 | 3.56E−69 |
| AC093162.3 | 9.36 | 2.13E−53 |
| RPS7P3 | 9.32 | 4.62E−192 |
| CCDC140 | 9.28 | 1.12E−61 |
| RP11-894P9.1 | 9.17 | 3.54E−52 |
| AC004920.2 | 9.06 | 1.23E−80 |
| GJB1 | 9.05 | 3.02E−58 |
| RP11-199A1.1 | 8.97 | 1.56E−43 |
| ECEL1P2 | 8.94 | 9.90E−137 |
| IL7 | 8.88 | 2.87E−48 |
| ASCL1 | 8.86 | 2.09E−156 |
| RP11-332H18.4 | 8.84 | 4.24E−74 |
| PHACTR3 | 8.82 | 1.25E−74 |
| LRRC37A16P | 8.78 | 1.04E−100 |
| PCDH12 | 8.70 | 2.29E−39 |
| RP11-445N18.3 | 8.64 | 1.09E−137 |
| RP11-609L23.2 | 8.56 | 7.74E−39 |
| FAM75C1 | 8.46 | 6.14E−36 |
| ITGA8 | 8.40 | 4.37E−145 |
| RP11-264B17.2 | 8.38 | 1.49E−33 |
| AC007620.3 | 8.34 | 2.99E−84 |
| RP11-513I15.6 | 8.30 | 1.17E−155 |
| RP11-10G12.1 | 8.29 | 4.88E−157 |
| MLANA | 8.25 | 1.52E−45 |
| RP11-348J24.2 | 8.19 | 3.32E−26 |
| FOXD2 | 8.19 | 2.06E−44 |
| CHCHD2P2 | 8.11 | 3.31E−97 |
| OTOP1 | 8.08 | 3.73E−11 |
| RP11-111F16.2 | 8.05 | 2.37E−63 |
| CTD-3110H11.1 | 8.04 | 1.16E−28 |
| CTD-2015H6.2 | 7.99 | 1.10E−29 |
| GPR17 | 7.99 | 2.19E−30 |
| WNT1 | 7.94 | 1.64E−26 |
| RP11-977G19.12 | 7.92 | 7.53E−24 |
| RP11-463C14.1 | 7.87 | 8.37E−81 |
| RP11-941H19.1 | 7.87 | 6.40E−178 |
| AC138035.2 | 7.84 | 2.89E−58 |
| ETS1 | 7.72 | 1.37E−186 |
| AL390877.1 | 7.70 | 1.23E−104 |
| RSL24D1P3 | 7.67 | 9.49E−22 |
| RP11-817O13.2 | 7.66 | 2.31E−22 |
| FMO1 | 7.55 | 4.20E−21 |
| SOX10 | 7.53 | 5.09E−183 |
| AC019129.1 | 7.53 | 9.84E−94 |
| SP5 | 7.50 | 5.23E−129 |
| RP11-621K7.1 | 7.48 | 9.98E−132 |
| CELF2-AS1 | 7.46 | 1.19E−21 |
| NPR3 | 7.45 | 1.40E−80 |
| COL11A2 | 7.41 | 3.84E−174 |
| HOXB3 | 7.40 | 1.31E−11 |
| MIR25 | 7.38 | 7.59E−09 |
| RP11-707P17.2 | 7.36 | 1.35E−32 |
| NEUROG1 | 7.34 | 7.71E−107 |
| ALX4 | 7.33 | 2.80E−38 |
| AC092171.4 | 7.31 | 3.28E−73 |
| RPL41P1 | 7.30 | 8.69E−86 |
| RP11-638F5.1 | 7.28 | 3.23E−24 |
| RP11-349N19.2 | 7.27 | 1.45E−147 |
| MCMDC2 | 7.27 | 1.17E−17 |
| WDR88 | 7.24 | 1.44E−18 |
| AC009963.6 | 7.22 | 3.02E−17 |
| NOSTRIN | 7.22 | 3.61E−16 |
| ERMN | 7.20 | 1.36E−10 |
| CHRND | 7.20 | 1.55E−15 |
| RP11-154D6.1 | 7.20 | 5.32E−17 |
| RBMS3-AS3 | 7.19 | 4.88E−14 |
| RP11-572C15.3 | 7.19 | 1.69E−18 |
| ABCA8 | 7.19 | 5.61E−12 |
| FAM184B | 7.12 | 1.89E−103 |
| LAT2 | 7.12 | 1.57E−15 |
| RP3-510O8.4 | 7.11 | 4.67E−16 |
| POU4F1 | 7.09 | 1.48E−74 |
| FXYD3 | 7.06 | 2.52E−25 |
| RP11-354M1.3 | 7.05 | 1.18E−81 |
| MORC2-AS1 | 7.05 | 4.34E−26 |
| FAM86GP | 7.04 | 7.28E−77 |
| SFRP5 | 7.04 | 0.008910204 |
| CTC-209H22.2 | 7.04 | 7.36E−67 |
| RP11-244J10.1 | 7.02 | 2.42E−156 |
| RP11-355O1.7 | 7.01 | 2.89E−118 |
| RP13-270P17.2 | 7.01 | 6.59E−28 |
| EMCN | 7.00 | 7.35E−38 |
| CYP26A1 | 6.97 | 0.001696401 |
| RP11-204L24.2 | 6.96 | 6.29E−30 |
| RP11-495K9.9 | 6.95 | 1.15E−29 |
| RP11-775B15.3 | 6.94 | 1.42E−45 |
| CTD-2010I16.1 | 6.89 | 2.03E−17 |
| RP11-450D21.1 | 6.87 | 1.72E−69 |
| AC092933.3 | 6.86 | 3.63E−108 |
| RP11-266L9.2 | 6.86 | 6.70E−16 |
| RFX6 | 6.86 | 5.50E−11 |
| RPL5P33 | 6.84 | 4.55E−51 |
| RP11-834C11.3 | 6.80 | 1.01E−08 |
| CTC-484M2.1 | 6.78 | 5.33E−148 |
| HNF1A | 6.77 | 9.59E−24 |
| NR1I3 | 6.74 | 3.06E−12 |
| RP11-478C6.4 | 6.73 | 7.22E−141 |
| RP11-650L12.2 | 6.72 | 6.58E−11 |
| RBMS3 | 6.71 | 5.03E−115 |
| SPP1 | 6.71 | 2.99E−141 |
| AC005013.1 | 6.71 | 2.24E−19 |
| RP11-430L17.1 | 6.70 | 2.82E−133 |
| TM6SF1 | 6.69 | 3.27E−52 |
| CHI3L2 | 6.69 | 2.48E−10 |
| APOD | 6.66 | 2.14E−26 |
| CTD-2298J14.2 | 6.66 | 1.91E−12 |
| ANKRD36BP1 | 6.66 | 7.18E−46 |
| RP11-299L17.4 | 6.66 | 8.02E−78 |
| RP11-263F19.1 | 6.63 | 1.90E−117 |
| RP11-707G14.6 | 6.62 | 5.06E−14 |
| OSTCP4 | 6.61 | 6.74E−40 |
| HOXB2 | 6.59 | 1.12E−70 |
| LRTM1 | 6.59 | 3.25E−14 |
| RP11-728F11.4 | 6.57 | 2.01E−19 |
| PRG4 | 6.57 | 5.67E−13 |
| NELL1 | 6.56 | 1.05E−07 |
| RP11-98L12.2 | 6.55 | 9.71E−11 |
| AC044860.1 | 6.54 | 1.50E−23 |
| RP11-54F2.1 | 6.53 | 2.27E−10 |
| OLIG3 | 6.51 | 9.39E−05 |
| PRDM12 | 6.49 | 7.46E−107 |
| FAM212A | 6.48 | 5.37E−90 |
| TLX3 | 6.46 | 1.24E−24 |
| RP4-584D14.5 | 6.43 | 8.49E−18 |
| FAM78B | 6.42 | 2.62E−97 |
| CTC-451P13.1 | 6.42 | 3.03E−137 |
| RPL19P21 | 6.42 | 7.25E−110 |
| RP4-584D14.6 | 6.39 | 2.38E−10 |
| RP1-266L20.2 | 6.39 | 8.06E−46 |
| ERBB3 | 6.38 | 1.81E−144 |
| CYP19A1 | 6.37 | 2.85E−17 |
| KB-1639H6.3 | 6.36 | 2.08E−37 |
| TPI1P3 | 6.36 | 1.87E−24 |

TABLE 3-continued

Top 200 most differentially expressed transcripts
in hESC-derived ENC (vagal/enteric NC) (day 11) versus
hESC-derived CNS (day 11) from RNA seq data

| Gene ID | log2FoldChange | pval |
|---|---|---|
| AC010615.1 | 6.34 | 7.18E−11 |
| RP11-364L4.1 | 6.33 | 7.43E−136 |
| MIR4737 | 6.32 | 6.58E−18 |
| RP11-61J19.4 | 6.32 | 1.35E−18 |
| ROPN1B | 6.32 | 5.61E−30 |
| TNFRSF19 | 6.30 | 3.99E−138 |
| ITGA4 | 6.28 | 5.15E−135 |
| RHOJ | 6.28 | 2.55E−106 |
| RP1-59D14.5 | 6.27 | 2.35E−24 |
| RP11-259G18.3 | 6.25 | 6.55E−27 |
| EIF4A1P13 | 6.24 | 3.36E−10 |
| RP11-180A12.1 | 6.24 | 2.35E−09 |
| C20orf151 | 6.22 | 8.04E−10 |
| MAP3K5 | 6.22 | 4.49E−28 |
| ALPP | 6.22 | 4.25E−12 |
| RP11-133F8.2 | 6.21 | 5.86E−17 |
| CD37 | 6.21 | 3.30E−58 |
| FTH1P5 | 6.21 | 4.11E−116 |
| LMOD2 | 6.19 | 2.09E−08 |
| RP11-382J24.2 | 6.19 | 5.76E−65 |
| SLC9A3 | 6.17 | 5.42E−73 |
| RP11-849F2.5 | 6.16 | 6.50E−17 |
| SEPHS1P1 | 6.16 | 4.43E−28 |
| APOA2 | 6.16 | 0.004139383 |
| RP11-667K14.3 | 6.15 | 1.73E−08 |
| RP11-945C19.4 | 6.14 | 9.42E−08 |
| GABRG2 | 6.12 | 1.14E−48 |
| RP11-578F5.1 | 6.12 | 7.44E−133 |
| EDAR | 6.11 | 2.83E−08 |
| CTD-2266L18.1 | 6.11 | 4.30E−10 |
| FTH1P12 | 6.11 | 1.85E−108 |
| S100B | 6.08 | 5.74E−104 |
| EGFLAM | 6.08 | 3.53E−60 |
| RP11-350E12.4 | 6.07 | 2.82E−16 |
| RP11-348P10.1 | 6.05 | 1.75E−07 |
| RP11-57C19.2 | 6.05 | 2.38E−78 |
| COL23A1 | 6.04 | 9.92E−78 |
| MASP2 | 6.04 | 6.80E−56 |
| CTD-2186M15.1 | 6.03 | 2.05E−106 |
| RPS7P8 | 6.01 | 4.03E−109 |
| RP11-645C24.2 | 6.00 | 5.80E−29 |
| AC093106.7 | 6.00 | 1.47E−119 |
| DRGX | 5.97 | 1.03E−09 |
| HMGB1P37 | 5.95 | 5.20E−78 |
| POM121L10P | 5.95 | 2.16E−08 |
| RP11-283C24.1 | 5.95 | 2.58E−43 |
| RP11-23E10.4 | 5.94 | 5.94E−25 |
| LINC00595 | 5.92 | 1.23E−16 |
| CTD-2341M24.1 | 5.92 | 8.54E−07 |
| AC009410.1 | 5.92 | 1.19E−07 |
| ART3 | 5.91 | 7.17E−24 |
| MIR647 | 5.91 | 9.85E−09 |

TABLE 4

Top 200 most differentially expressed transcripts
in hESC-derived CNC (cranial NC) (day 11) versus
hESC-derived CNS (day 11) from RNA seq data

| id | log2FoldChange | pval |
|---|---|---|
| FOXD3 | 12.91 | 3.54E−175 |
| RP4-792G4.2 | 12.27 | 4.58E−154 |
| FOXD2 | 11.48 | 3.69E−119 |
| RNA28S5 | 11.41 | 4.59E−96 |
| GJB1 | 11.24 | 2.50E−113 |
| CCDC140 | 10.67 | 1.09E−93 |
| MLANA | 10.49 | 3.15E−104 |
| RXRG | 10.47 | 5.07E−157 |
| POU4F1 | 10.40 | 2.17E−142 |
| TFAP2B | 10.28 | 1.22E−245 |

TABLE 4-continued

Top 200 most differentially expressed transcripts
in hESC-derived CNC (cranial NC) (day 11) versus
hESC-derived CNS (day 11) from RNA seq data

| id | log2FoldChange | pval |
|---|---|---|
| RP11-200A13.2 | 10.12 | 8.43E−77 |
| C1orf192 | 10.09 | 7.33E−77 |
| PHACTR3 | 9.85 | 1.36E−98 |
| OR7E12P | 9.77 | 2.81E−72 |
| RP11-894P9.1 | 9.73 | 2.88E−62 |
| UGT2B7 | 9.72 | 2.54E−69 |
| PAX3 | 9.71 | 3.47E−219 |
| NEUROG1 | 9.64 | 3.63E−178 |
| RP11-638F5.1 | 9.49 | 1.56E−56 |
| TLX3 | 9.47 | 1.19E−73 |
| SYNC | 9.39 | 9.40E−104 |
| INSC | 9.26 | 4.16E−163 |
| PPP1R17 | 9.25 | 8.39E−120 |
| RPS7P3 | 9.19 | 1.02E−187 |
| IL7 | 9.17 | 2.91E−53 |
| LRRC37A16P | 9.13 | 1.97E−110 |
| WNT1 | 9.02 | 1.98E−34 |
| DRGX | 9.00 | 8.91E−30 |
| AC004920.2 | 8.99 | 4.44E−79 |
| AC093162.3 | 8.96 | 6.01E−47 |
| ITGA8 | 8.95 | 2.12E−162 |
| TMEM204 | 8.86 | 4.95E−57 |
| LRCOL1 | 8.79 | 8.50E−102 |
| RP11-199A1.1 | 8.73 | 3.69E−40 |
| SP5 | 8.71 | 1.91E−167 |
| RP11-445N18.3 | 8.55 | 7.29E−135 |
| CERKL | 8.54 | 2.19E−124 |
| FAM75C1 | 8.50 | 1.48E−36 |
| RP11-513I15.6 | 8.42 | 1.47E−159 |
| RP11-463C14.1 | 8.39 | 1.44E−93 |
| AC007620.3 | 8.38 | 2.59E−85 |
| SEC1P | 8.32 | 5.41E−88 |
| RP11-10G12.1 | 8.32 | 5.79E−158 |
| CTD-3110H11.1 | 8.31 | 1.46E−31 |
| CELF2-AS1 | 8.31 | 4.15E−30 |
| TMEM215 | 8.29 | 3.29E−64 |
| RP11-351J23.1 | 8.28 | 1.69E−46 |
| KBTBD5 | 8.26 | 5.64E−29 |
| ISL1 | 8.22 | 1.65E−57 |
| RP11-609L23.2 | 8.20 | 2.72E−34 |
| LRRK2 | 8.19 | 4.24E−133 |
| RP11-111F16.2 | 8.17 | 6.99E−66 |
| ABCC2 | 8.04 | 3.31E−178 |
| AC138035.2 | 8.02 | 7.92E−62 |
| COL11A2 | 8.01 | 2.69E−194 |
| CYP19A1 | 8.00 | 1.57E−37 |
| ROPN1B | 7.96 | 5.56E−56 |
| CHCHD2P2 | 7.94 | 6.61E−93 |
| RP11-264B17.2 | 7.90 | 2.69E−28 |
| WDR88 | 7.84 | 2.04E−23 |
| GPR17 | 7.82 | 1.45E−28 |
| RP11-707P17.2 | 7.74 | 1.38E−37 |
| RP11-941H19.1 | 7.68 | 1.87E−171 |
| TRPM1 | 7.65 | 1.94E−101 |
| AL390877.1 | 7.64 | 3.95E−103 |
| PCDH12 | 7.61 | 2.01E−26 |
| RP11-707G14.6 | 7.59 | 5.01E−21 |
| TBX2 | 7.56 | 1.49E−33 |
| NOSTRIN | 7.56 | 2.46E−18 |
| HHIP | 7.54 | 3.28E−96 |
| CDH15 | 7.53 | 1.27E−66 |
| POU4F2 | 7.53 | 4.81E−29 |
| CTD-2015H6.2 | 7.51 | 5.14E−25 |
| LRTM1 | 7.44 | 1.81E−20 |
| RSL24D1P3 | 7.42 | 8.78E−20 |
| RP13-270P17.2 | 7.40 | 3.87E−32 |
| CTD-2010I16.1 | 7.39 | 3.02E−21 |
| FMO1 | 7.38 | 7.00E−20 |
| RP11-817O13.2 | 7.36 | 6.97E−20 |
| NOTUM | 7.34 | 9.70E−137 |
| RP11-349N19.2 | 7.33 | 1.67E−149 |
| RP11-977G19.12 | 7.32 | 4.88E−19 |
| OTOP1 | 7.29 | 2.91E−09 |
| SIX1 | 7.25 | 4.05E−121 |

TABLE 4-continued

Top 200 most differentially expressed transcripts in hESC-derived CNC (cranial NC) (day 11) versus hESC-derived CNS (day 11) from RNA seq data

| id | log2FoldChange | pval |
|---|---|---|
| RPL41P1 | 7.25 | 9.13E−85 |
| RP11-621K7.1 | 7.24 | 1.94E−124 |
| AC019129.1 | 7.22 | 5.66E−86 |
| POU4F3 | 7.22 | 6.10E−39 |
| RP3-510O8.4 | 7.21 | 9.48E−17 |
| FAM184B | 7.19 | 1.21E−105 |
| RP11-154D6.1 | 7.15 | 9.02E−17 |
| RP11-348J24.2 | 7.13 | 1.00E−17 |
| AC092171.4 | 7.11 | 7.19E−69 |
| MORC2-AS1 | 7.11 | 8.71E−27 |
| TPI1P3 | 7.10 | 2.67E−30 |
| RP11-775B15.3 | 7.09 | 4.44E−48 |
| EMCN | 7.08 | 1.47E−39 |
| LAT2 | 7.03 | 4.69E−15 |
| CTC-209H22.2 | 7.01 | 2.04E−66 |
| CHRND | 7.00 | 5.32E−15 |
| ECEL1P2 | 6.99 | 1.26E−82 |
| RP11-261N11.8 | 6.98 | 9.96E−14 |
| CTD-2314G24.2 | 6.97 | 1.01E−23 |
| PIK3C2G | 6.95 | 4.03E−22 |
| NR1I3 | 6.93 | 3.22E−13 |
| MCMDC2 | 6.93 | 1.56E−15 |
| TLX2 | 6.93 | 8.34E−58 |
| NTN5 | 6.92 | 7.03E−139 |
| HNF1A | 6.91 | 3.01E−25 |
| RP11-572C15.3 | 6.90 | 1.52E−16 |
| AC044860.1 | 6.89 | 4.82E−27 |
| SOX10 | 6.84 | 9.99E−160 |
| RP11-244J10.1 | 6.83 | 4.54E−150 |
| RP11-123K19.1 | 6.81 | 1.72E−11 |
| ANKRD36BP1 | 6.80 | 2.44E−48 |
| RP11-355O1.7 | 6.75 | 1.41E−110 |
| OTOGL | 6.75 | 3.59E−54 |
| PRDM12 | 6.74 | 3.76E−114 |
| RP11-61J19.4 | 6.74 | 2.94E−22 |
| RP11-495K9.9 | 6.73 | 2.36E−27 |
| CTD-2298J14.2 | 6.73 | 7.10E−13 |
| F13A1 | 6.73 | 1.38E−68 |
| RP11-354M1.3 | 6.71 | 7.42E−74 |
| NPR3 | 6.67 | 5.97E−69 |
| CTC-484M2.1 | 6.67 | 2.66E−144 |
| SLC9A3 | 6.65 | 4.85E−85 |
| CD37 | 6.65 | 1.64E−67 |
| FOXI2 | 6.63 | 4.38E−38 |
| TM6SF1 | 6.61 | 6.85E−51 |
| FAM86GP | 6.60 | 4.70E−67 |
| RP11-728F11.4 | 6.58 | 1.40E−19 |
| RUNX1T1 | 6.58 | 2.78E−84 |
| TYR | 6.56 | 5.95E−34 |
| OSTCP4 | 6.55 | 4.42E−39 |
| RPL5P33 | 6.55 | 2.32E−46 |
| AC092933.3 | 6.55 | 2.48E−99 |
| RP11-478C6.4 | 6.54 | 7.27E−135 |
| ABHD12B | 6.54 | 1.04E−43 |
| RP11-430L17.1 | 6.52 | 1.01E−127 |
| OR5BH1P | 6.52 | 6.73E−17 |
| SLC45A2 | 6.50 | 3.95E−46 |
| SLCO1C1 | 6.50 | 5.36E−14 |
| C20orf151 | 6.49 | 4.89E−11 |
| MGLL | 6.49 | 4.45E−131 |
| PRG4 | 6.48 | 1.48E−12 |
| AC009963.6 | 6.39 | 2.73E−12 |
| RP11-263F19.1 | 6.39 | 2.19E−110 |
| RP11-450D21.1 | 6.39 | 2.85E−61 |
| RP4-584D14.5 | 6.37 | 1.95E−17 |
| LMOD2 | 6.36 | 5.67E−09 |
| TNFRSF19 | 6.36 | 5.00E−140 |
| RP11-838N2.4 | 6.36 | 3.33E−14 |
| RP11-259G18.3 | 6.35 | 4.57E−28 |
| LMX1B | 6.34 | 8.80E−87 |
| RPL19P21 | 6.33 | 2.33E−107 |
| RP1-266L20.2 | 6.32 | 7.59E−45 |
| FAM181B | 6.32 | 1.36E−49 |
| SLC34A3 | 6.31 | 7.33E−18 |
| RP11-299L17.4 | 6.31 | 2.02E−69 |
| RP11-645C24.2 | 6.30 | 1.04E−32 |
| AIM1 | 6.28 | 1.26E−56 |
| MIR4737 | 6.28 | 1.24E−17 |
| NEUROD1 | 6.26 | 2.13E−74 |
| RP1-59D14.5 | 6.25 | 3.09E−24 |
| RP11-266L9.2 | 6.25 | 2.31E−12 |
| CHST9-AS1 | 6.23 | 9.96E−11 |
| C1QL3 | 6.23 | 1.71E−45 |
| RP11-667K14.3 | 6.22 | 8.74E−09 |
| CTC-451P13.1 | 6.22 | 7.92E−131 |
| GLTPD2 | 6.21 | 6.80E−15 |
| CTD-2266L18.1 | 6.21 | 1.31E−10 |
| SLN | 6.19 | 5.30E−65 |
| AC008746.3 | 6.17 | 6.29E−07 |
| RP11-98L12.2 | 6.17 | 3.36E−09 |
| RP11-71H17.7 | 6.16 | 8.22E−51 |
| POM121L10P | 6.15 | 3.43E−09 |
| ETS1 | 6.14 | 9.38E−134 |
| TTN | 6.14 | 2.76E−98 |
| RP11-849F2.5 | 6.14 | 9.29E−17 |
| RP11-197K6.1 | 6.13 | 1.00E−12 |
| ERVW-1 | 6.13 | 1.04E−11 |
| SEPHS1P1 | 6.13 | 9.50E−28 |
| EDAR | 6.11 | 2.84E−08 |
| RP11-244F12.3 | 6.11 | 2.25E−07 |
| C20orf166-AS1 | 6.10 | 3.95E−55 |
| ABCC9 | 6.09 | 1.91E−13 |
| RP11-307C19.1 | 6.09 | 9.92E−08 |
| RP11-364L4.1 | 6.08 | 8.68E−128 |
| ERMN | 6.08 | 3.20E−07 |
| FTH1P5 | 6.08 | 4.51E−112 |
| RP11-180A12.1 | 6.07 | 9.90E−09 |
| AC009410.1 | 6.07 | 3.61E−08 |
| MASP2 | 6.05 | 2.74E−56 |
| RP11-138J23.1 | 6.05 | 3.99E−07 |
| KB-1639H6.3 | 6.05 | 3.06E−33 |
| FOXP2 | 6.04 | 4.57E−45 |
| RP5-881L22.5 | 6.03 | 2.85E−08 |
| RP11-297P16.3 | 6.03 | 6.51E−08 |
| SNCG | 6.03 | 2.93E−86 |
| IGSF10 | 6.02 | 4.51E−16 |

TABLE 5

Top 200 most differentially expressed transcripts in hESC-derived MNC (melanocyte-biased) (day 11) versus hESC-derived CNS (day 11) from RNA seq data

| Gene ID | log2FoldChange | pval |
|---|---|---|
| MLANA | 16.00 | 9.42E−285 |
| TMEM204 | 12.91 | 2.29E−167 |
| FOXD3 | 12.56 | 7.00E−164 |
| TRPM1 | 12.43 | 1.33E−256 |
| RNA28S5 | 12.15 | 3.30E−107 |
| RXRG | 12.05 | 8.78E−208 |
| EMCN | 11.87 | 3.86E−163 |
| GJB1 | 11.85 | 6.53E−130 |
| TYR | 11.67 | 1.84E−162 |
| TMEM215 | 11.51 | 2.55E−149 |
| RP4-792G4.2 | 11.21 | 2.68E−122 |
| SLC45A2 | 11.21 | 3.08E−174 |
| TBX2 | 11.18 | 2.80E−64 |
| INSC | 10.99 | 4.91E−220 |
| PHACTR3 | 10.60 | 1.47E−116 |
| CCDC140 | 10.55 | 8.85E−91 |
| TFAP2B | 10.49 | 8.98E−253 |
| CYP19A1 | 10.31 | 3.66E−78 |
| PAX3 | 10.14 | 6.69E−234 |
| RP11-838N2.4 | 10.13 | 3.43E−61 |

TABLE 5-continued

Top 200 most differentially expressed transcripts in hESC-derived MNC (melanocyte-biased) (day 11) versus hESC-derived CNS (day 11) from RNA seq data

| Gene ID | log2FoldChange | pval |
| --- | --- | --- |
| RP11-200A13.2 | 9.97 | 2.39E-73 |
| LRRC37A16P | 9.95 | 9.97E-134 |
| RP3-527G5.1 | 9.87 | 4.69E-60 |
| UGT2B7 | 9.81 | 3.26E-71 |
| C1orf192 | 9.71 | 1.55E-68 |
| PTGDS | 9.65 | 1.60E-202 |
| ABCC2 | 9.46 | 7.13E-226 |
| RP11-638F5.1 | 9.39 | 1.01E-54 |
| GPNMB | 9.29 | 4.26E-198 |
| RP11-894P9.1 | 9.13 | 2.23E-51 |
| GPR17 | 9.11 | 5.84E-45 |
| IL7 | 9.10 | 6.18E-52 |
| RPS7P3 | 9.09 | 1.09E-184 |
| BCAN | 9.07 | 1.39E-227 |
| AC093162.3 | 8.99 | 2.25E-47 |
| LRRN4CL | 8.96 | 4.24E-110 |
| SLCO1C1 | 8.86 | 3.56E-34 |
| OR7E12P | 8.77 | 2.57E-52 |
| ST6GALNAC2 | 8.74 | 1.68E-176 |
| CERKL | 8.67 | 4.04E-128 |
| CHCHD2P2 | 8.66 | 4.21E-112 |
| A2M | 8.63 | 3.57E-214 |
| SYNC | 8.63 | 5.24E-84 |
| AC004920.2 | 8.60 | 2.21E-70 |
| GLRA2 | 8.56 | 2.83E-73 |
| BHLHE41 | 8.49 | 6.66E-142 |
| RP11-609L23.2 | 8.48 | 8.69E-38 |
| ACP5 | 8.43 | 8.14E-174 |
| PITX2 | 8.43 | 1.22E-24 |
| KBTBD5 | 8.42 | 1.38E-30 |
| RP11-513I15.6 | 8.41 | 2.26E-159 |
| POU4F1 | 8.37 | 1.58E-100 |
| RP11-10G12.1 | 8.32 | 4.84E-158 |
| PCDH12 | 8.24 | 1.45E-33 |
| RP11-111F16.2 | 8.22 | 5.92E-67 |
| WNT1 | 8.20 | 2.71E-28 |
| RP11-445N18.3 | 8.19 | 5.11E-124 |
| BIRC7 | 8.19 | 3.73E-125 |
| RP11-463C14.1 | 8.19 | 1.81E-88 |
| SP5 | 8.17 | 2.85E-150 |
| RP11-199A1.1 | 8.17 | 1.39E-32 |
| AC007620.3 | 8.14 | 1.46E-79 |
| FAM75C1 | 8.12 | 8.70E-32 |
| S100B | 8.09 | 3.52E-167 |
| LZTS1 | 8.01 | 7.40E-179 |
| ERVW-1 | 8.01 | 9.43E-24 |
| ETS1 | 8.00 | 3.96E-196 |
| LRTM1 | 8.00 | 3.99E-25 |
| RP11-817O13.2 | 7.97 | 4.32E-25 |
| CELF2-AS1 | 7.94 | 3.41E-26 |
| SLC6A17 | 7.92 | 1.87E-128 |
| ROPN1B | 7.89 | 9.59E-55 |
| CEACAM1 | 7.89 | 6.19E-99 |
| AC138035.2 | 7.76 | 1.31E-56 |
| RP11-941H19.1 | 7.72 | 8.09E-173 |
| FOXD2 | 7.71 | 5.87E-36 |
| FSTL5 | 7.69 | 1.07E-94 |
| CHRND | 7.68 | 6.93E-17 |
| SGCD | 7.68 | 3.93E-29 |
| NEUROG1 | 7.66 | 1.55E-116 |
| CAPN3 | 7.66 | 9.80E-80 |
| C7 | 7.64 | 1.11E-15 |
| AC019129.1 | 7.63 | 1.74E-96 |
| RP11-264B17.2 | 7.61 | 3.28E-25 |
| PPP1R17 | 7.60 | 7.86E-79 |
| FCRLA | 7.57 | 1.06E-65 |
| RP11-707G14.6 | 7.56 | 9.26E-21 |
| CTD-2266L18.1 | 7.56 | 4.21E-18 |
| CHST9-AS1 | 7.55 | 8.77E-18 |
| CTD-2015H6.2 | 7.55 | 3.04E-25 |
| GRAP2 | 7.53 | 5.29E-15 |
| RSL24D1P3 | 7.51 | 1.95E-20 |
| ITGA8 | 7.51 | 1.07E-117 |
| RP11-347E10.1 | 7.49 | 6.22E-29 |
| TMEM117 | 7.43 | 3.79E-116 |
| AIM1 | 7.43 | 1.15E-79 |
| TYRP1 | 7.43 | 3.87E-86 |
| AC092171.4 | 7.40 | 2.98E-75 |
| LRRK2 | 7.39 | 8.00E-110 |
| GALNTL6 | 7.38 | 7.18E-32 |
| CTC-209H22.2 | 7.37 | 2.35E-74 |
| PZP | 7.37 | 2.15E-13 |
| FMO1 | 7.34 | 1.79E-19 |
| FAM212A | 7.33 | 3.14E-113 |
| RP11-977G19.12 | 7.32 | 5.83E-19 |
| DCT | 7.30 | 3.34E-170 |
| RP11-621K7.1 | 7.29 | 4.97E-126 |
| OAS1 | 7.27 | 9.42E-14 |
| SOX10 | 7.26 | 5.14E-174 |
| RP11-707P17.2 | 7.24 | 3.60E-31 |
| RPL41P1 | 7.23 | 4.51E-84 |
| RP11-340F14.5 | 7.21 | 1.45E-34 |
| RP11-349N19.2 | 7.20 | 4.46E-145 |
| NOTUM | 7.19 | 5.32E-132 |
| CRH | 7.19 | 2.82E-21 |
| AL390877.1 | 7.18 | 8.79E-91 |
| CTD-2010I16.1 | 7.17 | 2.02E-19 |
| RP11-266L9.2 | 7.16 | 7.54E-18 |
| RP11-495K9.9 | 7.16 | 5.13E-32 |
| RHOJ | 7.14 | 1.72E-132 |
| ERMN | 7.14 | 2.23E-10 |
| TFAP2A | 7.14 | 5.75E-155 |
| IL12RB2 | 7.12 | 2.66E-76 |
| RP3-523C21.1 | 7.11 | 1.12E-18 |
| CTD-2298J14.2 | 7.11 | 6.56E-15 |
| MITF | 7.09 | 1.59E-114 |
| P2RX7 | 7.09 | 4.98E-95 |
| HEY2 | 7.06 | 1.67E-104 |
| DRGX | 7.04 | 1.02E-15 |
| AC009963.6 | 7.01 | 7.67E-16 |
| ANKRD36BP1 | 7.01 | 9.39E-52 |
| RP11-283G6.3 | 7.00 | 1.02E-09 |
| DLEU7 | 6.99 | 2.10E-65 |
| RP11-354M1.3 | 6.99 | 4.77E-80 |
| TLX3 | 6.97 | 2.69E-31 |
| RP11-775B15.3 | 6.97 | 5.76E-46 |
| EIF4A1P13 | 6.96 | 1.62E-13 |
| RP11-299L17.4 | 6.95 | 6.78E-85 |
| UNC13C | 6.94 | 5.97E-18 |
| WDR88 | 6.94 | 2.05E-16 |
| RP11-182J1.14 | 6.93 | 8.26E-43 |
| TP63 | 6.93 | 7.87E-55 |
| OSTCP4 | 6.91 | 1.82E-44 |
| PIK3C2G | 6.89 | 1.63E-21 |
| LAT2 | 6.85 | 6.11E-14 |
| RP11-154D6.1 | 6.83 | 1.06E-14 |
| ISL1 | 6.83 | 2.07E-40 |
| RP11-351J23.1 | 6.83 | 4.97E-28 |
| LRG1 | 6.81 | 1.14E-08 |
| RP11-645C24.2 | 6.80 | 2.60E-39 |
| RP11-332H18.4 | 6.80 | 2.36E-40 |
| RP11-61J19.4 | 6.79 | 1.51E-22 |
| COL11A2 | 6.78 | 4.65E-153 |
| HNF1A | 6.77 | 9.95E-24 |
| ABCA8 | 6.76 | 2.30E-10 |
| NYX | 6.75 | 3.63E-30 |
| ABCB5 | 6.75 | 3.09E-16 |
| RP11-133F8.2 | 6.75 | 6.29E-21 |
| LY96 | 6.72 | 1.88E-08 |
| CTC-484M2.1 | 6.71 | 9.41E-146 |
| FAM184B | 6.71 | 2.95E-92 |
| CHI3L2 | 6.71 | 2.19E-10 |
| ECEL1P2 | 6.70 | 7.77E-75 |
| MEGF10 | 6.67 | 7.71E-62 |
| RP11-355O1.7 | 6.65 | 1.27E-107 |
| RP11-503C24.6 | 6.65 | 1.81E-20 |
| ATP10B | 6.62 | 9.82E-38 |
| MORC2-AS1 | 6.61 | 6.02E-22 |

TABLE 5-continued

Top 200 most differentially expressed transcripts
in hESC-derived MNC (melanocyte-biased) (day 11) versus
hESC-derived CNS (day 11) from RNA seq data

| Gene ID | log2FoldChange | pval |
|---|---|---|
| RP11-450D21.1 | 6.61 | 5.81E−65 |
| CTD-3110H11.1 | 6.61 | 1.02E−15 |
| RP11-382N13.6 | 6.60 | 1.32E−18 |
| GDNF | 6.59 | 1.81E−73 |
| FTH1P5 | 6.58 | 1.27E−127 |
| MCMDC2 | 6.57 | 2.24E−13 |
| RPL19P21 | 6.57 | 2.67E−114 |
| RP11-572C15.3 | 6.56 | 2.34E−14 |
| PRRX1 | 6.56 | 5.58E−60 |
| POM121L10P | 6.55 | 9.11E−11 |
| FTH1P12 | 6.54 | 9.59E−122 |
| AC092933.3 | 6.54 | 3.74E−99 |
| FBXL21 | 6.54 | 6.37E−19 |
| APOD | 6.51 | 3.02E−25 |
| RP11-98L12.2 | 6.51 | 1.44E−10 |
| C20orf151 | 6.51 | 4.73E−11 |
| RP11-244J10.1 | 6.50 | 5.66E−139 |
| LINC00518 | 6.50 | 1.27E−31 |
| TMEM171 | 6.50 | 4.14E−09 |
| SLC9A3 | 6.48 | 8.24E−81 |
| HHIP | 6.48 | 1.58E−70 |
| GSN-AS1 | 6.43 | 2.20E−09 |
| BCL11A | 6.43 | 1.02E−93 |
| POU4F1-AS1 | 6.41 | 5.36E−09 |
| GLB1L3 | 6.41 | 5.63E−43 |
| XXyac-YX155B6.2 | 6.41 | 4.97E−16 |
| KCNJ15 | 6.40 | 8.77E−08 |
| RP11-430L17.1 | 6.40 | 7.28E−124 |
| ERBB3 | 6.39 | 1.59E−144 |
| SLC34A3 | 6.38 | 2.74E−18 |
| KB-1639H6.3 | 6.35 | 3.00E−37 |
| CTD-2514K5.2 | 6.34 | 3.48E−26 |

One key functional property of the ENC is the ability to migrate extensively after delaminating from the neural tube at the vagal NC level and to colonize the entire length of the gut[3]. Injection of RFP-labeled CD49D+ purified hPSC-derived ENC precursors into the developing chick embryo (FIG. 1H) at the level of the vagal NC resulted in the migration along the trunk of the embryo and colonization of the chick gut (in 22 embryos out of 57 injected) by human cells. In contrast, stage-matched CNC or MNC precursor showed either more diverse migration routes including into cranial regions of the embryo ("CNC) or a migration path largely limited to the dermis (MNC) (FIG. 2I). Only 2 out of 20 embryos injected with CNC showed the presence of some human cells in chick gut. Therefore, molecular, phenotypic and migration data confirm the feasability to enrich for vagal/ENC from hPSCs.

Within The PNS, ENS precursors are unique in their ability to give rise to diverse neuron subsets producing dozens of distinct neurotransmitters and hormones. To address whether hESC-derived ENC precursors are capable of differentiating into a broad range of neuron subtypes, purified CD49D+ ENC precursors were maintained in 3D spheroids for 4 days followed by spontaneous differentiation in adherent cultures in the presence of ascorbic acid (AA) and glial cell line-derived neurotrophic factor (GDNF) (FIG. 3A). The 3D spheroid intermediate culture step was required to retain high levels of SOX10::GFP expression after isolation of CD49D+ cells (FIG. 3B). After replating of the 3D spheroids under differentiation conditions, immature neurons expressing the pan-neuronal marker Tuj1 and the enteric neuron precursor marker PHOX2A emerged (day 20 of differentiation; FIG. 3B). The majority of PHOX2A+ cells were also positive for TRKC (NTRK3), a surface marker expressed in enteric neuron precursors[12] suitable for subsequent enrichment for PHOX2A+ and ASCL1+ precursors (FIGS. 4A and 4B). Temporal expression analysis (FIGS. 4C-4E) showed maintenance of ENC neuronal precursor marker expression by day 40 of differentiation (FIGS. 3C and 3D) followed by a robust increase in the percentage of mature neurons by day 60 (FIGS. 3E and 3F). In agreement with their enteric neuron identity, a broad range of neurotransmitter phenotypes were observed, including 5HT+, GABA+ and NOS+ neurons. The presence of these neurotransmitters in cultures derived from purified CD49D+ RA treated NC precursors indicates ENC origin, since these neurotransmitters are not expressed in other NC derivatives outside of the ENS. Indeed, no 5HT+ neurons were observed in parallel cultures derived from HOX-negative, CD49D+ cells derived under CNC conditions (FIGS. 5A and 5B). CNC-derived precursors differentiated into tyrosine hydroxylase (TH) expressing neurons (FIG. 5C) and gave rise to a high proportion of TRKB (NTRK2)-positive rather than TRKC-positive precursors suggesting enrichment for sympathetic neuron lineages (FIG. 6D). In contrast, the majority of ENC derived precursors expressed TRKC rather than TRKB (FIG. 5E).

Figure 7C:
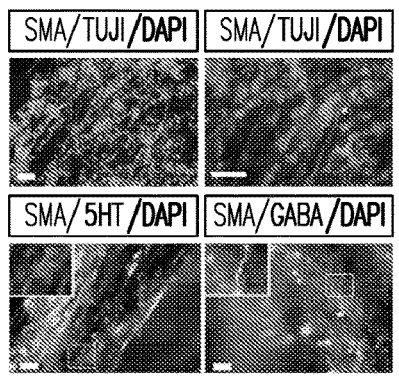
Figure 7B:
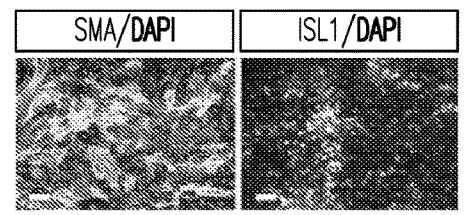
Figure 7D:
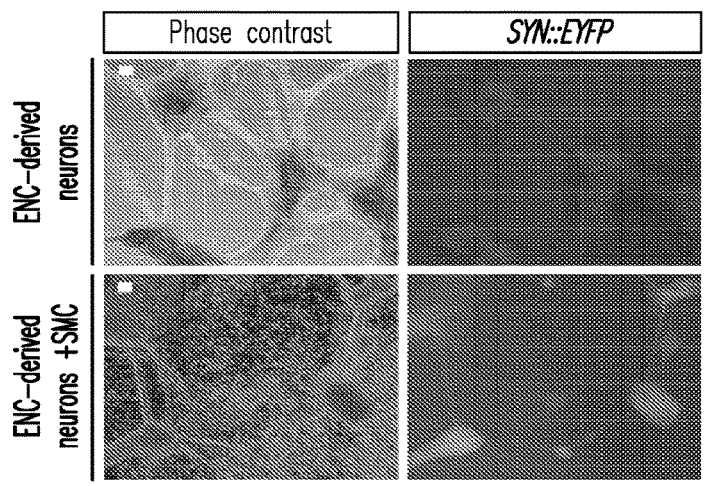
Figure 7E:
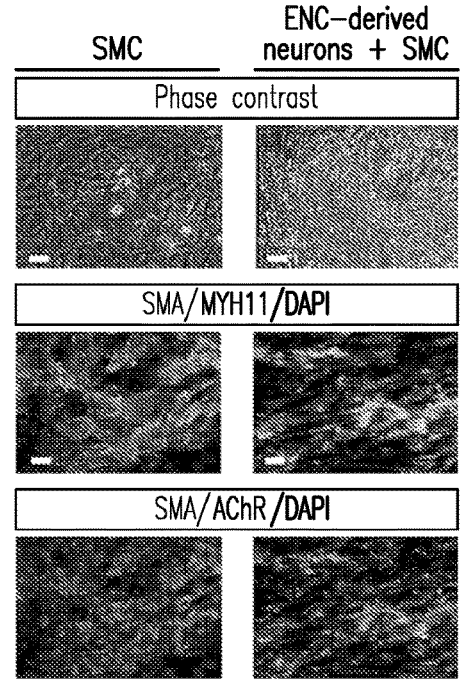

A major function of the ENS is control of peristaltic gut movements via coordinated activation of smooth muscle layers. The functionality of in vitro derived enteric neurons was investigated by assessing their connectivity with smooth muscle cells (SMCs). hESC-derived SMCs were generated via a mesoderm intermediate following exposure to activin A and BMP4 in vitro[13] and culture in the presence of TGFβ (FIG. 7A). The resulting SMC progenitors expressed ISL1 suggesting splanchnic mesoderm identity[14] and were immunoreactive for smooth muscle actin (SMA) (FIG. 7B). For connectivity studies, enteric neurons were derived from a hESC line expressing channelrhodopsin-2 (ChR2)-EYFP under control of the human Synapsin promoter. Use of an optogenetic reporter line allowed for light-induced control of neuronal activity (FIG. 3G). GABA+ and 5HT+ neurons in these co-cultures were closely associated with SMCs compatible with establishing physical connectivity (FIG. 7C). Co-culture of day 25 neurons with SMCs triggered accelerated neuronal maturation as illustrated by the increased expression of SYN::EYFP (FIG. 7D). Conversely, hESC-derived SMCs also showed signs of accelerated maturation under co-culture conditions as illustrated by the expression of mature smooth muscle markers such as myosin heavy chain 11 (MYH11) and acetylcholine receptor (AchR; FIG. 7E) and the ability to contract in response to acetylcholine, carbachol or KCl treatment (FIGS. 8A and 8B). No spontaneous contractions were observed in co-cultures of SMCs and ENC-derived neurons in the absence of light or pharmacological stimulation (day 90 of co-culture). In contrast, 5-10 seconds following light-mediated activation of ChR2 (10 Hz frequency), a wave of SMC contractions could be triggered in SYN::Chr2-YFP neuron containing cultures (FIGS. 3H, 3I, and 8C). Interestingly, both light- and drug-induced SMC contractions were slow and involved the movement of sheet-like structures suggesting coordination among cells possibly via gap junction mediated coupling of SMCs[15]. These studies demonstrate functional connectivity between hESC-derived enteric neurons and SMCs. In vivo interactions of the ENS within the gut, however, are more complex and involve multiple cell types. As a first step in modeling those interactions in 3D, a tissue engineering approach was used, combining in vitro derived human ENC precursors (CD49D+; day 15) with murine primary intestinal tissue (FIG. 3J) without preculture. Using previously established protocols to form organoid units[16], the recombined tissue constructs were seeded onto a scaffold and implanted onto the omentum of immunodeficient hosts for further maturation in vivo[16]. Human cells were readily detected within gut-like structures based on the expression of human-specific markers including SC121 and human synaptophysin. Importantly, cells were located both in submucosal and muscle layers (FIG. 3K), showing their ability to interact with both target cell types.

The repopulation of the gut using in vitro derived ENS lineages could yield novel therapeutic opportunities for ENS disorders such as HD. Previous studies tested the transplantation of variety of candidate cell sources into the fetal or postnatal colon[19-21]. Murine, fetal-derived ENC precursors resulted in the most promising data with evidence for functional integration but limited in vivo migration potential[22]. Furthermore, primary ENC precursors are of very limited scalability and cannot be readily obtained from human sources. To assess the ability of hESC-derived enteric NC precursors to migrate within the postnatal or adult colon, orthotopic (OT) injections of CD49D+ RFP-labeled precursors in NOD-scid IL2Rgamma$^{null}$ (NSG) mice were performed (FIG. 6A). Cells were injected into the wall of the cecum aiming for the muscle layer (FIG. 6A) resulting in a well-defined deposit of RFP+ cells at 1 hour after injection (FIG. 9A; left panel; FIG. 6B; top panel). Remarkably, by 2-4 weeks after transplantation, RFP+ cells had migrated extensively and repopulated the host colon over its entire length from the cecum to the rectum (FIG. 6B). The grafted enteric NC precursors gave rise to clusters along the colon (FIG. 9A; right panel) expressing TUJ1 (FIG. 6C). In contrast, stage-matched CNS and CNC precursors grafted under identical conditions showed only limited migration behavior (FIGS. 9B and 9C).

Figure 6E:
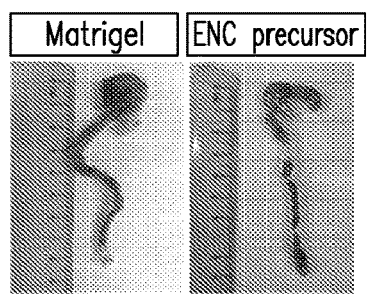
Figure 6F:
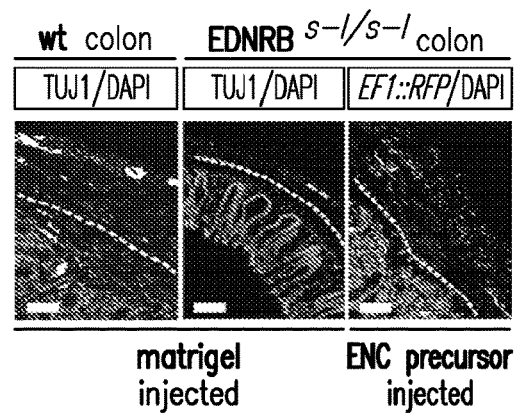
Figure 6G:
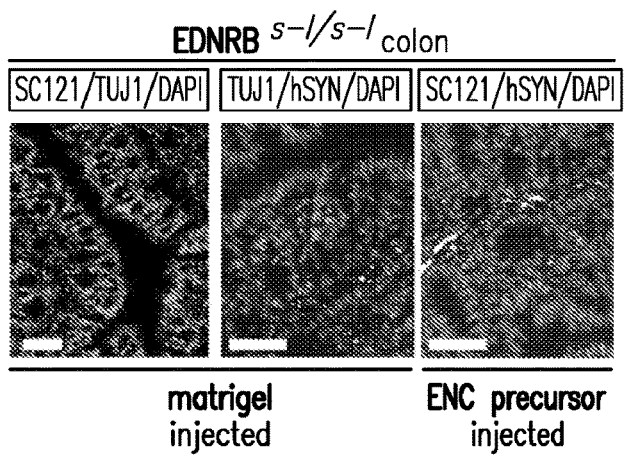
Figure 6H:
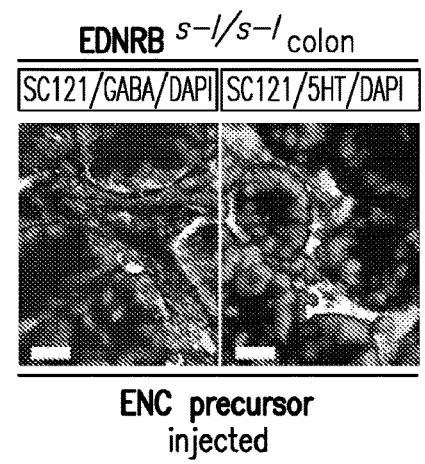
Figure 9J:
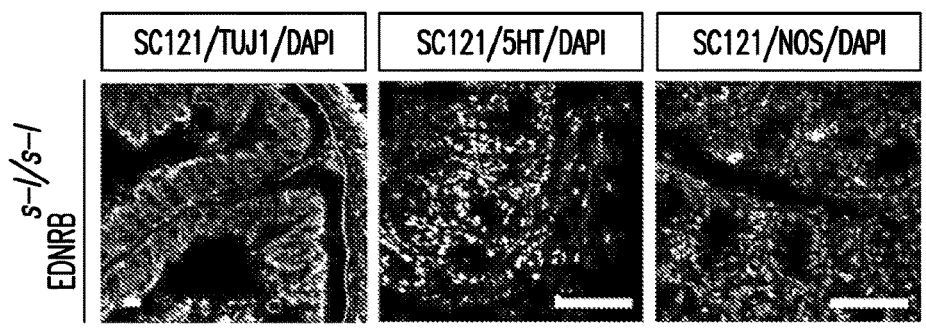

Given the extraordinary ability of the grafted cells to repopulate the host colon, in vivo studies were performed to assess the therapeutic benefit of these enteric NC precursors in an animal model of HD. One widely used genetic model of HD is the EDNRB$^{s-l/s-l}$ mouse[23]. These mice develop a megacolon, because the lack of proper ENS function leads to aberrant peristalsis. As a consequence, mutant mice show a high mortality by 4-6 weeks of age. EDNRB$^{s-l/s-l}$ mice were injected at 2-3 weeks after birth with RFP+ hESC-derived enteric NC precursors (treatment group) or with matrigel vehicle (control group). The majority of control-injected animals (n=6) died over a period of 4-5 weeks (FIG. 6D) with the characteristic megacolon pathology (FIG. 6E). In contrast, all animals injected with hESC-derived NC precursors (n=6) survived (FIG. 6D). Grafted animals were assessed for the extent of graft survival and migration at 6-8 weeks of age. Whole mount fluorescence imaging confirmed the migration of hESC-derived enteric NC precursors within the HD colon with RFP+ cells detected throughout the colon (FIGS. 9D and 9E). In preliminary studies, a trend towards an improved GI transit time was also observed, measured using carmine dye gavage in grafted versus the small subset of matrigel treated animals that survived beyond 6 weeks of treatment (FIG. 9F). Histological analyses at 6 weeks and 3 months after transplantation confirmed myenteric and submucosal localization of the transplanted human cells in HD colon. While human cell location mimicked aspects of endogenous ENS, there was a preference towards submucosal region (FIG. 6F; FIG. 9G upper panel). Human cells were also detected in the distal colon (FIG. 9G, lower panel) in regions where endogenous TUJ1+ cells were greatly decreased. Immunocytochemistry for SC121 and human-specific synaptophysin, not detected in matrigel injected animals (FIG. 6G, left panel), confirmed the presence of human cells in the colon tissue and indicated expression of pre-synaptic markers on the grafted cells (FIG. 6G, right panel). In addition to the expression of neuronal markers such as TUJ1 (FIG. 9G), expression of GFAP was also observd using the human specific SC-123 antibody (FIG. 9H). Finally co-expression of neuron-subtype markers including 5-HT, GABA and NOS with the human specific markers SC121 were observed within the host colonic wall (FIGS. 6H, 9I, and 9J). These transplantation studies indicate that hESC-derived enteric NC precursors migrate extensively within the colon of EDNRB$^{s-l/s-l}$ and are capable of improving survival of host animals.

Figure 10A:
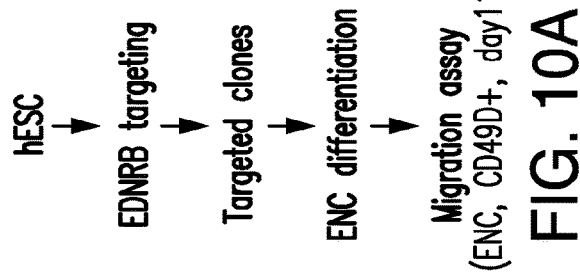
Figure 10G:
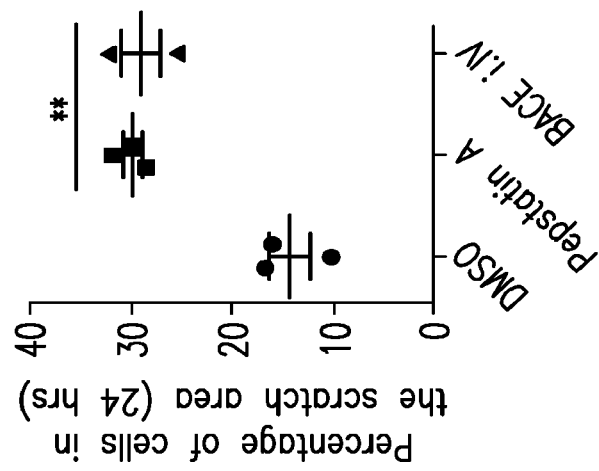
Figure 10F:
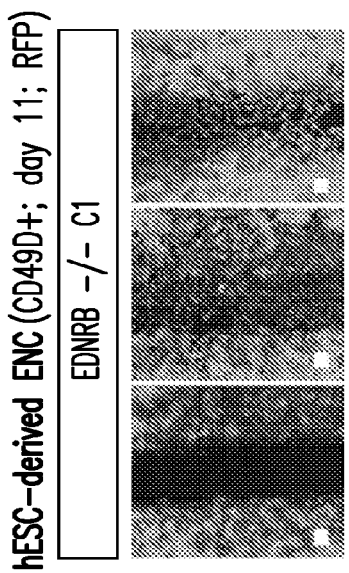

These findings demonstrate that wild-type hPSC-derived ENS precursors can repopulate the colon of HD mice. However, HD-causing mutations often affect the migration of ENS precursor in a cell autonomous manner[3,24]. Therefore, the development of a patient-matched cell therapy for HD may require complementary genetic or pharmacological strategies to overcome defects in ENS precursor migration prior to transplantation. As the causative genetic defects in HD patients are often not known or complex[3,25], and given the need to act quickly in treating HD children, gene correction prior to transplantation may not be a valid option. The inventors therefore assessed whether hPSC-derived ENS precursors can be used to model HD and serve as a platform to screen for candidate compounds that could overcome disease related migration defects. As a first step isogenic hESC lines with homozygous loss-of-function mutations in EDNRB were established using CRISPR/Cas-based gene targeting techniques[26,27] (FIGS. 9A, 9B and 10A). Loss of function mutations in EDNRB is a well-known genetic cause in a subset of HD patients[28]. Enteric NC precursors could be derived at comparable efficiencies from EDNRB-mutant and control lines (FIG. 9C). However, CD49D+ enteric NC precursors from four EDNRB$^{-/-}$ clones showed a striking migration defect in the scratch assay compared to the WT non-targeted isogenic line, modeling aspects of the HD-related ENS phenotype[29,30] (FIGS. 10B and 10C). The inventors next assessed whether EDNRB-/- ENCs display major differences in cell proliferation or survival as compared to wild-type ENCs. At 24 hours after replating (the time point assessed in the scratch assay), significant differences for either assay were not observed (FIGS. 9D and 9E). By 72 hours, EDNRB$^{-/-}$ ENCs did show reduced proliferation while cell viability remained unaffected (FIGS. 9D and 9E).

Figure 10H:
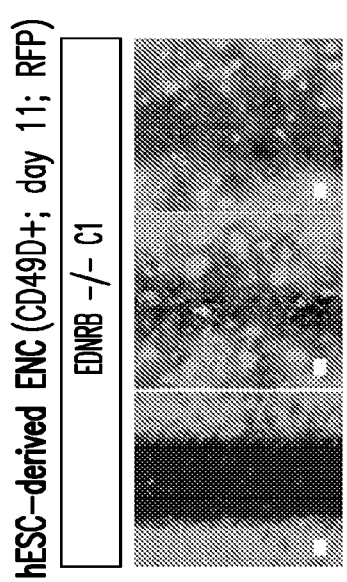
Figure 10I:
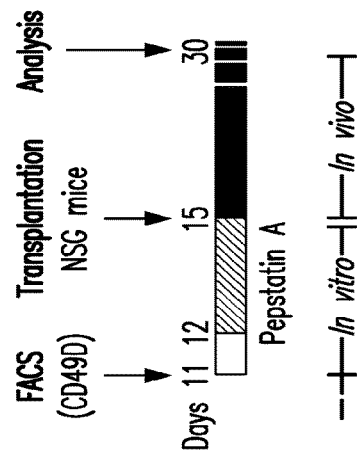
Figure 10J:
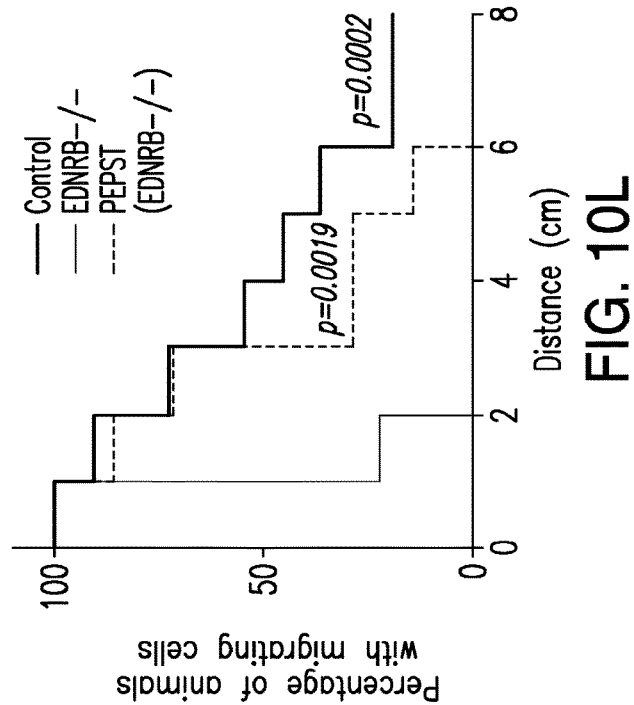
Figure 10K:
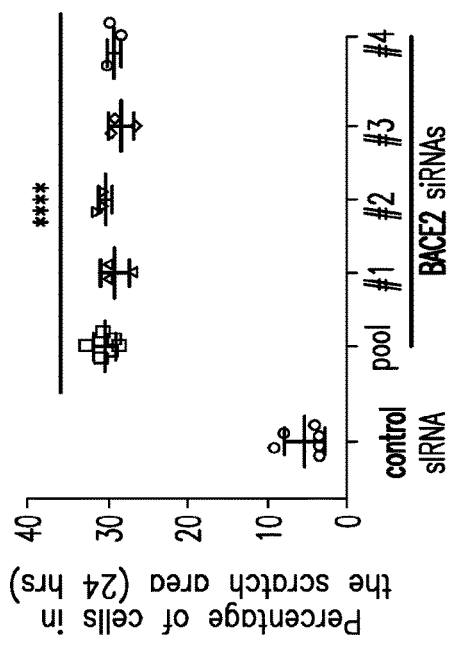
Figure 10L:
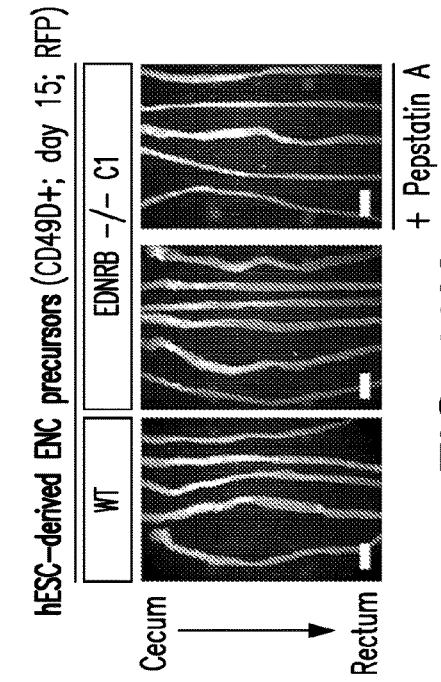
Figure 11A:
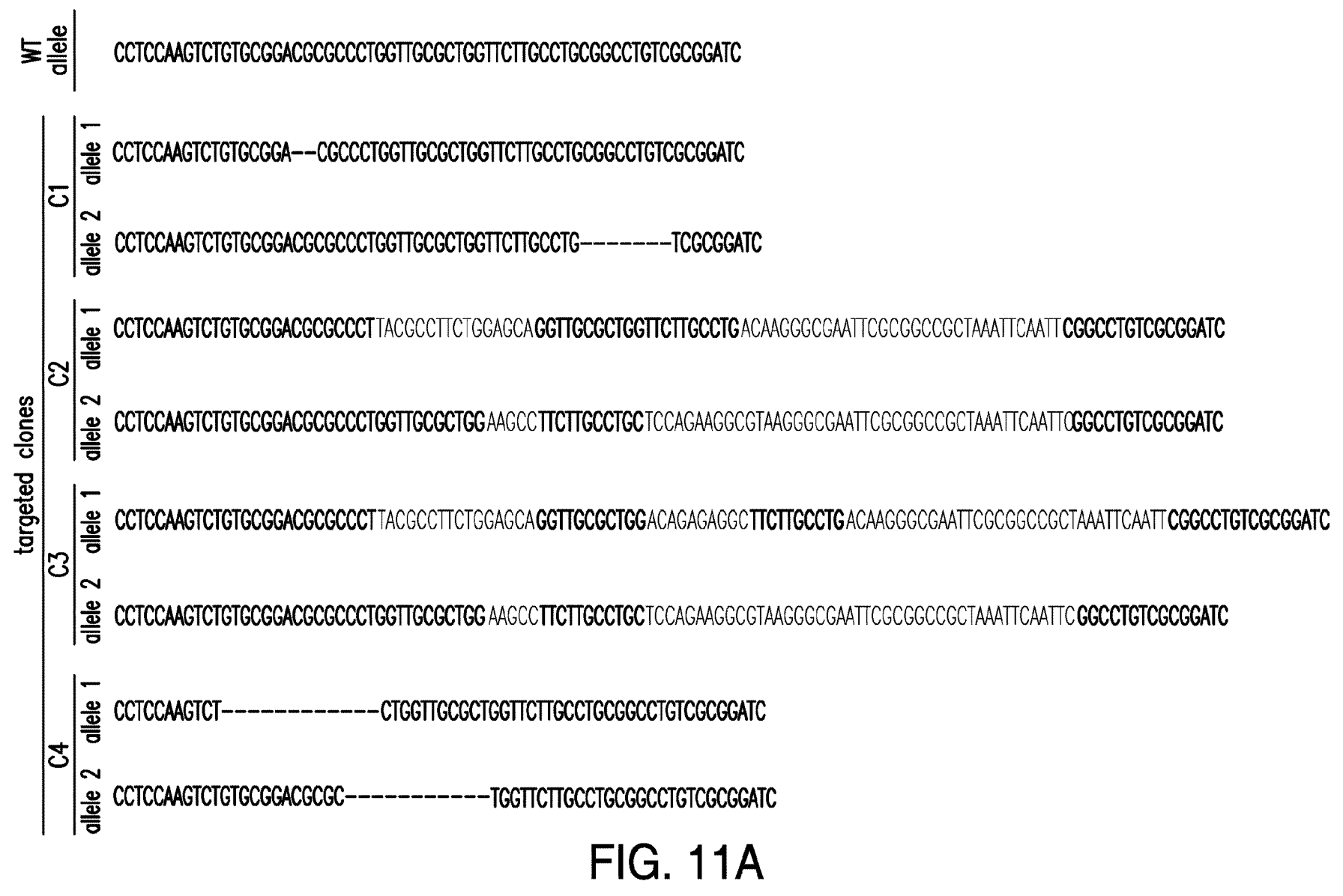
Figure 11B:
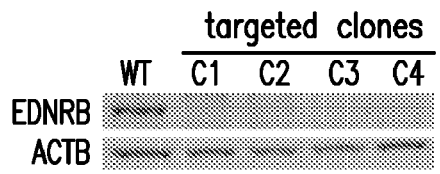
Figure 11C:
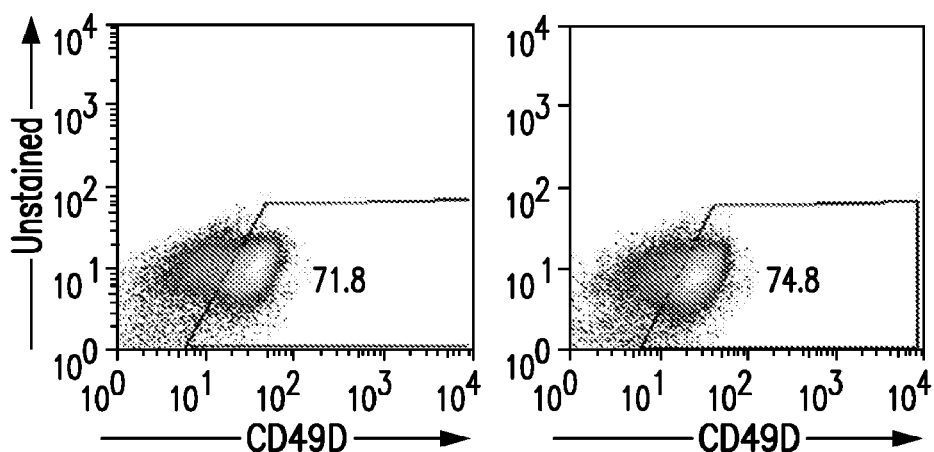
Figure 11D:
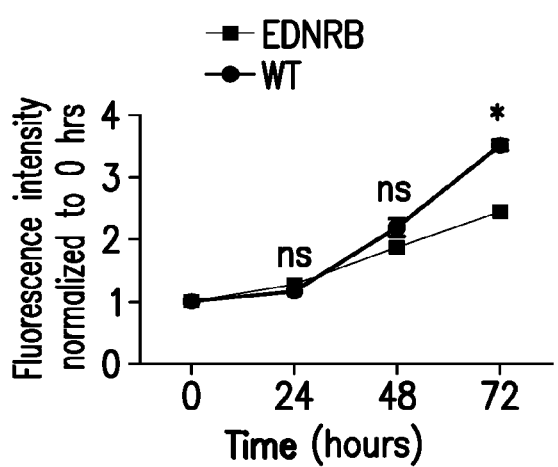
Figure 11E:
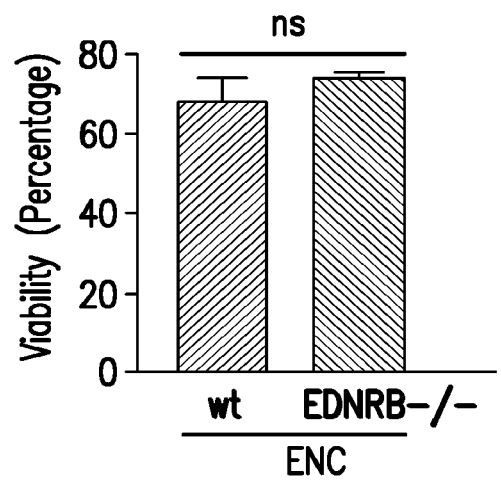
Figure 12A:
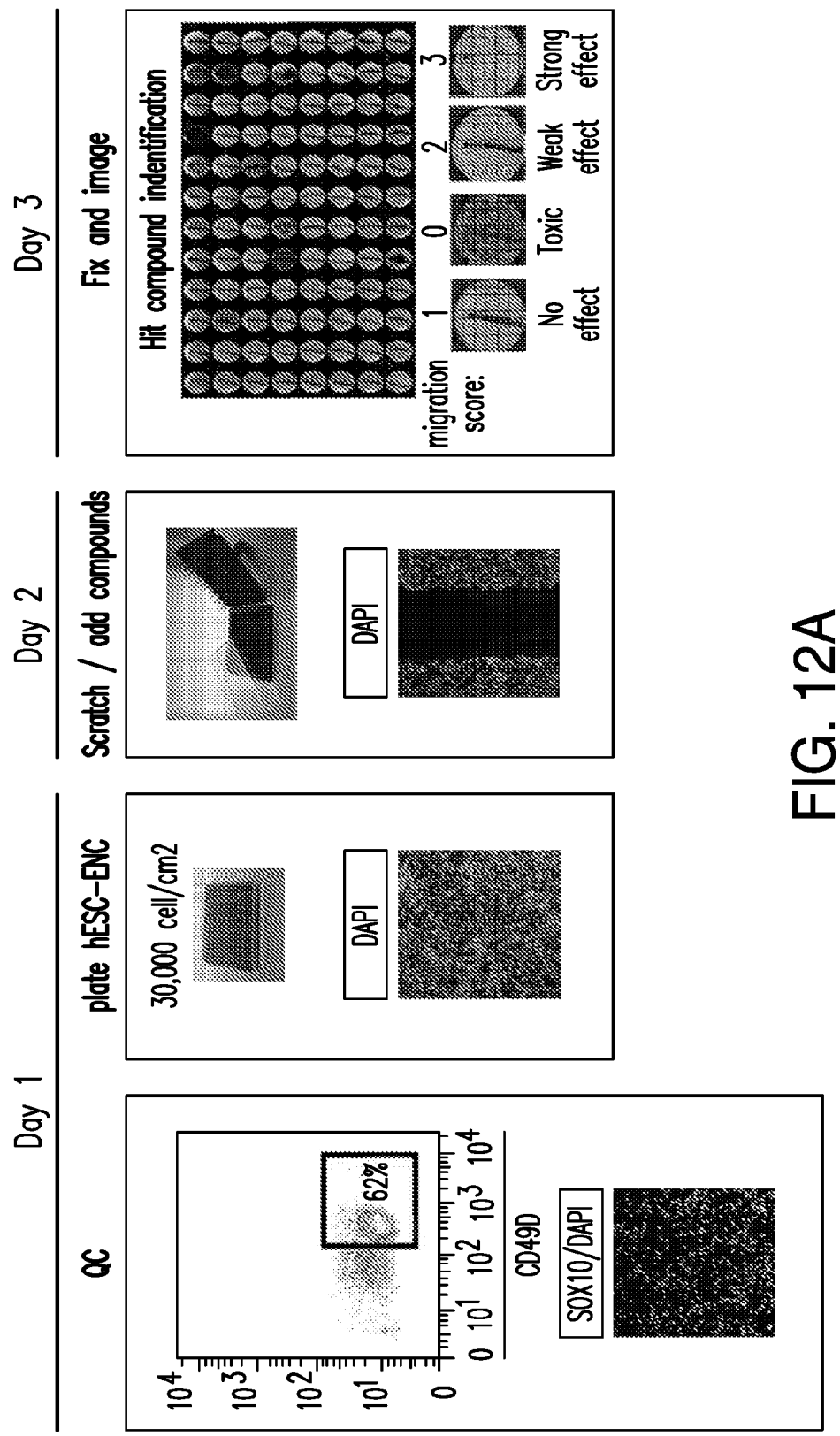
Figure 12B:
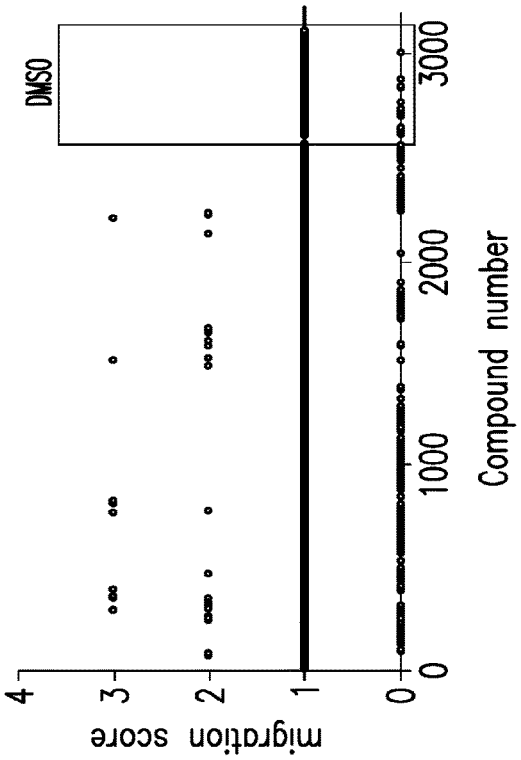
Figure 12C:
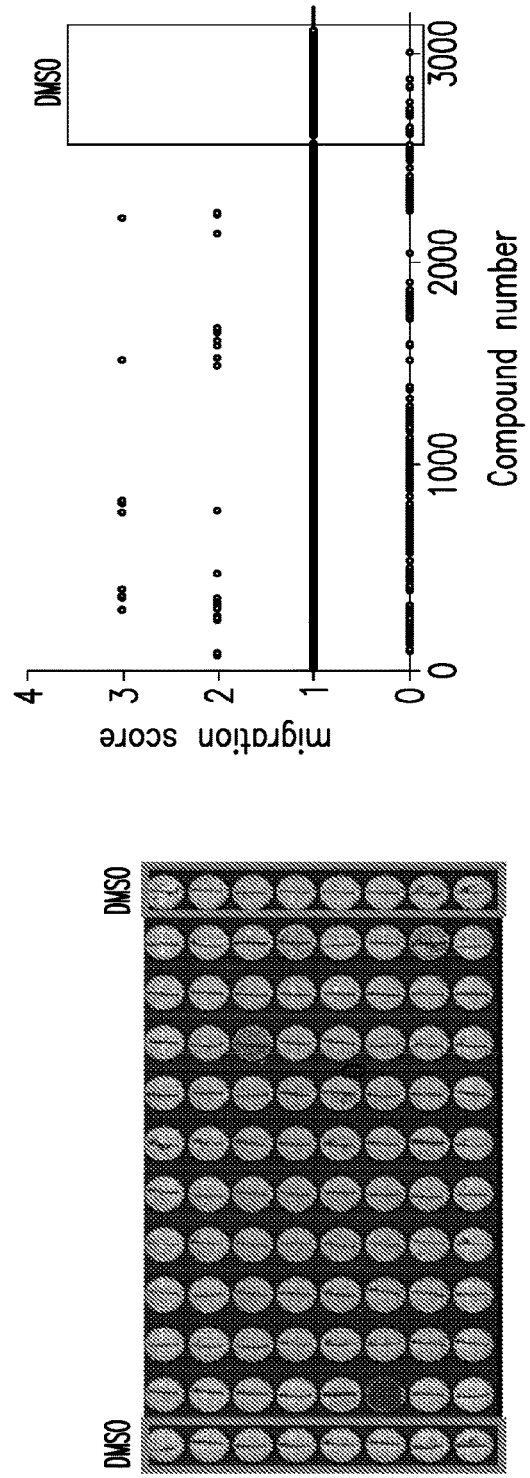
Figure 12D:
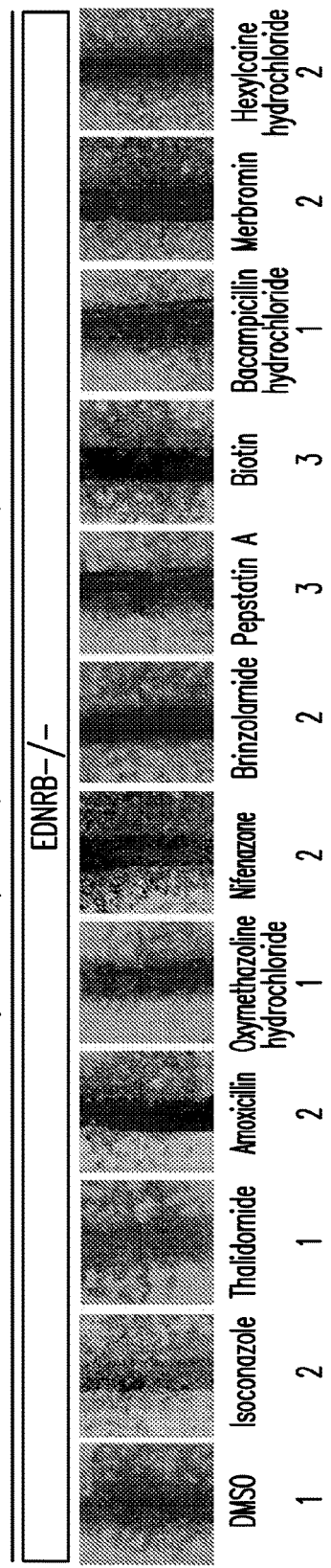
Figure 13E:
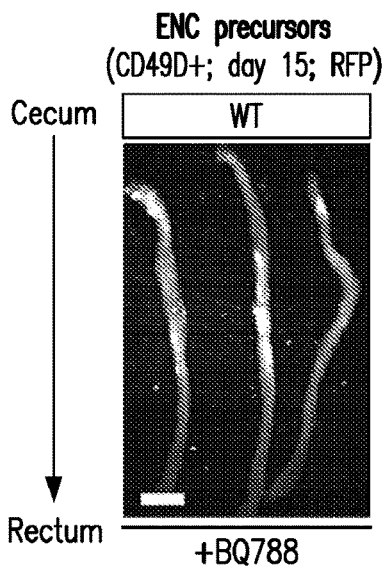
Figure 13F:
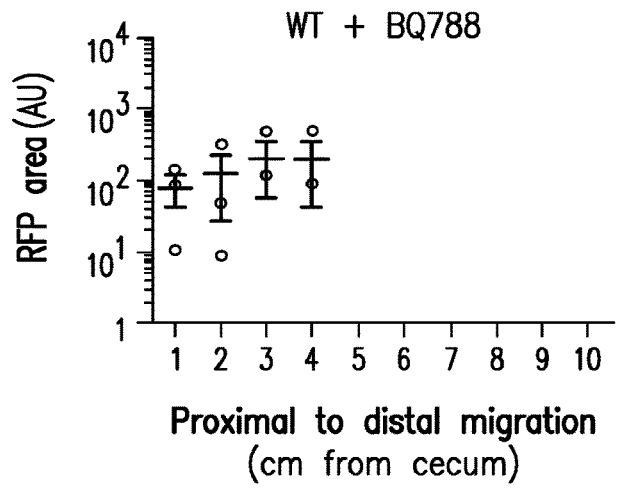

A small molecule screen was carried out to identify compounds capable of rescuing the migration defects observed in EDNRB mutant enteric NC precursors (FIGS. 10D and 11). A library of 1280 compounds (Prestwick Chemical Library®) comprised of FDA-approved compounds was screened to facilitate future translation. Results were binned into compounds with no effect, toxic effects, modest effects or strong effects (FIGS. 10D and 12A-12C). The hits were further validated by repeating the scratch assay under non-HTS conditions (FIG. 12D) and compounds with reproducible strong effects were chosen for further follow-up. Among those validated compounds the molecule Pepstatin A was particularly focused on, which showed a dose-dependent, near complete rescue of the migration defect in EDNRB$^{-/-}$ hESC derived NC precursors (FIG. 10E). Pepstatin A is a known inhibitor of acid proteases and various signaling pathways including ERK and NFAT1c[31]. Among potential Pepstatin targets, BACE2 was explored because the RNAseq data showed upregulation in hESC-derived NC lineages (FIG. 13A) and because BACE-2 had been recently shown to modulate the migration of NC derivatives in the developing zebrafish embryo[32]. To address whether BACE2 mediates the effects of Pepstatin A, the effect of structurally unrelated small molecules targeting BACE2 was tested. Exposure to the BACE inhibitor IV rescued the migration defect in the scratch assay (FIGS. 10F and 10G) similar to Pepstatin A. Furthermore, BACE2 knockdown using 4 different siRNAs confirmed that suppression of BACE-2 rescues migration defects in EDNRB$^{-/-}$ cells (FIGS. 10H, 10I, and 13B). Finally, the inventors tested whether Pepstatin A exposure in vitro (as outlined in FIG. 10J) is sufficient to rescue the in vivo migration behavior of EDNRB$^{-/-}$ ENC precursors. NC precursor derived from EDNRB$^{-/-}$ cells exhibited a significant in vivo migration defect following transplantation into the adult colon (FIGS. 10K and 10L). In contrast, EDNRB-null precursors pretreated with Pepstatin A for 72 hours before transplantation showed a significant rescue of the in vivo migration behavior (FIGS. 10K, 10L, and 13C). Interestingly, wild-type derived ENC precursors treated with pharmacological inhibitors of EDNRB showed similar migration defects in vitro and in vivo (FIGS. 13A-13C), further supporting a role for EDNRB in human ENC migration and HD (FIGS. 13D-13F).

DISCUSSION

The studies described in this example describe an efficient strategy to derive and prospectively purify enteric NC precursors from human ESCs. In agreement with studies in model organisms[1,3], it was demonstrated that hESC-derived enteric NC gives rise to a broad range of neurotransmitter phenotypes characteristic of the ENS. Such remarkable neuron subtype diversity in the ENS is distinct from sensory, sympathetic or parasympathetic PNS lineages, which predominantly generate glutamatergic, catecholaminergic or cholinergic neurons respectively. The ability to model human ENS development in vitro should enable the large scale production of defined human enteric neuron subtypes, a technology not currently available from any other human cell source. For example hPSC-derived enteric 5HT-neurons could serve as a tool to model GI side effects of CNS-acting drugs such as Prozac[33].

The potential cell therapeutic applications of hESC-derived enteric NC lineages in HD was primarily focused on. One of the most remarkable findings was the extensive in vivo migratory potential of human enteric NC precursors in the adult host colon. While most of in vivo studies in NSG mice (a total of 102 animals grafted) were limited to a 5-6 week survival period, animals analyzed at 3 months or 4 months after transplantation showed comparable in vivo properties without any evidence of tumor formation or other graft-related adverse effects. The therapeutic potential of the cells is illustrated by their ability to rescue the survival of EDNRB$^{s-l/s-l}$ mice. The potential for widespread engraftment of the cells may enable permanent, bona fide repair of the aganglionic portions of the gut.

The identification of Pepstatin A and BACE2 inhibition in rescuing HD-related migration defects represents a proof-of-concept for the use of hESC-derived enteric NC precursors in drug discovery. The mechanism of BACE-2 inhibition on migration remains to be elucidated. Possible targets of BACE proteases include neuregulins and ErbB receptors previously implicated in NC lineage migration[34-36]. BACE inhibitors are currently under clinical development for various indications including the treatment of Alzheimer's disease[37]. The therapeutic potential of BACE inhibitors is tested in mouse models of HD. For example, whether those compounds can directly modulate endogenous precursors, independent of any cell-based intervention is tested. Such a strategy may enable the prevention of aganglionosis during pregnancy or target repair of enteric neuron function at postnatal stages. The studies described in this example were focused on combining Pepstatin A as a neoadjuvant treatment to enable improved migration of EDNRB$^{-/-}$ enteric NC precursors. Whether Pepstatin A pretreatment can rescue lethality or other disease-associated phenotypes in HD mice is tested. The findings raise the prospect that compounds can enhance migration of enteric NC precursors across various HD-related genetic defects. In conclusion, these studies present a powerful differentiation strategy that enables access to human ENS development and establishes novel cell- and drug-based therapies in HD. Human PSCs represent a promising platform to explore the "second brain[1]" in human health and disease.

7. REFERENCES

1 Gershon, M. *The Second Brain-A Groundbreaking New Understanding of Nervous Disorders of the Stomach and Intestine*. (Harper Collins, 1999).
2 Furness, J. B. The enteric nervous system and neurogastroenterology. *Nature Reviews Gastroenterology & Hepatology* 9, 286-294, (2012).
3 Heanue, T. A. & Pachnis, V. Enteric nervous system development and Hirschsprung's disease: advances in genetic and stem cell studies. *Nat Rev Neurosci* 8, 466-479, (2007).
4 Chambers, S. M. et al. Combined small-molecule inhibition accelerates developmental timing and converts human pluripotent stem cells into nociceptors. *Nat Biotechnol* 30, 715-720, (2012).
5 Mica, Y., Lee, G., Chambers, S. M., Tomishima, M. J. & Studer, L. Modeling neural crest induction, melanocyte specification, and disease-related pigmentation defects in hESCs and patient-specific iPSCs. *Cell Rep* 3, 1140-1152, (2013).
6 Menendez, L., Yatskievych, T. A., Antin, P. B. & Dalton, S. Wnt signaling and a Smad pathway blockade direct the differentiation of human pluripotent stem cells to multipotent neural crest cells. *Proceedings of the National Academy of Sciences of the United States of America* 108, 19240-19245, (2011).
7 Lee, G. et al. Isolation and directed differentiation of neural crest stem cells derived from human embryonic stem cells. *Nat Biotechnol* 25, 1468-1475, (2007).
8 Chan, K. K. et al. Hoxb3 vagal neural crest-specific enhancer element for controlling enteric nervous system development. *Dev Dyn* 233, 473-483, (2005).
9 Fu, M., Lui, V. C., Sham, M. H., Cheung, A. N. & Tam, P. K. HOXB5 expression is spatially and temporarily regulated in human embryonic gut during neural crest cell colonization and differentiation of enteric neuroblasts. *Dev Dyn* 228, 1-10, (2003).
10 Wichterle, H., Lieberam, I., Porter, J. A. & Jessell, T. M. Directed differentiation of embryonic stem cells into motor neurons. *Cell* 110, 385-397, (2002).
11 Chambers, S. M. et al. Highly efficient neural conversion of human ES and iPS cells by dual inhibition of SMAD signaling. *Nat Biotechnol* 27, 275-280, (2009).
12 Chalazonitis, A. et al. Neurotrophin-3 induces neural crest-derived cells from fetal rat gut to develop in vitro as neurons or glia. *J Neurosci* 14, 6571-6584, (1994).

13 Laflamme, M. A. et al. Cardiomyocytes derived from human embryonic stem cells in pro-survival factors enhance function of infarcted rat hearts. *Nat Biotechnol* 25, 1015-1024, (2007).

14 Nathan, E. et al. The contribution of Islet1-expressing splanchnic mesoderm cells to distinct branchiomeric muscles reveals significant heterogeneity in head muscle development. *Development* 135, 647-657, (2008).

15 Christ, G. J., Moreno, A. P., Melman, A. & Spray, D. C. Gap junction-mediated intercellular diffusion of Ca2+ in cultured human corporal smooth muscle cells. *Am J Physiol* 263, C373-383, (1992).

16 Barthel, E. R. et al. Tissue engineering of the intestine in a murine model. *Journal of visualized experiments: JoVE*, e4279, (2012).

17 Di Lorenzo, C., Solzi, G. F., Flores, A. F., Schwankovsky, L. & Hyman, P. E. Colonic motility after surgery for Hirschsprung's disease. *The American journal of gastroenterology* 95, 1759-1764, (2000).

18 Drake, R. L. V., W.; Mitchell, A. W. M. *Gray's Anatomy for Students*. (Churchill Livingstone, 2010).

19 Hotta, R., Natarajan, D., Burns, A. J. & Thapar, N. Stem cells for GI motility disorders. *Curr Opin Pharmacol* 11, 617-623, (2011).

20 Gershon, M. D. Transplanting the enteric nervous system: a step closer to treatment for aganglionosis. *Gut* 56, 459-461, (2007).

21 Schafer, K. H., Micci, M. A. & Pasricha, P. J. Neural stem cell transplantation in the enteric nervous system: roadmaps and roadblocks. *Neurogastroenterol Motil* 21, 103-112, (2009).

22 Hotta, R. et al. Transplanted progenitors generate functional enteric neurons in the postnatal colon. *J Clin Invest* 123, 1182-1191, (2013).

23 Gariepy, C. E., Cass, D. T. & Yanagisawa, M. Null mutation of endothelin receptor type B gene in spotting lethal rats causes aganglionic megacolon and white coat color. *Proceedings of the National Academy of Sciences of the United States of America* 93, 867-872, (1996).

24 Kruger, G. M. et al. Temporally distinct requirements for endothelin receptor B in the generation and migration of gut neural crest stem cells. *Neuron* 40, 917-929, (2003).

25 Tam, P. K. & Garcia-Barcelo, M. Genetic basis of Hirschsprung's disease. *Pediatric surgery international* 25, 543-558, (2009).

26 Jinek, M. et al. RNA-programmed genome editing in human cells. *eLife* 2, e00471, (2013).

27 Cong, L. et al. Multiplex genome engineering using CRISPR/Cas systems. *Science* 339, 819-823, (2013).

28 Chakravarti, A. Endothelin receptor-mediated signaling in hirschsprung disease. *Hum Mol Genet* 5, 303-307, (1996).

29 Tobin, J. L. et al. Inhibition of neural crest migration underlies craniofacial dysmorphology and Hirschsprung's disease in Bardet-Biedl syndrome. *Proceedings of the National Academy of Sciences of the United States of America* 105, 6714-6719, (2008).

30 Zhang, Y., Kim, T. H. & Niswander, L. Phactr4 regulates directional migration of enteric neural crest through PP1, integrin signaling, and cofilin activity. *Genes Dev* 26, 69-81, (2012).

31 Yoshida, H. et al. Pepstatin A, an aspartic proteinase inhibitor, suppresses RANKL-induced osteoclast differentiation. *J Biochem* 139, 583-590, (2006).

32 Haas, H. A. Extending the search for folk personality constructs: the dimensionality of the personality-relevant proverb domain. *J Pers Soc Psychol* 82, 594-609, (2002).

33 Gershon, M. D. & Tack, J. The serotonin signaling system: from basic understanding to drug development for functional GI disorders. *Gastroenterology* 132, 397-414, (2007).

34 Vassar, R. et al. Function, therapeutic potential and cell biology of BACE proteases: current status and future prospects. *J Neurochem* 130, 4-28, (2014).

35 Torii, T. et al. In vivo knockdown of ErbB3 in mice inhibits Schwann cell precursor migration. *Biochem Biophys Res Commun* 452, 782-788, (2014).

36 Wakatsuki, S., Araki, T. & Sehara-Fujisawa, A. Neuregulin-1/glial growth factor stimulates Schwann cell migration by inducing alpha5 beta1 integrin-ErbB2-focal adhesion kinase complex formation. *Genes Cells* 19, 66-77, (2014).

37 Cully, M. Deal watch: Lilly buys back into the BACE race for Alzheimer's disease. Nature reviews. *Drug discovery* 13, 804, (2014).

38 Zeltner, N., Lafaille, F. G., Fattahi, F. & Studer, L. Feeder-free derivation of neural crest progenitor cells from human pluripotent stem cells. *Journal of visualized experiments: JoVE*, (2014).

39 Hosoda, K. et al. Targeted and natural (piebald-lethal) mutations of endothelin-B receptor gene produce megacolon associated with spotted coat color in mice. *Cell* 79, 1267-1276, (1994).

40 Ran, F. A. et al. Double nicking by RNA-guided CRISPR Cas9 for enhanced genome editing specificity. *Cell* 154, 1380-1389, (2013).

41 Berthold, M. et al. in *Data Analysis, Machine Learning and Applications Studies in Classification, Data Analysis, and Knowledge Organization* (eds Christine Preisach, Hans Burkhardt, Lars Schmidt-Thieme, & Reinhold Decker) Ch. 38, 319-326 (Springer Berlin Heidelberg, 2008).

42 Dreser, N. et al. Grouping of histone deacetylase inhibitors and other toxicants disturbing neural crest migration by transcriptional profiling. *Neurotoxicology* 50, 56-70, (2015).

Various patents and other publications are cited herein, the contents of which are hereby incorporated by reference in their entireties.

What is claimed is:

1. An in vitro method for inducing differentiation of human stem cells to vagal neural crest lineage cells expressing PAX3 and at least one enteric neural crest lineage marker selected from the group consisting of HOXB3 and HOXB5, comprising:
contacting human stem cells with at least one inhibitor of TGFβ/Activin-Nodal signaling and at least one activator of Wnt signaling, and further contacting said cells with at least one molecule that induces vagal neural crest patterning in a concentration of from about 5 μM to 100 μM for at least about 2 days to produce a population of vagal neural crest lineage cells that express PAX3 and at least one enteric neural crest lineage marker selected from the group consisting of HOXB3 and HOXB5;
wherein the initial contact of said cells with said at least one molecule that induces vagal neural crest patterning is between about 2 days and about 6 days from the initial contact of said cells with said at least one activator of Wnt signaling;
wherein said at least one molecule that induces vagal neural crest patterning is selected from the group consisting of retinoic acid, retinol, retinal, tretinoin, isotretinoin, alitretinoin, etretinate, acitretin, tazarotene, bexarotene, adapalene, activators of FGF signaling, and combinations thereof.

2. The method of claim 1, comprising contacting said cells with said at least one molecule that induces vagal neural crest patterning for about 6 days.

3. The method of claim 1, comprising initially contacting said cells with said at least one molecule that induces vagal neural crest patterning within an about 8-day period from the initial contact of said cells with said at least one activator of Wnt signaling.

4. The method of claim 1, comprising initially contacting said cells with said at least one molecule that induces vagal neural crest patterning about 4 days from the initial contact of said cells with said at least one activator of Wnt signaling.

5. The method of claim 1, wherein said stem cells are differentiated into said population of differentiated cells that express said at least one enteric neural crest lineage marker on or after about 11 days from their initial contact with said at least one inhibitor of TGFβ/Activin-Nodal signaling.

6. The method of claim 1, comprising contacting said stem cells with at least one inhibitor of SMAD signaling.

7. The method of claim 6, comprising contacting said stem cells with said at least one inhibitor of TGFβ/Activin-Nodal signaling and said at least one inhibitor of SMAD signaling concurrently.

8. The method of claim 6, wherein said at least one inhibitor of SMAD signaling comprises LDN193189.

9. The method of claim 1, comprising initially contacting said cells with said at least one activator of Wnt signaling within an about 4-day period from the initial contact of said stem cells with said at least one inhibitor of TGFβ/Activin-Nodal signaling.

10. The method of claim 9, comprising initially contacting said cells with said at least one activator of Wnt signaling about 2 days from the initial contact of said stem cells with said at least one inhibitor of TGFβ/Activin-Nodal signaling.

11. The method of claim 1, comprising initially contacting said stem cells with said at least one inhibitor of TGFβ/Activin-Nodal signaling on the same day as the initial contact of said cells with said at least one activator of Wnt signaling.

12. The method of claim 1, wherein said at least one inhibitor of TGFβ/Activin-Nodal signaling comprises SB431542.

13. The method of claim 1, wherein said at least one activator of Wnt signaling comprises CHIR99021.

14. The method of claim 1, wherein said at least one molecule that induces vagal neural crest patterning comprises at least one activator of FGF signaling.

15. The method of claim 1, comprising contacting said cells with one molecule that induces vagal neural crest patterning.

16. The method of claim 15, wherein said one molecule that induces vagal neural crest patterning is retinoic acid.

17. The method of claim 1, wherein said activators of FGF signaling are selected from the group consisting of FGF2, FGF4, FGF7, and FGF8.

18. The method of claim 1, wherein said differentiated cells further express at least one marker selected from the group consisting of EDNRB, RET, PHOX2A, PHOX2B, NTRK-3, HAND2, and ASCL1.

19. The method of claim 1, wherein said differentiated cells further express at least one SOX10$^+$ neural crest lineage marker.

20. The method of claim 19, wherein said at least one SOX10$^+$ neural crest lineage marker is CD49D.

21. The method of claim 1, wherein said human stem cells are selected from the group consisting of human embryonic stem cells, human induced pluripotent stem cells, human parthenogenetic stem cells, primordial germ cell-like pluripotent stem cells, epiblast stem cells, and F-class pluripotent stem cells.

22. The method of claim 1, further comprising subjecting said population of differentiated cells to conditions favoring maturation of said differentiated cells into a population of cells that express at least one enteric neuron marker.

23. The method of claim 22, wherein said conditions favoring maturation of said differentiated cells into said population of cells expressing the at least one enteric neuron marker comprise culturing said differentiated cells in a suitable cell culture medium.

24. The method of claim 22, wherein said at least one enteric neuron marker is selected from the group consisting of Tuj1, MAP2, PHOX2A, PHOX2B, TRKC, ASCL1, HAND2, EDNRB, 5HT, GABA, NOS, SST, TH, CHAT, DBH, Substance P, VIP, NPY, GnRH, and CGRP.

25. The method of claim 23, wherein said suitable cell culture medium comprises at least one molecule that enhances maturation of enteric neural crest (ENC) precursors to enteric neurons.

26. The method of claim 25, wherein said at least one molecule that enhances maturation of ENC precursors to enteric neurons is selected from the group consisting of growth factors and Wnt activators.

27. The method of claim 26, wherein said growth factors are selected from the group consisting of activators of FGF signaling, glial cell line derived neurotrophic factor (GDNF), and ascorbic acid.

28. The method of claim 26, wherein said suitable cell culture medium comprises at least one activator of FGF signaling and at least one activator of Wnt signaling.

29. The method of claim 28, wherein said differentiated cells are cultured in said suitable cell culture medium comprising said at least one activator of FGF signaling and said at least one activator of Wnt signaling for about 4 days.

30. The method of claim 28, wherein the at least one activator of FGF signaling is selected from the group consisting of FGF2, FGF4, FGF8, and FGF7.

31. The method of claim 1, wherein said stem cells are differentiated into said population of differentiated cells that express said at least one enteric neural crest lineage marker about 11 days from their initial contact with said at least one inhibitor of TGFβ/Activin-Nodal signaling.

32. An in vitro method for inducing differentiation of human stem cells to vagal neural crest lineage cells expressing PAX3 and at least one enteric neural crest lineage marker selected from the group consisting of HOXB3 and HOXB5, comprising:
    contacting stem cells with at least one inhibitor of TGFβ/Activin-Nodal signaling and at least one activator of Wnt signaling, and further contacting said cells with at least one molecule that induces vagal neural crest patterning in a concentration of from about 5 µM to 100 µM for at least about 2 days, for between about 2 days and about 20 days, or for between about 2 days and about 6 days, to produce a population of vagal neural crest lineage cells that express PAX3 and at least one enteric neural crest lineage marker selected from the group consisting of HOXB3 and HOXB5,
    wherein the initial contact of said cells with said at least one molecule that induces vagal neural crest patterning is between about 2 days and about 6 days from the initial contact of said cells with said at least one activator of Wnt signaling;
    wherein the initial contact of said cells with said at least one molecule that induces vagal neural crest patterning is within an about 8-day period from the initial contact of said cells with said at least one activator of Wnt signaling, and
    wherein said at least one molecule that induces vagal neural crest patterning is selected from the group consisting of retinoic acid, retinol, retinal, tretinoin, isotretinoin, alitretinoin, etretinate, acitretin, tazarotene, bexarotene, adapalene, activators of FGF signaling, and combinations thereof.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial sequence
<220> FEATURE:
<223> OTHER INFORMATION: Synthetic oligonucleotide

```
<400> SEQUENCE: 1
aagtctgtgc ggacgcgccc tgg                                         23

<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 2
ccagatccgc gacaggccgc agg                                         23

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
acgccttctg gagcaggtag                                             20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
gtcaggcggg aagcctctct                                             20
```